(12) United States Patent
Uno

(10) Patent No.: US 11,814,395 B2
(45) Date of Patent: Nov. 14, 2023

(54) CONDENSED CYCLIC COMPOUND AND ORGANIC LIGHT-EMITTING DEVICE INCLUDING THE SAME

(71) Applicant: Samsung Display Co., Ltd., Yongin-Si (KR)

(72) Inventor: Takuya Uno, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 506 days.

(21) Appl. No.: 16/429,782

(22) Filed: Jun. 3, 2019

(65) Prior Publication Data
US 2019/0389877 A1 Dec. 26, 2019

(30) Foreign Application Priority Data

Jun. 22, 2018 (KR) ........................ 10-2018-0072153

(51) Int. Cl.
*C07D 493/04* (2006.01)
*C07D 495/04* (2006.01)
*H10K 50/13* (2023.01)
*H10K 85/60* (2023.01)
*H10K 50/15* (2023.01)

(52) U.S. Cl.
CPC ......... *C07D 493/04* (2013.01); *C07D 495/04* (2013.01); *H10K 50/13* (2023.02); *H10K 85/622* (2023.02); *H10K 85/633* (2023.02); *H10K 85/636* (2023.02); *H10K 85/656* (2023.02); *H10K 85/6572* (2023.02); *H10K 85/6574* (2023.02); *H10K 85/6576* (2023.02); *H10K 50/15* (2023.02)

(58) Field of Classification Search
CPC . C07D 493/04; C07D 495/04; H01L 51/0054; H01L 51/0059; H01L 51/006; H01L 51/0061; H01L 51/0071; H01L 51/0072; H01L 51/0073; H01L 51/0074; H01L 51/5012; H01L 51/504; H01L 51/5056; H10K 50/13; H10K 85/622; H10K 85/633; H10K 85/636; H10K 85/6572; H10K 85/6574; H10K 85/6576; H10K 85/656; H10K 50/11; H10K 85/631; H10K 85/657; H10K 50/12; H10K 85/40
See application file for complete search history.

(56) References Cited

U.S. PATENT DOCUMENTS 7,507,485 B2 * 3/2009 Oh .......................... C09B 15/00
428/690
8,318,323 B2 11/2012 Kato et al.
(Continued)

FOREIGN PATENT DOCUMENTS

CN 103524518 B 1/2014
EP 3130591 A1 2/2017
(Continued)

OTHER PUBLICATIONS

Gao, Peng (2009). "Thiophene-Containing Organic Semiconducting Heteroacenes for Electronic Applications." Johannes Gutenberg-Universitat in Mainz, pp. 1-280. (Year: 2009).*

*Primary Examiner* — Dawn L Garrett
(74) *Attorney, Agent, or Firm* — Lewis Roca Rothgerber Christie LLP

(57) ABSTRACT

Provided are a condensed cyclic compound and an organic light-emitting device including the same.

19 Claims, 4 Drawing Sheets

(56) References Cited

U.S. PATENT DOCUMENTS

| | | | |
|---|---|---|---|
| 9,461,249 B2* | 10/2016 | Vestweber | C07C 17/2632 |
| 2004/0124766 A1* | 7/2004 | Nakagawa | H01L 51/5234 |
| | | | 313/504 |
| 2008/0220285 A1* | 9/2008 | Vestweber | C07C 49/792 |
| | | | 564/426 |
| 2012/0138918 A1* | 6/2012 | Naraoka | C09K 11/06 |
| | | | 257/E51.026 |
| 2015/0171334 A1* | 6/2015 | Kato | H01L 51/0055 |
| | | | 257/40 |
| 2016/0197282 A1 | 7/2016 | Tanimoto et al. | |
| 2016/0351816 A1 | 12/2016 | Kim et al. | |
| 2017/0047526 A1 | 2/2017 | Chung et al. | |
| 2017/0222158 A1 | 8/2017 | Jung et al. | |
| 2017/0342318 A1 | 11/2017 | Kim et al. | |
| 2019/0152985 A1* | 5/2019 | Suh | H01L 51/0061 |

FOREIGN PATENT DOCUMENTS

| | | |
|---|---|---|
| JP | 2004-200141 A | 7/2004 |
| JP | 2012-028548 A | 2/2012 |
| JP | 5499972 B2 | 5/2014 |
| KR | 10-2011-0025906 A | 3/2011 |
| KR | 10-2012-0009984 A | 2/2012 |
| KR | 10-2012-0034140 A | 4/2012 |
| KR | 10-2015-0114636 A | 10/2015 |
| KR | 10-2015-0121337 A | 10/2015 |
| KR | 10-2016-0036158 A | 4/2016 |
| KR | 10-2016-0050700 A | 5/2016 |
| KR | 10-2017-0056425 A | 5/2017 |
| KR | 10-2017-0082459 A | 7/2017 |
| KR | 10-2017-0086243 A | 7/2017 |
| KR | 10-2017-0086277 A | 7/2017 |
| WO | 2009-148062 A1 | 12/2009 |
| WO | 2015-022988 A1 | 2/2015 |
| WO | 2016-068441 A1 | 5/2016 |
| WO | 2016-068450 A1 | 5/2016 |
| WO | 2016-108419 A1 | 7/2016 |
| WO | WO 2018/110989 A1 * | 6/2018 |

* cited by examiner

| 190 |
|---|
| 150 |
| 110 |

| 190 |
|---|
| 150 |
| 110 |
| 210 |

| 220 |
|-----|
| 190 |
| 150 |
| 110 |

| |
|---|
| 220 |
| 190 |
| 150 |
| 110 |
| 210 |

CONDENSED CYCLIC COMPOUND AND ORGANIC LIGHT-EMITTING DEVICE INCLUDING THE SAME

CROSS-REFERENCE TO RELATED APPLICATION

This application claims the benefit of Korean Patent Application No. 10-2018-0072153, filed on Jun. 22, 2018, in the Korean Intellectual Property Office, the disclosure of which is incorporated herein in its entirety by reference.

BACKGROUND

1. Field

One or more embodiments relate to a condensed cyclic compound and an organic light-emitting device including the same.

2. Description of the Related Art

Organic light-emitting devices are self-emission devices that produce full-color images, and also have wide viewing angles, high contrast ratios, short response times, and excellent characteristics in terms of brightness, driving voltage, and response speed, compared to devices in the art.

An example of such organic light-emitting devices may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transit from an excited state to a ground state, thereby generating light.

SUMMARY

One or more embodiments provide a condensed cyclic compound and an organic light-emitting device including the same.

Additional aspects will be set forth in part in the description which follows and, in part, will be apparent from the description, or may be learned by practice of the presented embodiments.

An aspect provides a condensed cyclic compound represented by Formula 1-1 or 1-2:

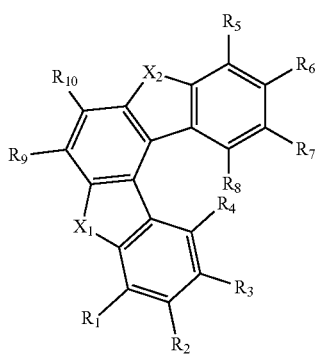
<Formula 1-1>

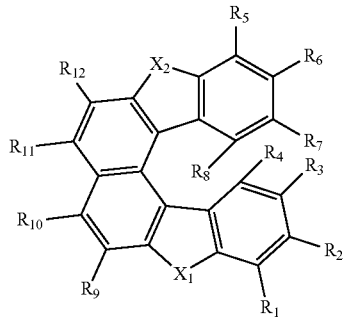
<Formula 1-2>

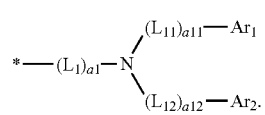
<Formula 2>

In Formulae 1-1, 1-2, and 2, $X_1$ and $X_2$ may each independently be selected from O, S, and $Si(R_{13})(R_{14})$, $L_1$, $L_{11}$, and $L_{12}$ may each independently be selected from *—O—*', a substituted or unsubstituted $C_3$-$C_{60}$ carbocyclic group, and a substituted or unsubstituted $C_1$-$C_{60}$ heterocyclic group, a1 may be an integer from 1 to 5, a11 and a12 may each independently be an integer from 0 to 4, $Ar_1$ and $Ar_2$ may each independently be selected from a substituted or unsubstituted $C_3$-$C_{60}$ carbocyclic group and a substituted or unsubstituted $C_1$-$C_{60}$ heterocyclic group, $R_1$ to $R_{14}$ may each independently be selected from a group represented by Formula 2, hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$B(Q_1)(Q_2)$, —$S(=O)_2(Q_1)$, and —$P(=O)(Q_1)(Q_2)$, at least one selected from $R_5$ to $R_8$ may be a group represented by Formula 2, $R_1$ to $R_4$ do not include a carbazole group, any two neighboring groups among $R_1$ to $R_{14}$ may optionally be linked to form a substituted or unsubstituted $C_3$-$C_{60}$ carbocyclic group or a $C_1$-$C_{60}$ heterocyclic group, at least one substituent of the substituted $C_3$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group may be selected from:

deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* and *' each indicate a binding site to a neighboring atom.

Another aspect provides an organic light-emitting device including: a first electrode; a second electrode facing the first electrode; and an organic layer between the first electrode and the second electrode and including an emission layer, wherein the organic layer includes at least one of the condensed cyclic compound.

BRIEF DESCRIPTION OF THE DRAWINGS

These and/or other aspects will become apparent and more readily appreciated from the following description of the embodiments, taken in conjunction with the accompanying drawings in which:

FIG. 1 is a schematic view of an organic light-emitting device according to an embodiment;

FIG. 2 is a schematic view of an organic light-emitting device according to another embodiment;

FIG. 3 is a schematic view of an organic light-emitting device according to another embodiment; and FIG. 4 is a schematic view of an organic light-emitting device according to another embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list. A condensed cyclic compound according to an embodiment is represented by Formula 1-1 or 1-2:

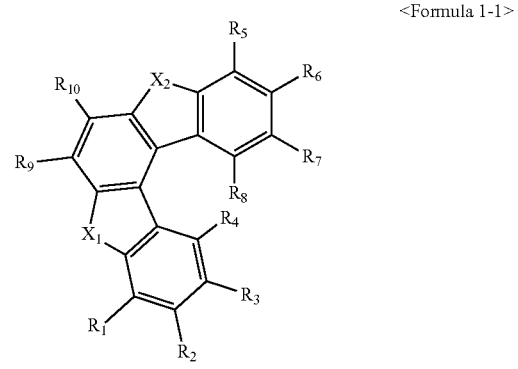

<Formula 1-1>

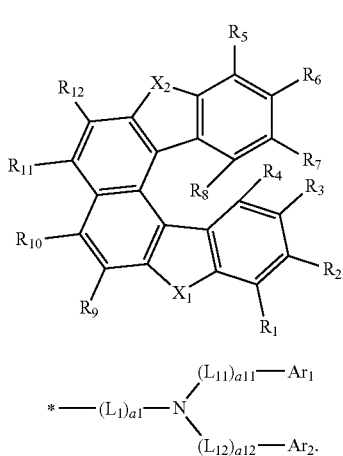

<Formula 1-2>

<Formula 2>

In Formulae 1-1 to 1-2 and 2, $X_1$ and $X_2$ may each independently be selected from O, S, and $Si(R_{13})(R_{14})$.

In one embodiment, i) each of $X_1$ and $X_2$ may be O, ii) each of $X_1$ and $X_2$ may be S, iii) $X_1$ may be O, and $X_2$ may be S or $Si(R_{13})(R_{14})$, iv) $X_1$ may be S, and $X_2$ may be O or $Si(R_{13})(R_{14})$, V) $X_1$ may be S or $Si(R_{13})(R_{14})$, and $X_2$ may be O, or vi) $X_1$ may be O or $Si(R_{13})(R_{14})$, and $X_2$ may be S.

In Formulae 1-1 to 1-2 and 2, $L_1$, $L_{11}$, and $L_{12}$ may each independently be selected from *—O—*', a substituted or unsubstituted $C_3$-$C_{60}$ carbocyclic group, and a substituted or unsubstituted $C_1$-$C_{60}$ heterocyclic group.

For example, $L_1$ may be selected from a substituted or unsubstituted $C_3$-$C_{60}$ carbocyclic group, and a substituted or unsubstituted $C_1$-$C_{60}$ heterocyclic group, but embodiments of the present disclosure are not limited thereto.

In one embodiment, $L_1$, $L_{11}$, and $L_{12}$ may each independently be selected from:

*—O—*', a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a benzosilole group, a dibenzosilole group, a quinoline group, an isoquinoline group, a benzimidazole group, an imidazopyridine group, and an imidazopyrimidine group;

a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a benzosilole group, a dibenzosilole group, a quinoline group, an isoquinoline group, a benzimidazole group, an imidazopyridine group, and an imidazopyrimidine group, each substituted with at least one selected from deuterium, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a pyridinyl group, a pyrazinyl group, a pyrimidinyl group, a pyridazinyl group, a quinolinyl group, an isoquinolinyl group, a benzofuranyl group, a benzothiophenyl group, —$Si(Q_{31})(Q_{32})(Q_{33})$, —$N(Q_{31})(Q_{32})$, and —$B(Q_{31})(Q_{32})$, and Qi and $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, and a pyridinyl group.

In one embodiment, $L_1$, $L_{11}$, and $L_{12}$ may each independently be selected from *—O—*' and groups represented by Formulae 3-1 to 3-29:

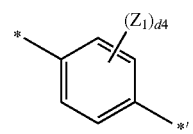

3-1

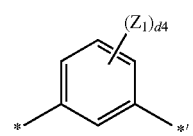

3-2

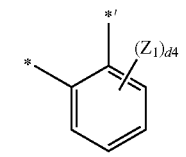

3-3

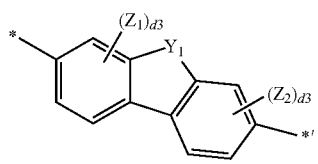

3-4

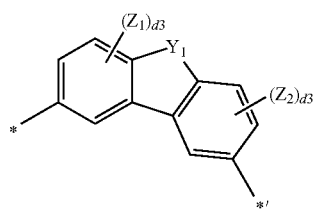

3-5

3-6
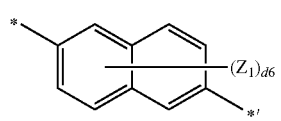
3-7
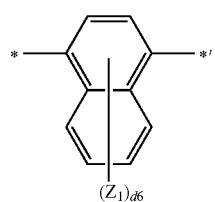
3-8
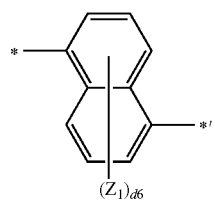
3-9
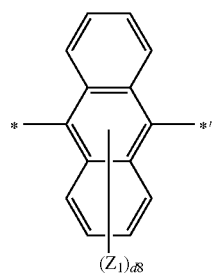
3-10
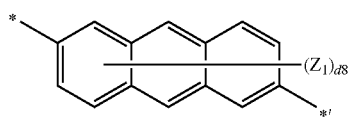
3-11
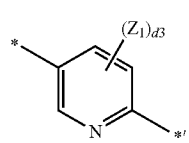
3-12
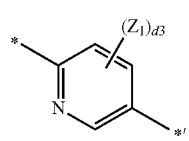
3-13
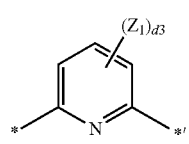
3-14
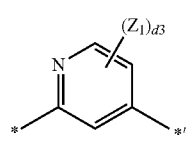
3-15
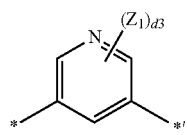
3-16
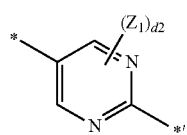
3-17
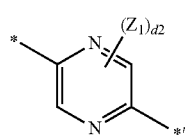
3-18
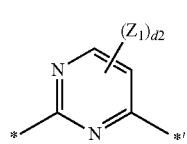
3-19
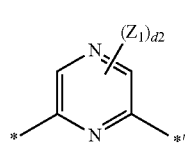
3-20
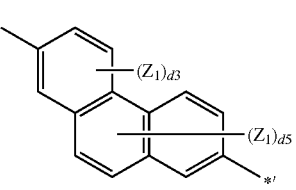
3-21
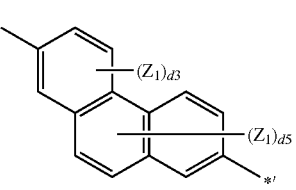
3-22
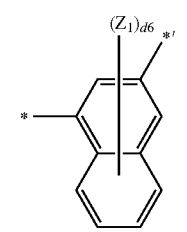
3-23
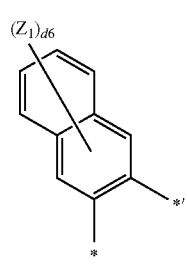

-continued

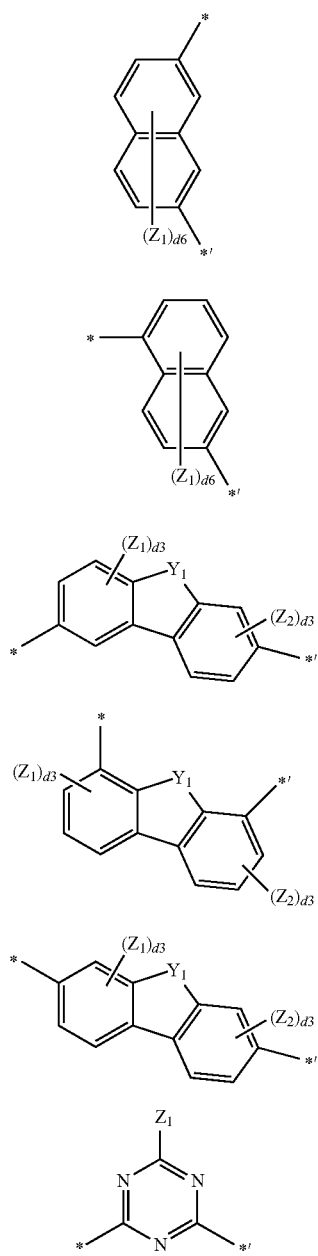

In Formulae 3-1 to 3-29,

Y$_1$ may be selected from C(Z$_3$)(Z$_4$), N(Z$_5$), Si(Z$_6$)(Z$_7$), O, and S, Z$_1$ to Z$_7$ may each independently be selected from hydrogen, deuterium, —F, —Cl, —Br, —I, a hydroxyl group, a cyano group, a C$_1$-C$_{20}$ alkyl group, a C$_1$-C$_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a pyrenyl group, a chrysenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a benzofuranyl group, a benzothiophenyl group, a benzosilolyl group, a dibenzosilolyl group, and —Si(Q$_{31}$)(Q$_{32}$)(Q$_{33}$), Q$_{31}$ to Q$_{33}$ may each independently be selected from a C$_1$-C$_{20}$ alkyl group, a C$_1$-C$_{20}$ alkoxy group, a phenyl group, a biphenyl group, a terphenyl group, a naphthyl group, and a pyridinyl group, d2 may be an integer from 0 to 2,
d3 may be an integer from 0 to 3,
d4 may be an integer from 0 to 4,
d6 may be an integer from 0 to 6,
d8 may be an integer from 0 to 8, and
* and *' each indicate a binding site to a neighboring atom.

For example, L$_1$ may be a group represented by Formula 3-1.

In Formulae 1-1 to 1-2 and 2, a1 may be an integer from 1 to 5, and a11 and a12 may each independently be an integer from 0 to 4.

In one embodiment, a1 may be 1 or 2.

In one embodiment, a11 and a12 may each independently be an integer from 0 to 2.

In Formulae 1-1 to 1-2 and 2, Ar$_1$ and Ar$_2$ may each independently be selected from a substituted or unsubstituted C$_3$-C$_{60}$ carbocyclic group and a substituted or unsubstituted C$_1$-C$_{60}$ heterocyclic group.

In one embodiment, Ar$_1$ and Ar$_2$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a triphenylenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, an adamantanyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, a benzonaphtho silolyl group, a dinaphtho silolyl group, a benzimidazolyl group, a phenanthrolinyl group, and an imidazopyridinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a triphenylenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, an adamantanyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, a benzonaphtho silolyl group, a dinaphtho silolyl group, a benzimidazolyl group, a phenanthrolinyl group, and an imidazopyridinyl group, each substituted with at least one selected from deuterium, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a triphenylenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, an adamantanyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, a benzonaphtho silolyl group, a dinaphtho silolyl group, a benzimidazolyl group, a phenanthrolinyl group, an imidazopyridinyl group, $-N(Q_{31})(Q_{32})$, $-Si(Q_{31})(Q_{32})(Q_{33})$, and $-P(=O)(Q_{31})(Q_{32})$; and $-N(Q_1)(Q_2)$, $-B(Q_1)(Q_2)$, $-S(=O)_2(Q_1)$, and $-P(=O)(Q_1)(Q_2)$, and $Q_1$, $Q_2$, and $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, and a pyridinyl group.

In Formulae 1-1 to 1-2 and 2, $Ar_1$ and $Ar_2$ may each independently be selected from a substituted or unsubstituted $C_3$-$C_{60}$ carbocyclic group and a substituted or unsubstituted $C_1$-$C_{60}$ heterocyclic group.

In one embodiment, $Ar_1$ and $Ar_2$ may each independently be selected from groups represented by Formulae 4-1 to 4-15:

4-1

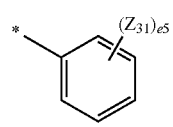

4-2

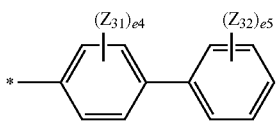

4-3

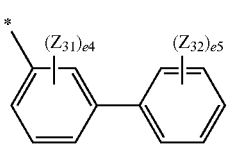

4-4

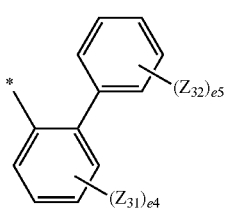

-continued 4-5

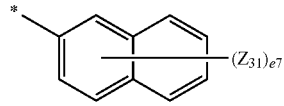

4-6

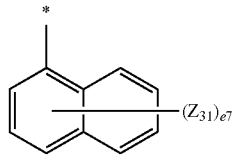

4-7

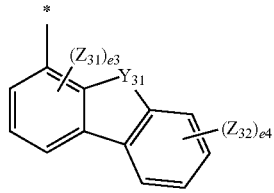

4-8

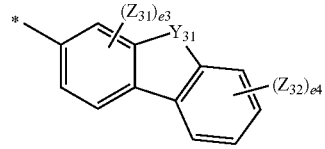

4-9

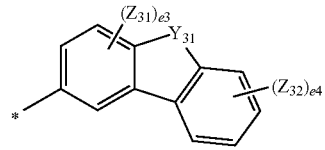

4-10

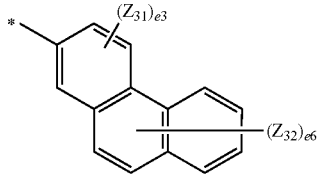

4-11

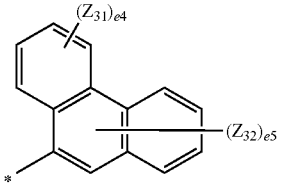

4-12

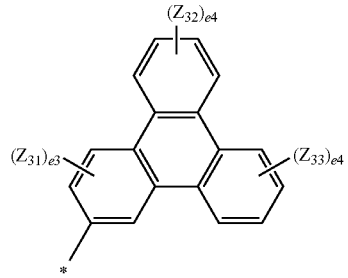

-continued 4-13

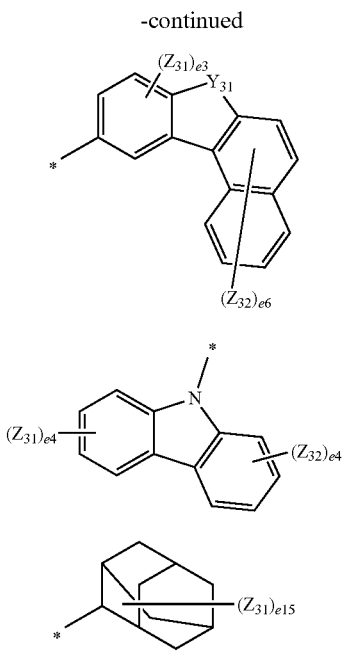

4-14

4-15

In Formulae 4-1 to 4-15, $Y_{31}$ may be selected from $C(Z_{34})(Z_{35})$, $N(Z_{36})$, $Si(Z_{37})(Z_{38})$, O, and S, $Z_{31}$ to $Z_{38}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a triazinyl group, a biphenyl group, a terphenyl group, a phenyl group substituted with a $C_1$-$C_{20}$ alkyl group, and —$Si(Q_{31})(Q_{32})(Q_{33})$, $Q_{31}$ to $Q_{33}$ may each independently be selected from a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and a phenyl group substituted with a $C_1$-$C_{20}$ alkyl group, e3 may be an integer from 0 to 3,
e4 may be an integer from 0 to 4,
e5 may be an integer from 0 to 5,
e6 may be an integer from 0 to 6,
e7 may be an integer from 0 to 7,
e15 may be an integer from 0 to 15, and
* indicates a binding site to a neighboring atom.

For example, in Formula 2, $Ar_1$ and $Ar_2$ may not be linked.

In Formulae 1-1 to 1-2, and 2, $R_1$ to $R_{14}$ may each independently be selected from a group represented by Formula 2, hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed heteropolycyclic group, —$Si(Q_1)(Q_2)(Q_3)$, —$B(Q_1)(Q_2)$, —$S(=O)_2(Q_1)$, and —$P(=O)(Q_1)(Q_2)$, at least one selected from selected from $R_5$ to $R_8$ may be a group represented by Formula 2, $R_1$ to $R_4$ may not include a carbazole group, any two neighboring groups among $R_1$ to $R_{14}$ may optionally be linked to form substituted or unsubstituted $C_3$-$C_{60}$ carbocyclic group or $C_1$-$C_{60}$ heterocyclic group.

In one embodiment, $R_1$ to $R_{14}$ may each independently be selected from:

a group represented by Formula 2, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a triphenylenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, an adamantanyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, a benzonaphtho silolyl group, a dinaphtho silolyl group, a benzimidazolyl group, a phenanthrolinyl group, and an imidazopyridinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a triphenylenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, an adamantanyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, a benzonaphtho silolyl group, a dinaphtho silolyl group, a benzimidazolyl group, a phenanthrolinyl group, and an imidazopyridinyl group, each substituted with at least one selected from deuterium, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a triphenylenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, an adamantanyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, a benzonaphtho silolyl group, a dinaphtho silolyl group, a benzimidazolyl group, a phenanthrolinyl group, an imidazopyridinyl group, —N($Q_{31}$)($Q_{32}$), —Si($Q_{31}$)($Q_{32}$)($Q_{33}$), and —P(=O)($Q_{31}$)($Q_{32}$); and —B($Q_1$)($Q_2$), —S(=O)$_2$($Q_1$), and —P(=O)($Q_1$)($Q_2$), and $Q_1$, $Q_2$, and $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, and a pyridinyl group.

For example, in Formula 1-1, i) $R_1$ to $R_4$ and $R_9$ to $R_{10}$ may be hydrogen, ii) $R_1$ to $R_4$ may be hydrogen, and $R_9$ to $R_{10}$ may linked to form a benzene group.

For example, in Formula 1-2, i) $R_1$ to $R_4$ and $R_9$ to $R_{12}$ may each independently be hydrogen, ii) $R_1$ to $R_4$ and $R_9$ to $R_{10}$ may each independently be hydrogen, and $R_{11}$ and $R_{12}$ may be linked to form a benzene group, iii) $R_1$ to $R_2$ and $R_9$ to $R_{12}$ may each independently be hydrogen, and $R_3$ and $R_4$ may be formed to form a benzene group or a pyridine group.

For example, i) $R_5$ may be a group represented by Formula 2, and $R_6$ to $R_8$ may each independently be hydrogen ii) $R_6$ may be a group represented by Formula 2, and $R_5$, $R_7$, and $R_8$ may each independently be hydrogen iii) $R_7$ may be a group represented by Formula 2, and $R_5$, $R_6$, and $R_8$ may each independently be hydrogen, and iv) $R_8$ a group represented by Formula 2, and $R_5$ to $R_7$ may each independently be hydrogen.

At least one substituent of the substituted $C_3$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group may be selected from:

deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and Qi to $Q_3$, $Q_{11}$ to $Q_{13}$, $Q_{21}$ to $Q_{23}$, and $Q_{31}$ to $Q_{33}$ may each independently be selected from hydrogen, deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group.

In one embodiment, the condensed cyclic compound may be selected from Compounds A1 to A119 and B1 to B119, but embodiments of the present disclosure are not limited thereto:

A1

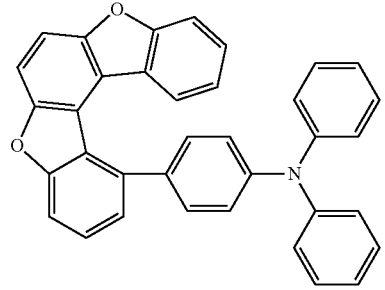

-continued
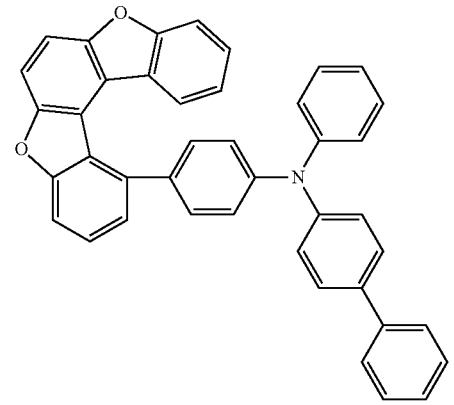
A2
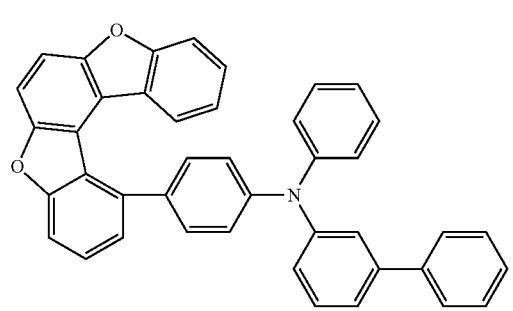
A3
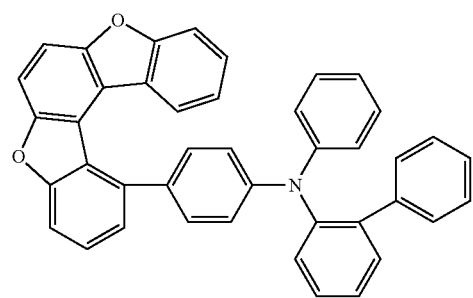
A4
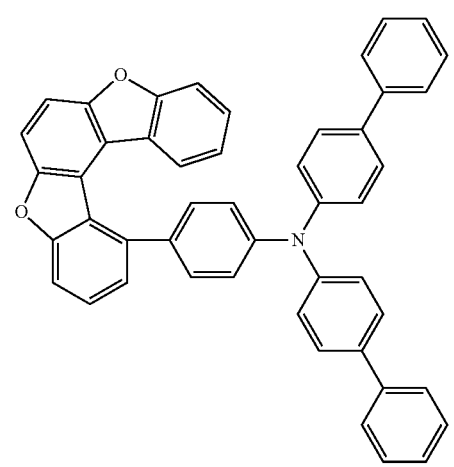
A5
-continued
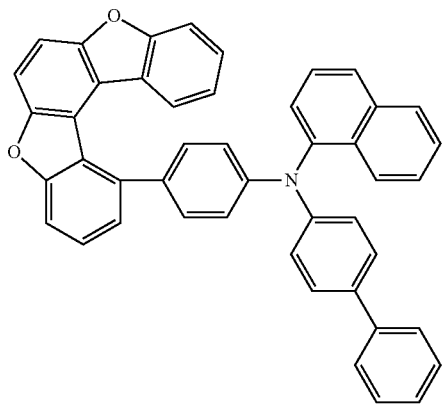
A6
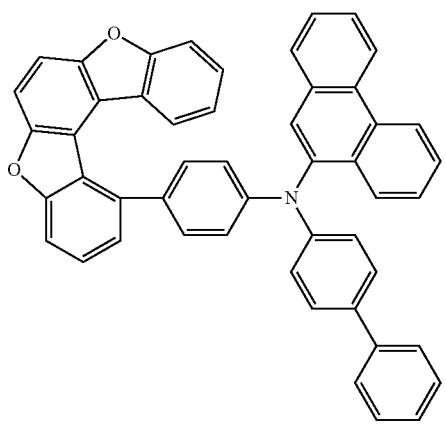
A7
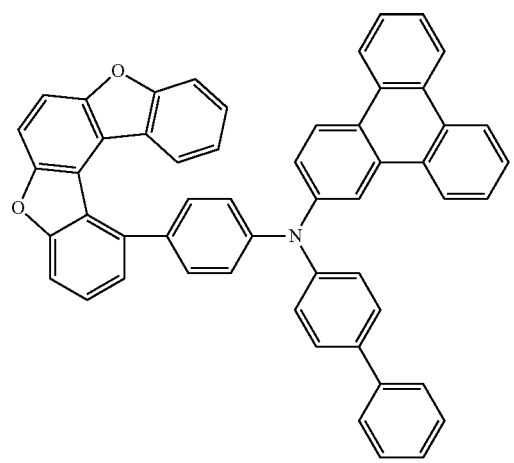
A8
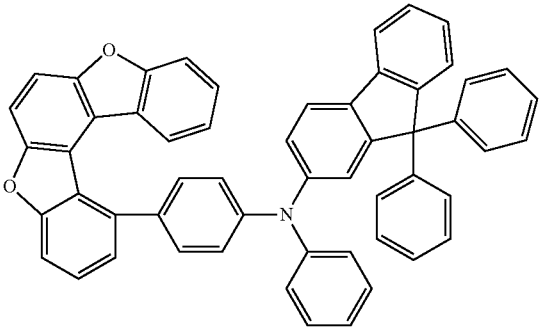
A9

-continued
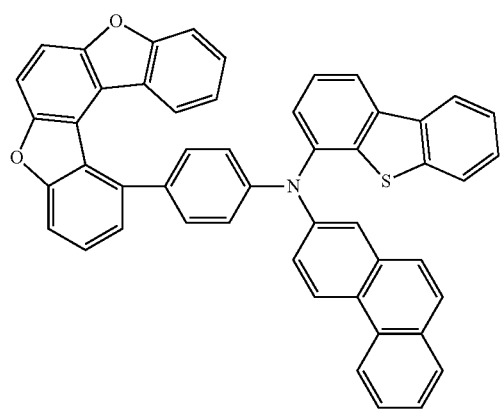
A10
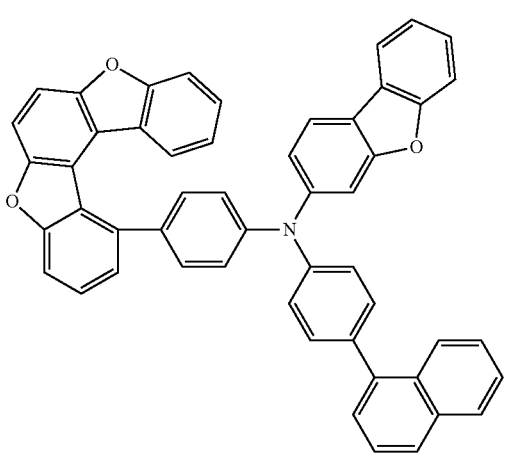
A11
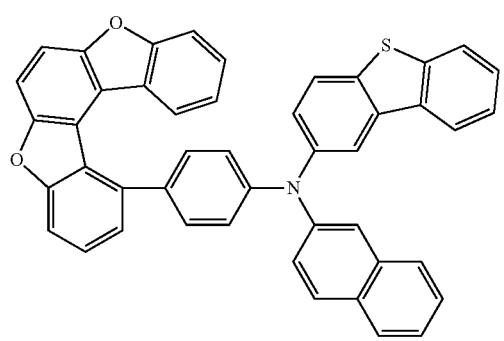
A12
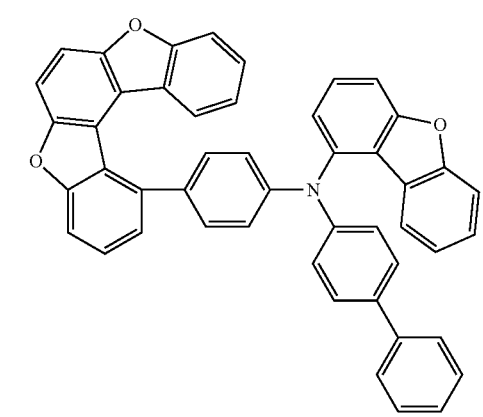
A13
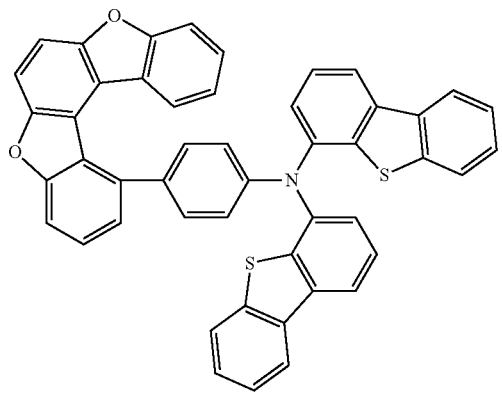
A14
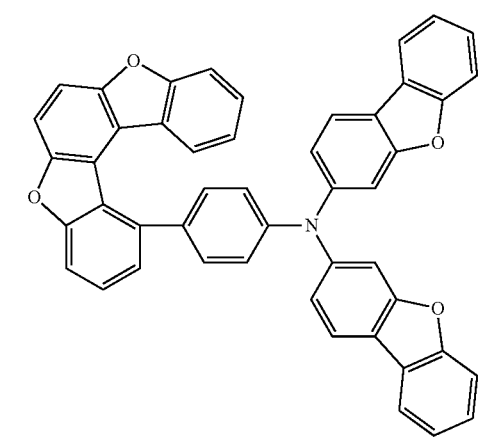
A15
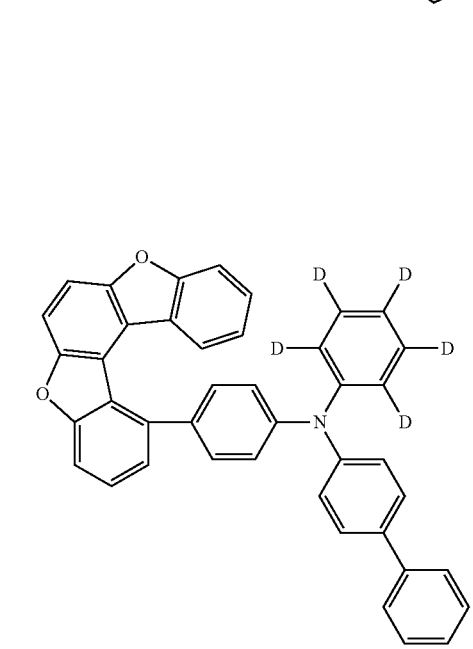
A16

A17
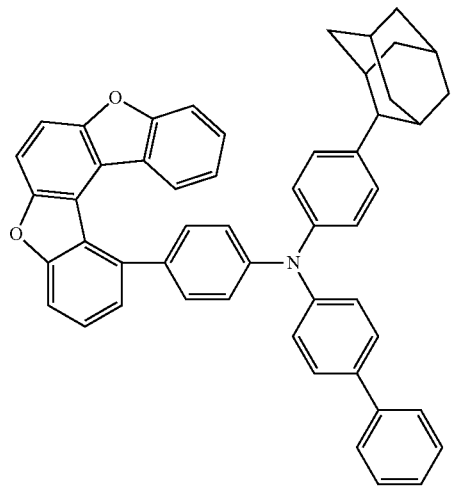
A20
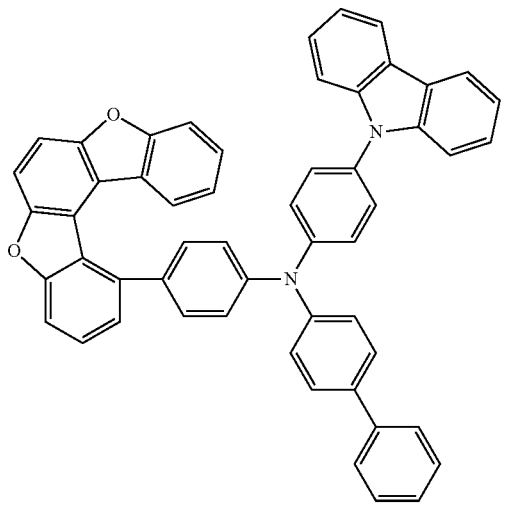
A18
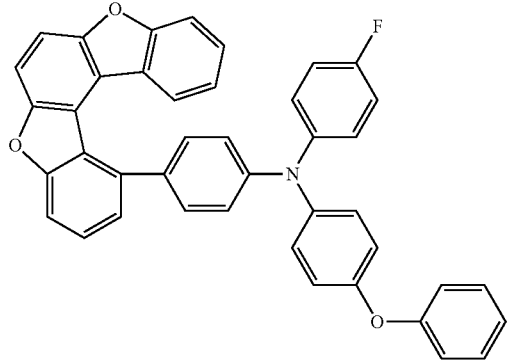
A21
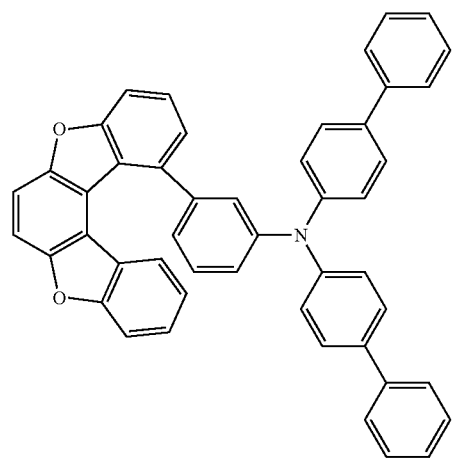
A19
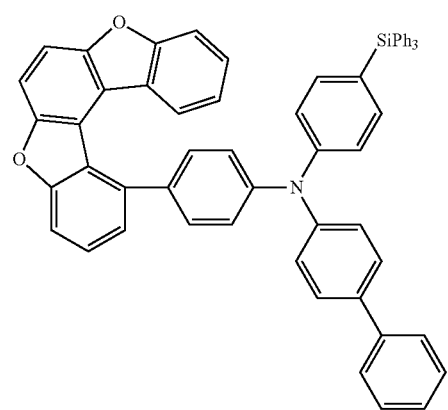
A22
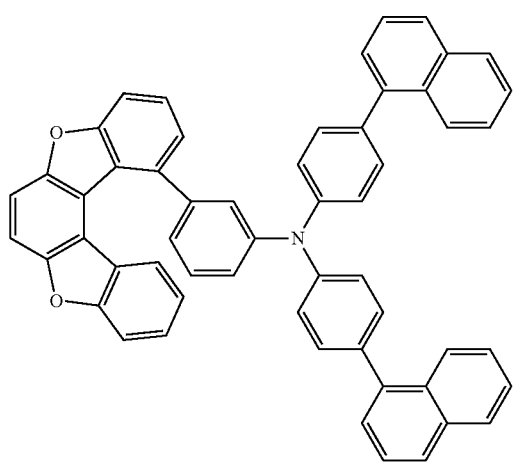

-continued
A23
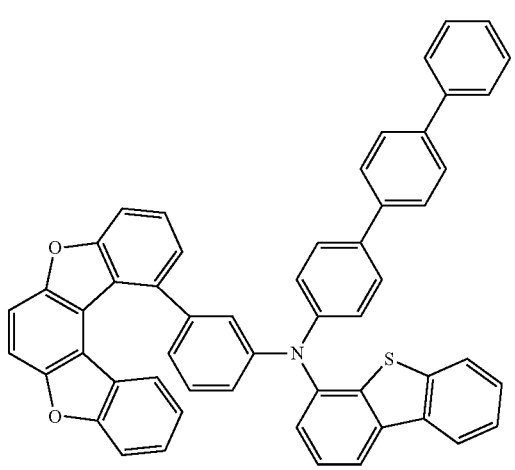
A24
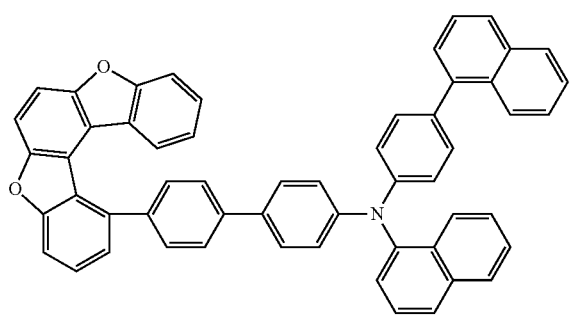
A25
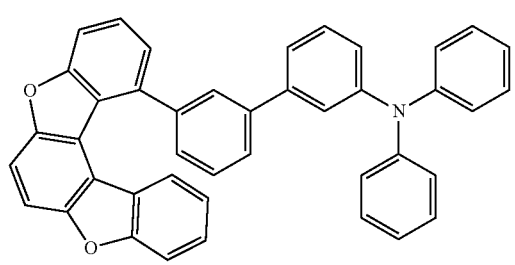
A26
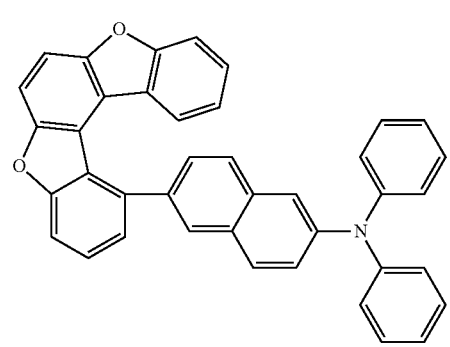
-continued
A27
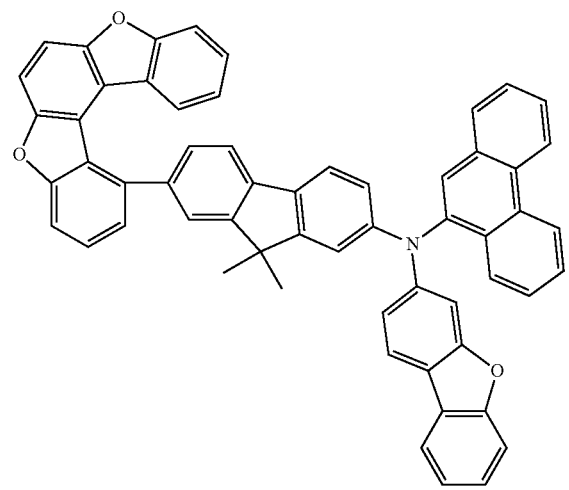
A28
A29
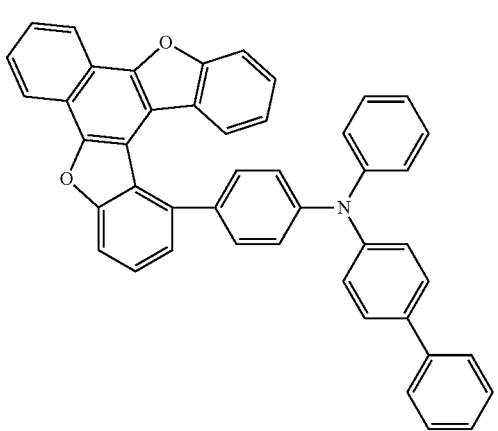

A30
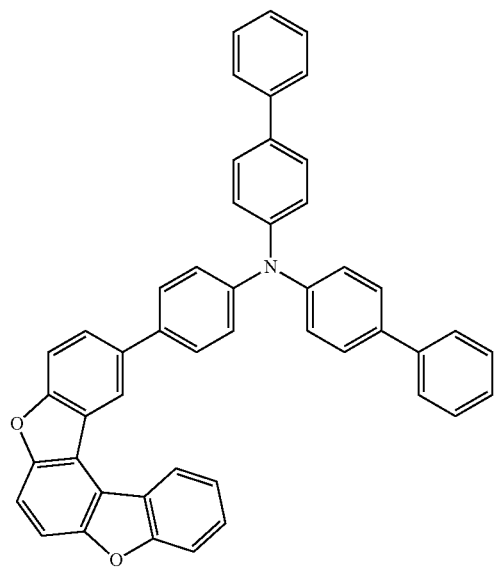
A31
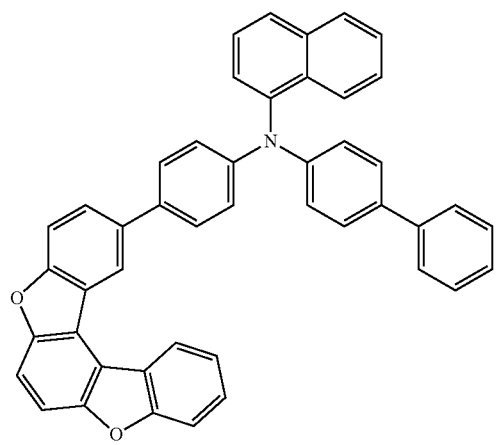
A32
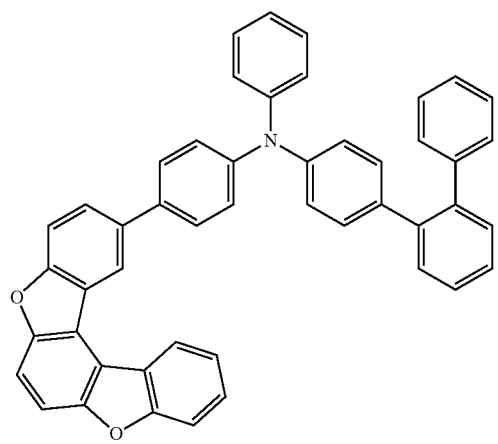
A33
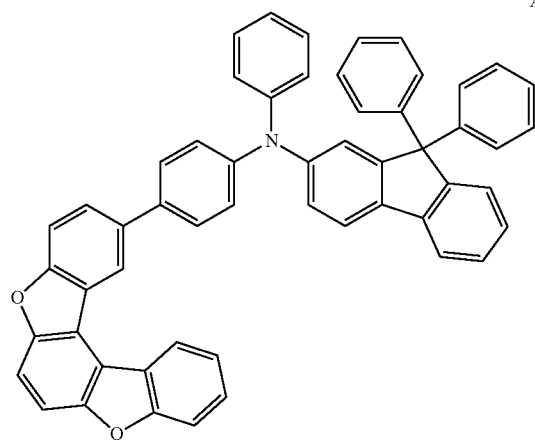
A34
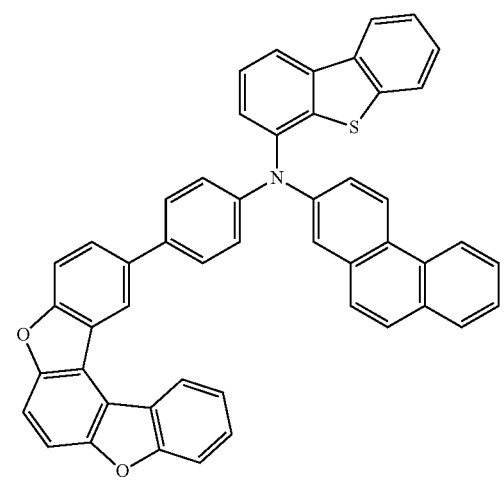
A35
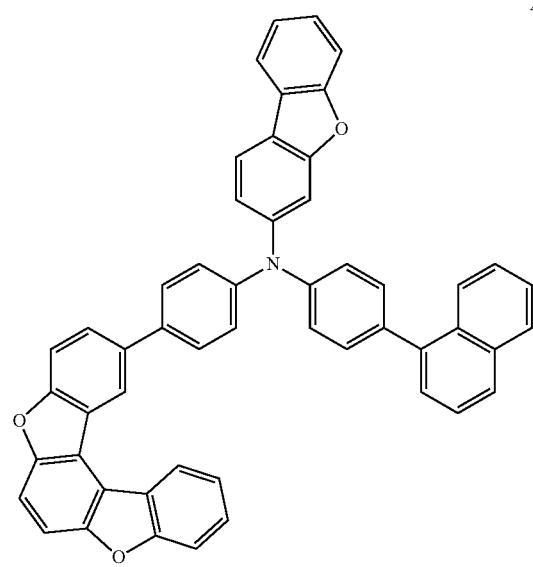

-continued
A36
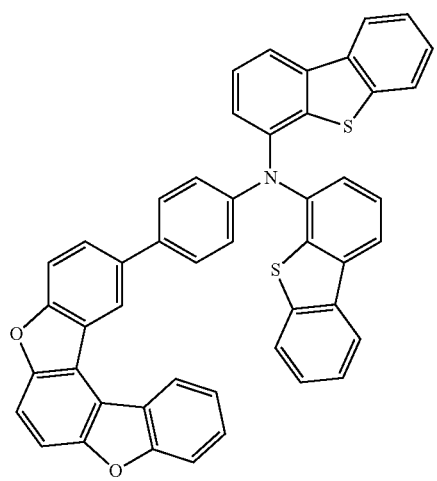
A37
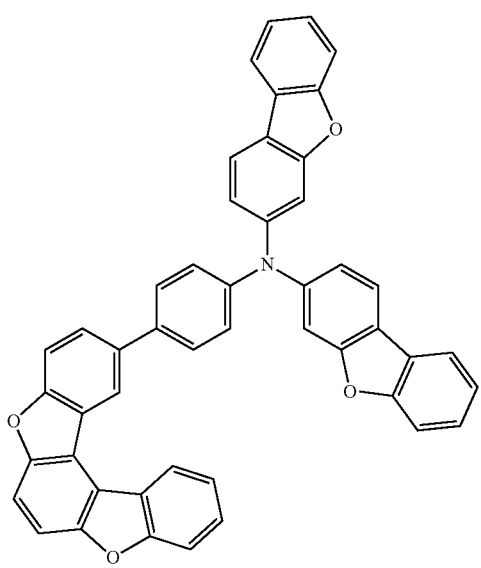
A38
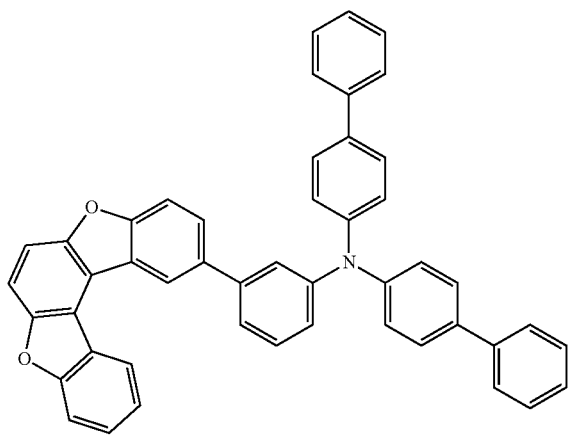
-continued
A39
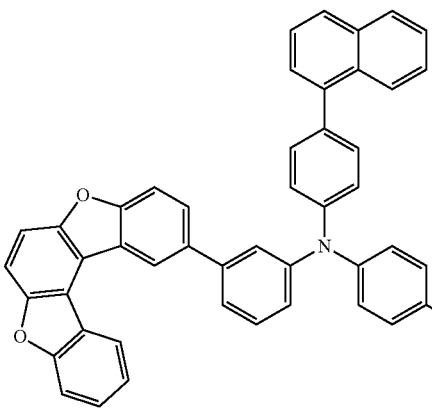
A40
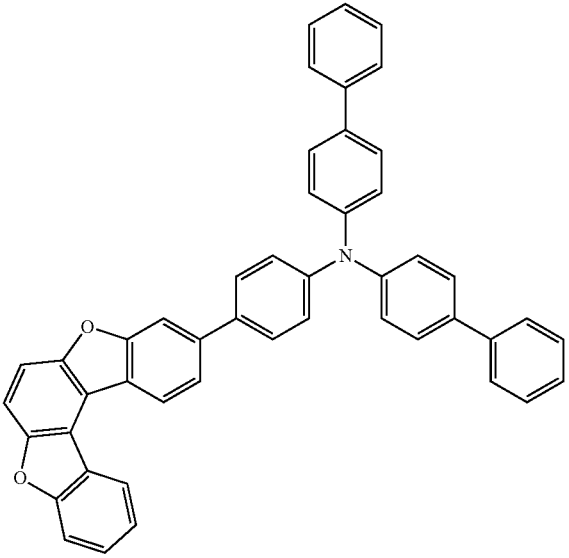
A41
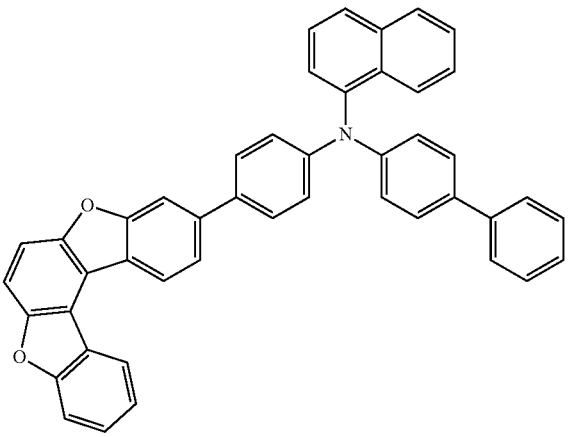

-continued
A42
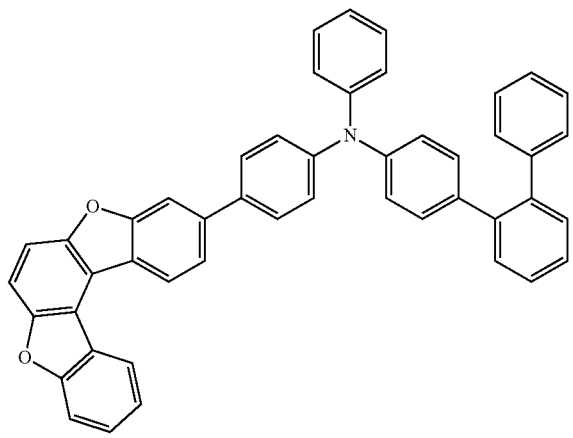
A43
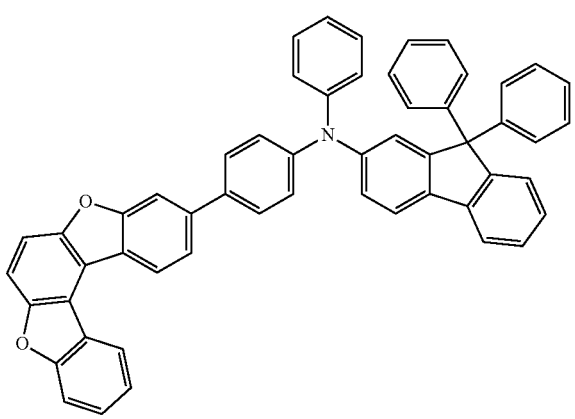
A44
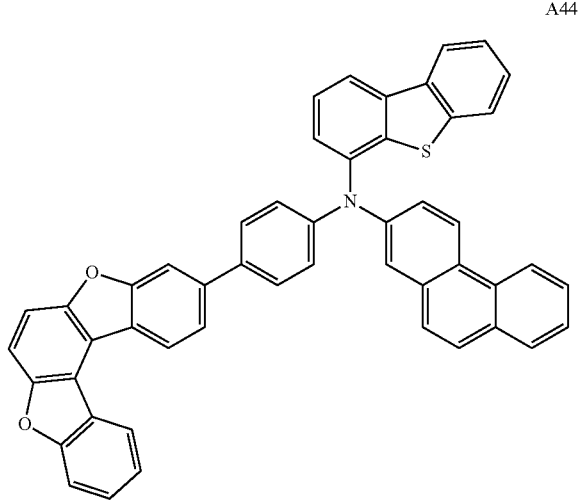
-continued
A45
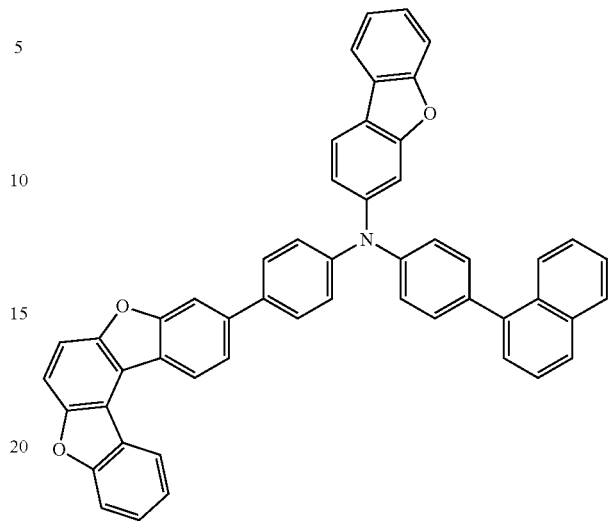
A46
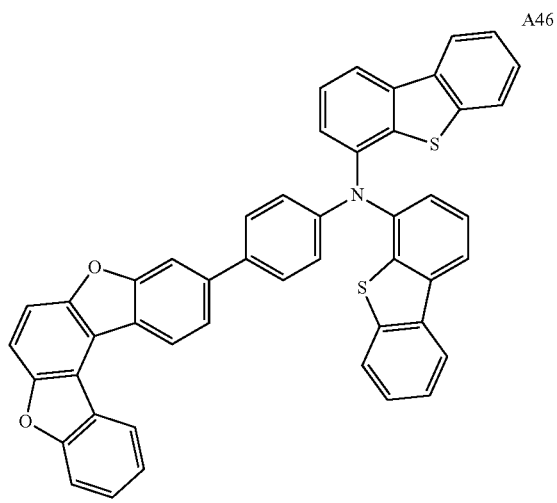
A47
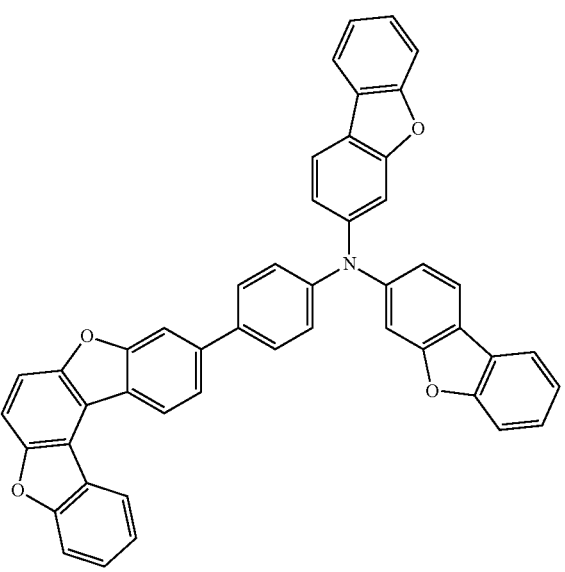

A48
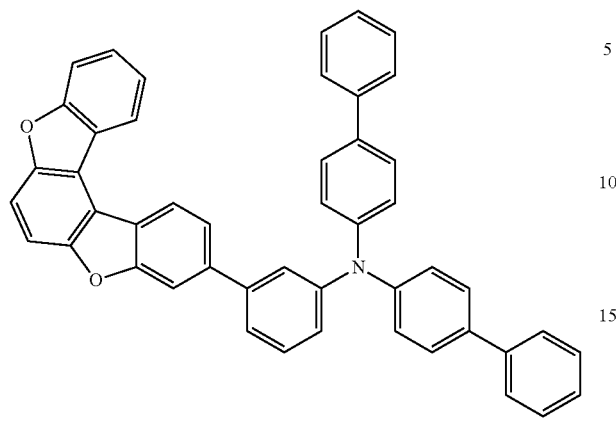
A49
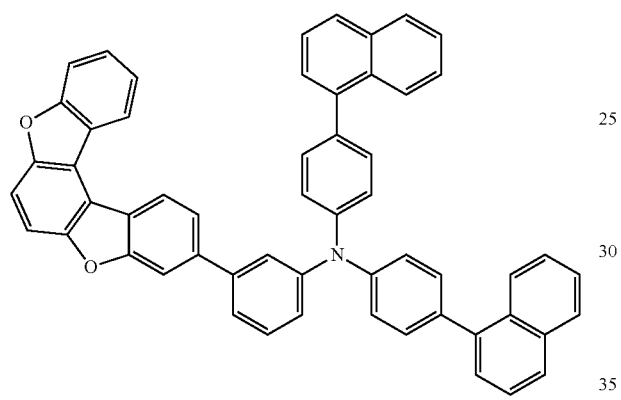
A50
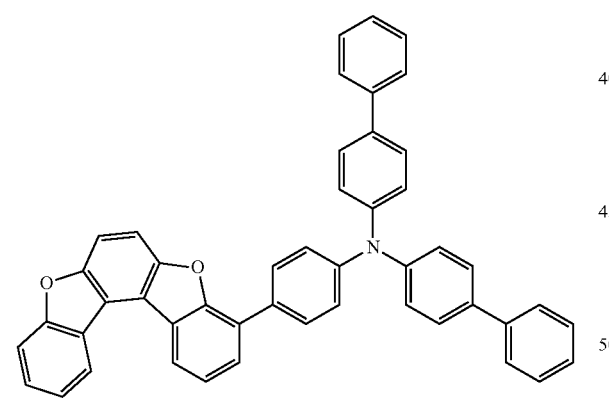
A51
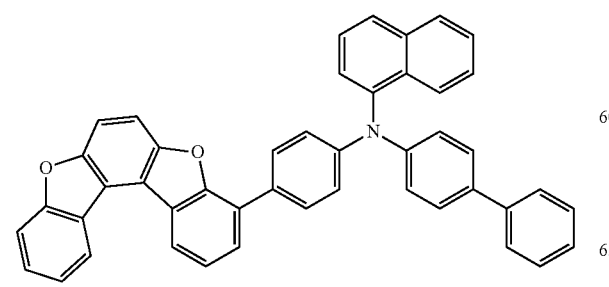
A52
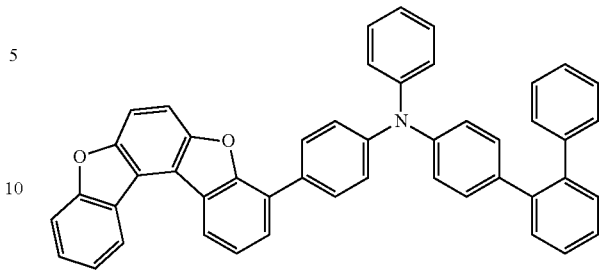
A53
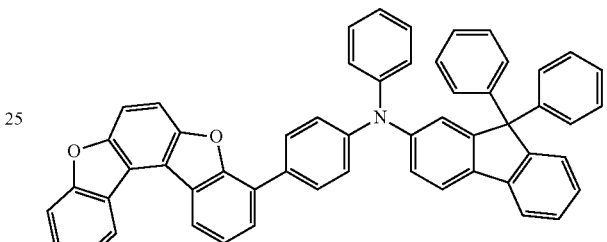
A54
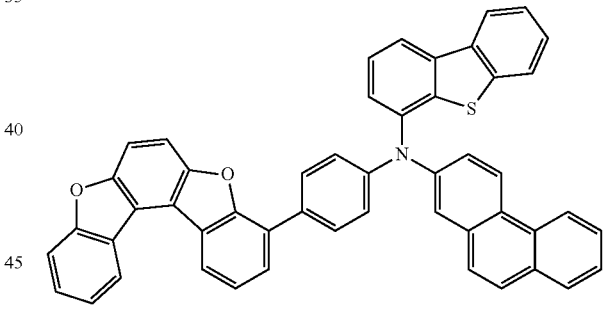
A55
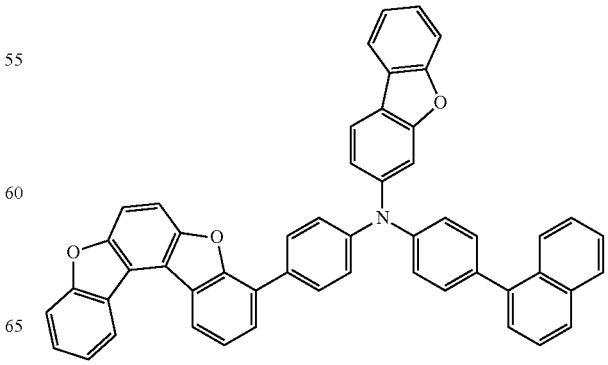

A56
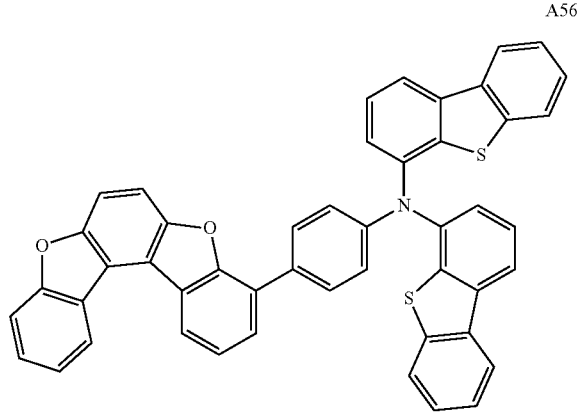
A59
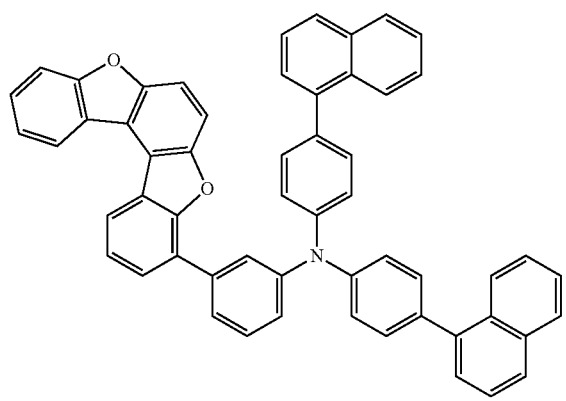
A57
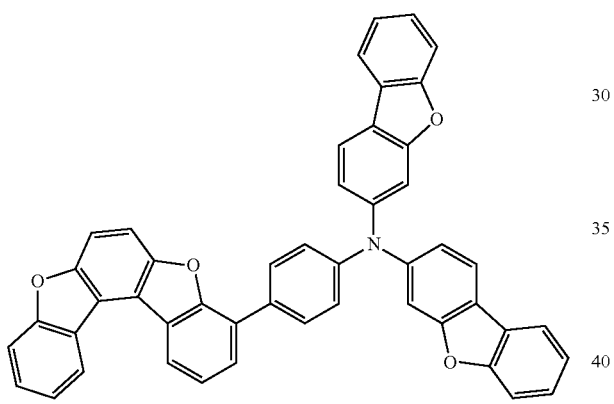
A60
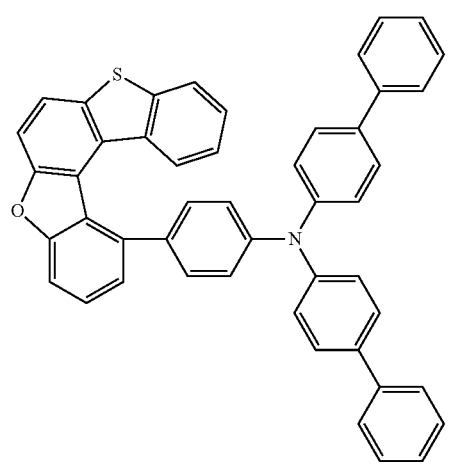
A58
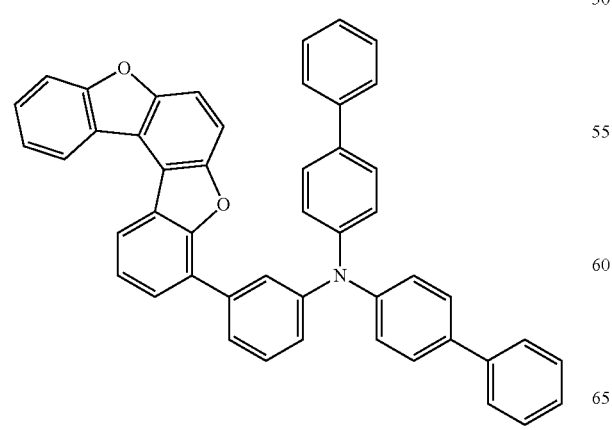
A61
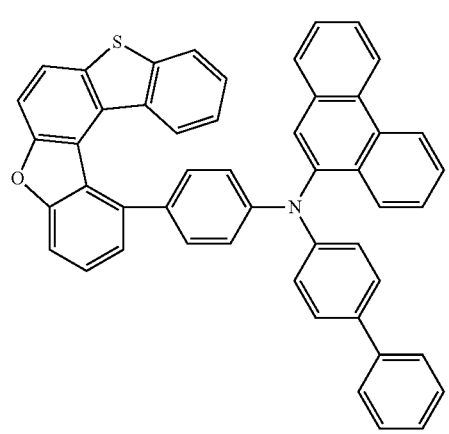

-continued
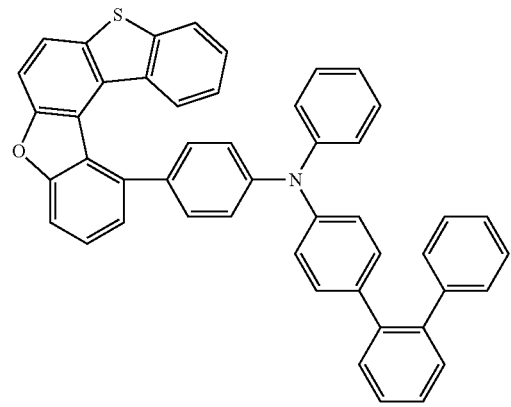
A62
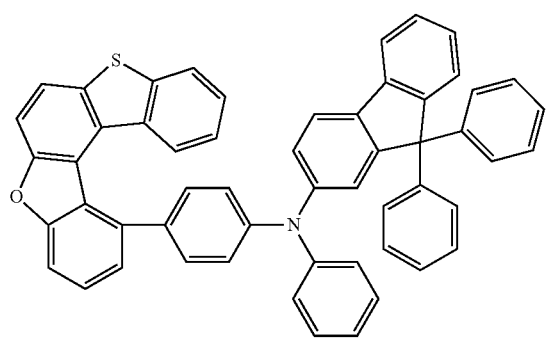
A63
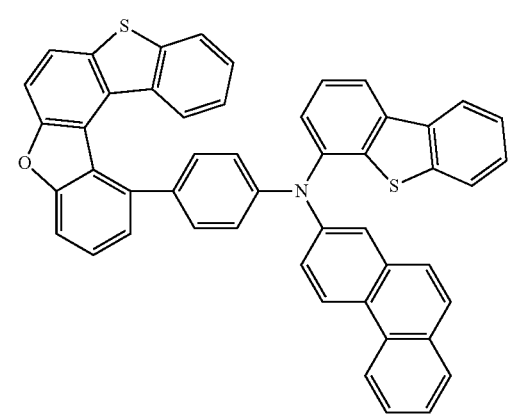
A64
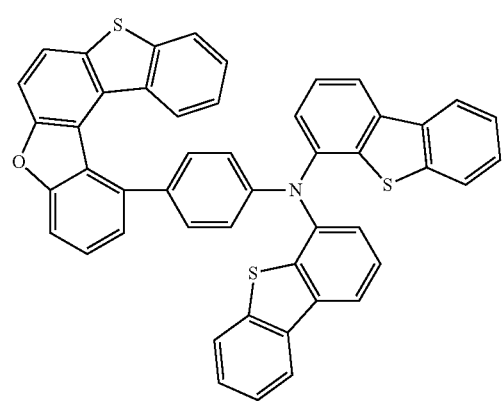
A65
-continued
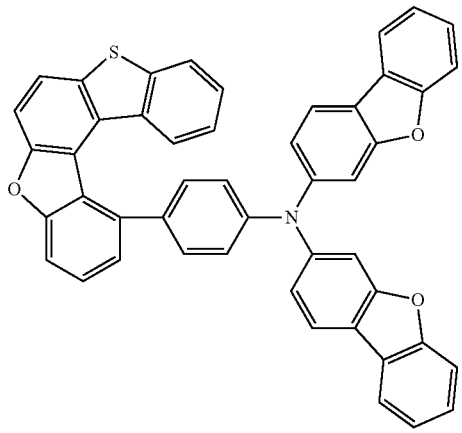
A66
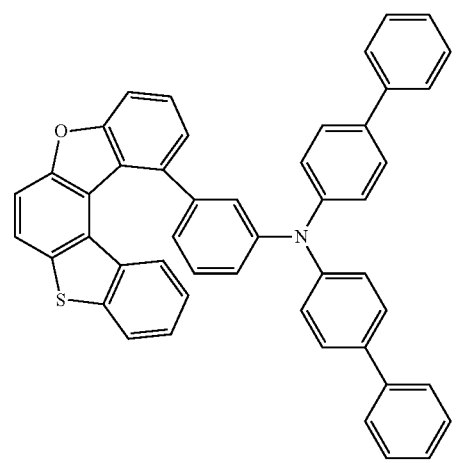
A67
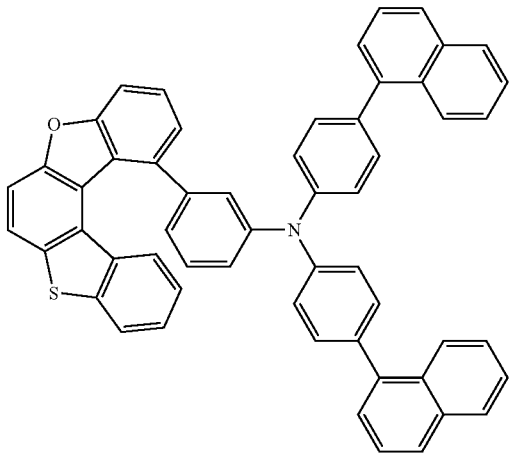
A68

A69
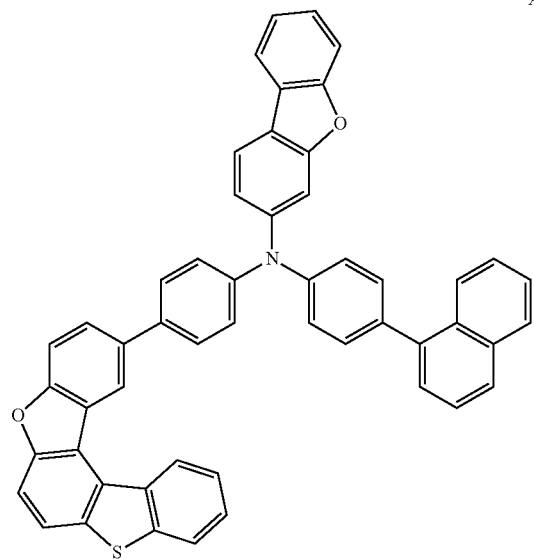
A70
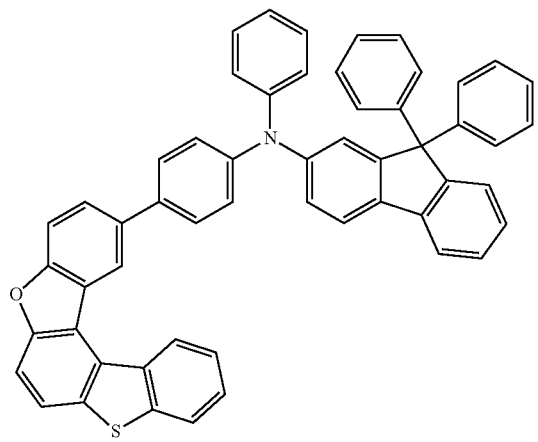
A71
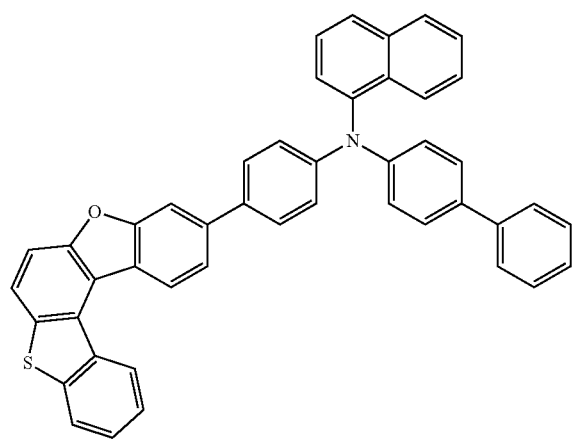
A72
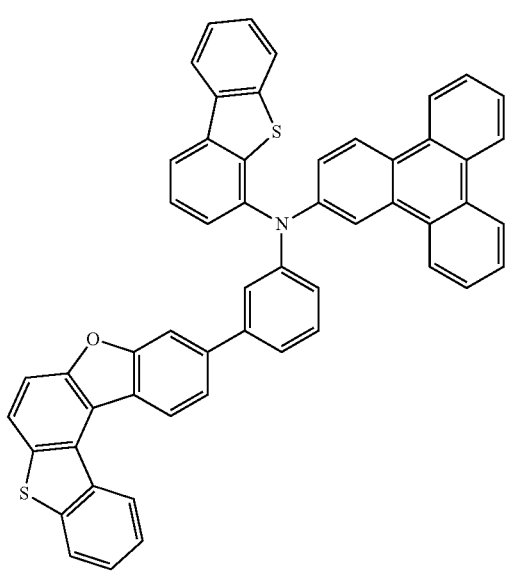
A73
A74
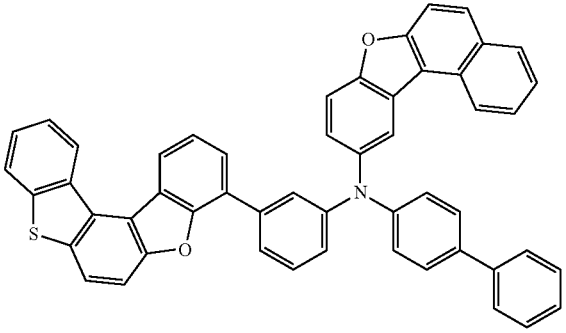

A75
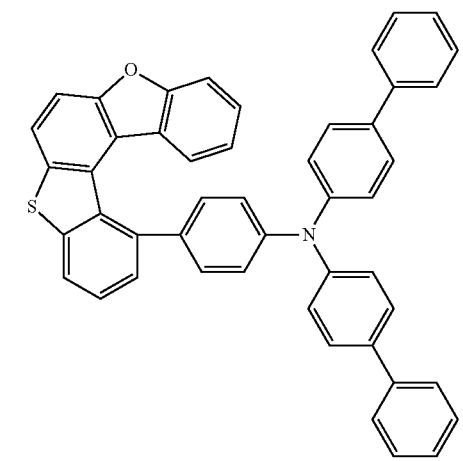
A76
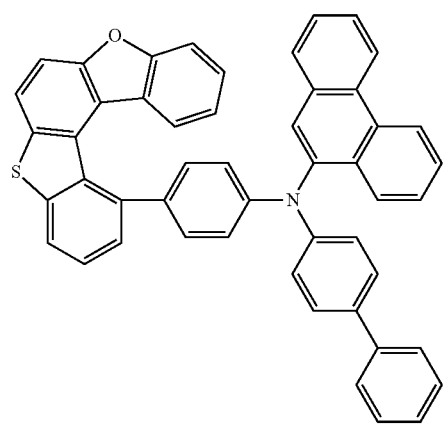
A77
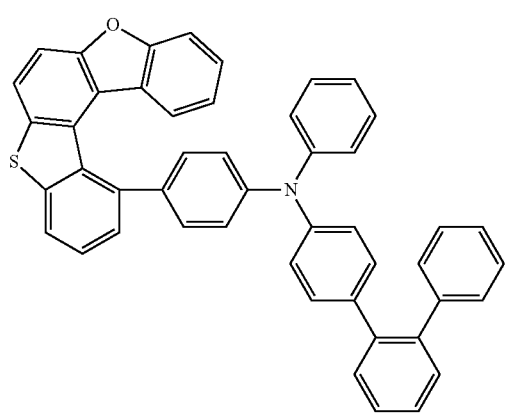
A78
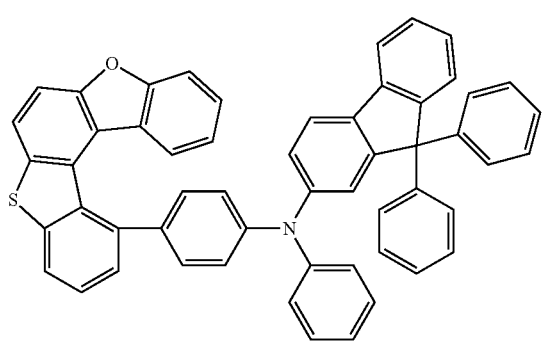
A79
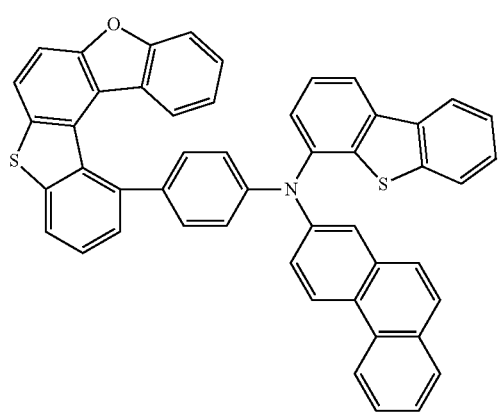
A80
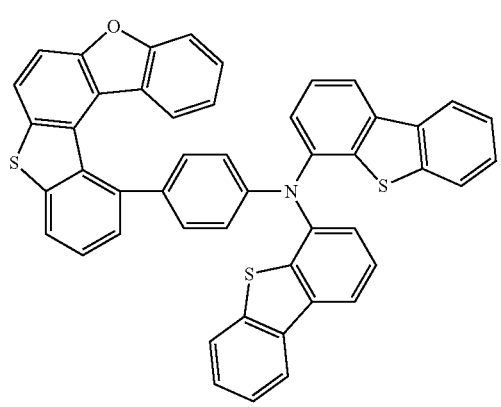
A81
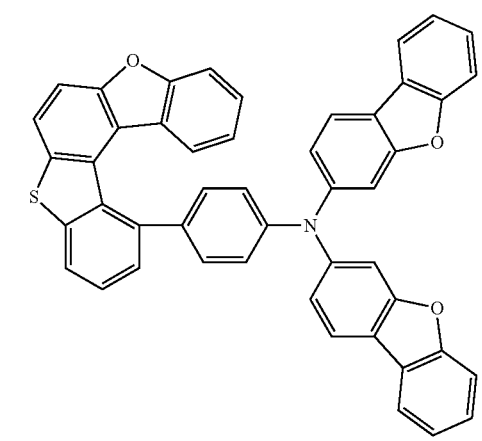

-continued
A82
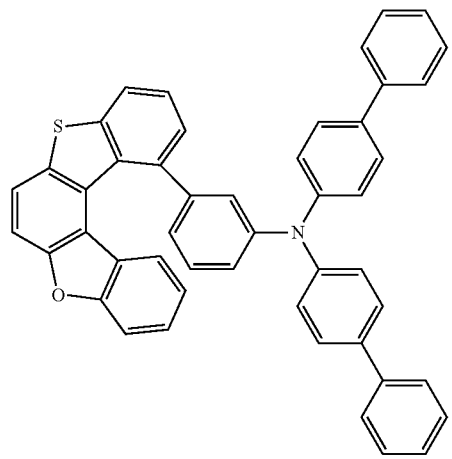
A83
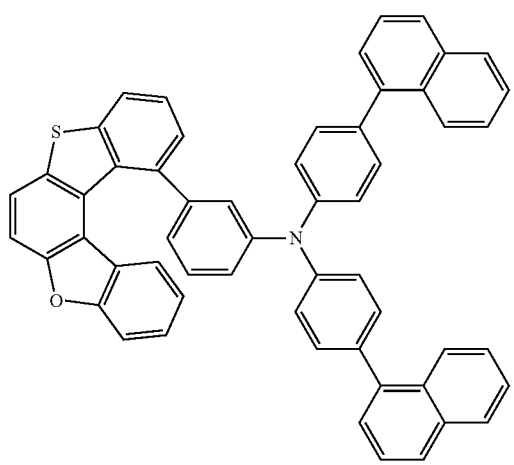
A84
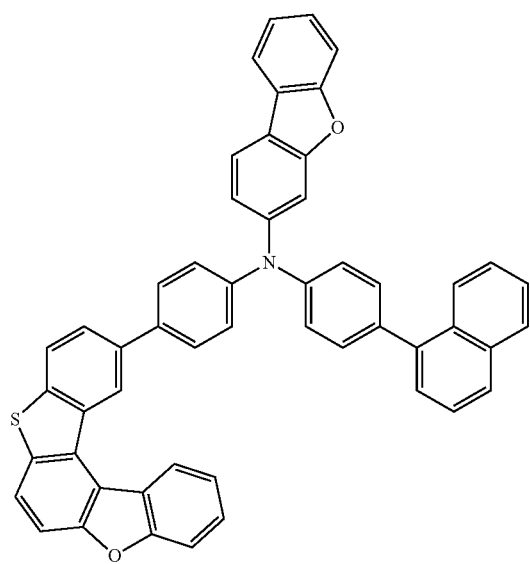
-continued
A85
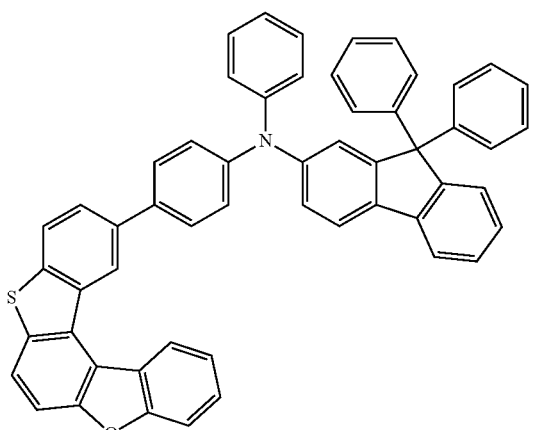
A86
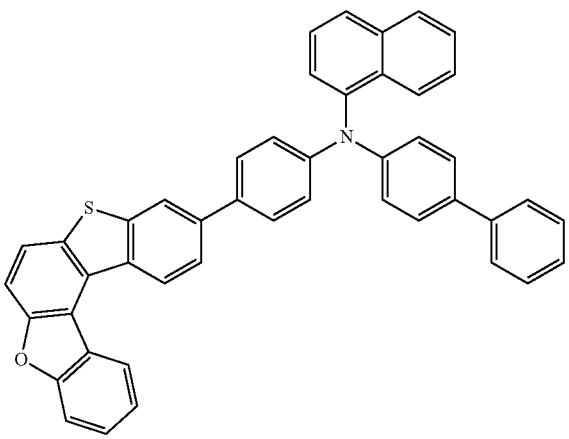
A87
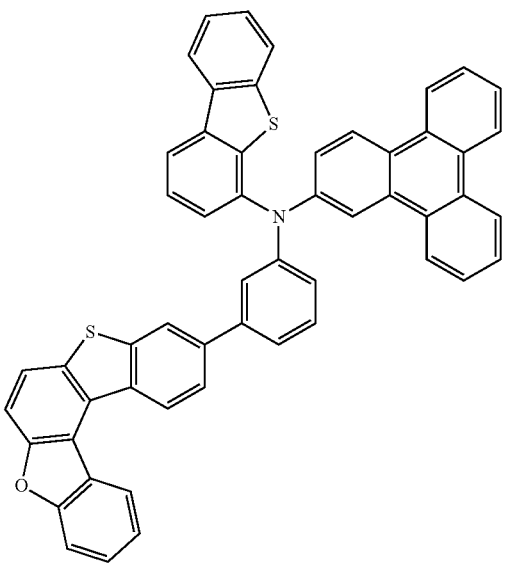

A88
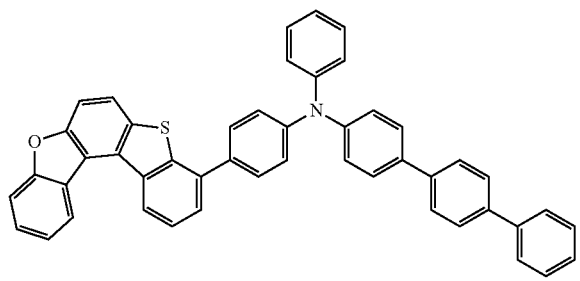
A89
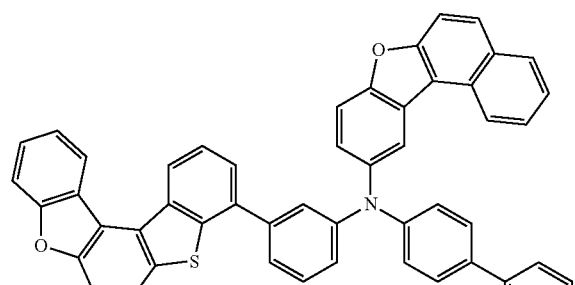
A90
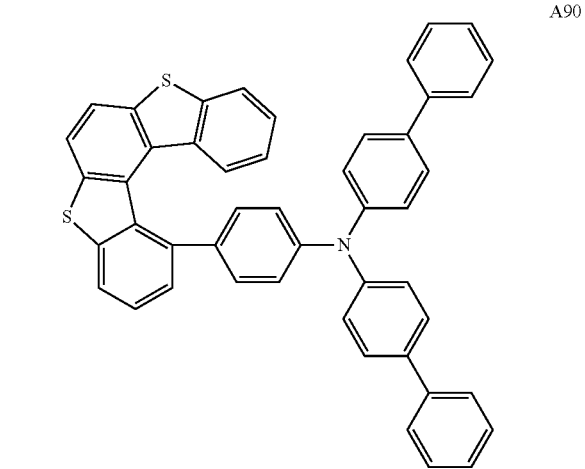
A91
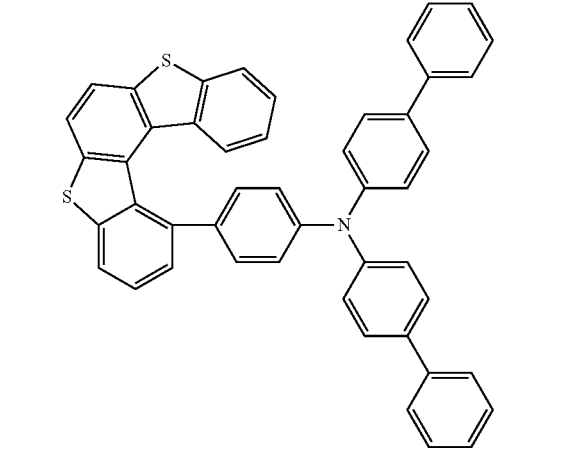
A92
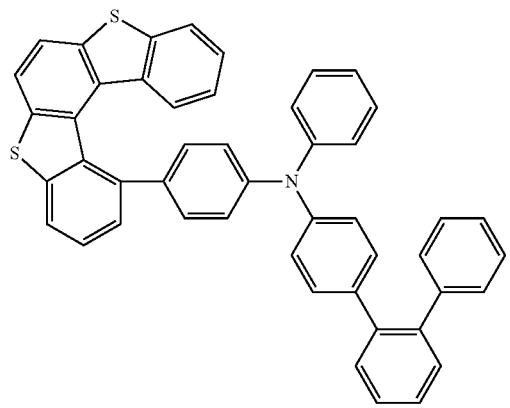
A93
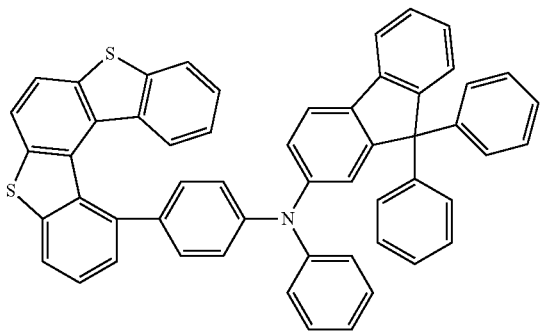
A94
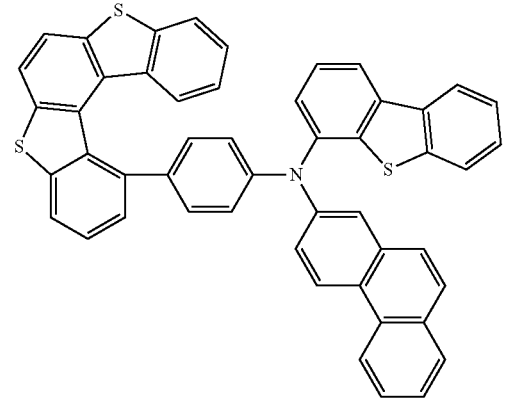
A95
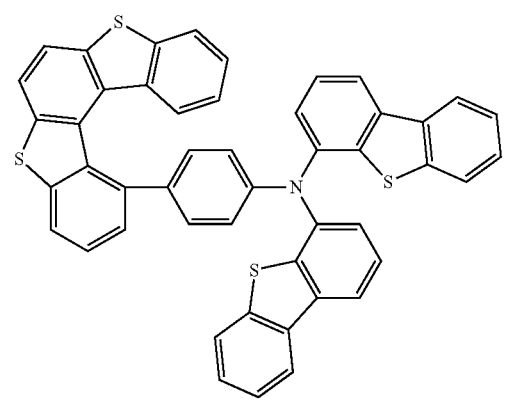

A96
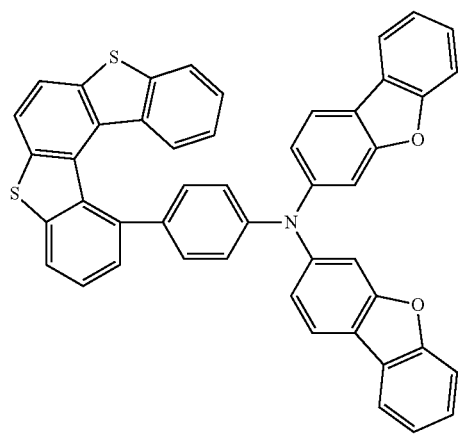
A97
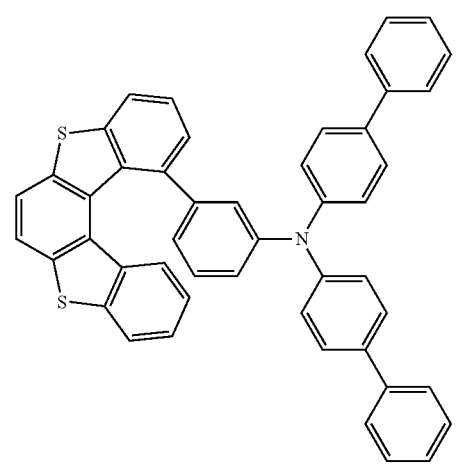
A98
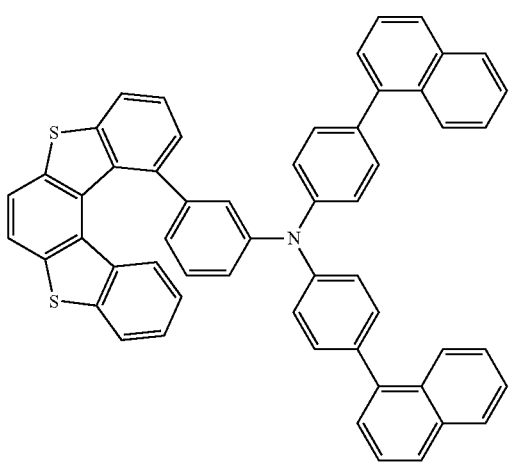
A99
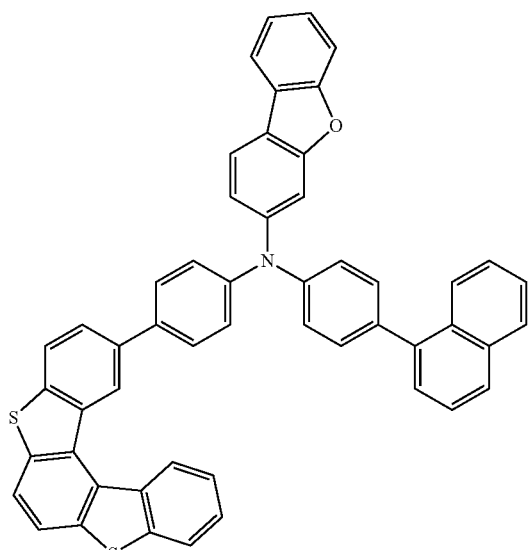
A100
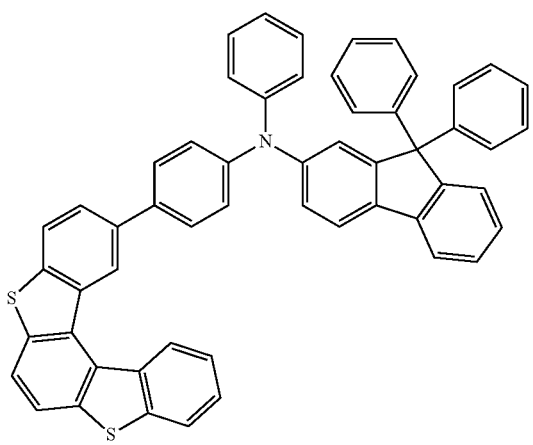
A101
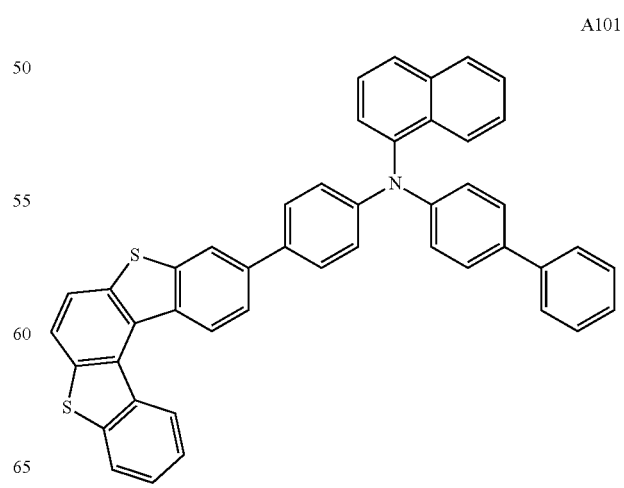

A102
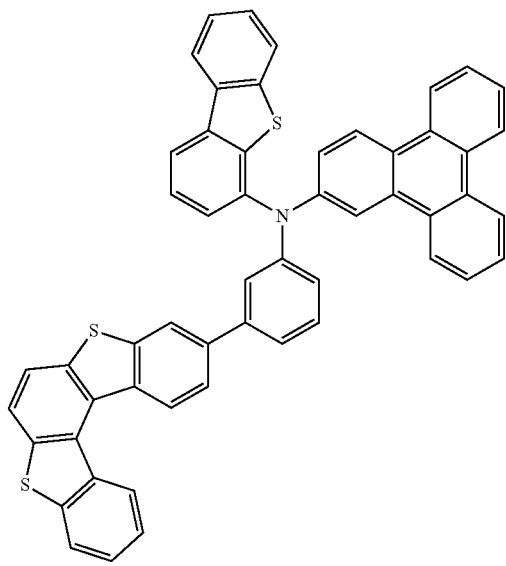
A105
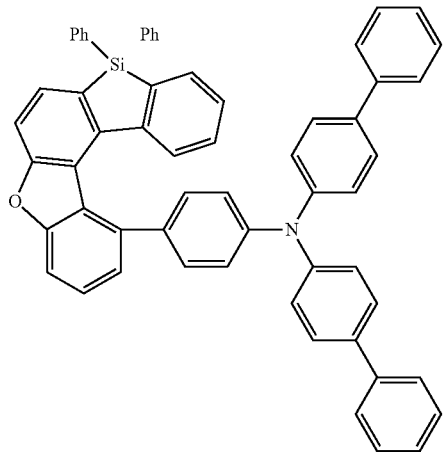
A103
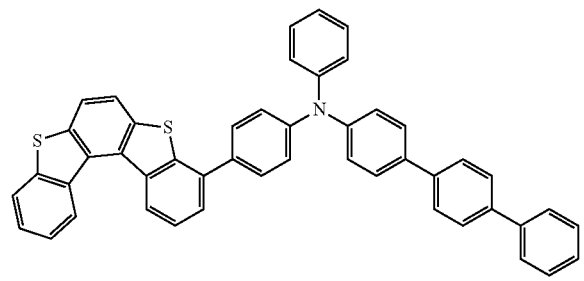
A106
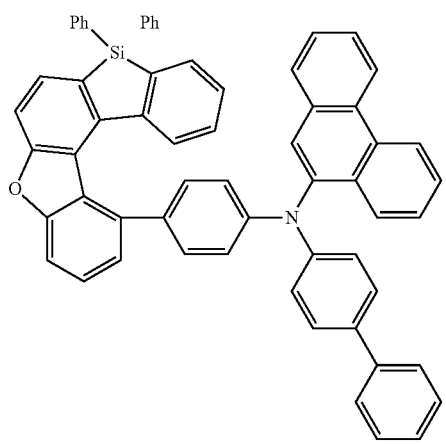
A104
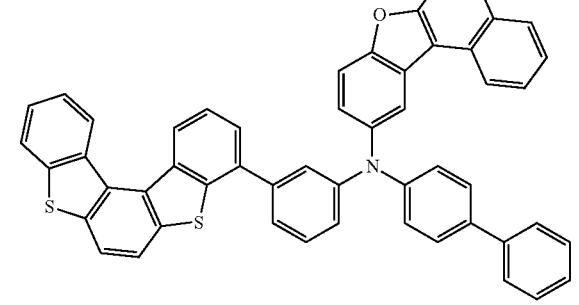
A107
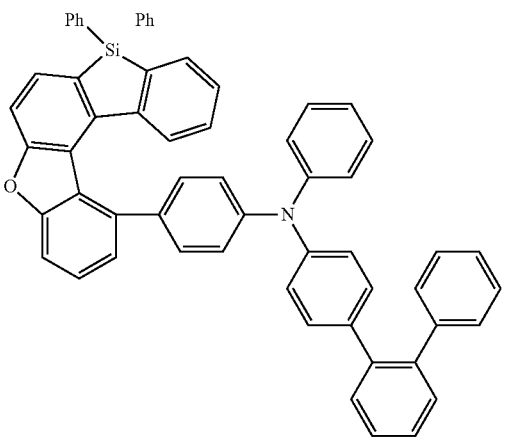

-continued
A108
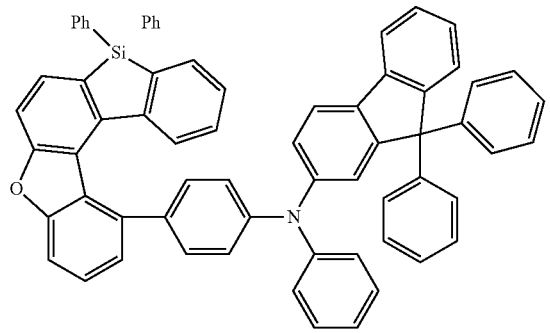
A109
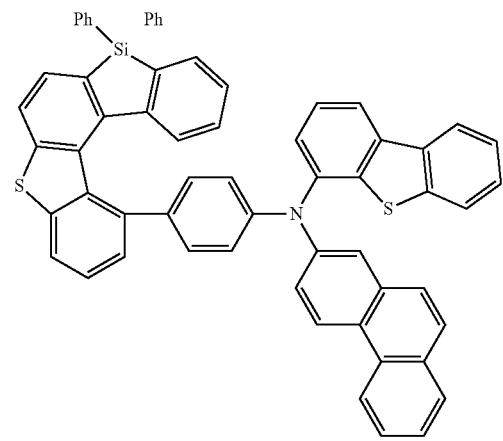
A110
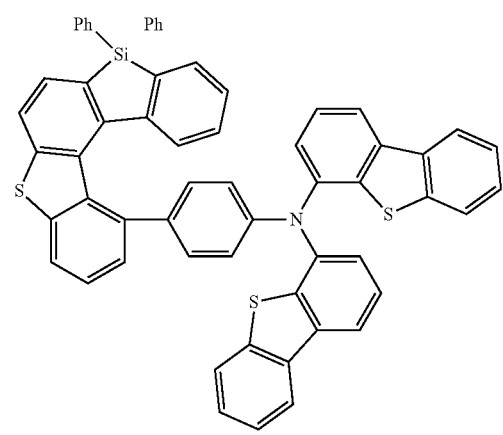
A111
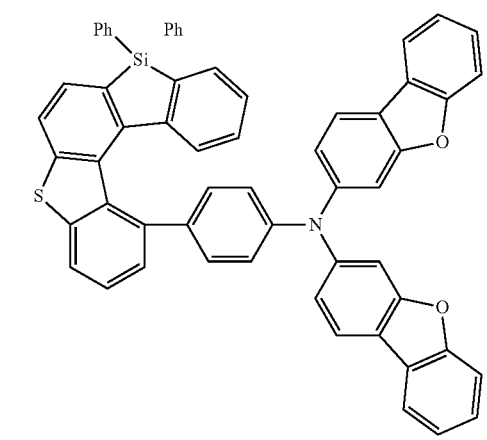
-continued
A112
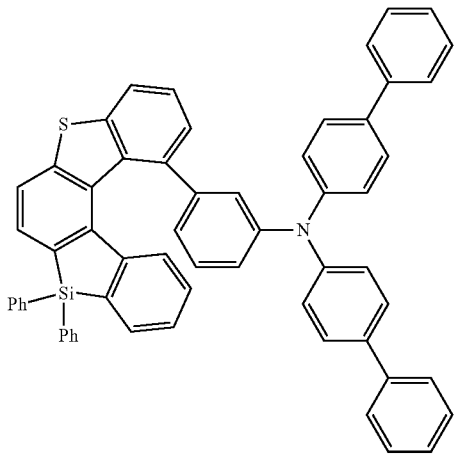
A113
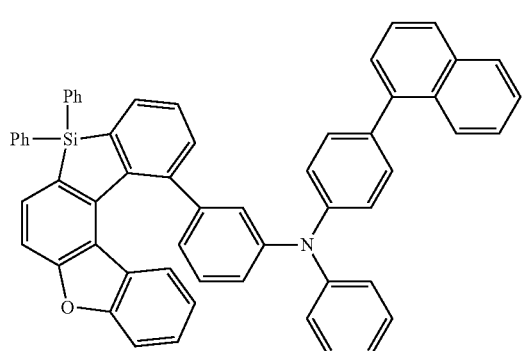
A114
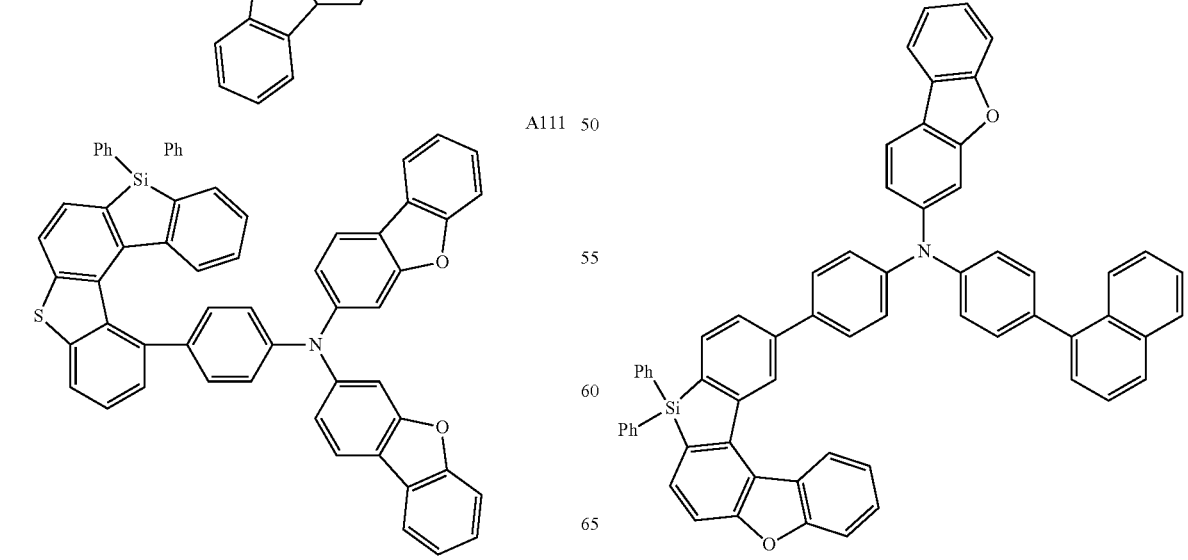

A115
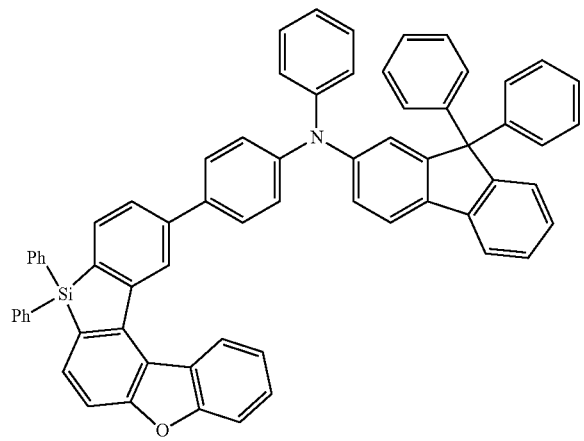
A116
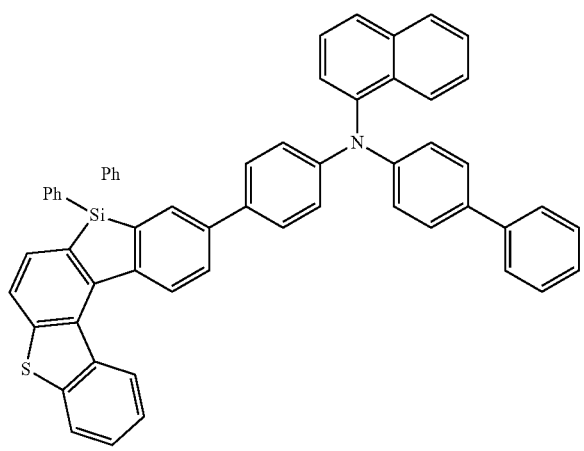
A117
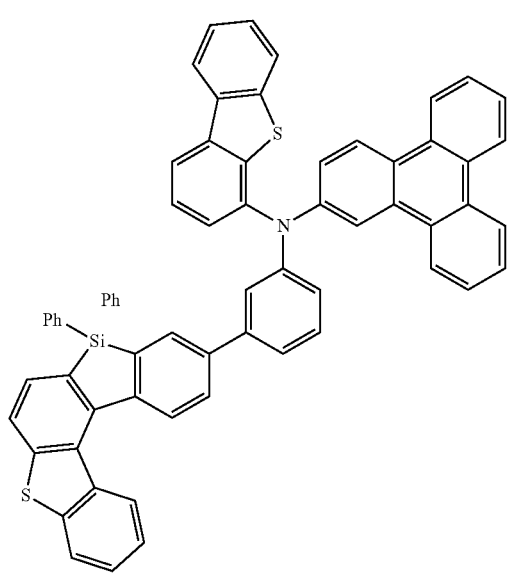
A118
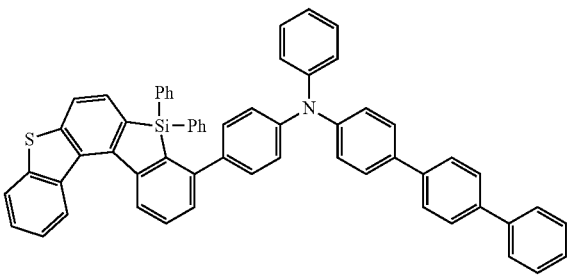
A119
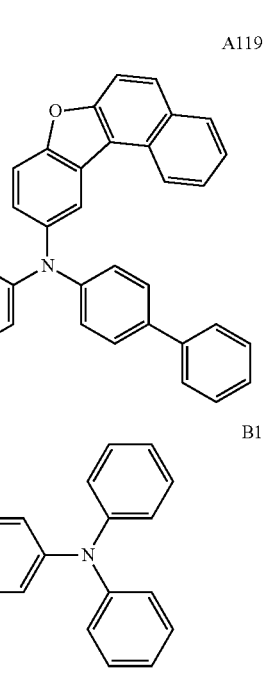
B1
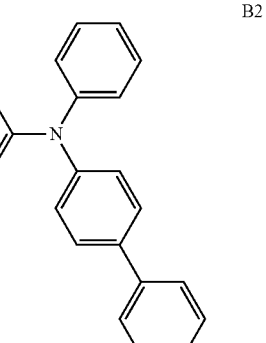
B2
B3
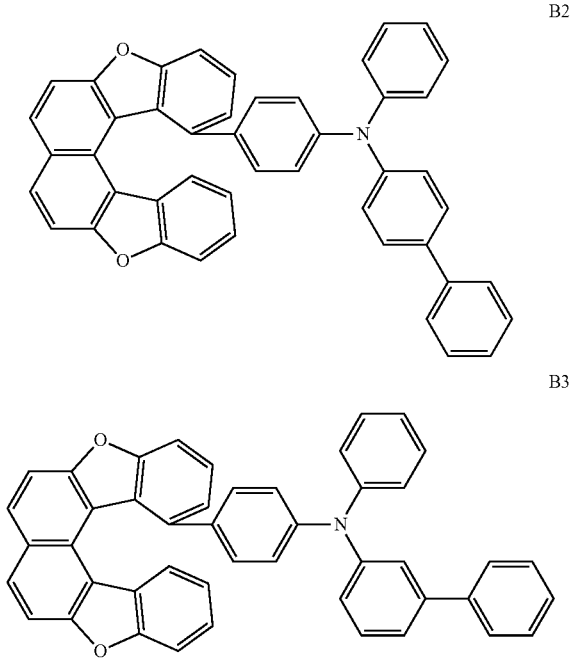

B4
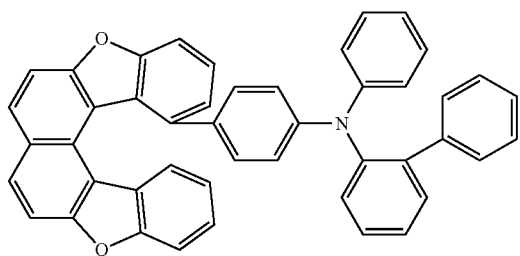
B5
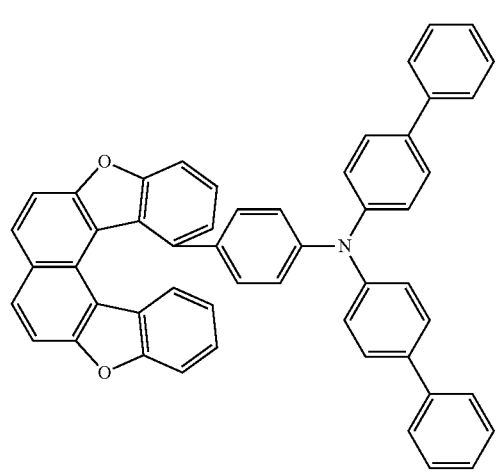
B6
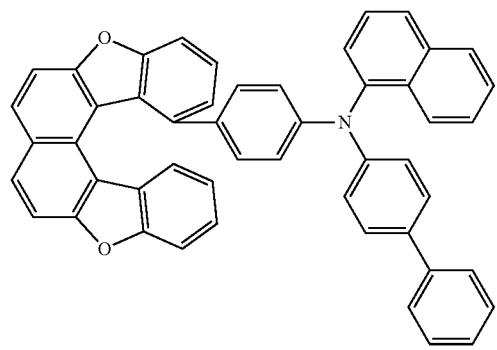
B7
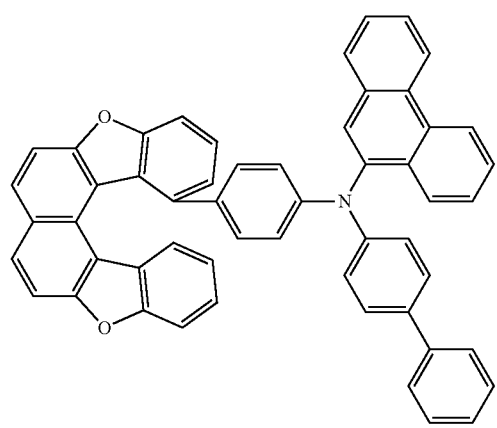
B8
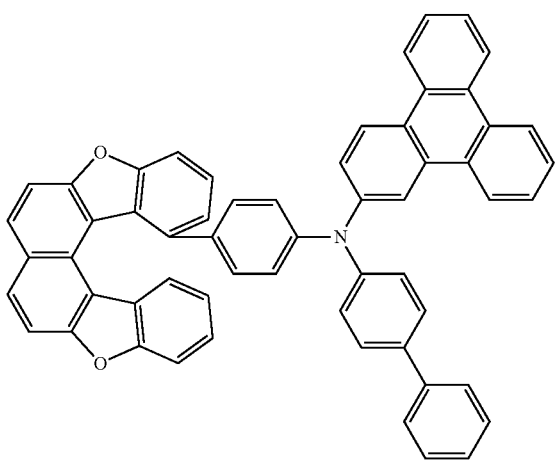
B9
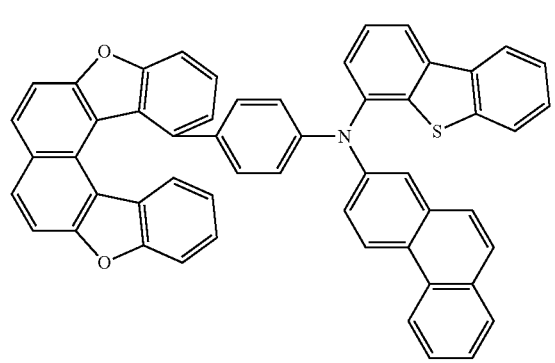
B10
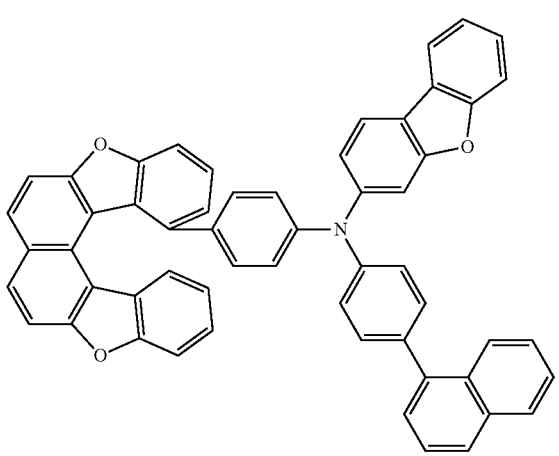
B11

B12
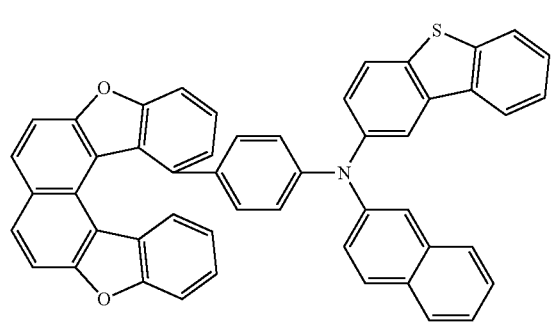
B13
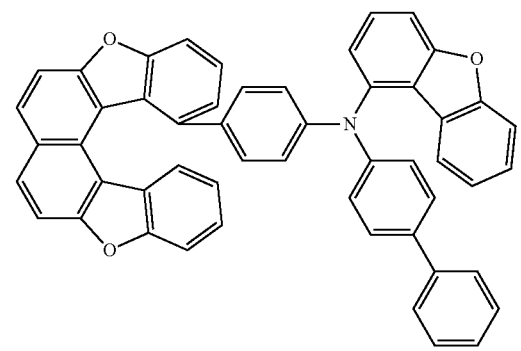
B14
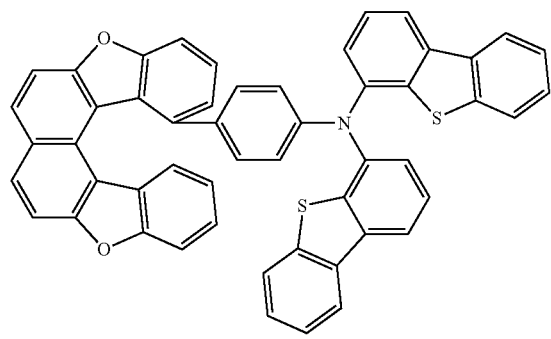
B15
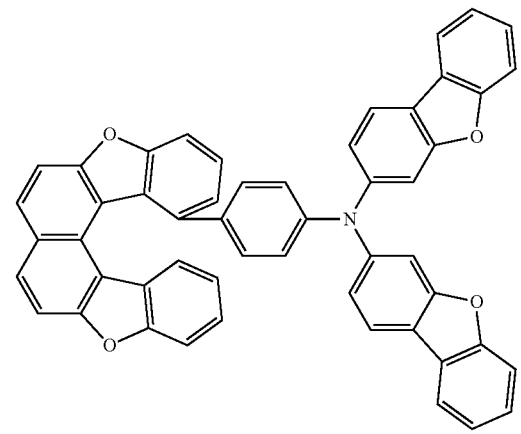
B16
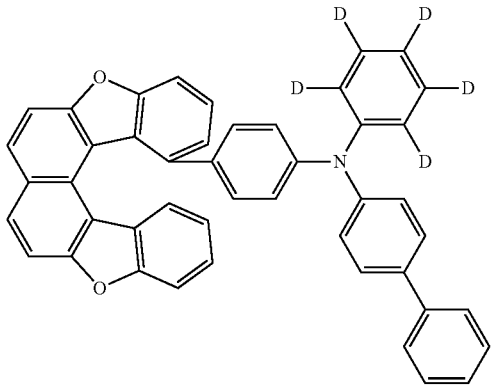
B17
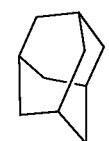
B18
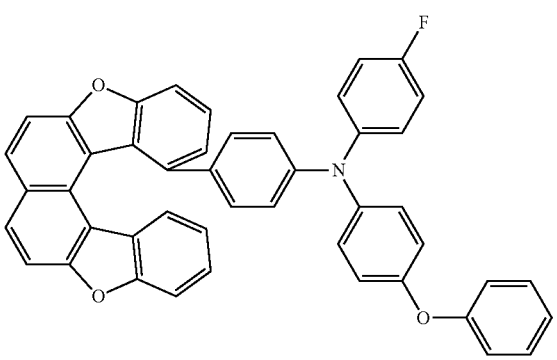

B19
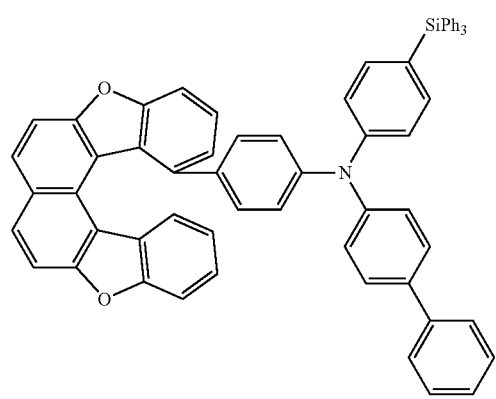
B20
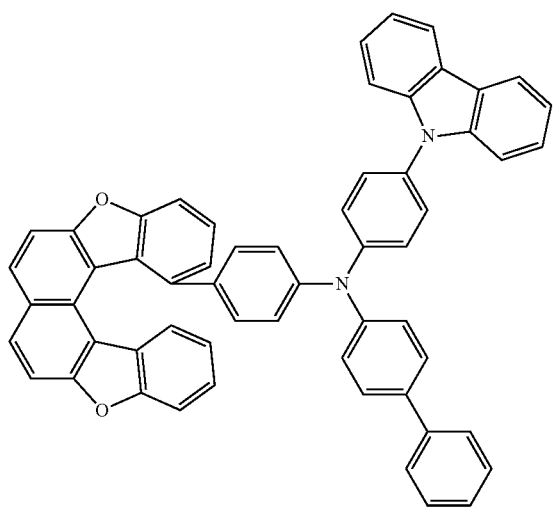
B21
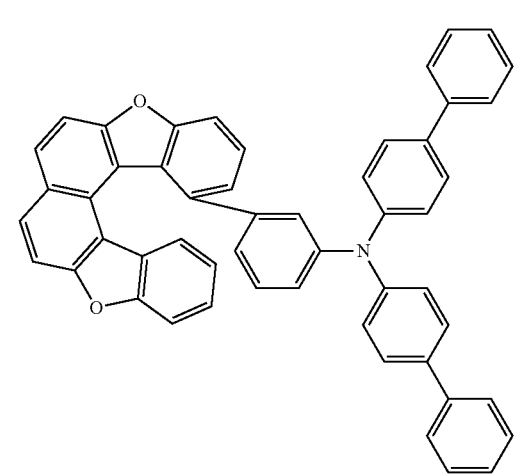
B22
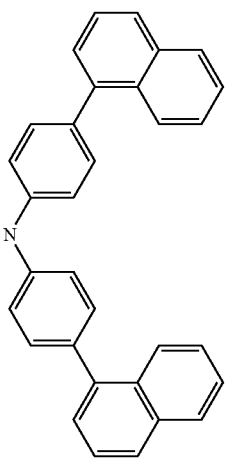
B23
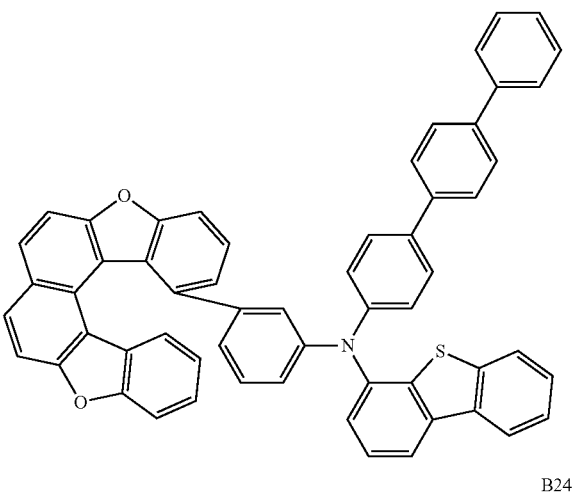
B24
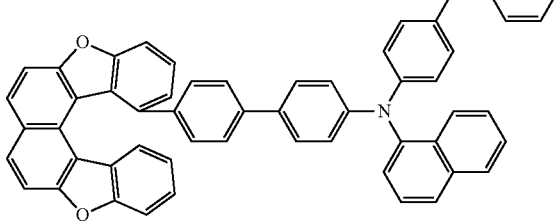
B25
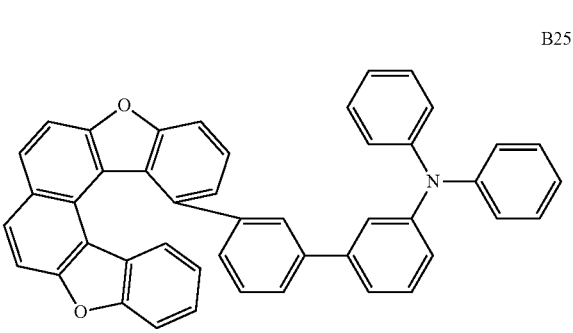

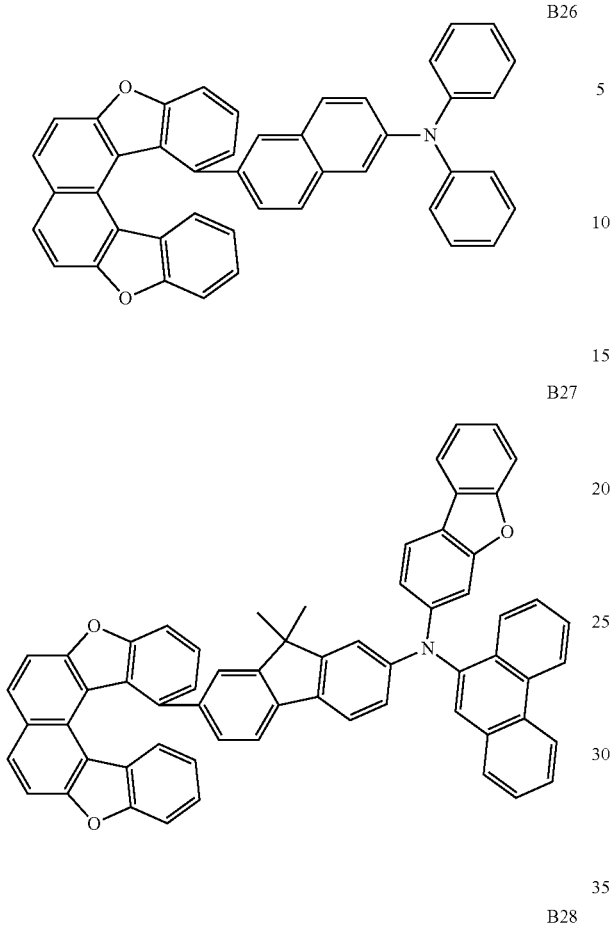
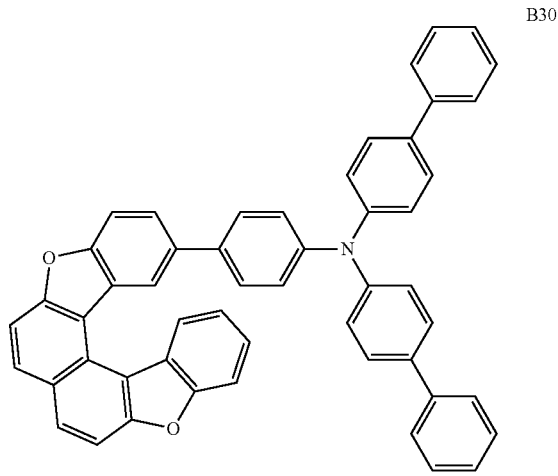
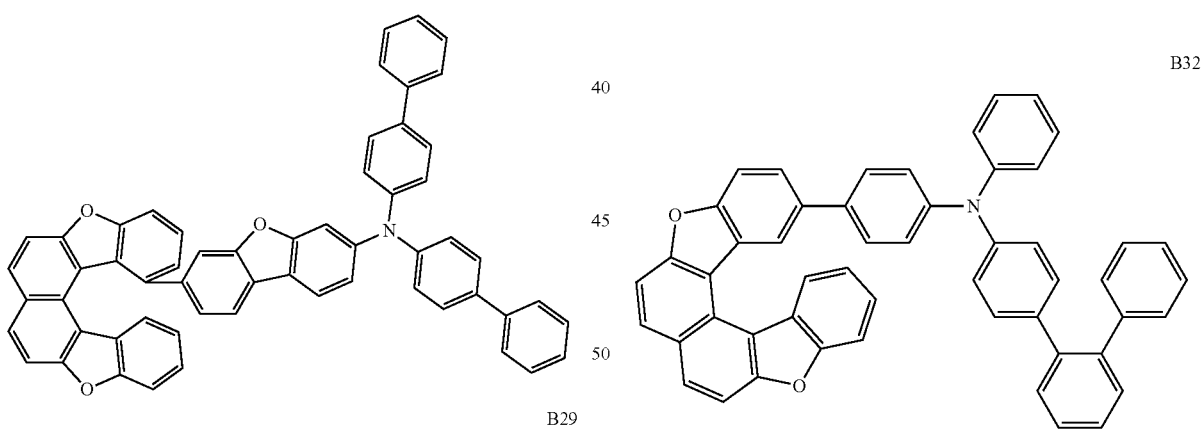
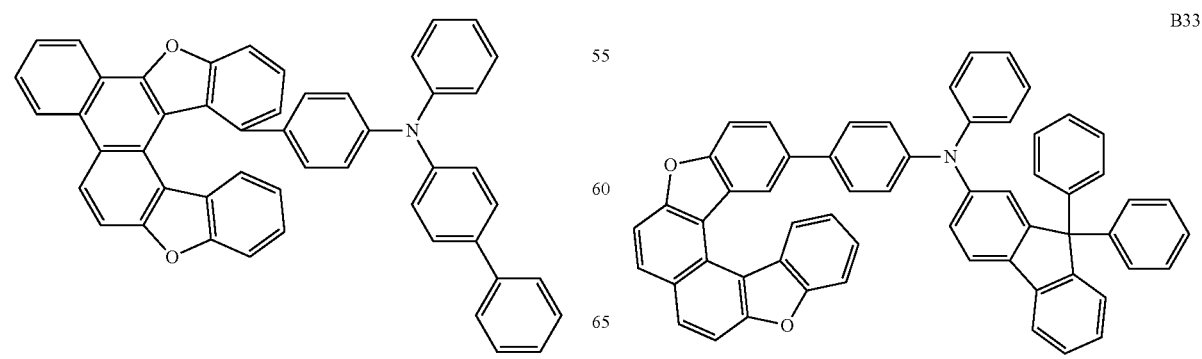

B34
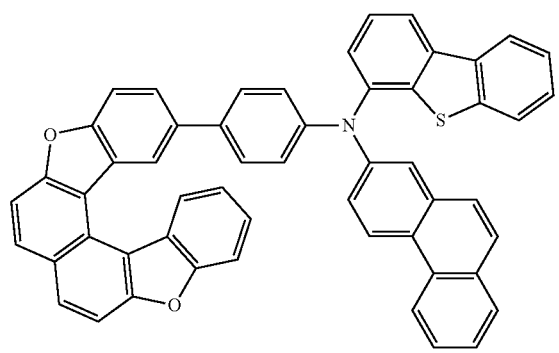
B37
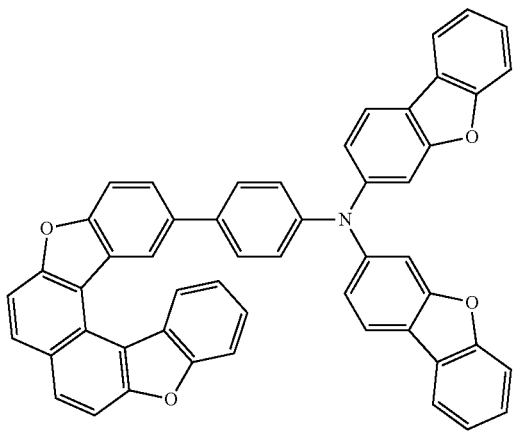
B35
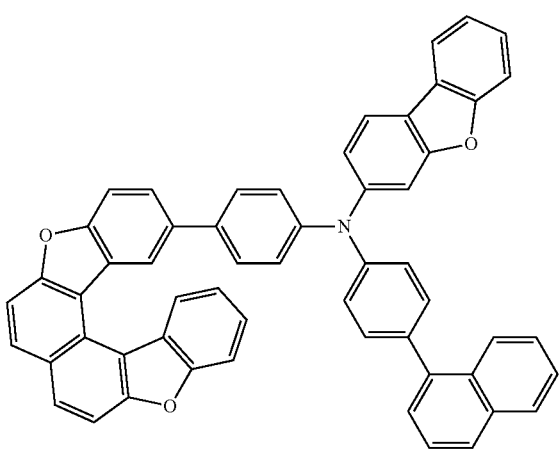
B38
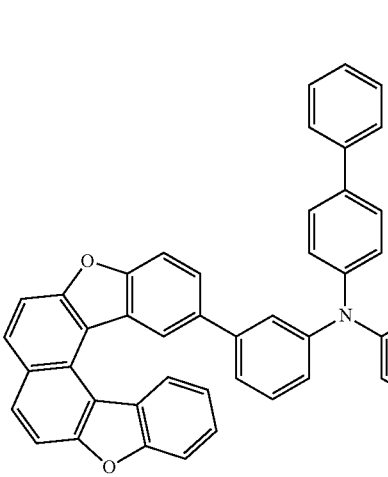
B36
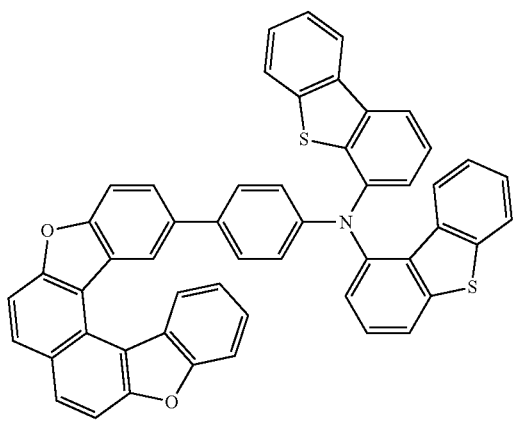
B39
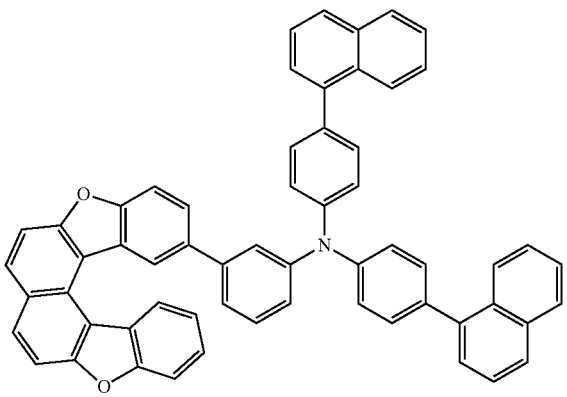

B40
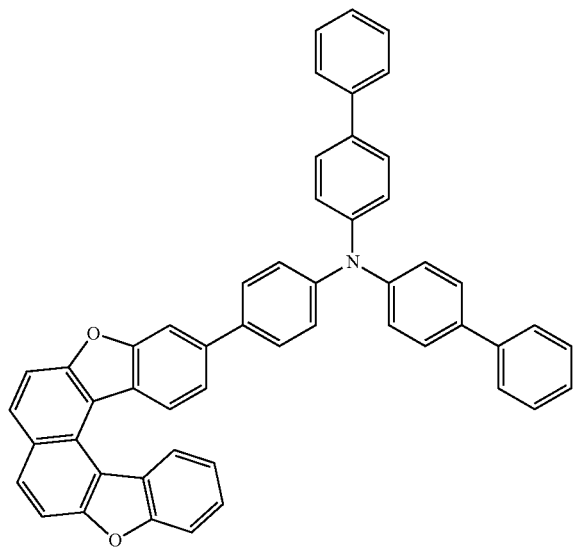
B41
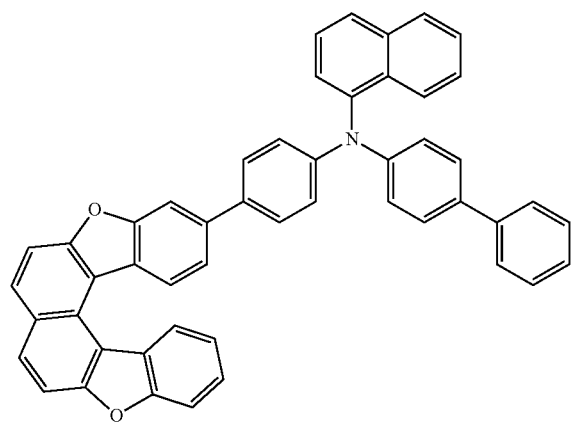
B42
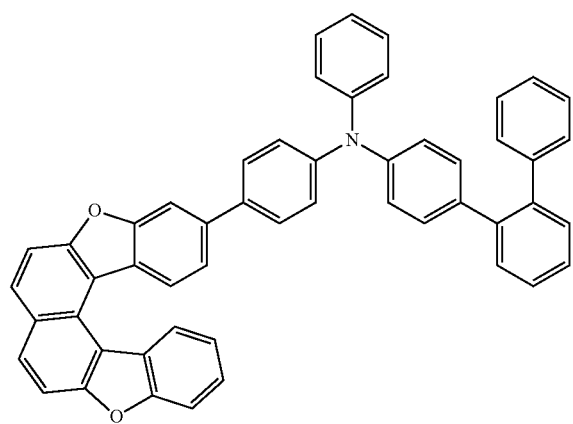
B43
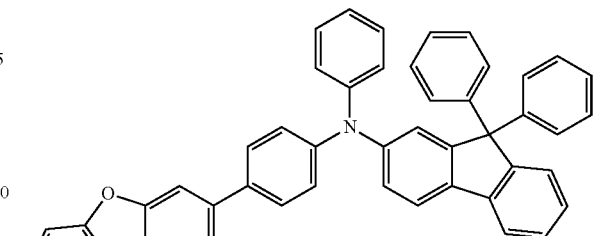
B44
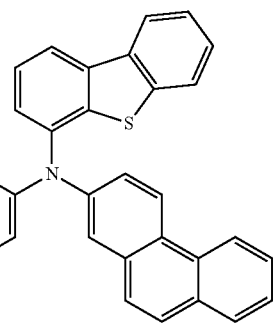
B45
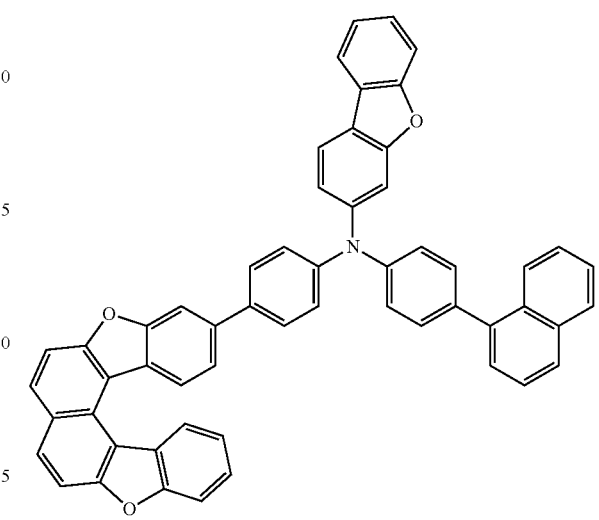

B46
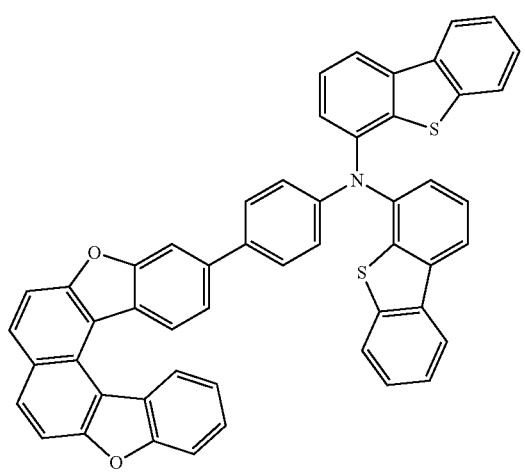
B47
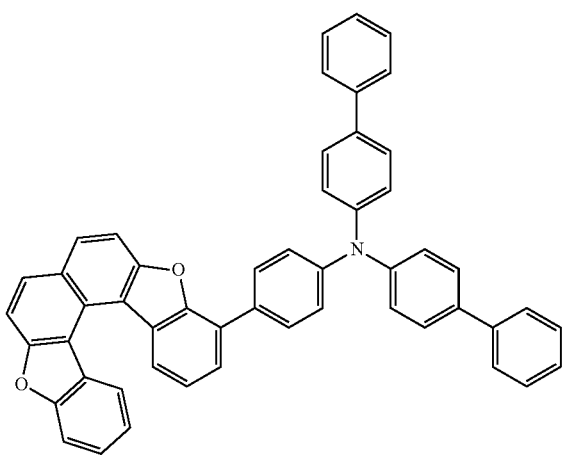
B48
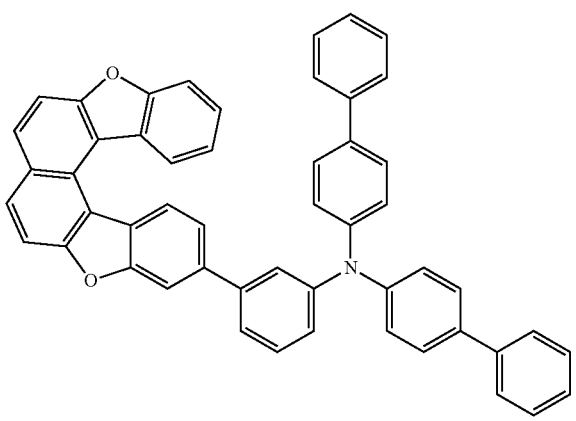
B49
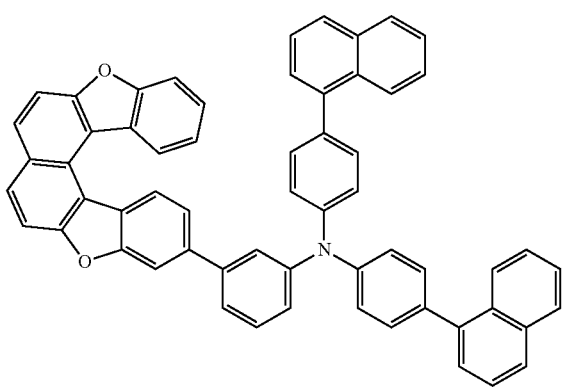
B50
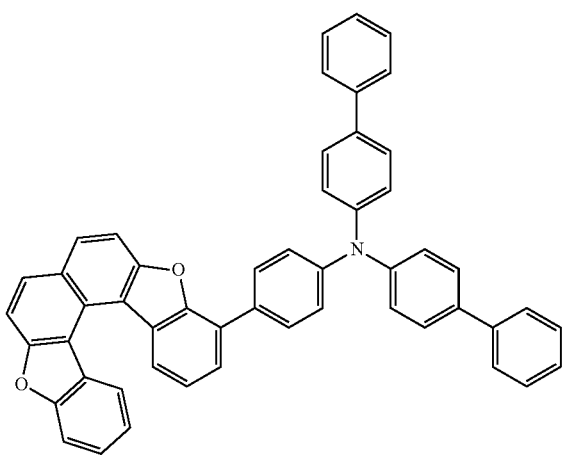
B51
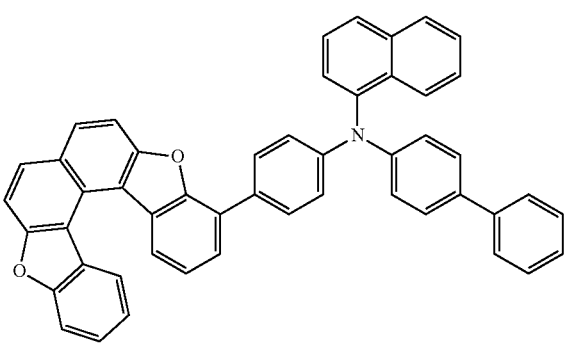
B52
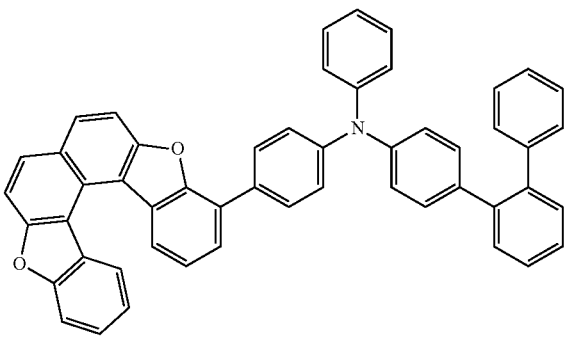

B53
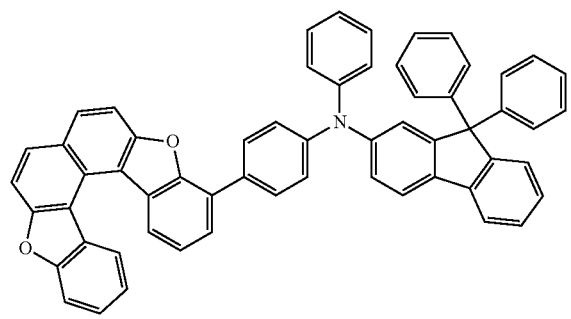
B54
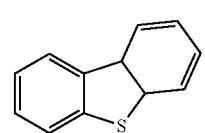
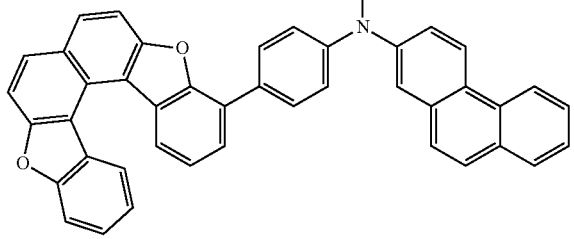
B55
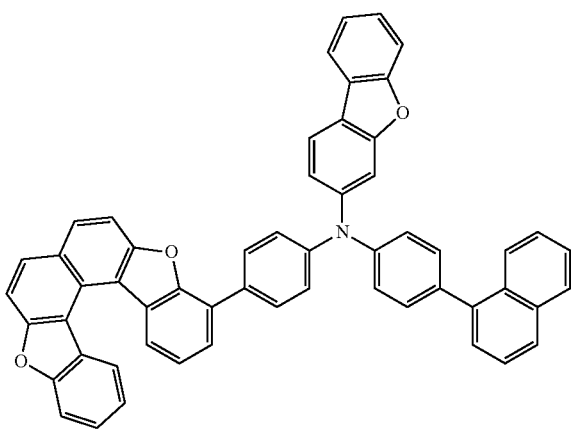
B56
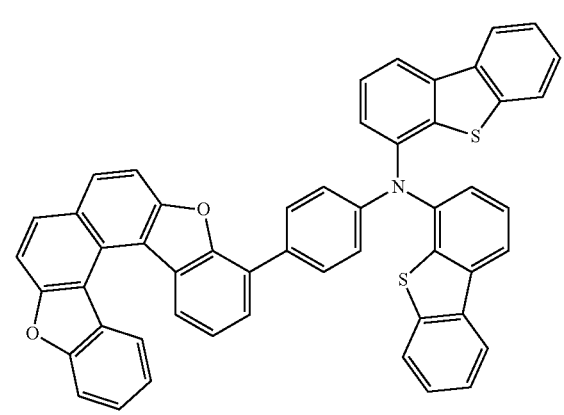
B57
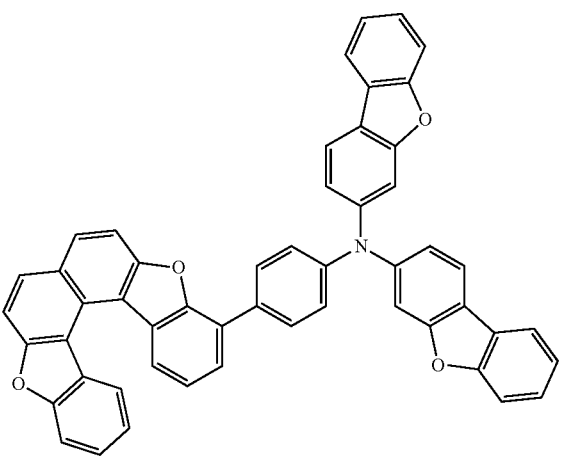
B58
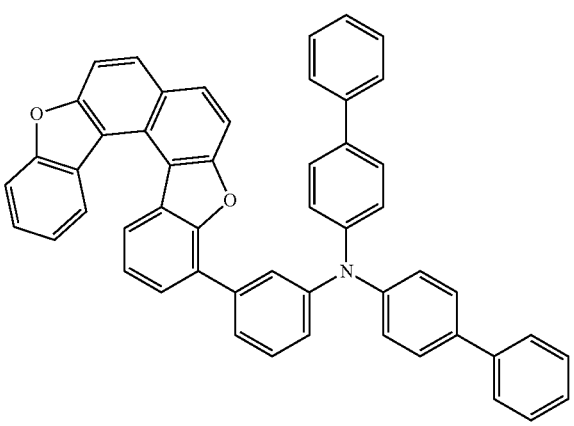
B59
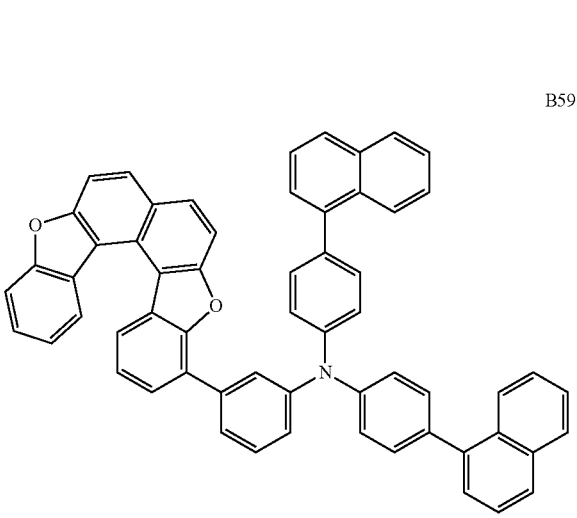

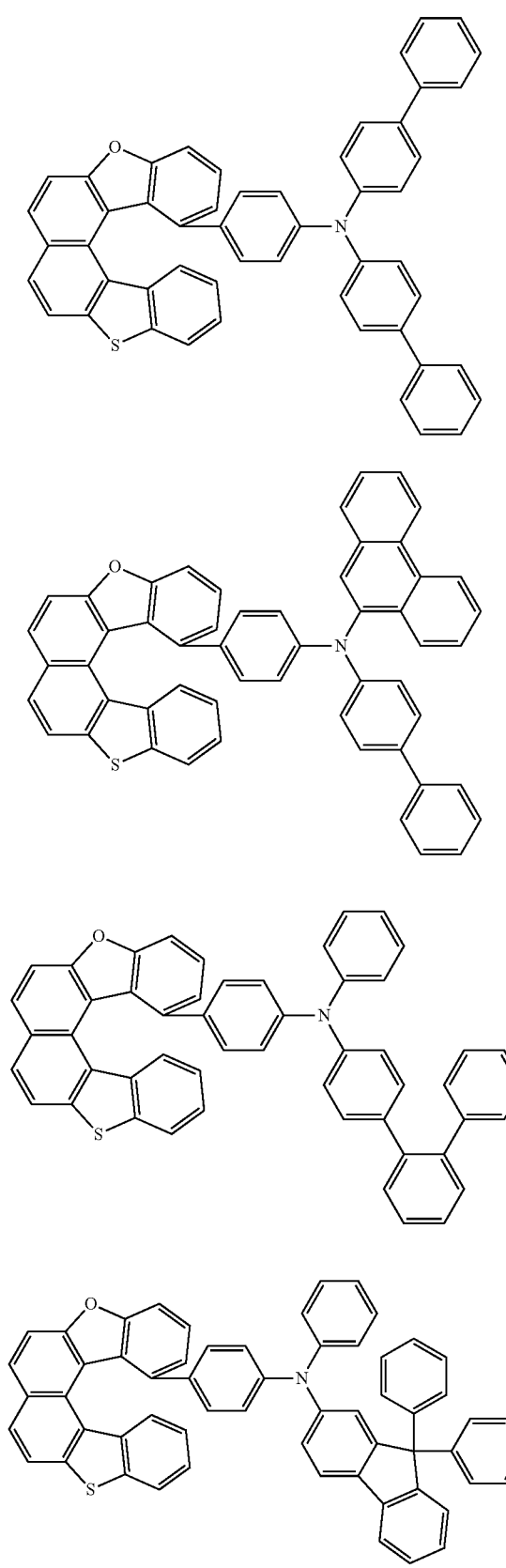
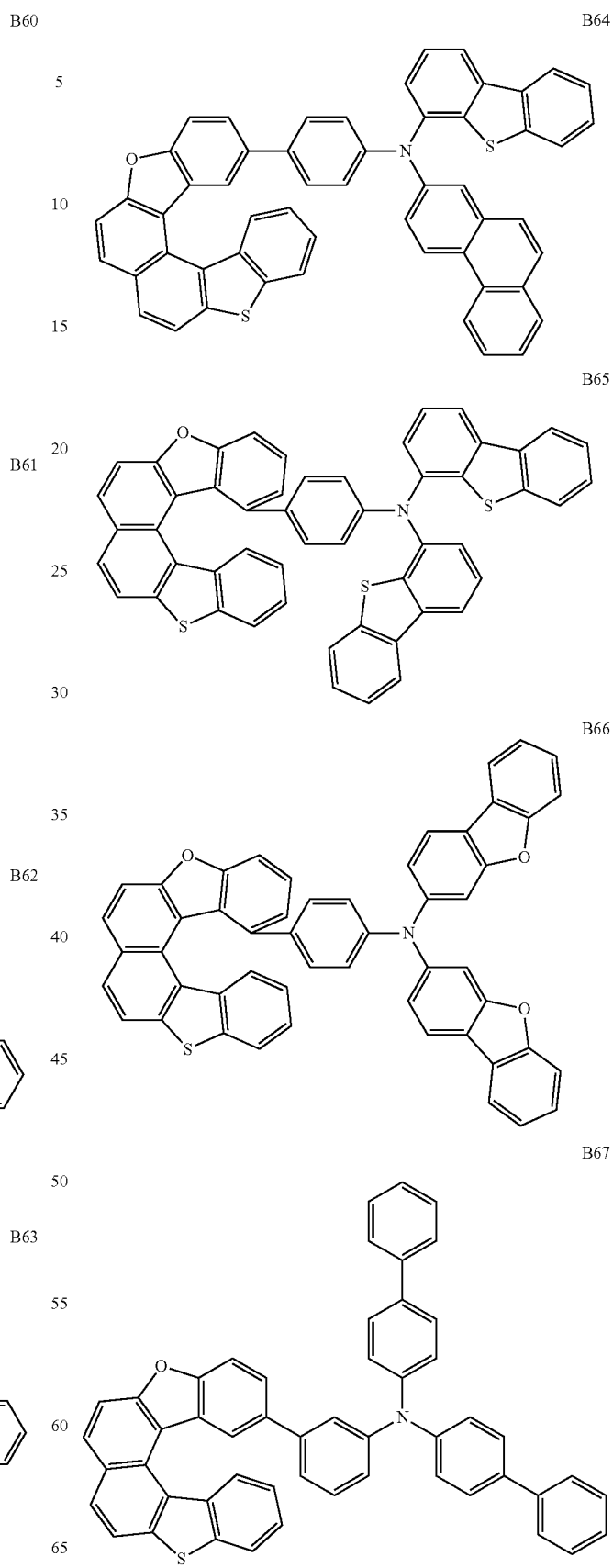

-continued
B68
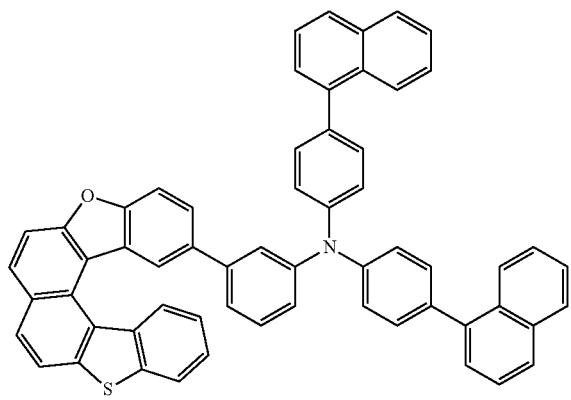
B69
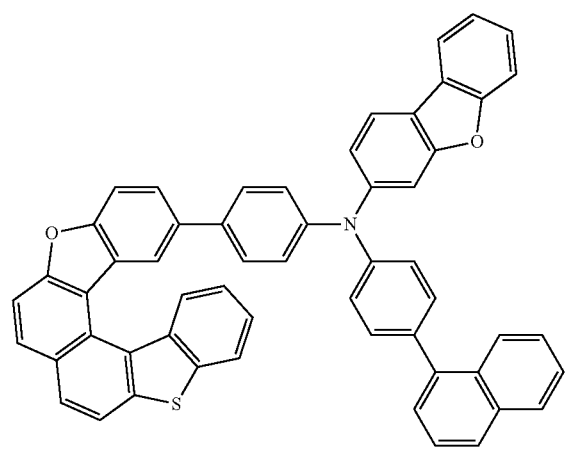
B70
B71
-continued
B72
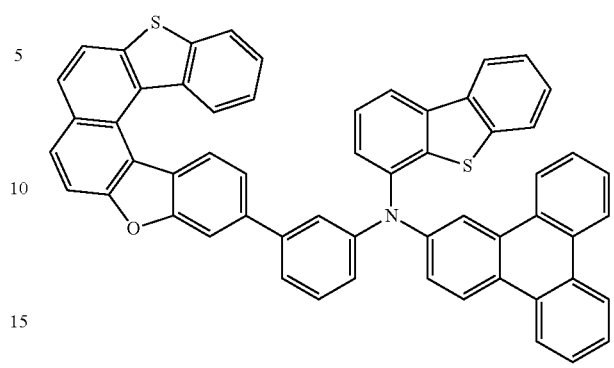
B73
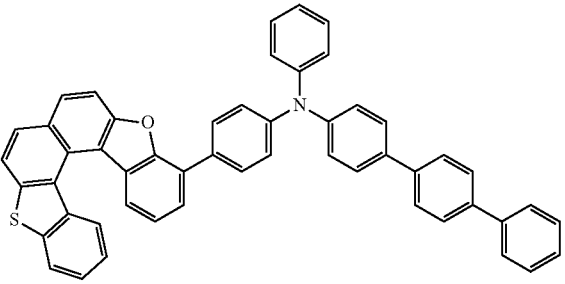
B74
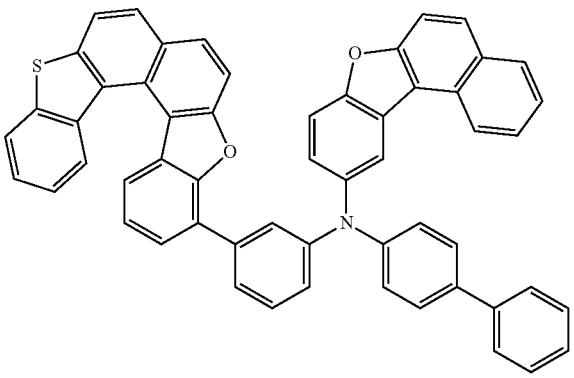
B75
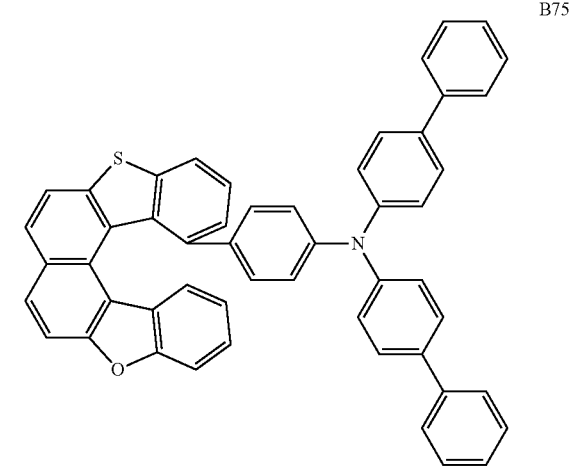

B76
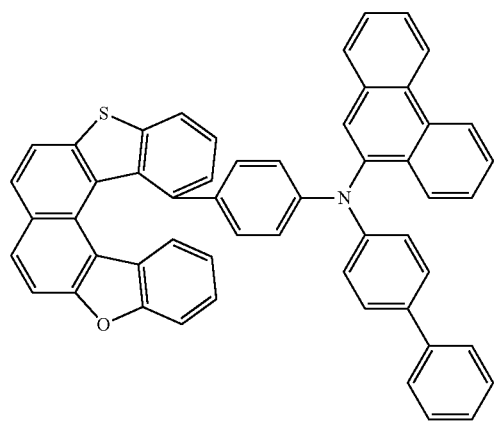
B77
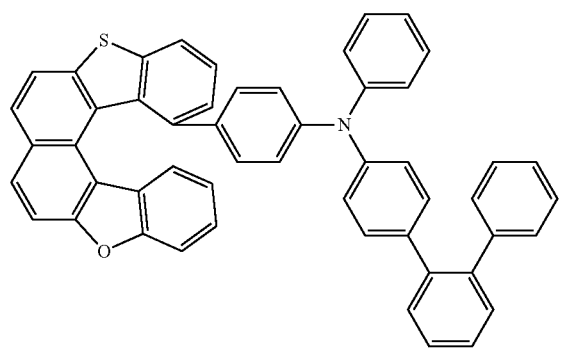
B78
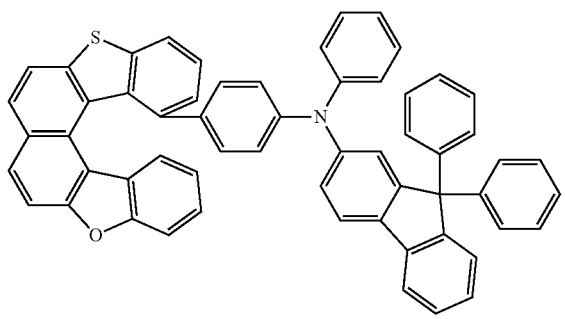
B79
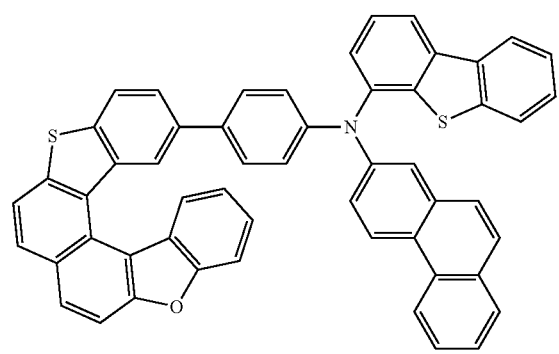
B80
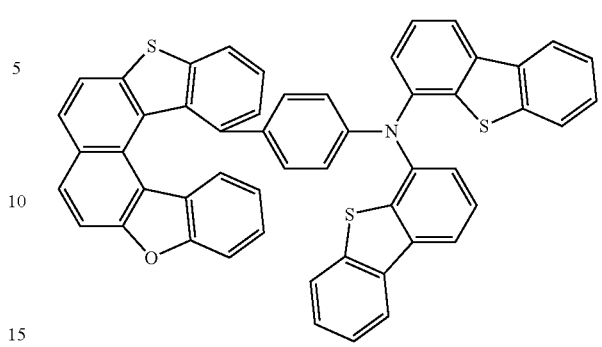
B81
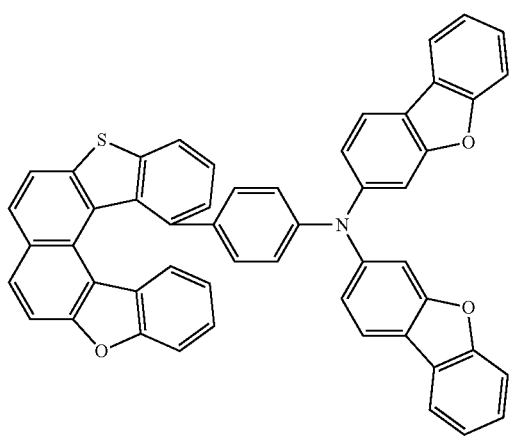
B82
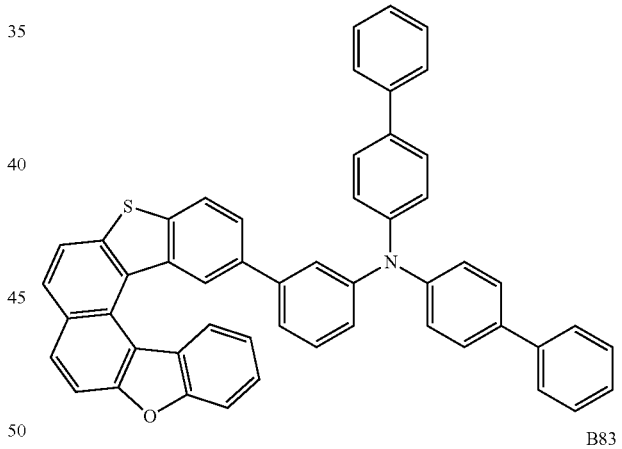
B83
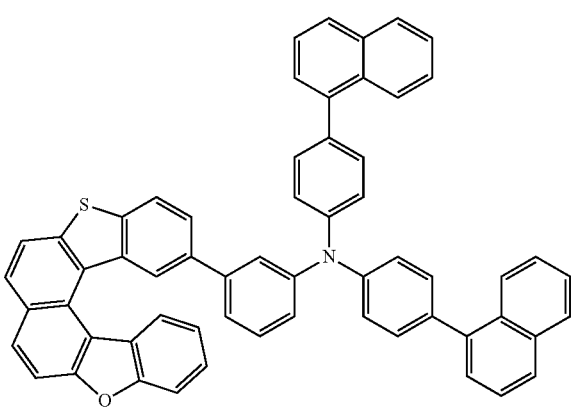

B84
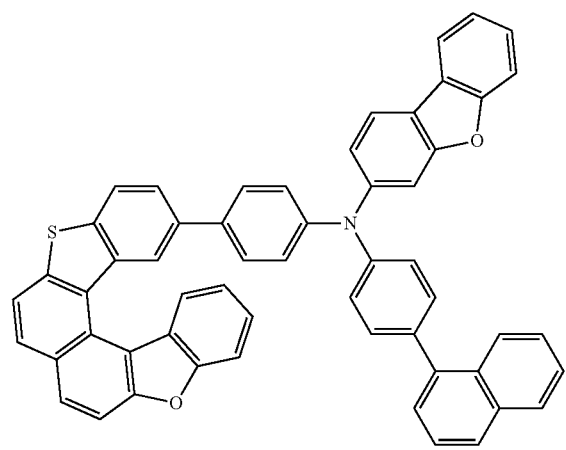
B85
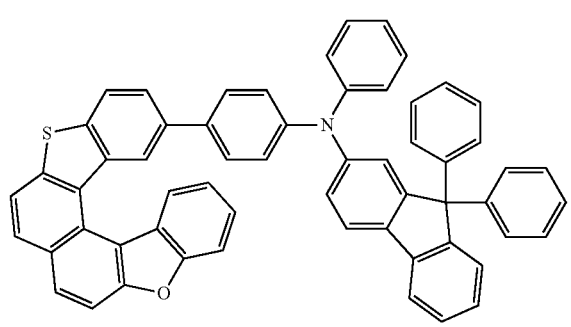
B86
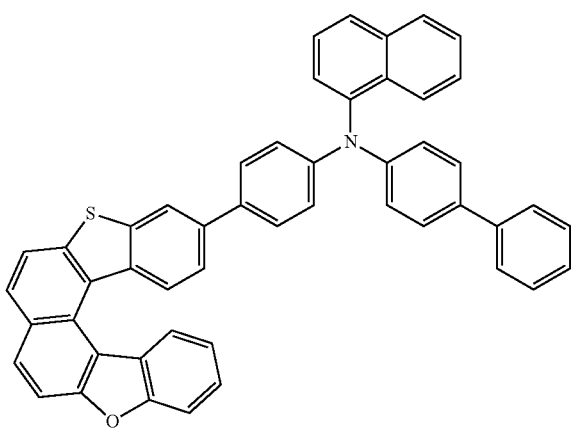
B87
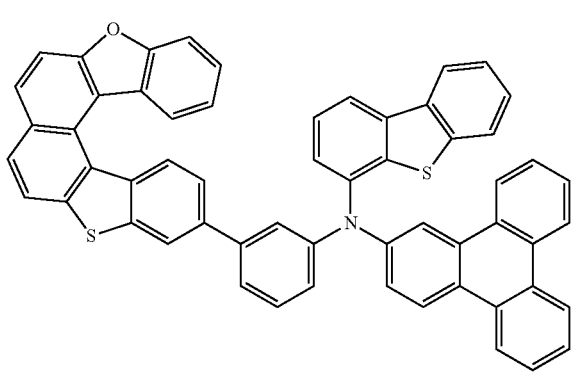
B88
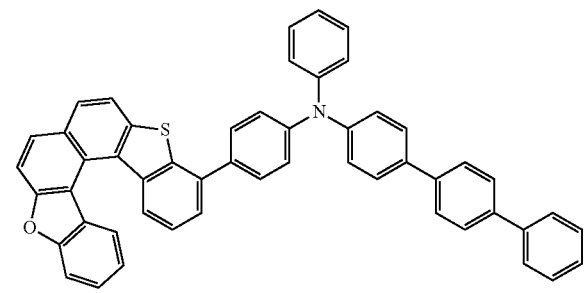
B89
B90
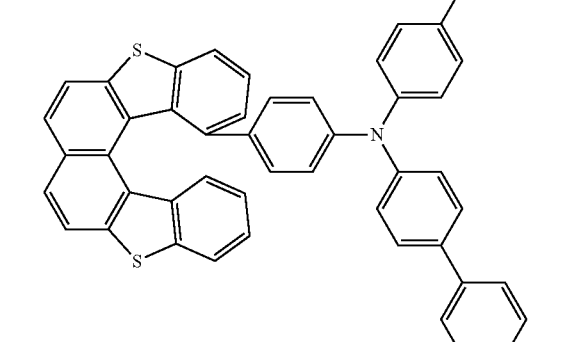
B91
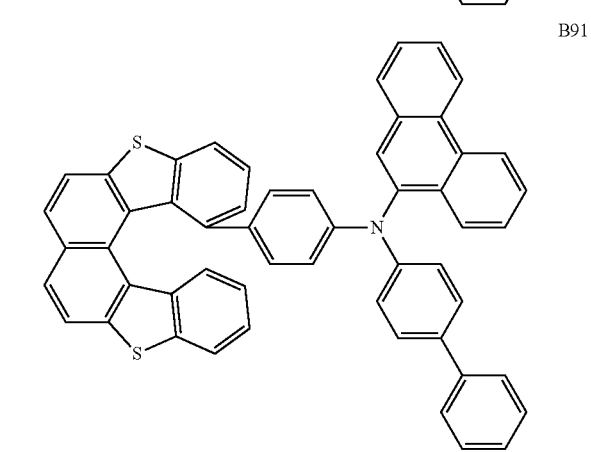

77
-continued
B92
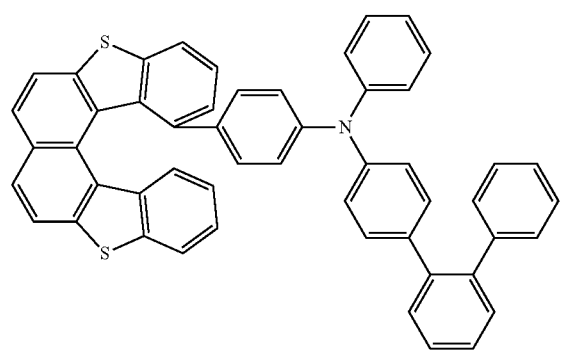
B93
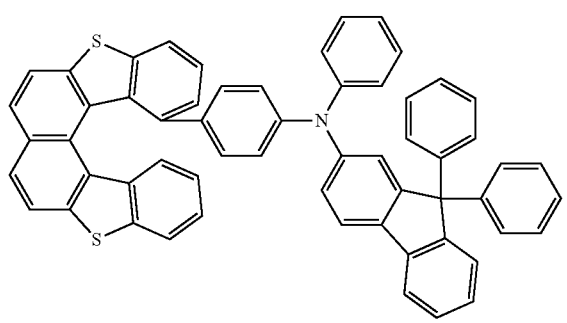
B94
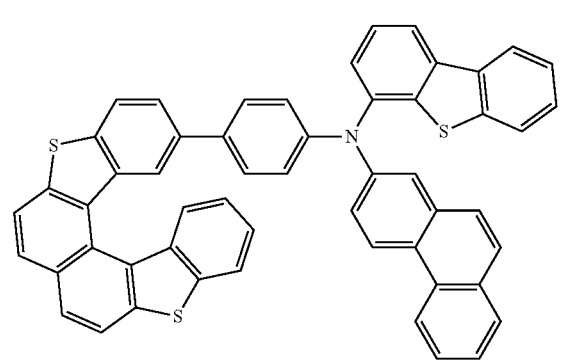
B95
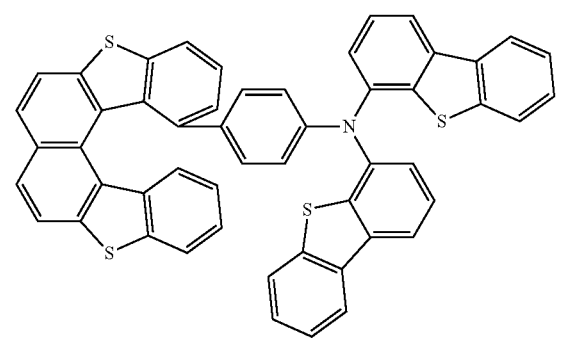
78
-continued
B96
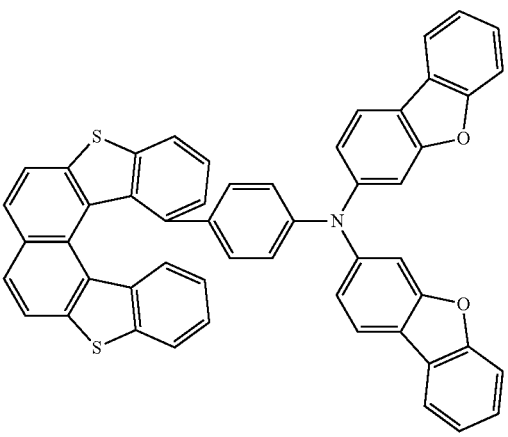
B97
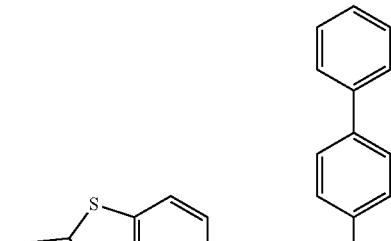
B98
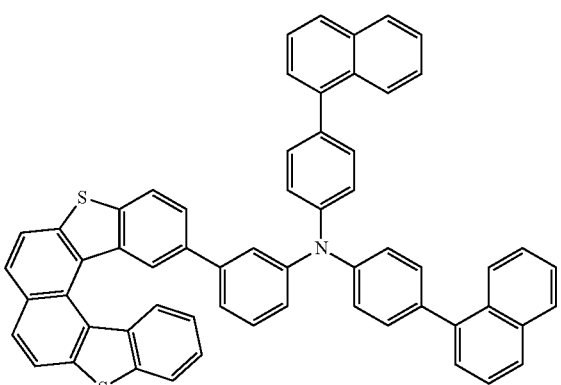

B99
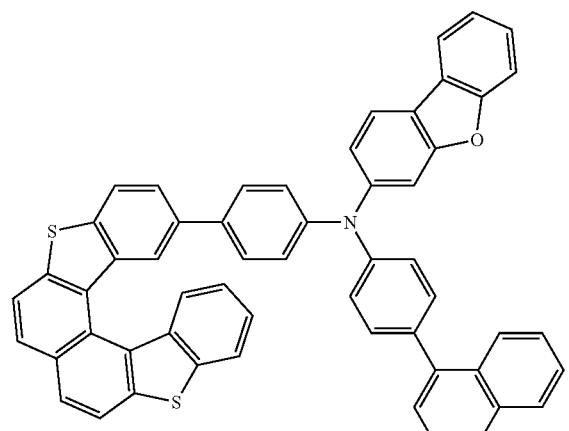
B100
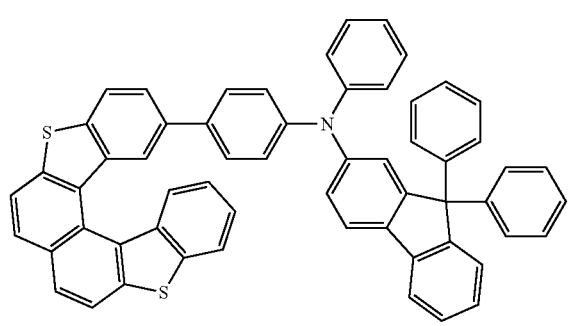
B101
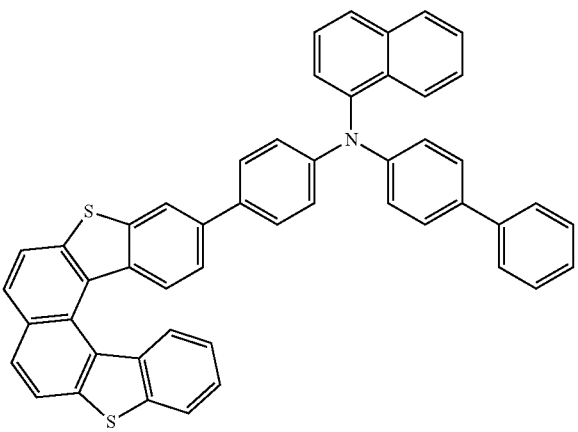
B102
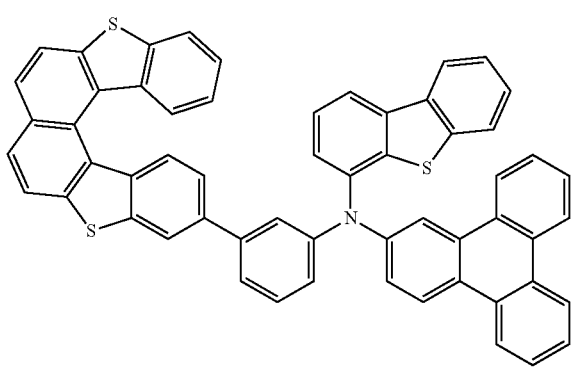
B103
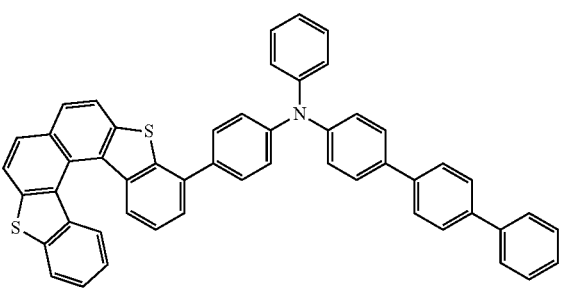
B104
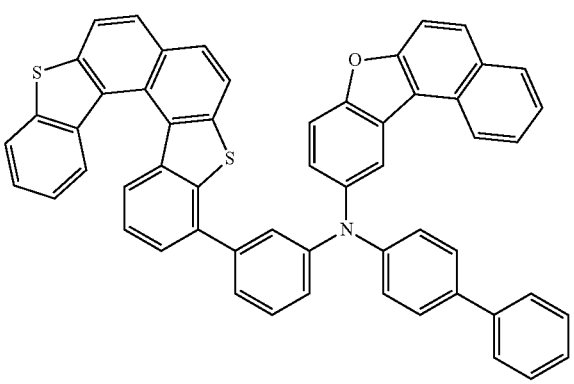
B105
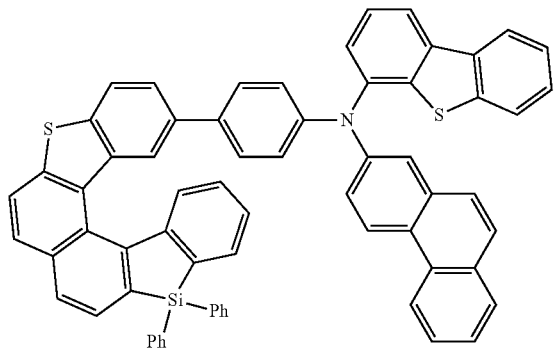
B106
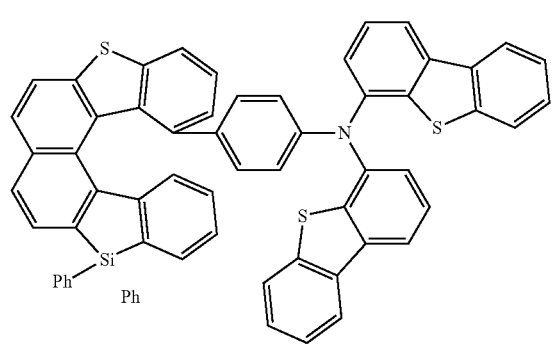

-continued
B107
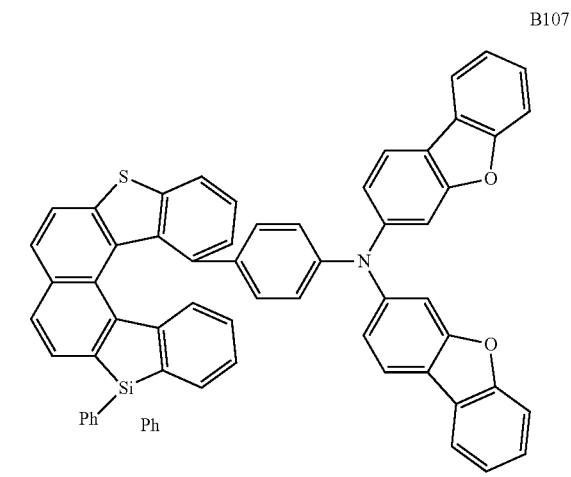
B108
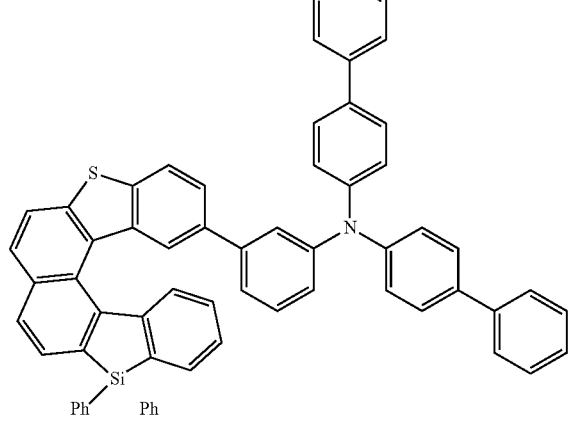
B109
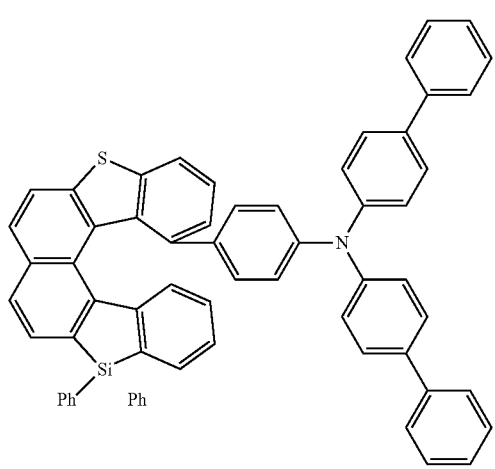
-continued
B110
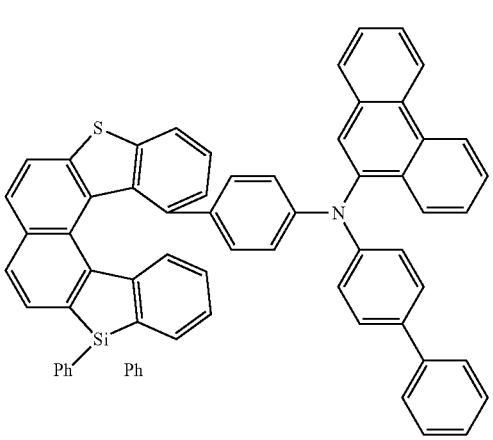
B111
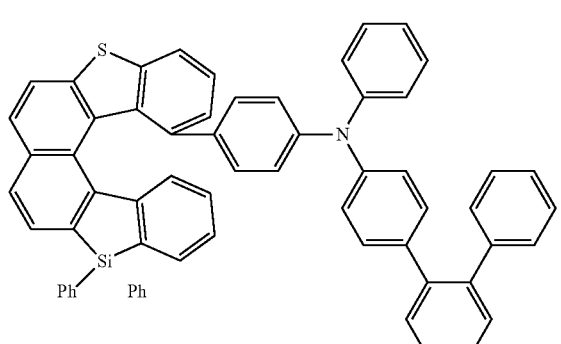
B112
B113
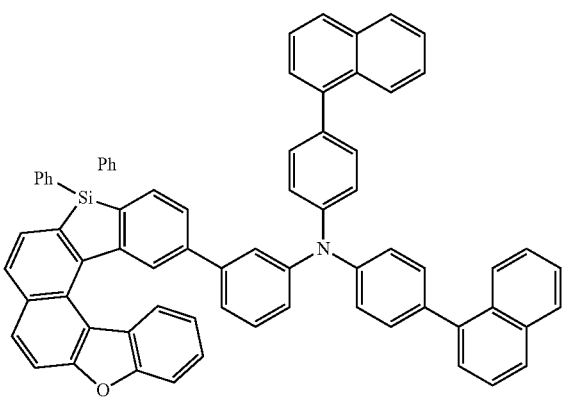

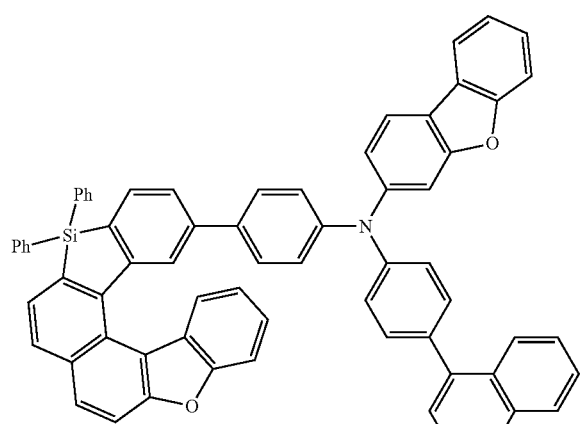

B114

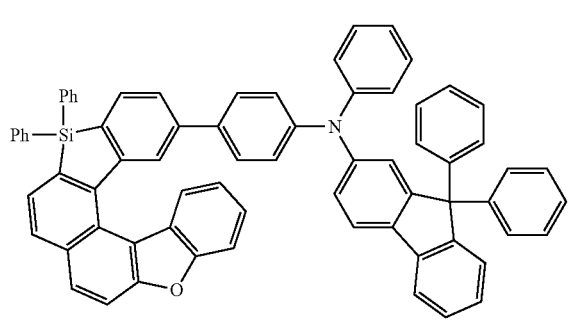

B115

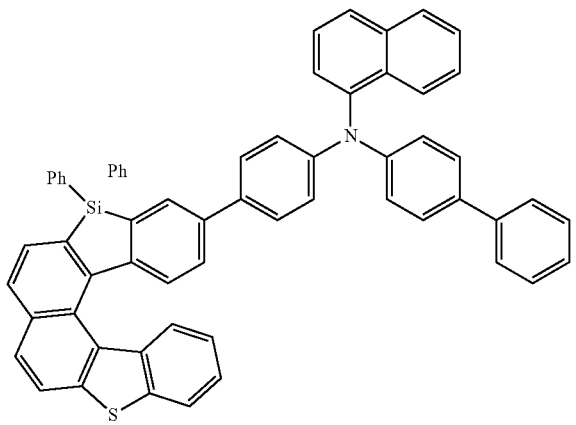

B116

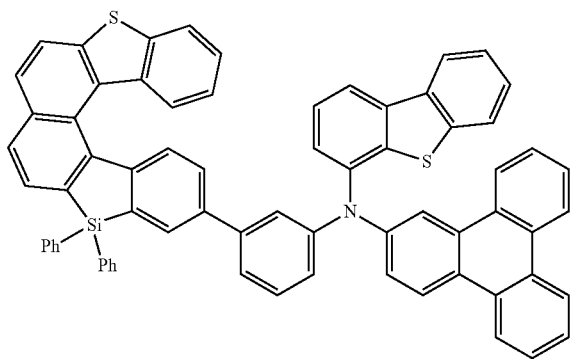

B117

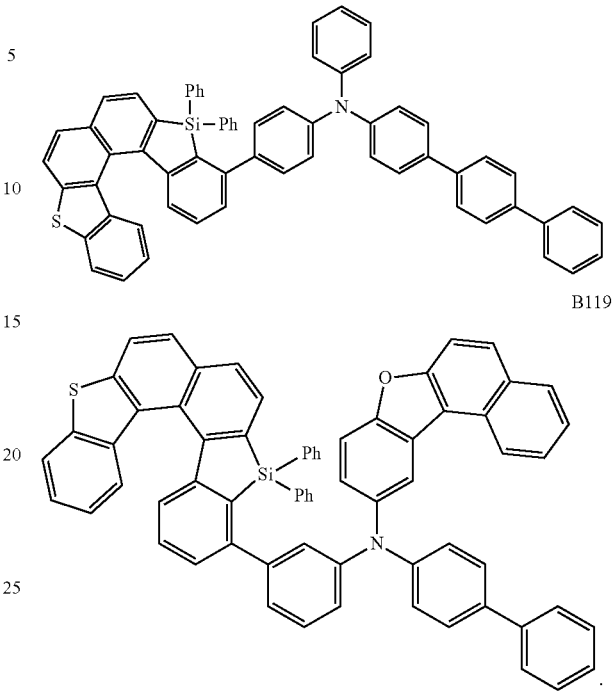

B118

B119

The condensed cyclic compound includes a heterohelicene moiety represented by Formula 1-1 or 1-2. Therethrough a π conjugation system is long, and thermal and charge resistance thereof are excellent, thereby exhibiting a long lifespan, and since a plurality of heteroatoms are included in the heterohelicene moiety, hole transport capability can be improved.

In addition, since the condensed cyclic compound includes the condensation moiety, the symmetry and crystallinity of the whole molecule are deteriorated, thereby improving the film characteristics.

Even when a condensed dibenzofuran (or dibenzothiophene, dibenzosilole) moiety is included as above, if the condensation moiety of the present disclosure is not included, the planarity of the whole molecule becomes too high to improve the crystallinity, the distance between molecules is shortened, the transfer of holes is slowed, resulting in poor luminescent efficiency.

In addition, the condensed cyclic compound limits the heteroatom included in the heterohelicene core to O, Si, or S. Thus, as compared with the case of including N as the heteroatom, excellent carrier balance can be provided, thereby improving the device efficiency.

In addition, the condensed cyclic compound essentially includes a linker between a group represented by Formula 1-1 or 1-2 and an amine group. In a case where no linker is included and thus the amine group is directly linked to a group represented by Formula 1-1 or 1-2, the distance between three aryl groups linked to the nitrogen atom is excessively close. Thus, the stability of molecule is deteriorated, and a three-dimensional structure capable of distorting three aryl groups is taken so as to solve a three-dimensional electronic repulsion. Thus, since HOMO orbital distribution becomes narrow, the efficiency and lifespan of the device are deteriorated.

In addition, since the condensed cyclic compound includes the amine group represented by Formula 2, it can be applied as a hole transport material having a long lifespan due to the aryl group having strong electron resistance, and the condensed cyclic compound limits the substitution position of the amine group to the terminus of the heterohelicene core. When the amine group is substituted at not the terminus of the core but the central site, the heteroatoms in the heterohelicene are directed toward the core of the whole molecule, and the interaction between molecules becomes weak. Thus, the hole transport capability is hardly increased, and in the HOMO orbital, the electron distribution of the core is excessively large. Thus, the contribution to the condensed cyclic compound of the amine group is relatively reduced. Consequently, it is difficult to exhibit characteristics arising from the amine group.

Furthermore, the carbazole group is not included in the terminus of the core of the condensed cyclic compound. If the carbazole group is included in the condensed cyclic compound, resulting that hole transport capability is not sufficient, and a three-dimensional structure in which the molecule is excessively distorted as a whole is taken. Thus, the compound becomes unstable in a radical state, and thus the efficiency and lifespan of the device using the compound are all deteriorated.

Therefore, an electronic device, for example, an organic light-emitting device, which includes the condensed cyclic compound represented by Formula 1, may have a low driving voltage, high efficiency, and a long lifespan.

A synthesis method for the condensed cyclic compound represented by Formula 1 would be apparent to those of ordinary skill in the art by referring to the following examples.

At least one condensed cyclic compound represented by Formula 1 may be used between a pair of electrodes constituting an organic light-emitting device. For example, the condensed cyclic compound may be included in at least one selected from a hole transport region and an emission layer. In one or more embodiments, the condensed cyclic compound of Formula 1 may be used as a material for a capping layer located outside a pair of electrodes of an organic light-emitting device.

For example, the organic light-emitting device may have i) a stacked structure including a first electrode, an organic layer, a second electrode, and a second capping layer which are sequentially stacked in this stated order, ii) a stacked structure including a first capping layer, a first electrode, an organic layer, and a second electrode which are sequentially stacked in this stated order, or iii) a stacked structure including a first capping layer, a first electrode, an organic layer, a second electrode, and a second capping layer which are sequentially stacked in this stated order, and at least one selected from the first capping layer and the second capping layer may include the condensed cyclic compound.

Accordingly, provided is an organic light-emitting device including: a first electrode, a second electrode facing the first electrode, and an organic layer between the first electrode and the second electrode, the organic layer including an emission layer and at least one condensed cyclic compound represented by Formula 1.

The expression "(an organic layer) includes at least one of the condensed cyclic compounds" used herein may include a case in which "(an organic layer) includes identical condensed cyclic compounds represented by Formula 1" and a case in which "(an organic layer) includes two or more different condensed cyclic compounds represented by Formula 1."

For example, the organic layer may include, as the condensed cyclic compound, only Compound A1. In this regard, Compound A1 may exist in a hole transport layer of the organic light-emitting device. In one or more embodiments, the organic layer may include, as the condensed cyclic compound, Compounds A1 and Compound A2. In this regard, Compound A1 and Compound A2 may exist in an identical layer (for example, Compound 1 and Compound 2 may all exist in a hole transport layer), or different layers (for example, Compound 1 may exist in an emission layer and Compound 2 may exist in a hole transport layer).

According to one embodiment, the first electrode of the organic light-emitting device may be an anode, the second electrode of the organic light-emitting device may be a cathode, the organic layer of the organic light-emitting device may further include a hole transport region between the first electrode and the emission layer and an electron transport region between the emission layer and the second electrode, the hole transport region may include at least one layer selected from a hole injection layer, a hole transport layer, a buffer layer, an emission auxiliary layer, and an electron blocking layer, and the electron transport region may include an electron transport region including at least one layer selected from a hole blocking layer, an electron transport layer, and an electron injection layer.

In one or more embodiments, the hole transport region may include the condensed cyclic compound represented by Formula 1.

In one or more embodiments, the hole transport region includes a hole transport layer, which includes the condensed cyclic compound.

In one embodiment, the hole transport region may include: a first hole transport layer disposed between the first electrode and the emission layer; and a second hole transport layer disposed between the first hole transport layer and the emission layer, and the first hole transport layer may include the condensed cyclic compound.

In one or more embodiments, the hole transport region may include: a first hole transport layer disposed between the first electrode and the emission layer; a second hole transport layer between the first hole transport layer and the emission layer, and the second hole transport layer may include the condensed cyclic compound.

In one embodiment, the emission layer may include a host and a dopant, and the dopant may be a fluorescent dopant or a phosphorescent dopant. For example, the host may include an anthracene-based compound, a pyrene-based compound, a fluoranthene-based compound, a chrysene-based compound, a dihydrobenzanthracene-based compound, a triphenylene-based compound, and any combination thereof.

At least one layer selected from the electron transport layer and the electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof.

In one embodiment, the emission layer may be a first emission layer for emitting a first color light, For example, the organic light-emitting device may further include i) at least one second emission layer for emitting a second color light or ii) at least one second emission layer for emitting the second color light and at least one third emission layer for emitting a third color light, between the first electrode and the second electrode, a maximum emission wavelength of the first color light, a maximum emission wavelength of the second color light, and a maximum emission wavelength of the third color light may be identical to or different from each other.

The term "organic layer" as used herein refers to a single layer and/or a plurality of layers between the first electrode and the second electrode of an organic light-emitting device. A material included in the "organic layer" is not limited to an organic material.

[Description of FIG. 1]

Figure 1:
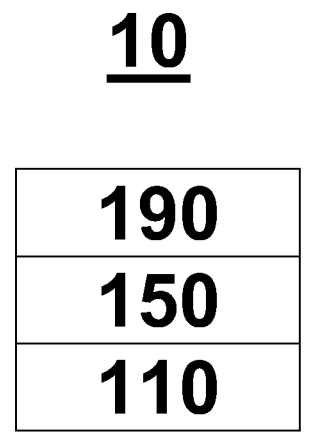

FIG. 1 is a schematic view of an organic light-emitting device 10 according to an embodiment. The organic light-emitting device 10 includes a first electrode 110, an organic layer 150, and a second electrode 190.

Hereinafter, the structure of the organic light-emitting device 10 according to an embodiment and a method of manufacturing the organic light-emitting device 10 will be described in connection with FIG. 1.

[First Electrode 110]

In FIG. 1, a substrate may be additionally disposed under the first electrode 110 or above the second electrode 190. The substrate may be a glass substrate or a plastic substrate, each having excellent mechanical strength, thermal stability, transparency, surface smoothness, ease of handling, and water resistance.

The first electrode 110 may be formed by depositing or sputtering a material for forming the first electrode 110 on the substrate. When the first electrode 110 is an anode, the material for forming the first electrode 110 may be selected from materials with a high work function to facilitate hole injection.

The first electrode 110 may be a reflective electrode, a semi-transmissive electrode, or a transmissive electrode. When the first electrode 110 is a transmissive electrode, a material for forming a first electrode may be selected from indium tin oxide (ITO), indium zinc oxide (IZO), tin oxide ($SnO_2$), zinc oxide (ZnO), and any combinations thereof, but embodiments of the present disclosure are not limited thereto. When the first electrode 110 is a semi-transmissive electrode or a reflective electrode, as a material for forming the first electrode 110, magnesium (Mg), silver (Ag), aluminum (Al), aluminum-lithium (Al—Li), calcium (Ca), magnesium-indium (Mg—In), magnesium-silver (Mg—Ag), or any combination thereof may be used. However, the material for forming the first electrode 110 is not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

[Organic Layer 150]

The organic layer 150 is disposed on the first electrode 110. The organic layer 150 may include an emission layer.

The organic layer 150 may further include a hole transport region between the first electrode 110 and the emission layer, and an electron transport region between the emission layer and the second electrode 190.

[Hole Transport Region in Organic Layer 150]

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer, a hole transport layer, an emission auxiliary layer, and an electron blocking layer.

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein for each structure, constituting layers are sequentially stacked from the first electrode 110 in this stated order, but the structure of the hole transport region is not limited thereto.

In one embodiment, the hole transport region may include the condensed cyclic compound.

The hole transport region may further include at least one selected from m-MTDATA, TDATA, 1-TNATA, 2-TNATA, NPB(NPD), p-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), PEDOT/PSS (poly(3,4-ethylenedioxythiophene)/poly(4-styrenesulfonate)), polyaniline/camphor sulfonic acid (PANI/CSA), polyaniline/poly(4-styrenesulfonate) (PANI/PSS), a compound represented by Formula 201, and a compound represented by Formula 202:

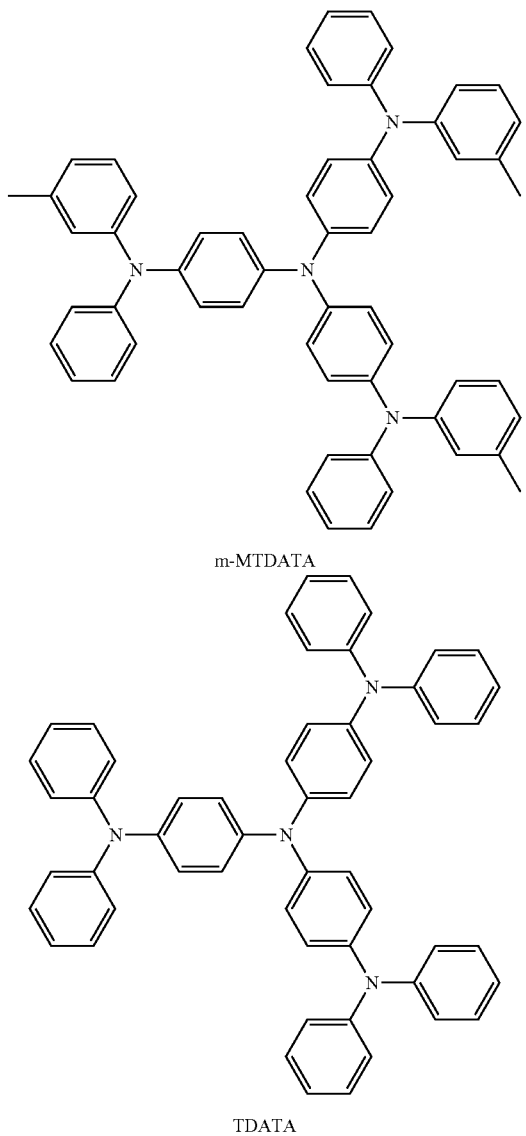

m-MTDATA

TDATA

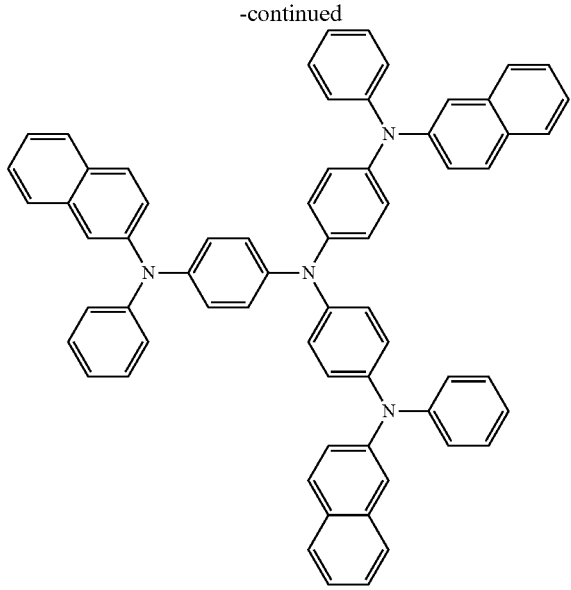
2-TNATA
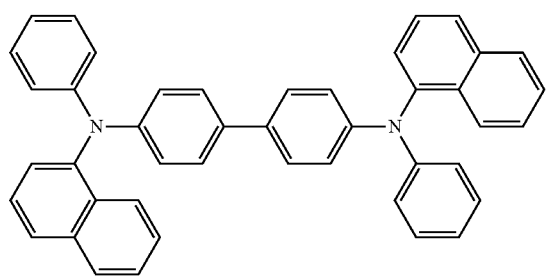
NPB
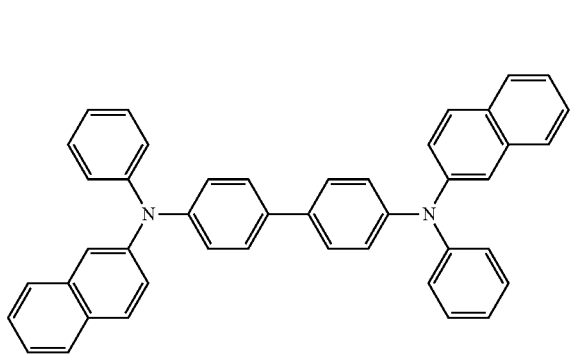
β-NPB
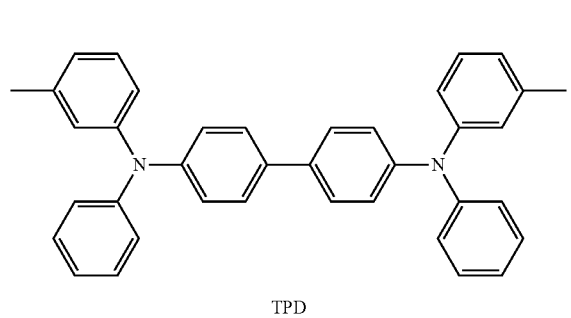
TPD
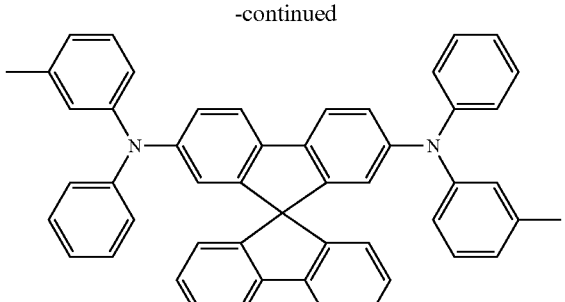
Spiro-TPD
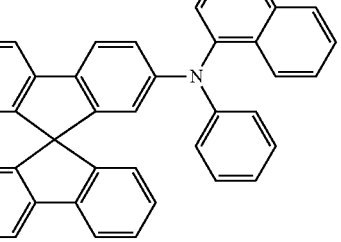
Spiro-NPB
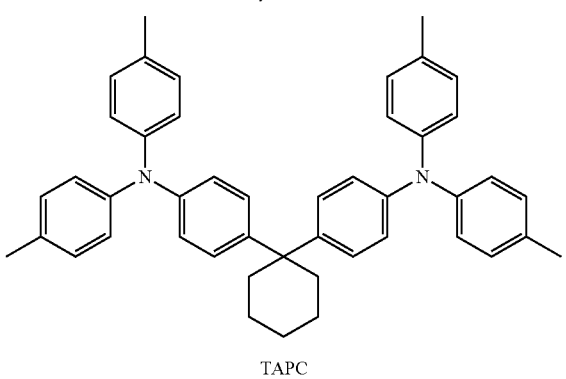
methylated NPB
TAPC
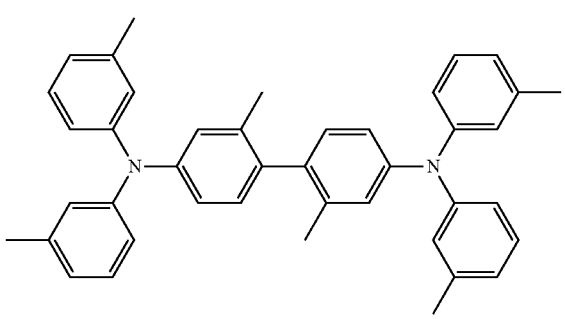
HMTPD

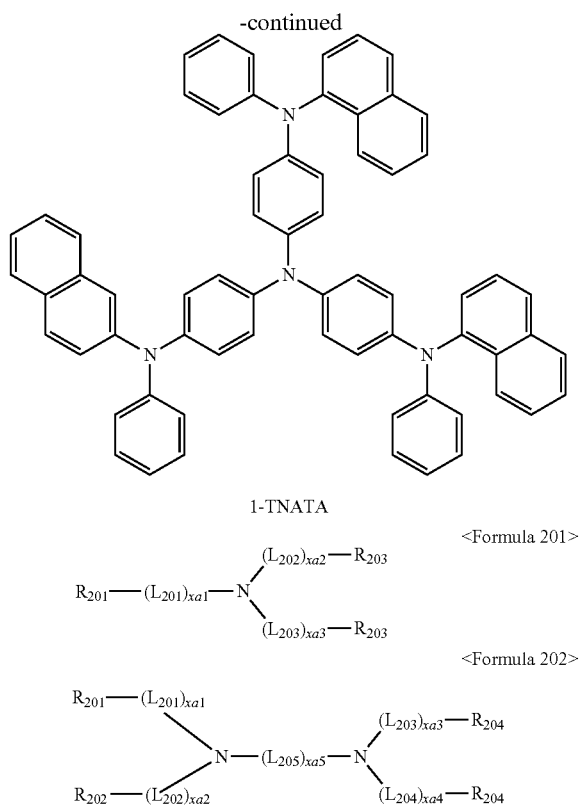

1-TNATA

<Formula 201>

$R_{201}$—$(L_{201})_{xa1}$—N$\begin{matrix}(L_{202})_{xa2}\text{—}R_{203}\\(L_{203})_{xa3}\text{—}R_{203}\end{matrix}$ <Formula 202>

$R_{201}$—$(L_{201})_{xa1}$
$R_{202}$—$(L_{202})_{xa2}$ N—$(L_{205})_{xa5}$—N$\begin{matrix}(L_{203})_{xa3}\text{—}R_{204}\\(L_{204})_{xa4}\text{—}R_{204}\end{matrix}$ In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 202, $R_{201}$ and $R_{202}$ may optionally be linked via a single bond, a dimethyl-methylene group, or a diphenyl-methylene group, and $R_{203}$ and $R_{204}$ may optionally be linked via a single bond, a dimethyl-methylene group, or a diphenyl-methylene group.

In one or more embodiments, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, $-Si(Q_{31})(Q_{32})(Q_{33})$, and $-N(Q_{31})(Q_{32})$, and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, $-Si(Q_{31})(Q_{32})(Q_{33})$, and $-N(Q_{31})(Q_{32})$, and $Q_{31}$ to $Q_{33}$ may each independently be defined the same as described above.

In one or more embodiments, in Formula 201, at least one selected from $R_{201}$ to $R_{203}$ may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

In one or more embodiments, in Formula 202, i) $R_{201}$ and $R_{202}$ may be linked via a single bond, and/or ii) $R_{203}$ and $R_{204}$ may be linked via a single bond.

In one or more embodiments, in Formula 202, at least one selected from $R_{201}$ to $R_{204}$ may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

The compound represented by Formula 201 may be represented by Formula 201A:

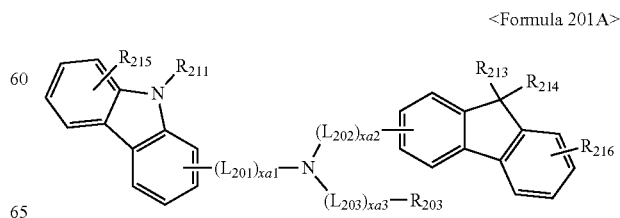

<Formula 201A>

In one embodiment, the compound represented by Formula 201 may be represented by Formula 201A(1) below, but embodiments of the present disclosure are not limited thereto:

In one embodiment, the compound represented by Formula 202 may be represented by Formula 202A-1:

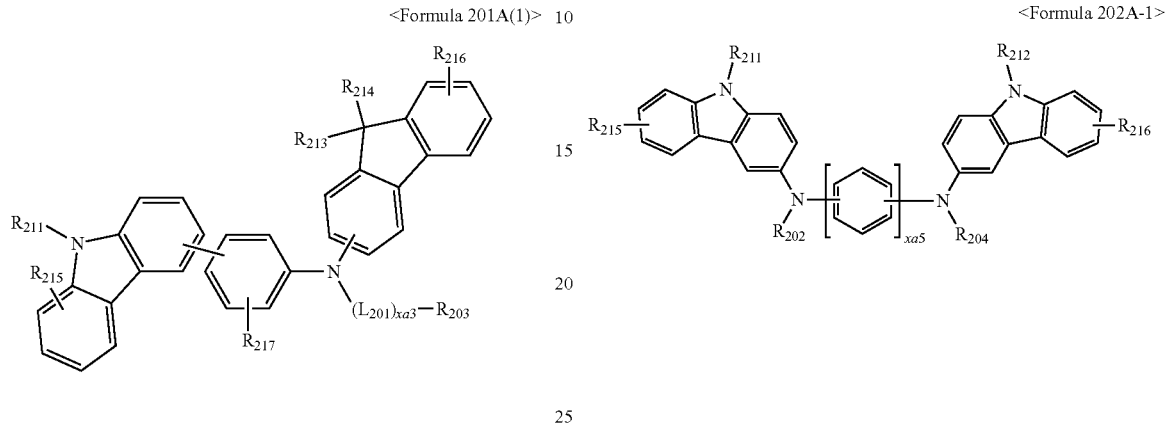

<Formula 201A(1)>

<Formula 202A-1>

In one embodiment, the compound represented by Formula 201 may be represented by Formula 201A-1 below, but embodiments of the present disclosure are not limited thereto:

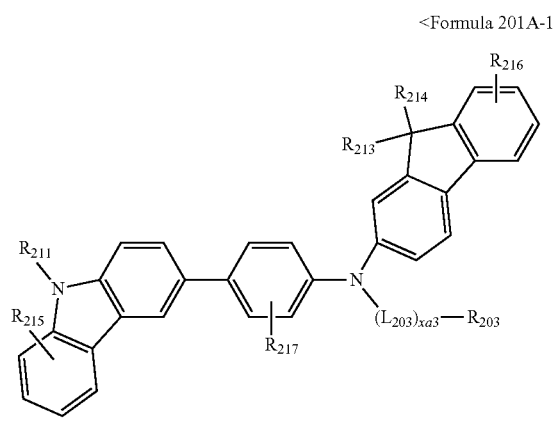

<Formula 201A-1>

In one embodiment, the compound represented by Formula 202 may be represented by Formula 202A:

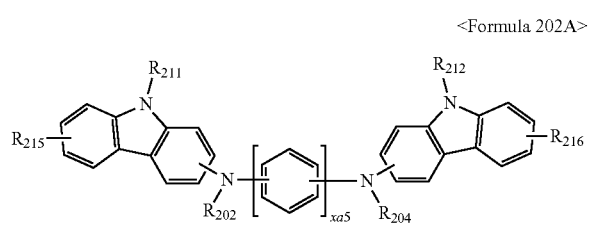

<Formula 202A>

In Formulae 201A, 201A(1), 201A-1, 202A, and 202A-1, $L_{201}$ to $L_{203}$, xa1 to xa3, xa5, and $R_{202}$ to $R_{204}$ are the same as described above, $R_{211}$ and $R_{212}$ may be understood by referring to the description provided herein in connection with $R_{203}$, $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but embodiments of the present disclosure are not limited thereto:

97
HT1
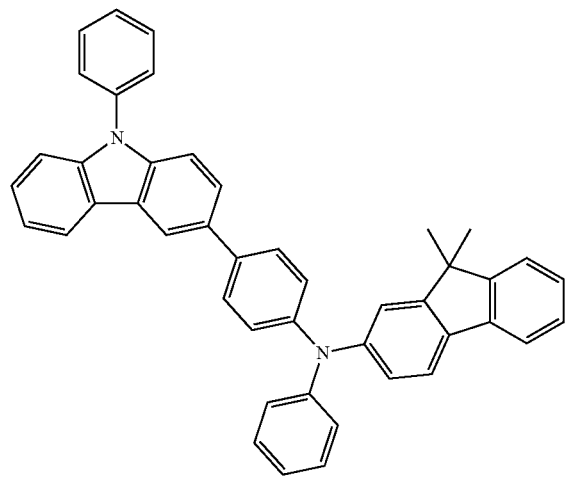
98
HT2
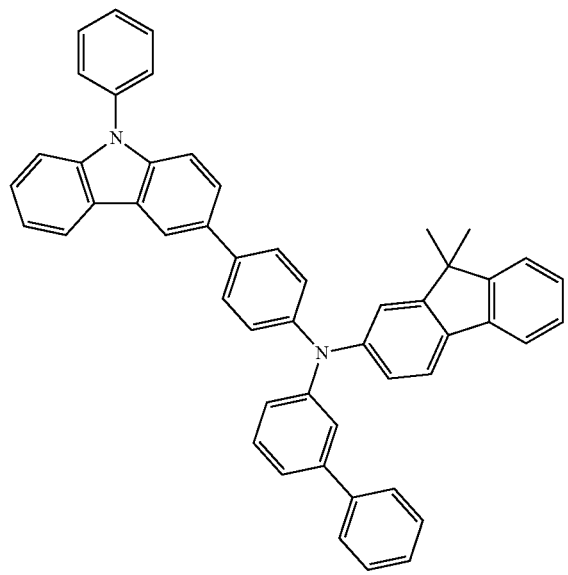
HT3
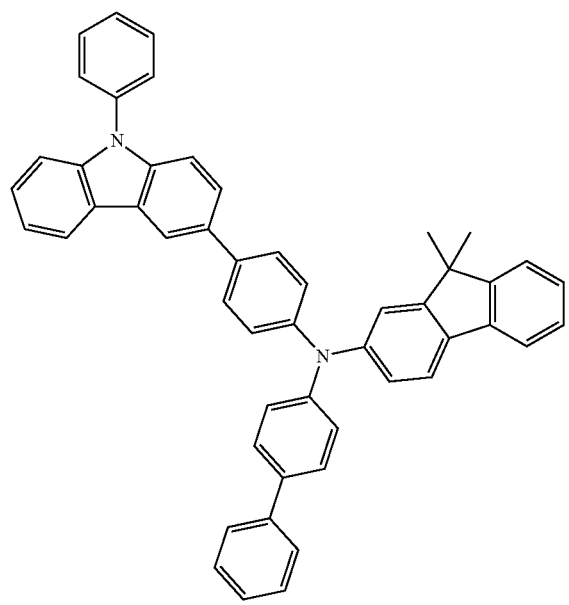
HT4
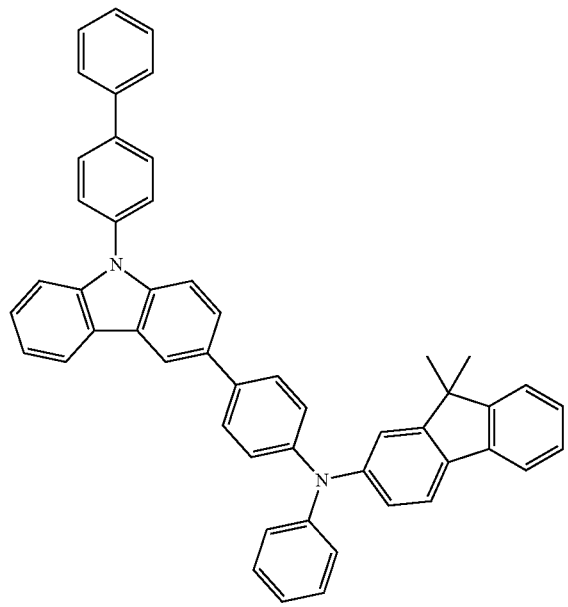

-continued
HT5
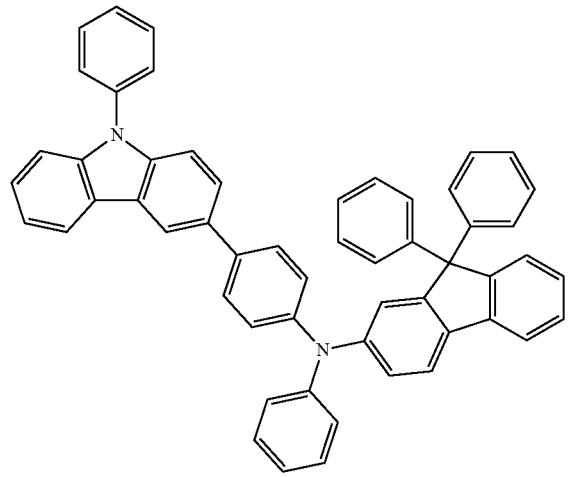
HT6
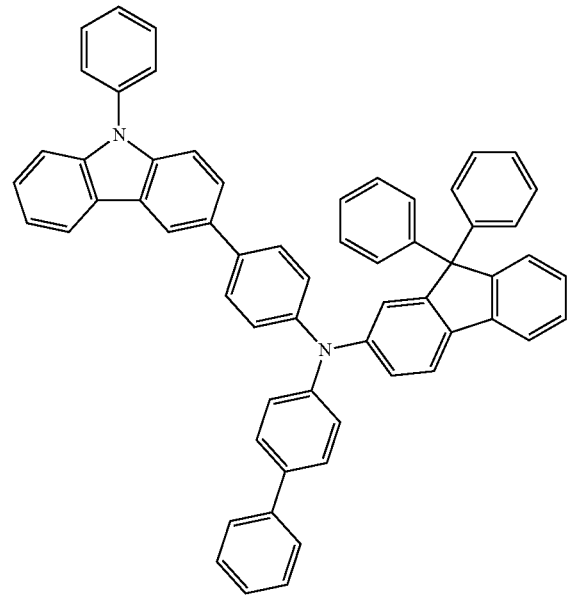
HT7
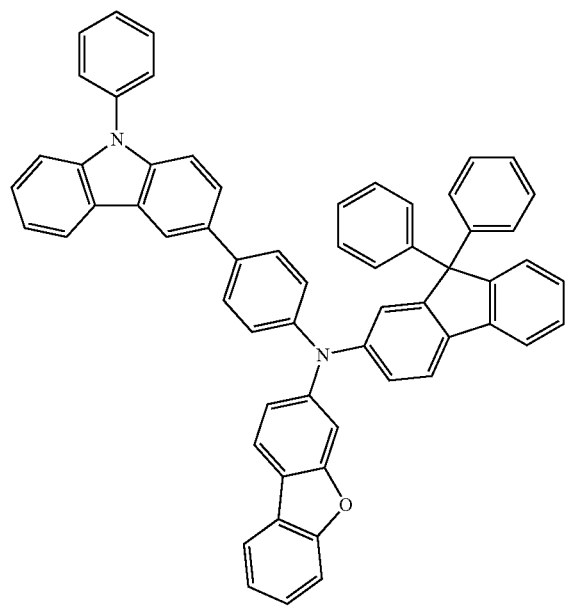
HT8
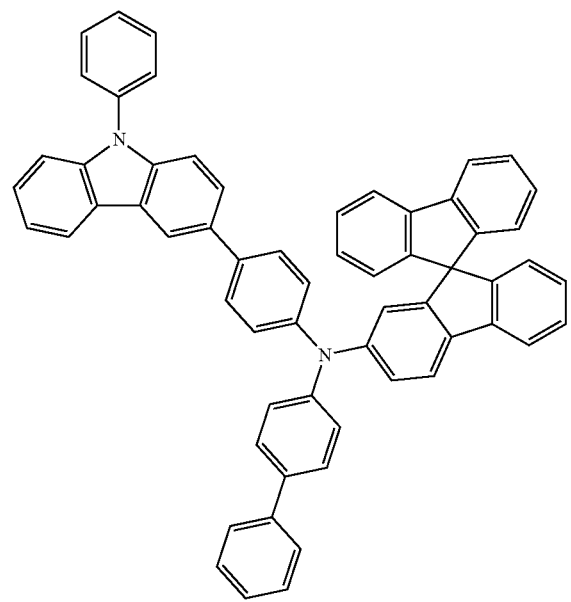

-continued
101    HT9
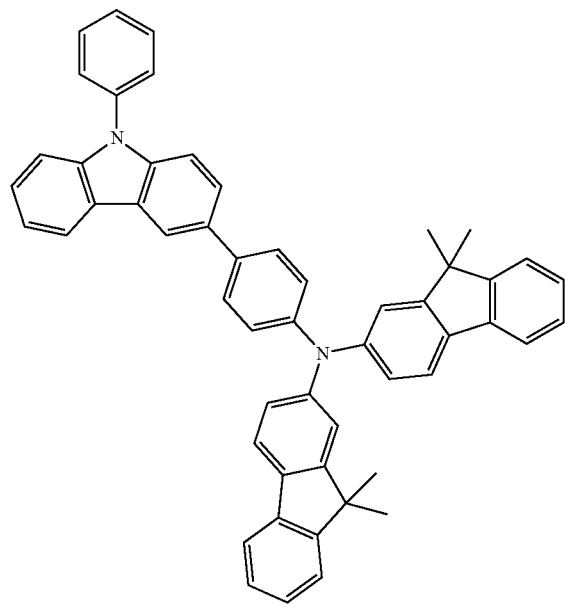
102    HT10
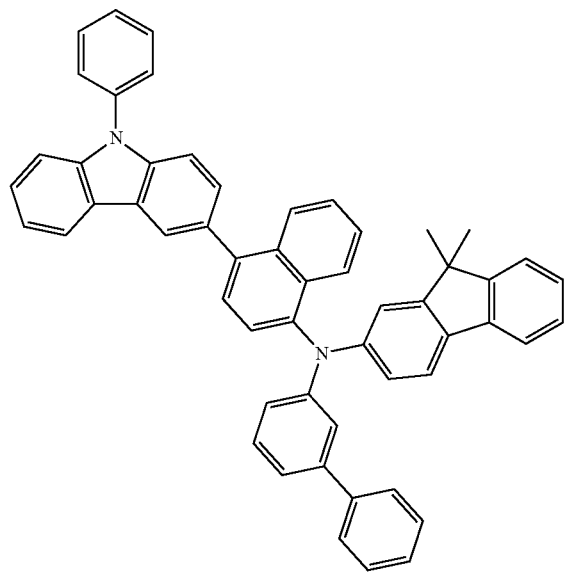
HT11
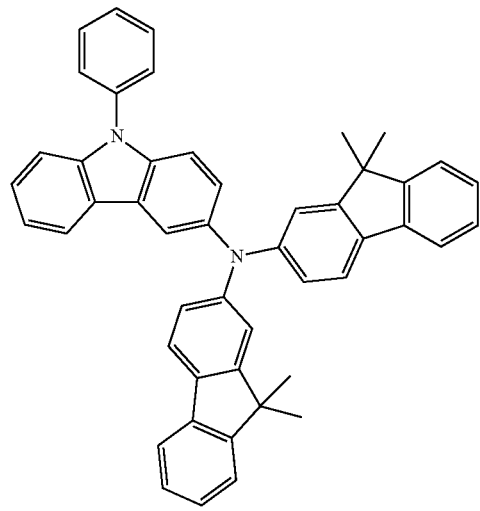
HT12
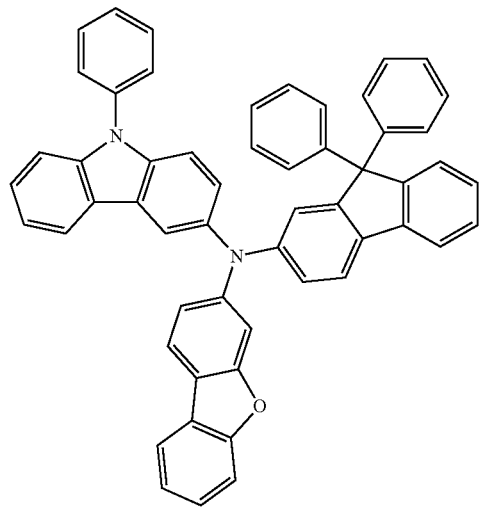

-continued
HT13
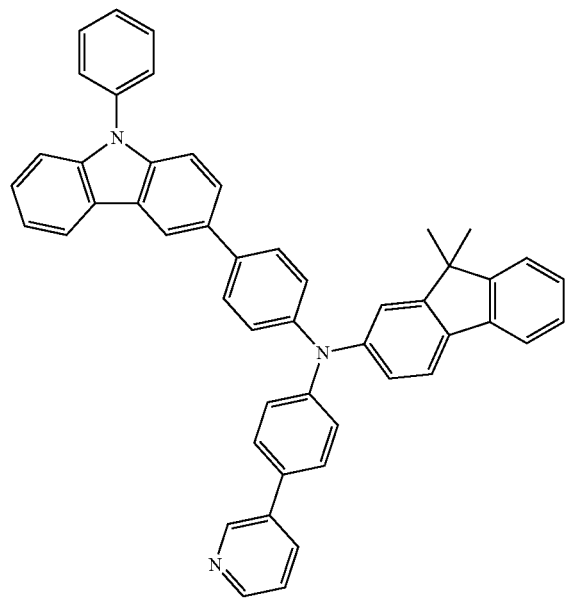
HT14
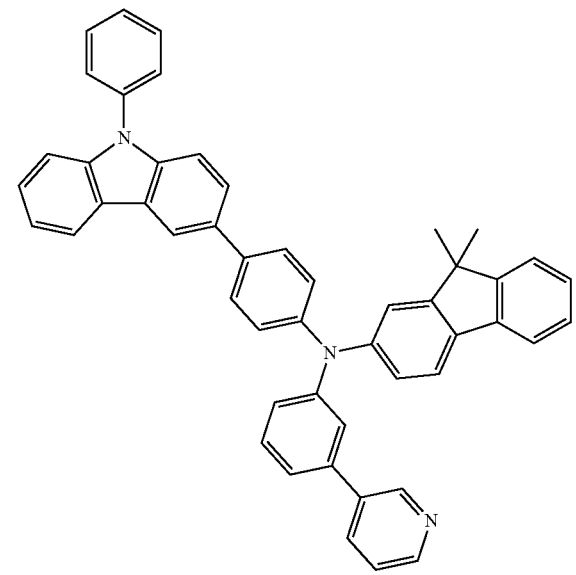
HT15
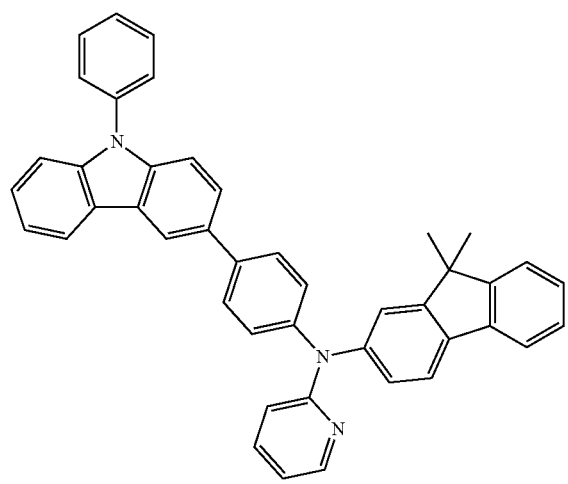
HT16
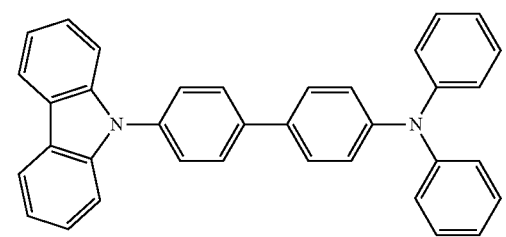
HT17
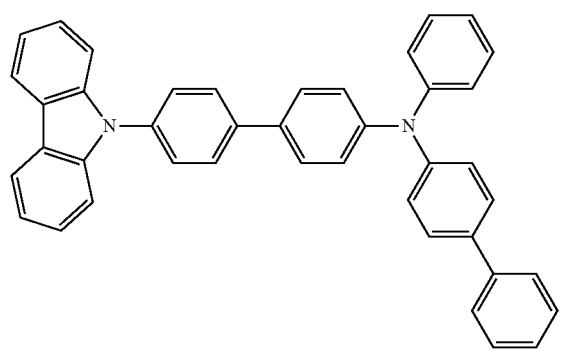
HT18
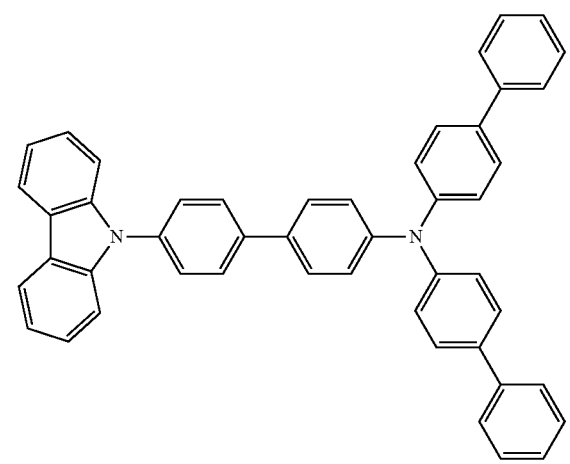

-continued
HT19
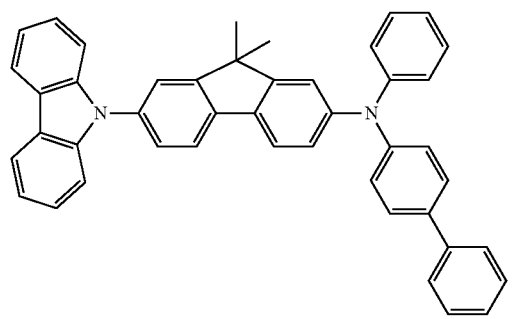
HT20
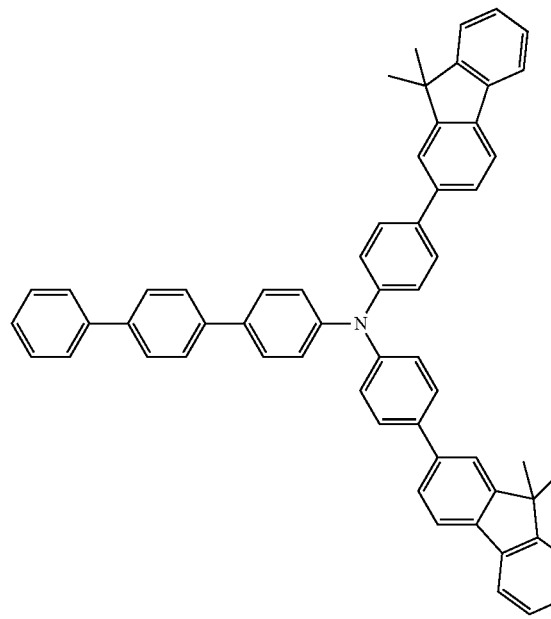
HT21
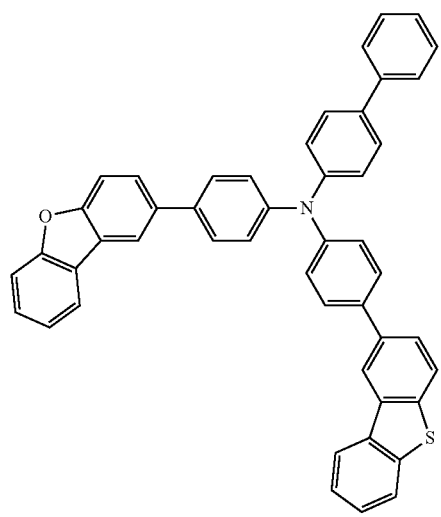
HT22
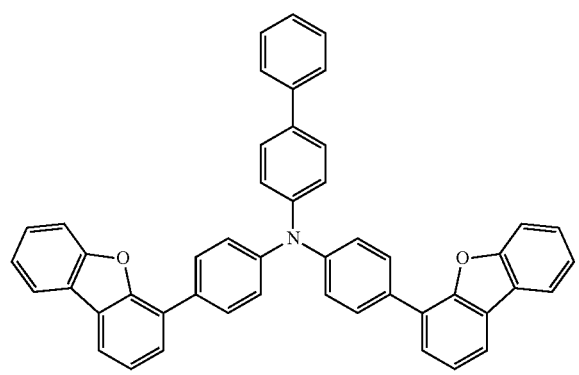
HT23
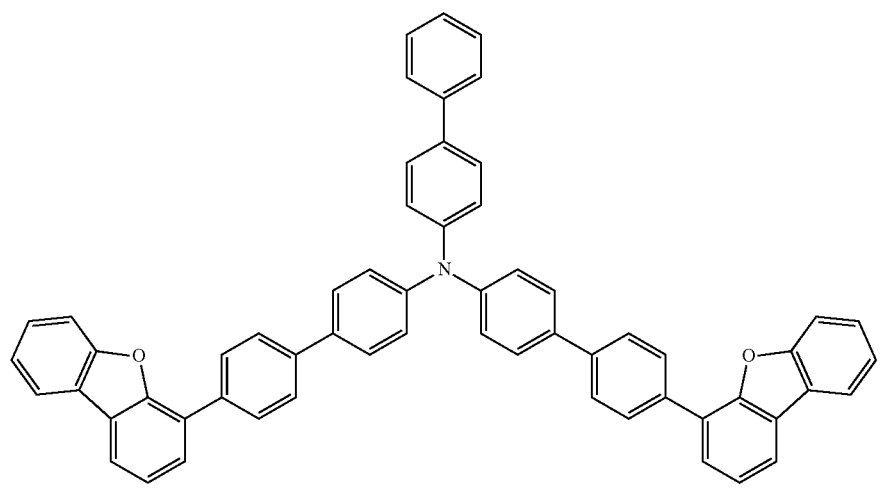

-continued
HT24
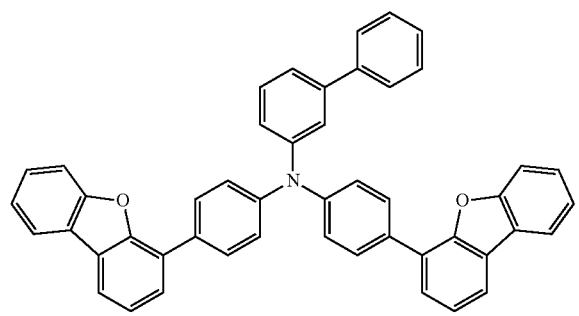
HT25
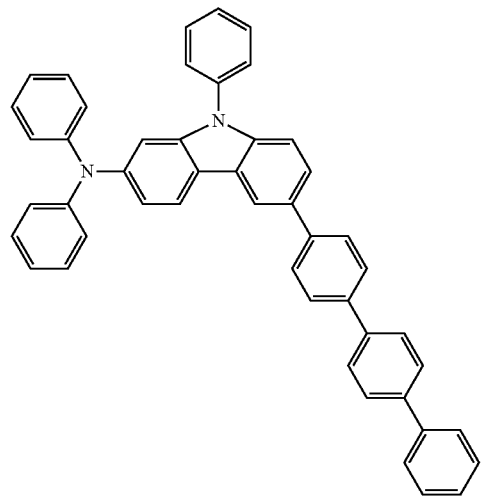
HT26
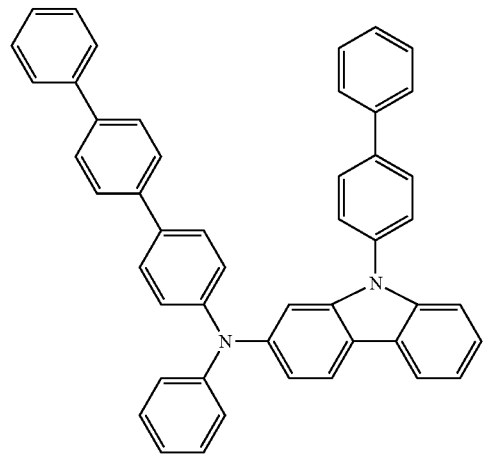
HT27
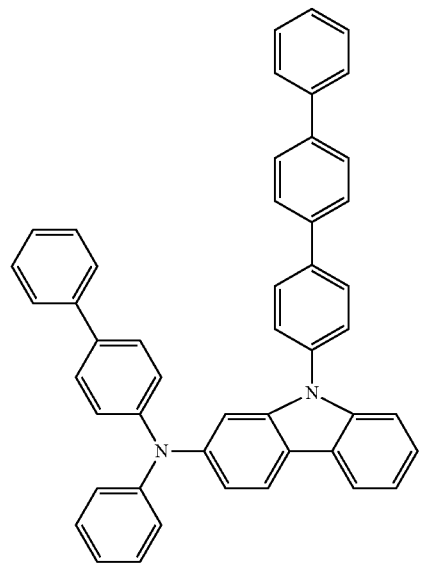
HT28
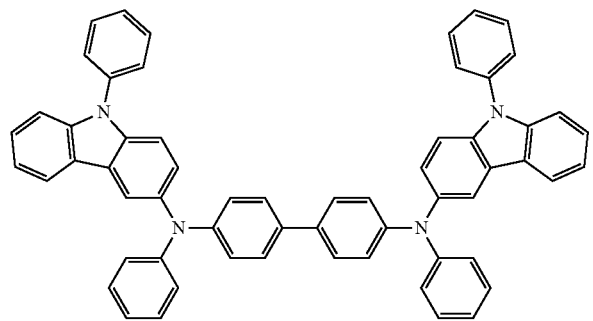
HT29
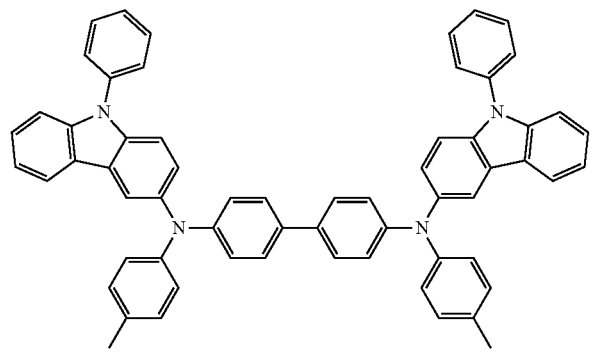

-continued
HT30
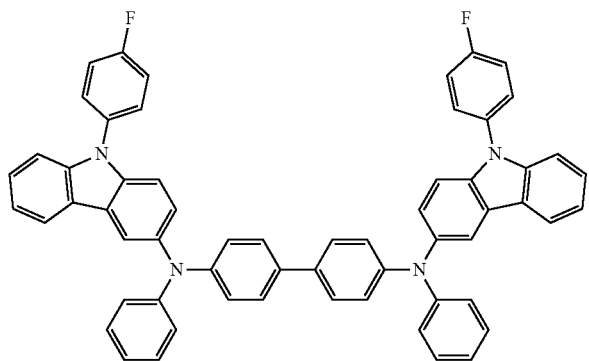
HT31
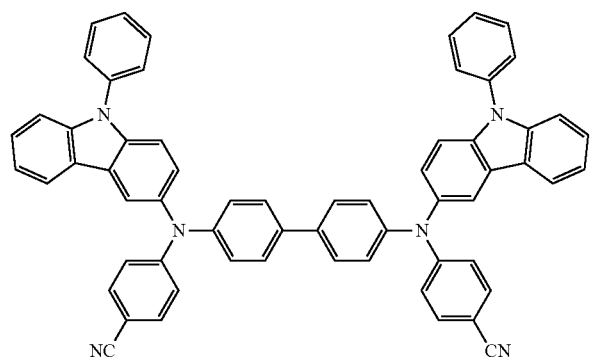
HT32
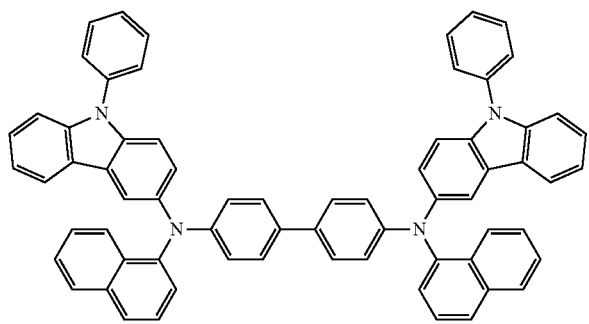
HT33
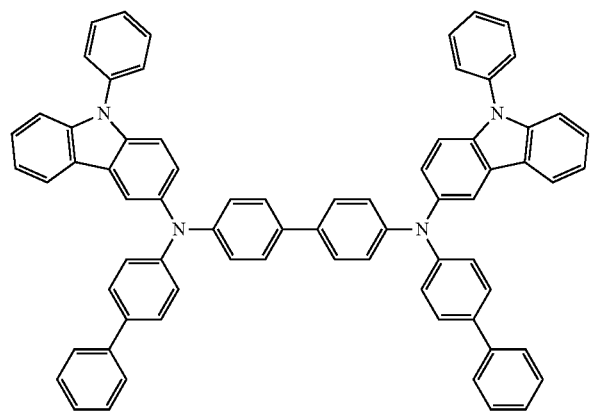
HT34
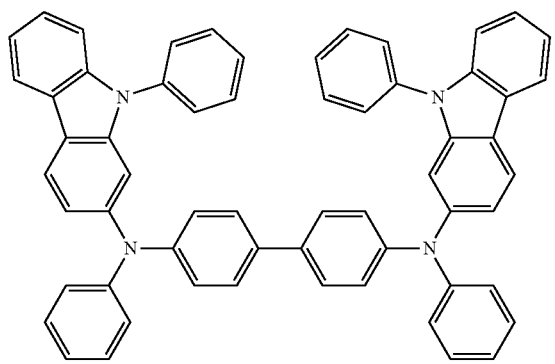
HT35
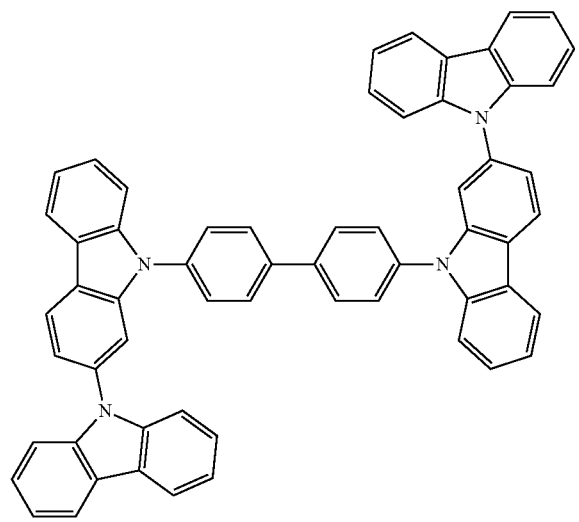

-continued

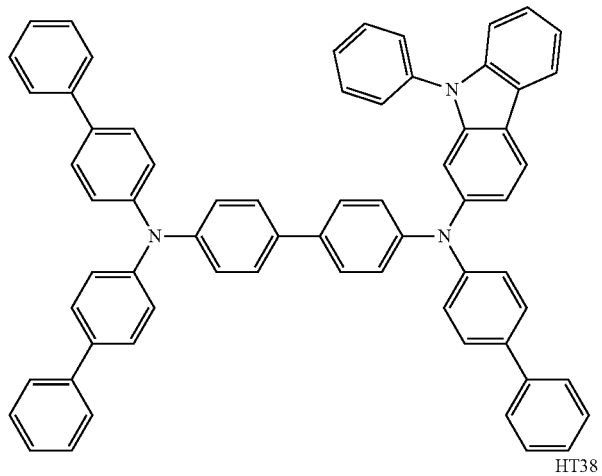
HT36

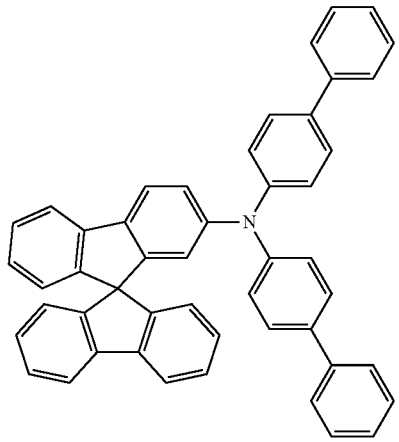
HT37

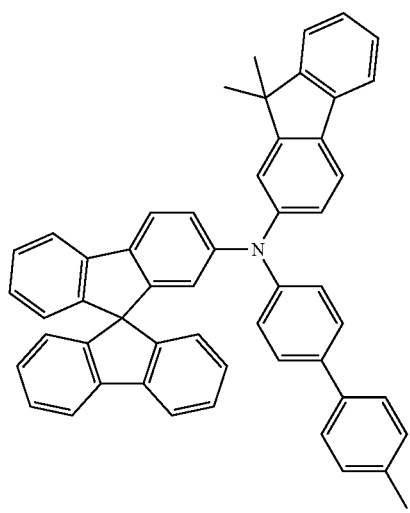
HT38

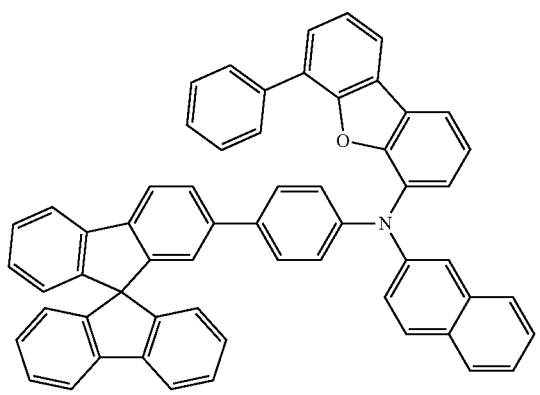
HT39

A thickness of the hole transport region may be in a range of about 100 Å to about 10,000 Å, for example, about 100 Å to about 1,000 Å. When the hole transport region includes at least one of a hole injection layer and a hole transport layer, the thickness of the hole injection layer may be in a range of about 100 Å to about 9,000 Å, and for example, about 100 Å to about 1,000 Å, and the thickness of the hole transport layer may be in a range of about 50 Å to about 2,000 Å, and for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may include the materials as described above.

[p-Dopant]

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In one embodiment, the p-dopant may have a lowest unoccupied molecular orbital (LUMO) level of −3.5 eV or less.

The p-dopant may include at least one selected from a quinone derivative, a metal oxide, and a cyano group-containing compound, but embodiments of the present disclosure are not limited thereto.

For example, the p-dopant may include at least one selected from:

a quinone derivative, such as tetracyanoquinodimethane (TCNQ) and 2,3,5,6-tetrafluoro-7,7,8,8-tetracyanoquinodimethane (F4-TCNQ);

a metal oxide, such as tungsten oxide or molybdenum oxide;

1,4,5,8,9,12-hexaazatriphenylene-hexacarbonitrile (HAT-CN); and a compound represented by Formula 221 below:

but embodiments of the present disclosure are not limited thereto:

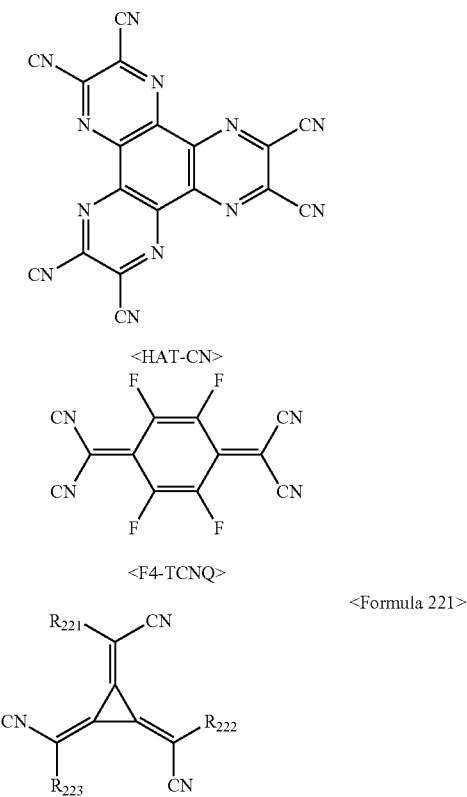

<HAT-CN>

<F4-TCNQ>

<Formula 221>

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from $R_{221}$ to $R_{223}$ may have at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br and a $C_1$-$C_{20}$ alkyl group substituted with —I.

[Emission Layer in Organic Layer 150]

When the organic light-emitting device 10 is a full-color organic light-emitting device, the emission layer may be patterned into a red emission layer, a green emission layer, or a blue emission layer, according to a sub-pixel. In one or more embodiments, the emission layer may have a stacked structure of two or more layers selected from a red emission layer, a green emission layer, and a blue emission layer, in which the two or more layers contact each other or are separated from each other. In one or more embodiments, the emission layer may include two or more materials selected from a red light-emitting material, a green light-emitting material, and a blue light-emitting material, in which the two or more materials are mixed with each other in a single layer to emit white light.

The emission layer may include a host and a dopant. The dopant may include at least one selected from a phosphorescent dopant and a fluorescent dopant.

In the emission layer, an amount of the dopant material may be in a range of about 0.01 parts to about 15 parts by weight based on 100 parts by weight of the host material, but embodiments of the present disclosure are not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

[Host in Emission Layer]

In one or more embodiments, the host may include a compound represented by Formula 301 below.

$$[Ar_{301}]_{xb11}\text{-}[(L_{301})_{xb1}\text{-}R_{301}]_{xb21} \qquad <\text{Formula 301}>$$

In Formula 301, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

xb1 may be an integer from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), xb21 may be an integer from 1 to 5, and $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In one embodiment, $Ar_{301}$ in Formula 301 may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group. However, embodiments of the present disclosure are not limited thereto.

When xb11 in Formula 301 is two or more, two or more Ar301(s) may be linked via a single bond.

In one or more embodiments, the compound represented by Formula 301 may be represented by Formula 301-1 or 301-2:

a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1, or 2, $L_{301}$, xb1, $R_{301}$, and $Q_{31}$ to $Q_{33}$ may each independently be defined the same as described above, $L_{302}$ to $L_{304}$ may each independently be defined the same as described above $L_{301}$, xb2 to xb4 may each independently be defined the same as described above xb1, and $R_{302}$ to $R_{304}$ may each independently be defined the same as described above $R_{301}$.

For example, in Formulae 301, 301-1, and 301-2, $L_{301}$ to $L_{304}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imida-

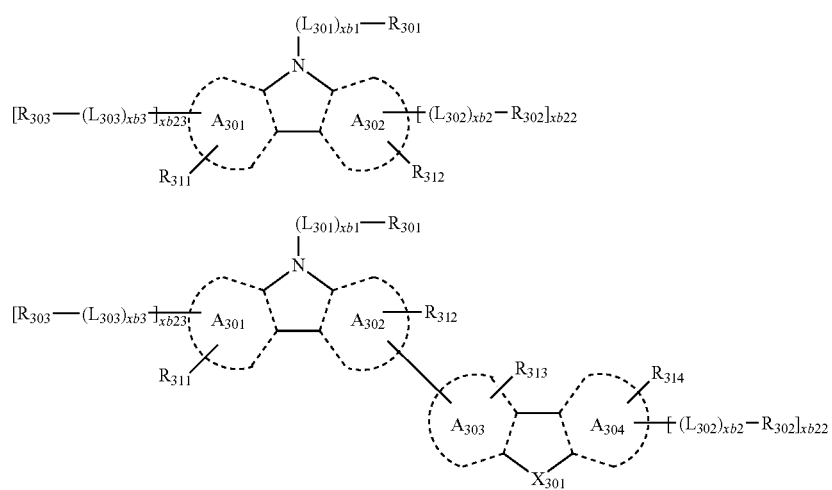

<Formula 301-1>

<Formula 301-2> wherein in Formulae 301-1 and 301-2, $A_{301}$ to $A_{304}$ may each independently be selected from a benzene, a naphthalene, a phenanthrene, a fluoranthene, a triphenylene, a pyrene, a chrysene, a pyridine, a pyrimidine, an indene, a fluorene, a spiro-bifluorene, a benzofluorene, a dibenzofluorene, an indole, a carbazole, benzocarbazole, dibenzocarbazole, a furan, a benzofuran, a dibenzofuran, a naphthofuran, a benzonaphthofuran, dinaphthofuran, a thiophene, a benzothiophene, a dibenzothiophene, a naphthothiophene, a benzonaphthothiophene, and a dinaphthothiophene, $X_{301}$ may be O, S, or N-[($L_{304}$)$_{xb4}$-$R_{304}$], $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, zolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be defined the same as described above.

In one embodiment, in Formulae 301, 301-1, and 301-2, $R_{301}$ to $R_{304}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$ ($Q_{31}$), and —P(=O)($Q_{31}$)($Q_{32}$), and $Q_{31}$ and $Q_{33}$ may each independently be defined the same as described above.

In one or more embodiments, the host may include an alkaline earth metal complex. For example, the host may be selected from a Be complex (for example, Compound H55), a Mg complex, and a Zn complex.

The host may include at least one selected from 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), a 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments of the present disclosure are not limited thereto:

H1

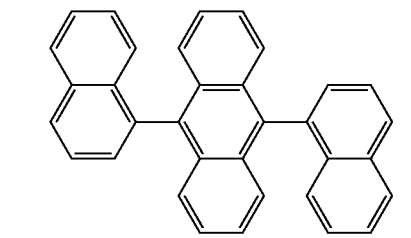

H2

H3

H4

H5

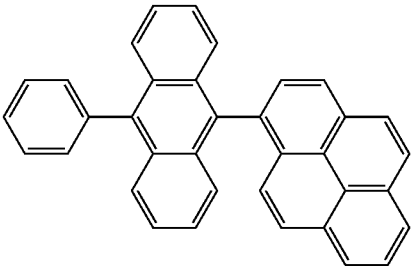

H6

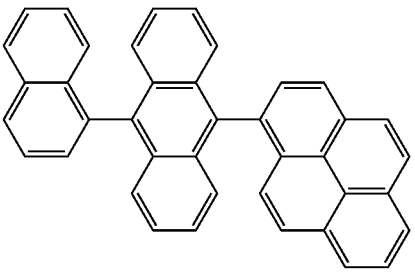

H7

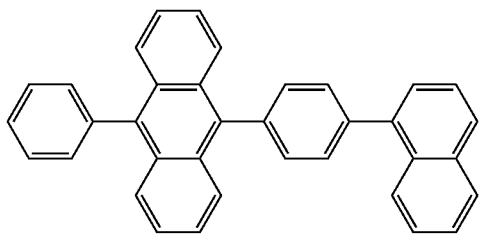

H8

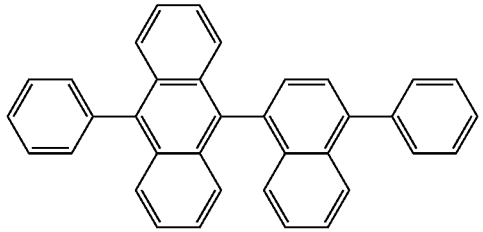

H9

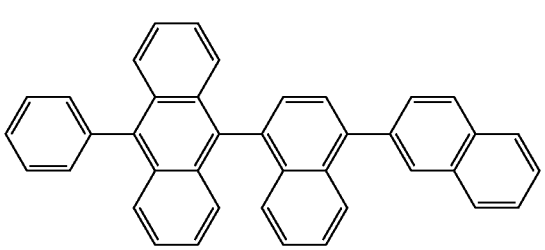

H10

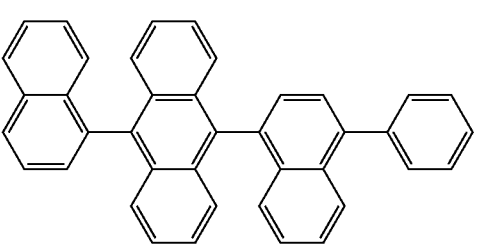

-continued
H11
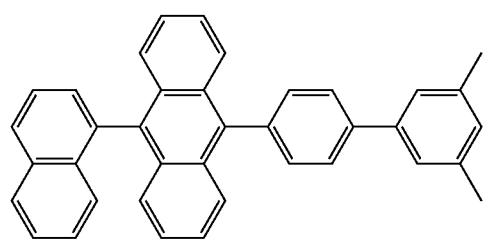
H12
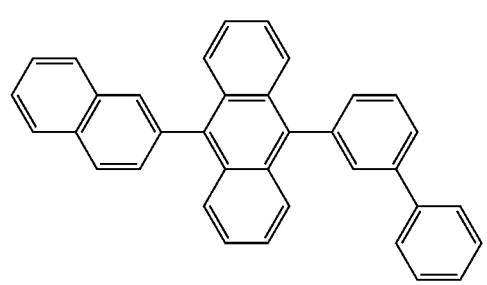
H13
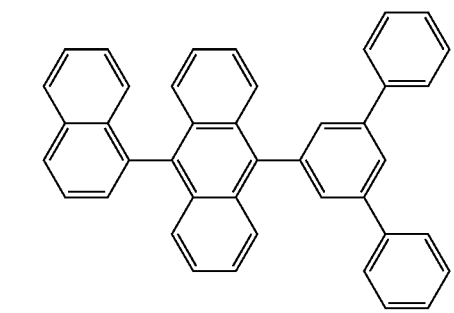
H14
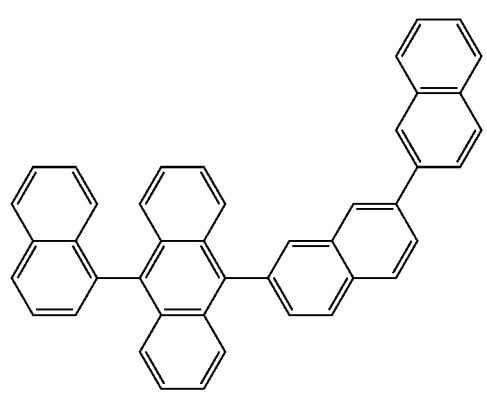
H15
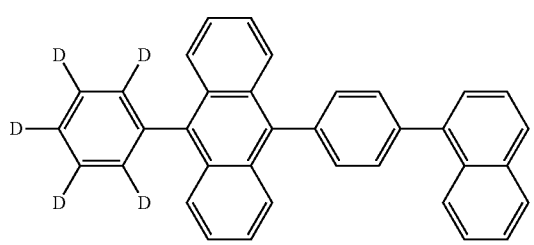
-continued
H16
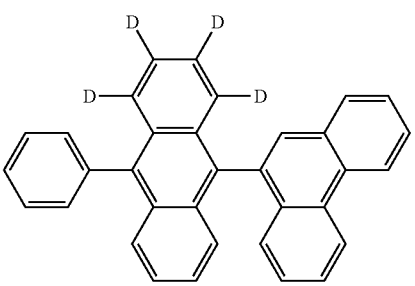
H17
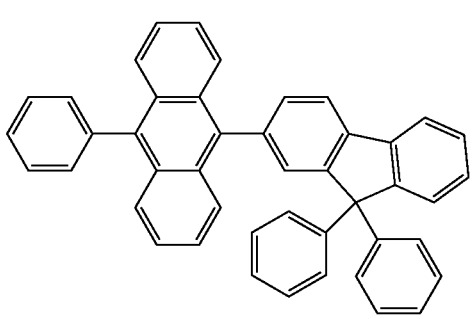
H18
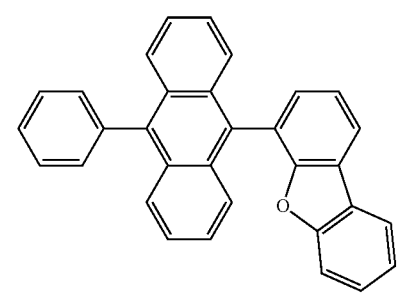
H19
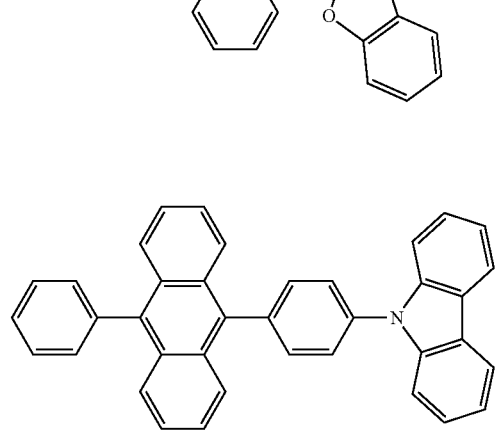
H20
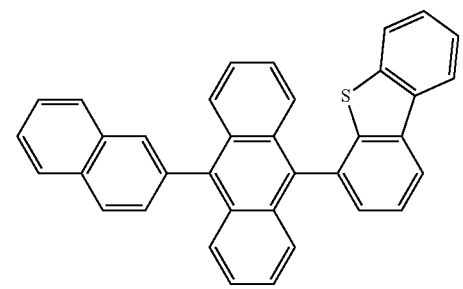

H21
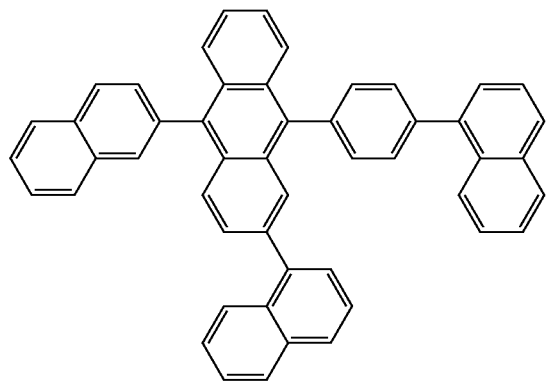
H22
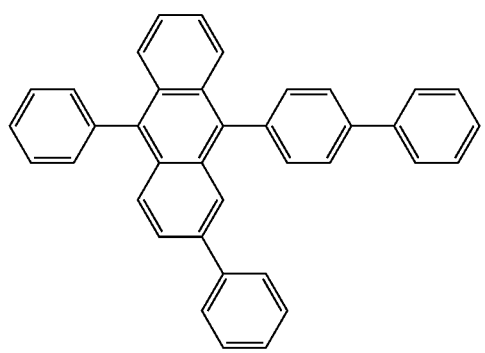
H23
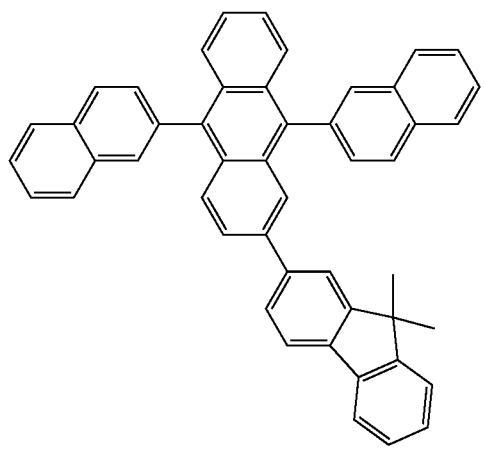
H24
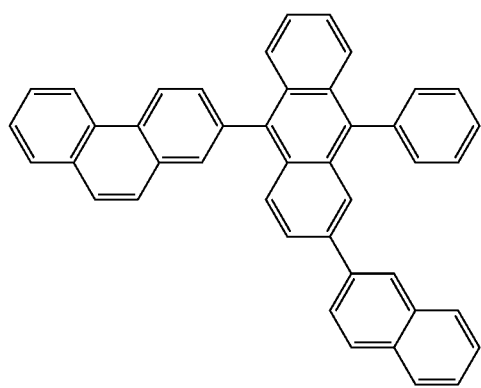
H25
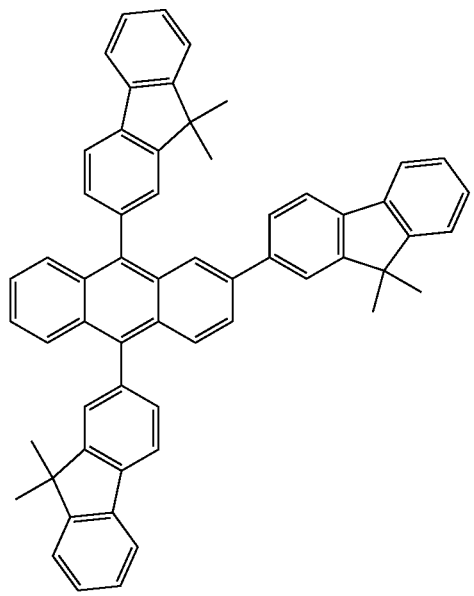
H26
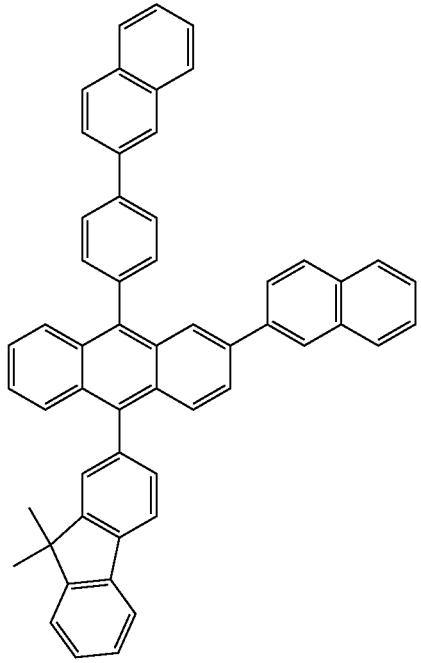

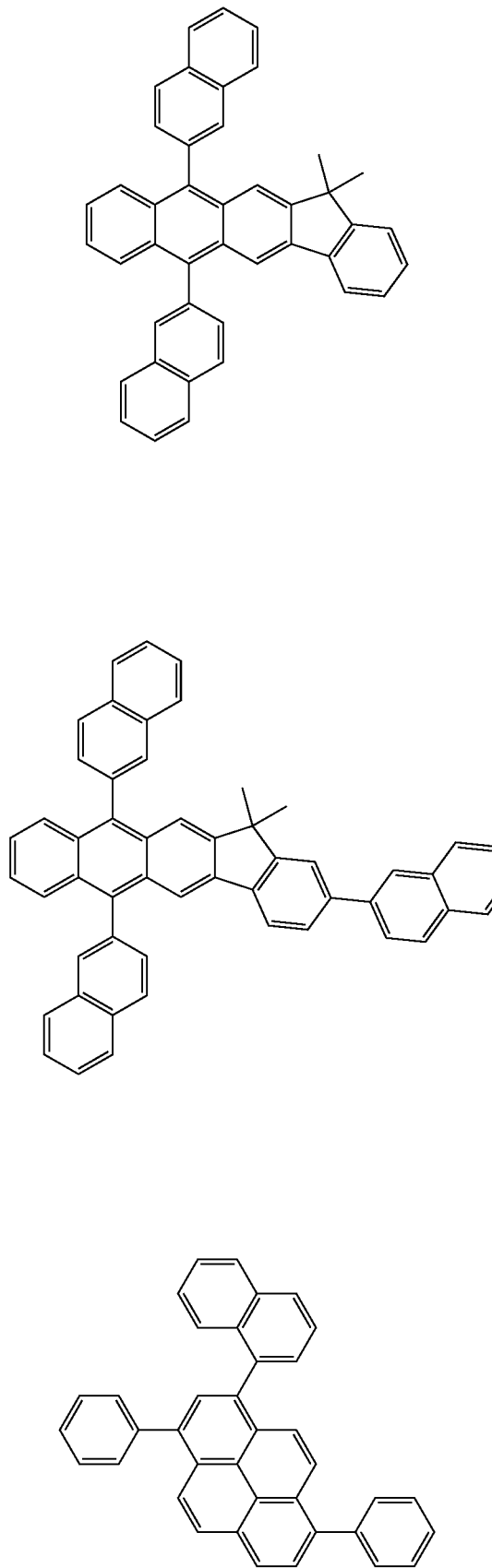
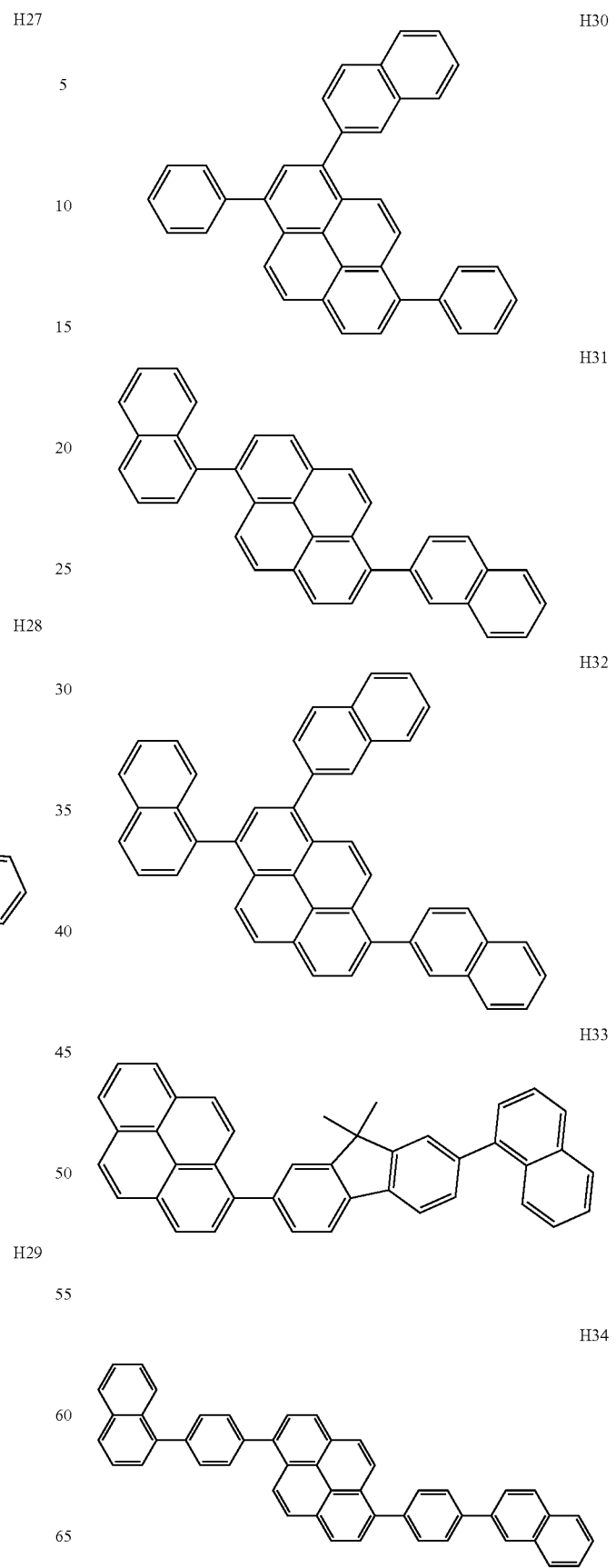

-continued
H35
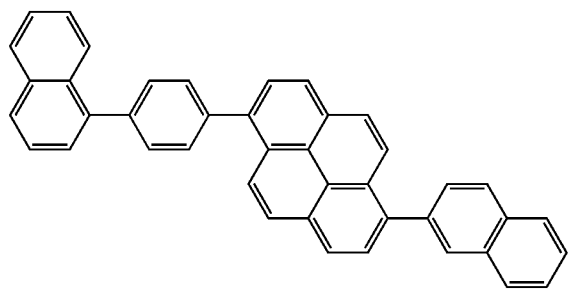
H36
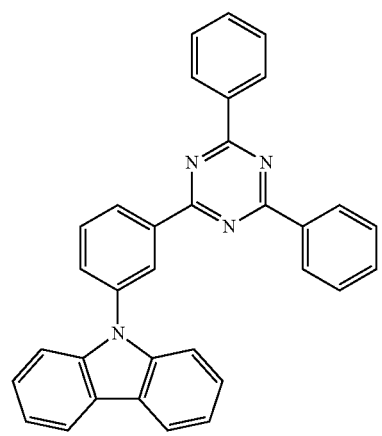
H37
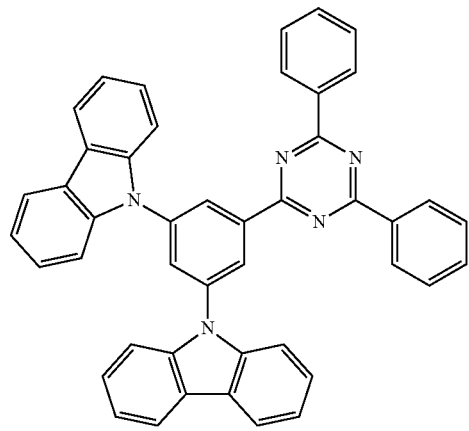
H38
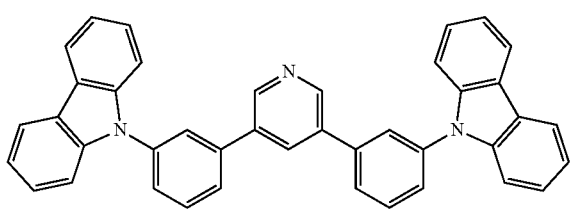
-continued
H39
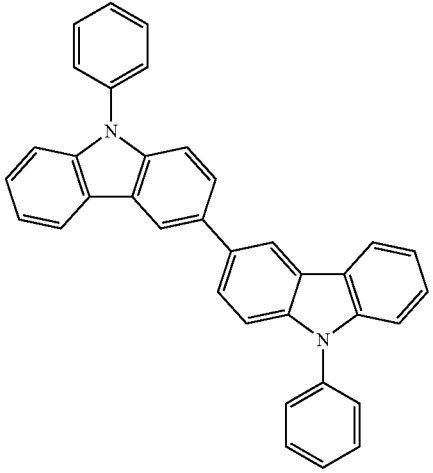
H40
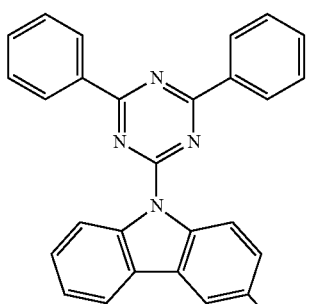
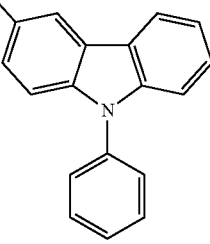
H41
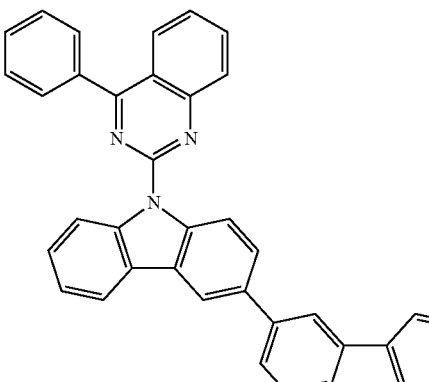
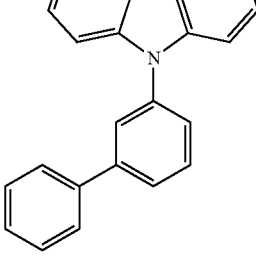

129
-continued
H42
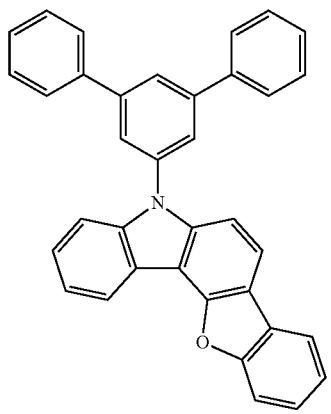
H43
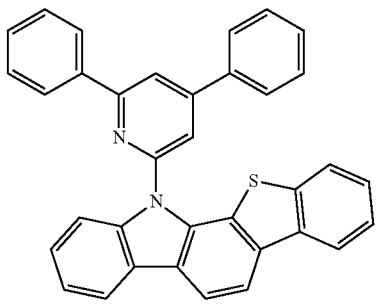
H44
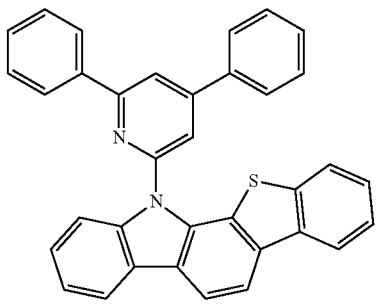
H45
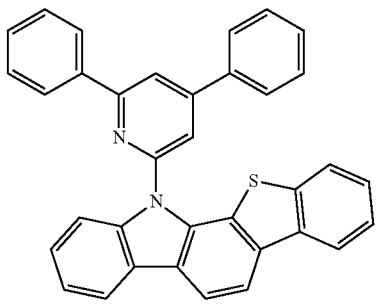
130
-continued
H46
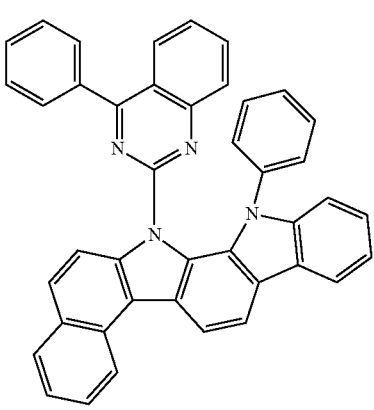
H47
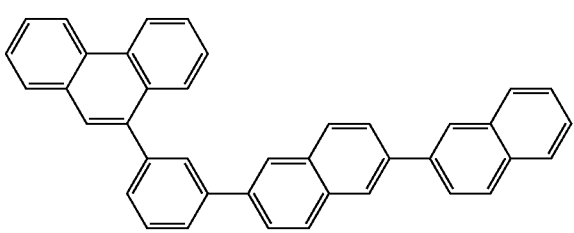
H48
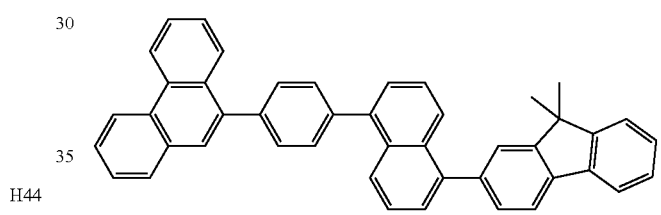
H49
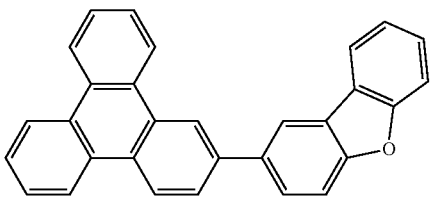
H50
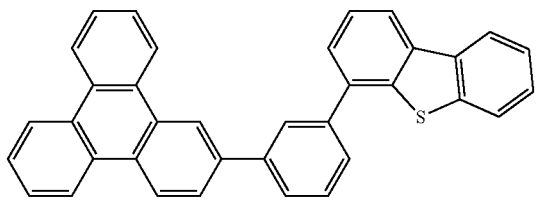
H51
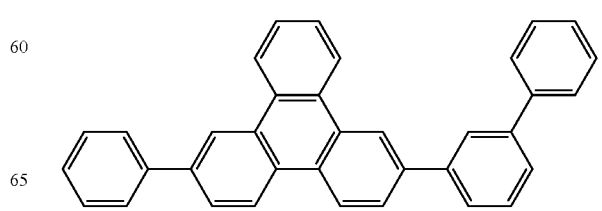

-continued

H52

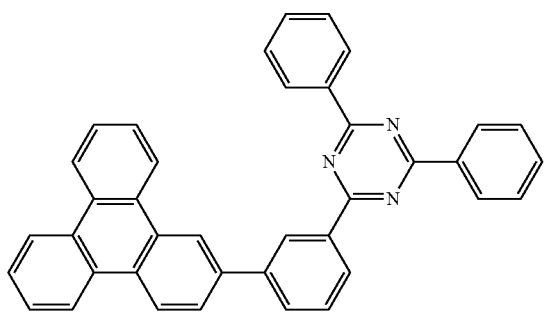

H53

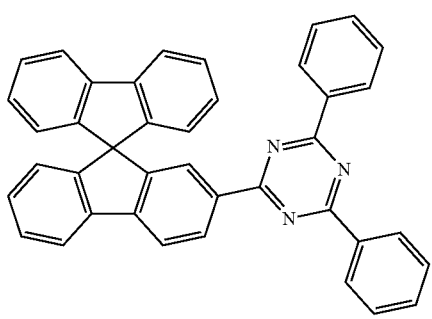

H54

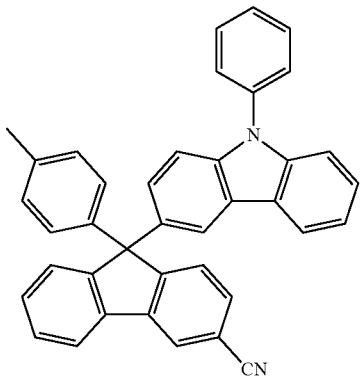

H55

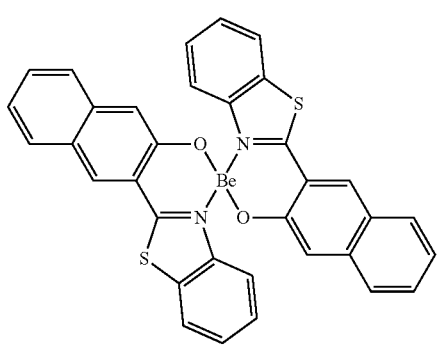

[Phosphorescent Dopant Included in Emission Layer in Organic Layer 150]

The phosphorescent dopant may include an organometallic complex represented by Formula 401 below:

$$M(L_{401})_{xc1}(L_{402})_{xc2} \quad \text{<Formula 401>}$$

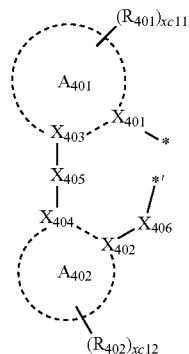

<Formula 402>

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, wherein, when xc1 is two or more, two or more $L_{401}$(s) may be identical to or different from each other, $L_{402}$ may be an organic ligand, and xc2 may be an integer from 0 to 4, wherein, when xc2 is two or more, two or more $L_{402}$(s) may be identical to or different from each other, $X_{401}$ to $X_{404}$ may each independently be nitrogen or carbon, $X_{401}$ and $X_{403}$ may be linked via a single bond or a double bond, and $X_{402}$ and $X_{404}$ may be linked via a single bond or a double bond, $A_{401}$ and $A_{402}$ may each independently be selected from a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)-*, *—C($Q_{411}$)($Q_{412}$)-*', *—C($Q_{411}$)=C($Q_{412}$)-*, *—C($Q_{411}$)=*', or *=C=*', wherein $Q_{411}$ and $Q_{412}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{40}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer from 0 to 10, and in Formula 402, * and *' each indicate a binding site to M in Formula 401.

In one embodiment, $A_{401}$ and $A_{402}$ in Formula 402 may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may each be nitrogen at the same time.

In one or more embodiments, $R_{402}$ and $R_{402}$ in Formula 401 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group, and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, and a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), and $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but are not limited thereto.

In one or more embodiments, when xc1 in Formula 401 is two or more, two $A_{401}$(s) in two or more $L_{401}$(s) may optionally be linked via $X_{407}$, which is a linking group, or two $A_{402}$(s) in two or more $L_{401}$(s) may optionally be linked via $X_{408}$, which is a linking group (see Compounds PD1 to PD4 and PD7). $X_{407}$ and $X_{408}$ may each independently be a single bond, *—O—*', *—S—*', *—C(=O)—*', *—N($Q_{413}$)-*', *—C($Q_{413}$)($Q_{414}$)-*', or *—C($Q_{413}$)=C($Q_{414}$)-*' (wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group), but are not limited thereto.

$L_{402}$ in Formula 401 may be a monovalent, divalent, or trivalent organic ligand. For example, $L_{402}$ may be selected from halogen, diketone (for example, acetylacetonate), carboxylic acid (for example, picolinate), —C(=O), isonitrile, —CN, and a phosphorus-containing material (for example, phosphine, or phosphite), but embodiments of the present disclosure are not limited thereto.

In one or more embodiments, the phosphorescent dopant may be selected from, for example, Compounds PD1 to PD25, but embodiments of the present disclosure are not limited thereto:

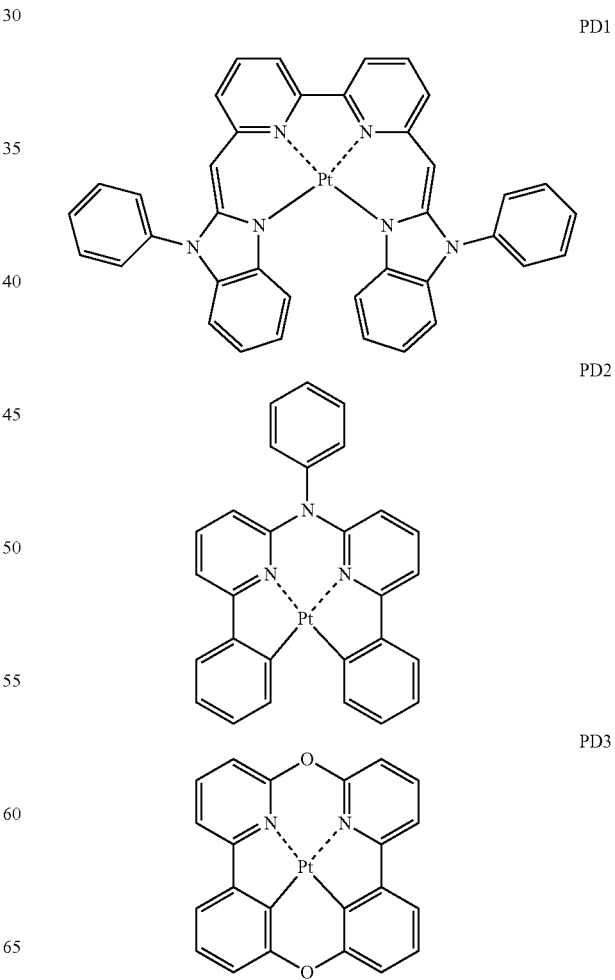

PD1

PD2

PD3

PD4 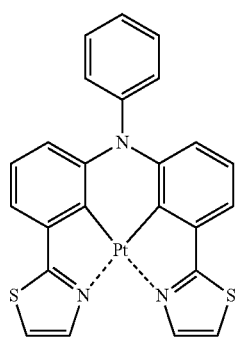
PD5 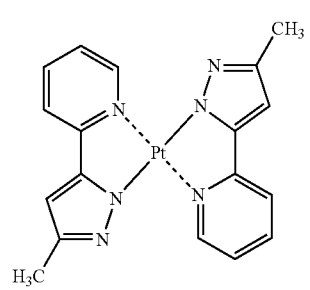
PD6 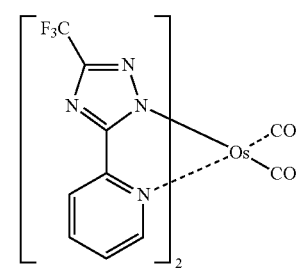
PD7 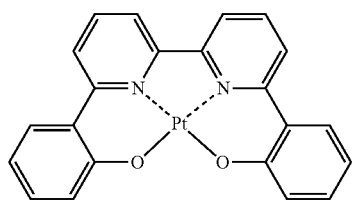
PD8 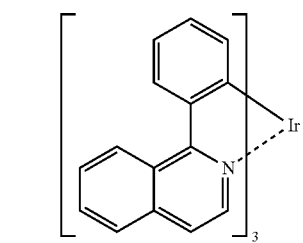
PD9 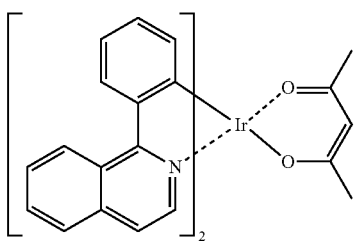
PD10 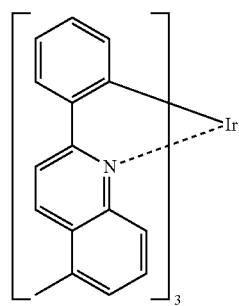
PD11 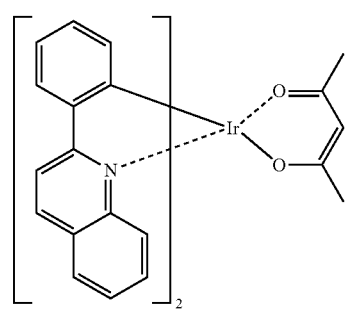
PD12 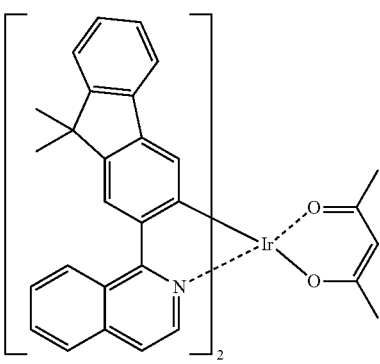
PD13 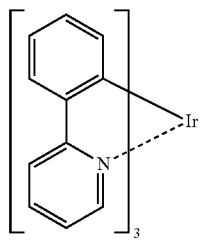
PD14 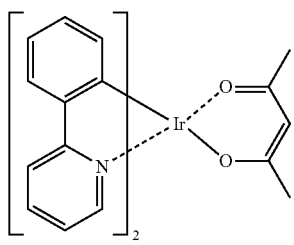

-continued
PD15
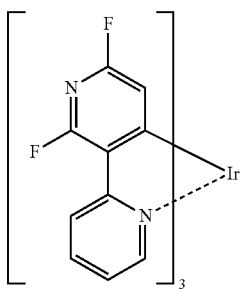
PD16
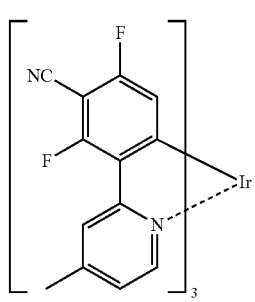
PD17
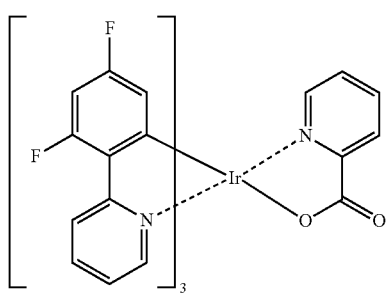
PD18
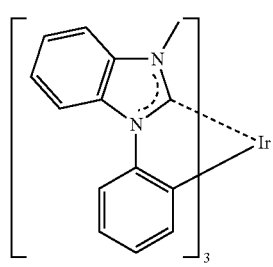
PD19
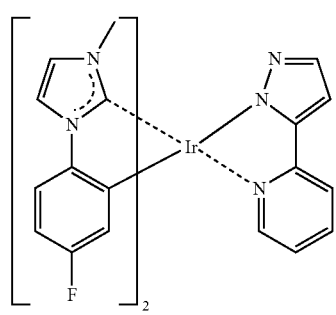
-continued
PD20
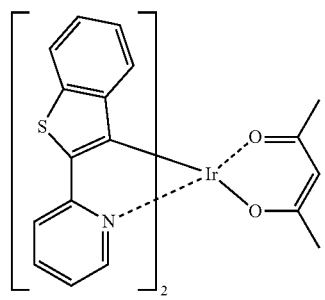
PD21
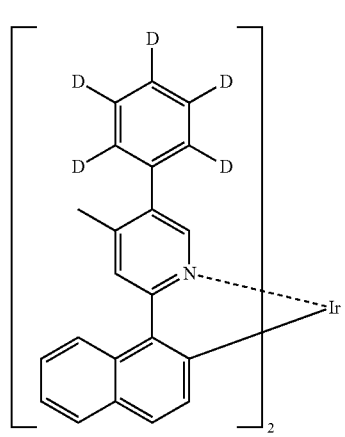
PD22
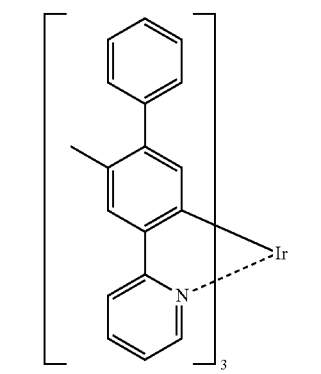
PD23
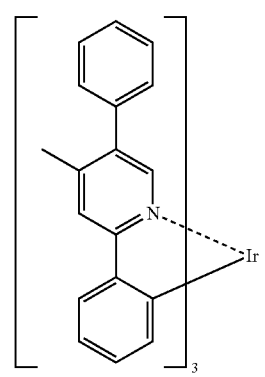

-continued

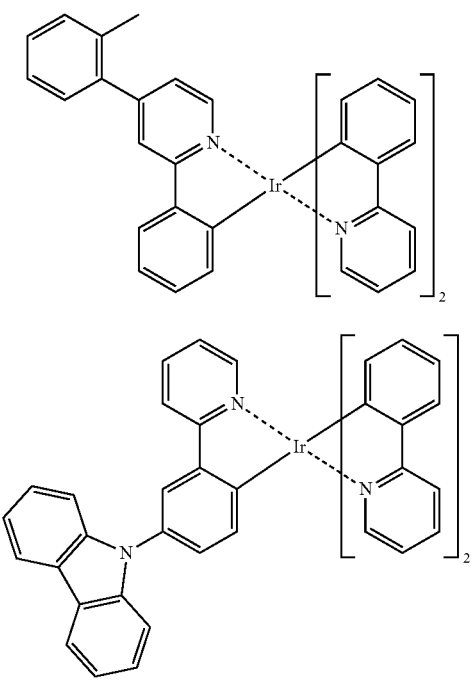

PD24

PD25

[Fluorescent Dopant in Emission Layer]

The fluorescent dopant may include an arylamine compound or a styrylamine compound.

The fluorescent dopant may include a compound represented by Formula 501 below.

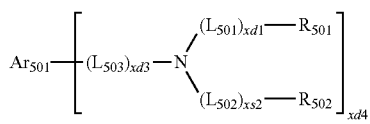

<Formula 501>

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer of 0 to 3;

$R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, xd4 may be an integer of 1 to 6.

In one embodiment, $Ar_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, $R_{501}$ and $R_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), and $Q_{31}$ to $Q_{33}$ may each be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2, but embodiments of the present disclosure are not limited thereto.

For example, the fluorescent dopant may be selected from Compounds FD1 to FD22:

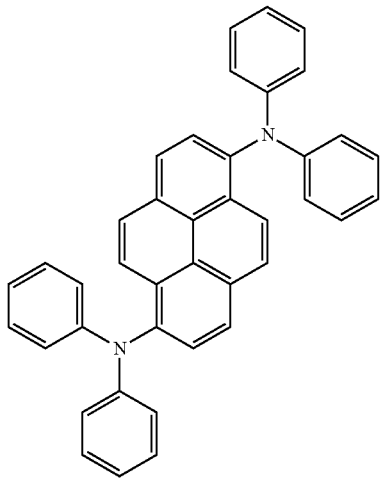

FD1

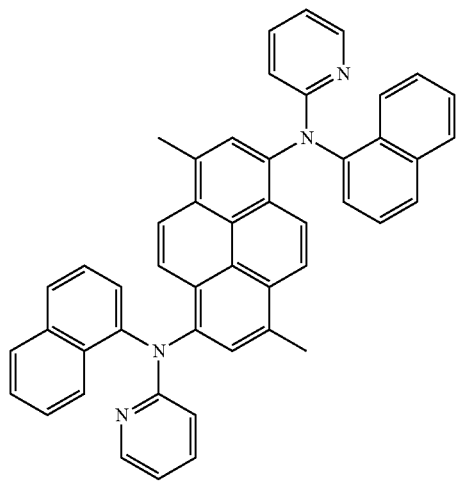

FD2

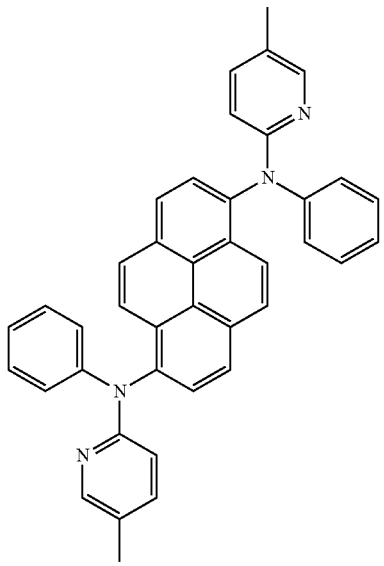

FD3

FD4
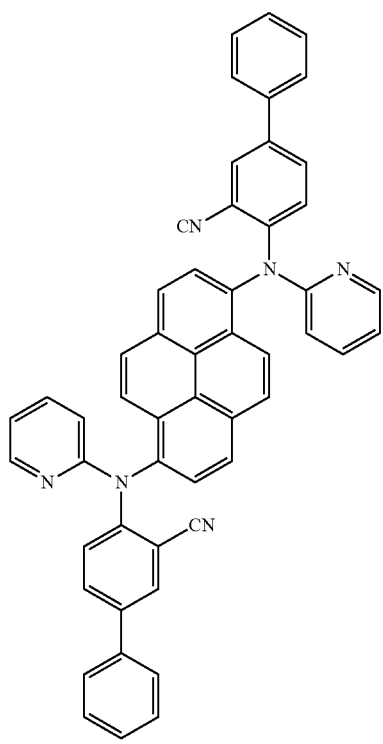
FD5
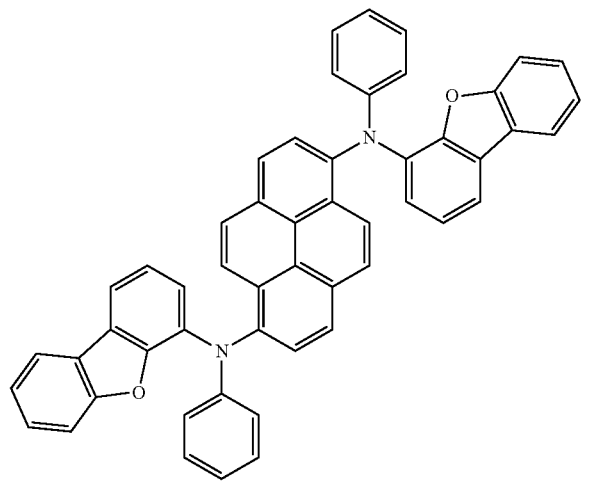
FD6
FD7
FD8
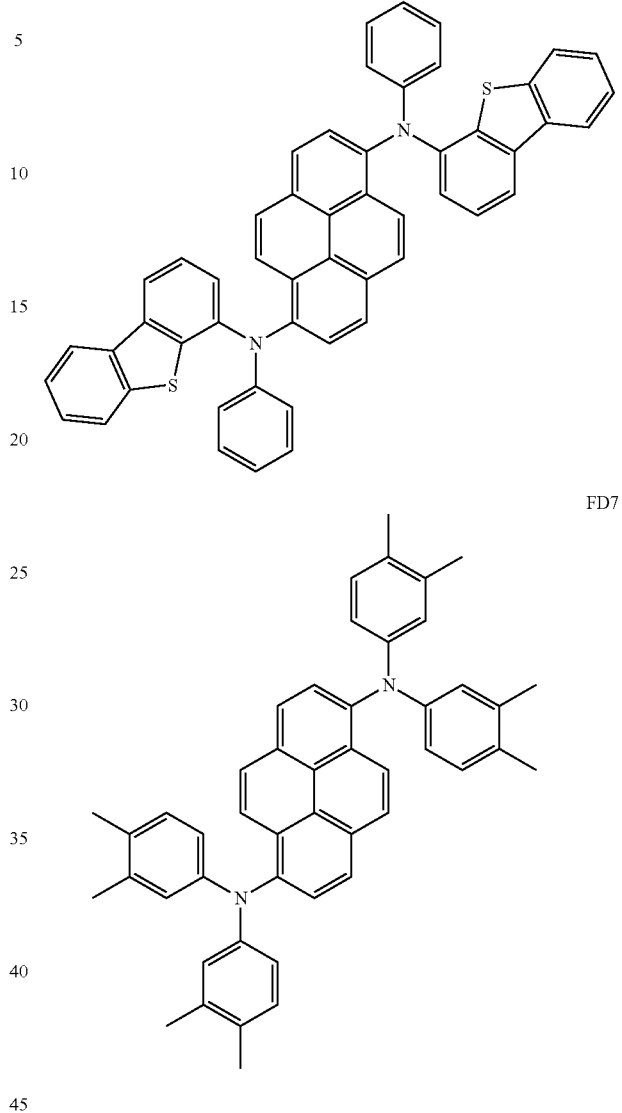

FD9
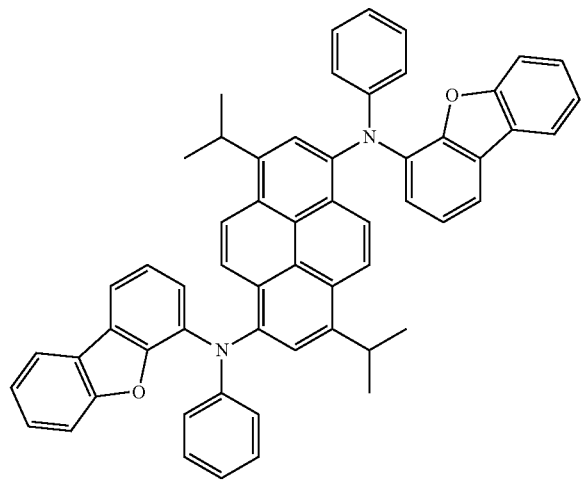
FD10
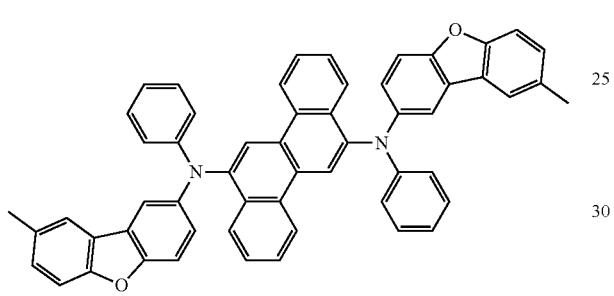
FD11
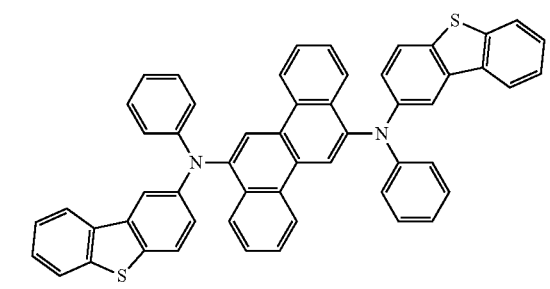
FD12
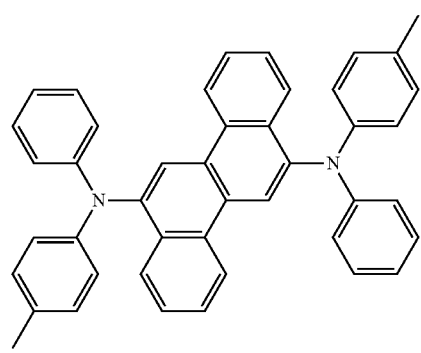
FD13
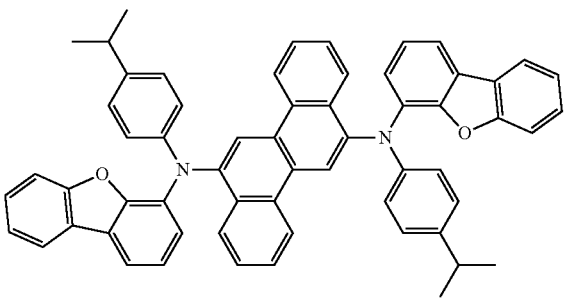
FD14
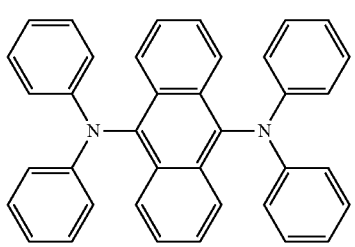
FD15
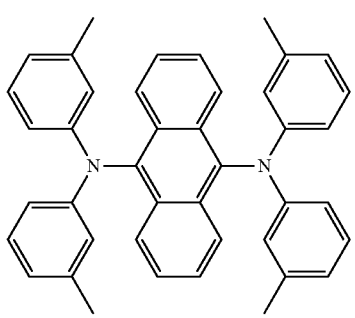
FD16
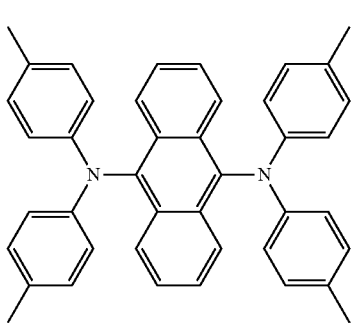
FD17
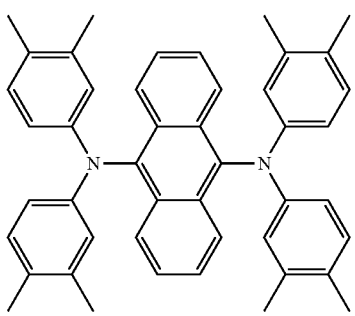

-continued
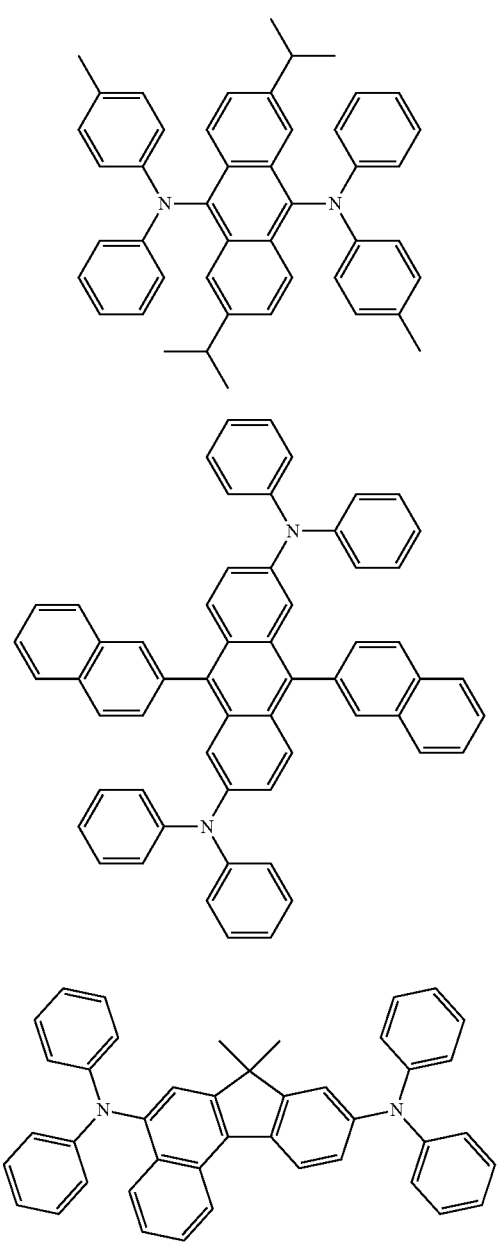
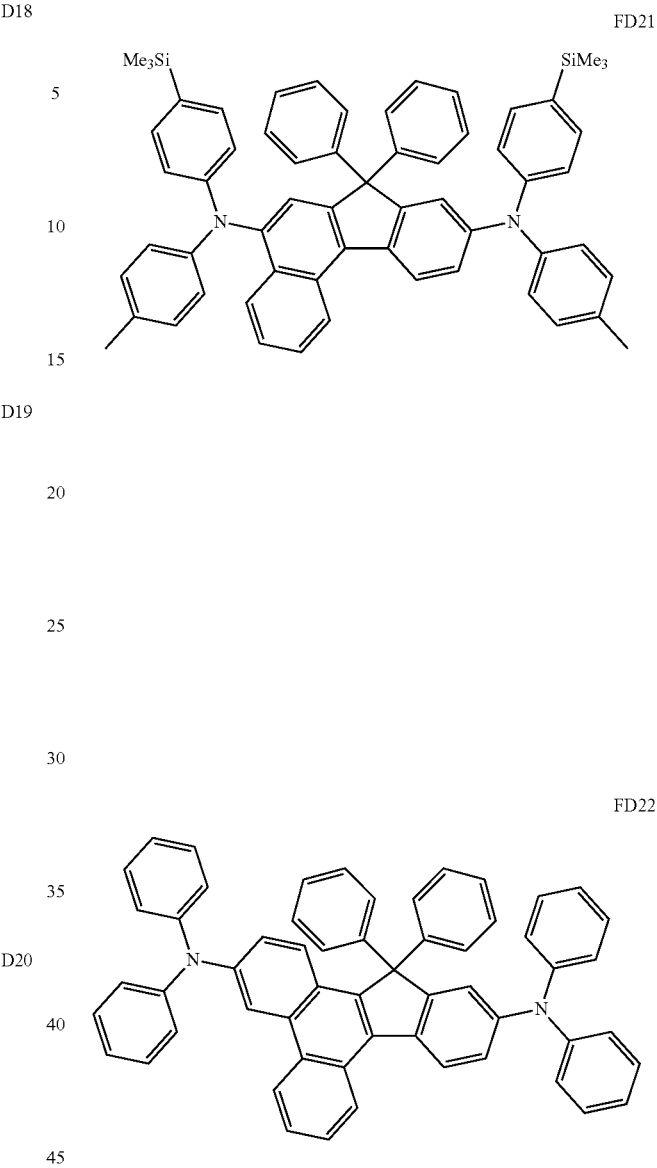
In one or more embodiments, the fluorescent dopant may be selected from the following compounds, but embodiments of the present disclosure are not limited thereto.
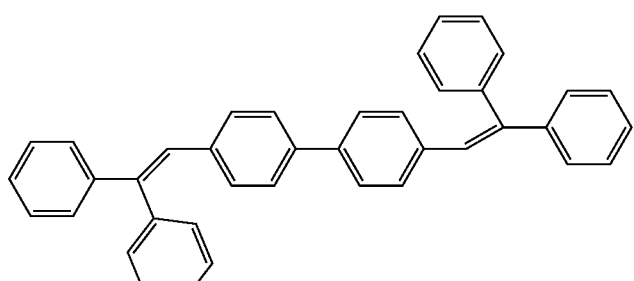

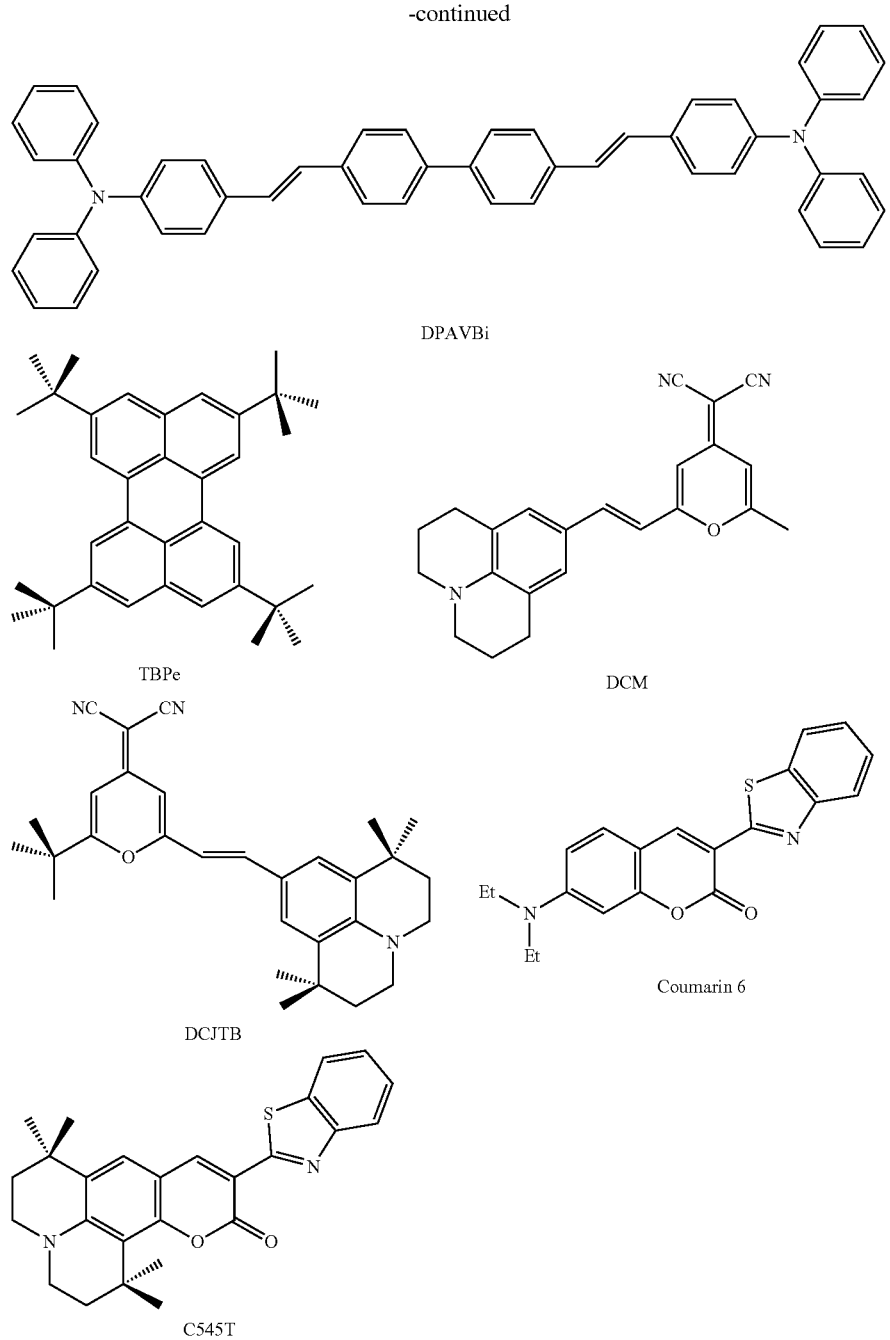

[Electron Transport Region in Organic Layer 150]

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer, but embodiments of the present disclosure are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from an emission layer. However, embodiments of the structure of the electron transport region are not limited thereto.

The electron transport region (for example, a buffer layer, a hole blocking layer, an electron control layer, or an electron transport layer in the electron transport region) may include a metal-free compound containing at least one rr electron-depleted nitrogen-containing ring.

The "π electron-depleted nitrogen-containing ring" indicates a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups each having at least one *—N=*' moiety are condensed with each other, or iii) a heteropolycyclic group in which at least one of 5-membered to 7-membered heteromonocyclic groups, each having at least one *—N=*' moiety, is condensed with at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, thiadiazole, an imidazopyridine, an imidazopyrimidine, and an azacarbazole, but embodiments of the present disclosure are not limited thereto.

For example, the electron transport region may include a compound represented by Formula 601:

$$[Ar_{601}]_{xe11}-[(L_{601})_{xe11}-R_{601}]_{xe21}.$$  <Formula 601>

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_{601})(Q_{602})(Q_{603})$, —C(=O)$(Q_{601})$, —S(=O)$_2(Q_{601})$, and —P(=O)$(Q_{601})(Q_{602})$, $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In one embodiment, at least one of $Ar_{601}$(s) in the number of xe11 and/or at least one of $R_{601}$(s) in the number of xe21 may include the π electron-depleted nitrogen-containing ring.

In one embodiment, ring $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si$(Q_{31})(Q_{32})(Q_{33})$, —S(=O)$_2(Q_{31})$, and —P(=O)$(Q_{31})(Q_{32})$, and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or more, two or more $Ar_{601}$(s) may be linked via a single bond.

In one or more embodiments, $Ar_{601}$ in Formula 601 may be an anthracene group.

In one or more embodiments, a compound represented by Formula 601 may be represented by Formula 601-1:

<Formula 601-1>

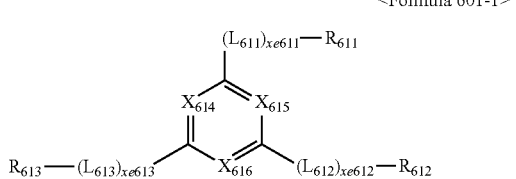

In Formula 601-1, $X_{614}$ may be N or $C(R_{614})$, $X_{615}$ may be N or $C(R_{615})$, $X_{616}$ may be N or $C(R_{616})$, and at least one selected from $X_{614}$ to $X_{616}$ may be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but are not limited thereto, but embodiments of the present disclosure are not limited thereto.

In one or more embodiments, xe1 and xe611 to xe613 in Formulae 601 and 601-1 may each independently be 0, 1, or 2.

In one or more embodiments, $R_{601}$ and $R_{611}$ to $R_{613}$ in Formula 601 and 601-1 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and
—S(=O)$_2$(Q$_{601}$) and —P(=O)(Q$_{601}$)(Q$_{602}$), and Q$_{601}$ and Q$_{602}$ may be the same as described above.

The electron transport region may include at least one compound selected from Compounds ET1 to ET36, but embodiments of the present disclosure are not limited thereto:

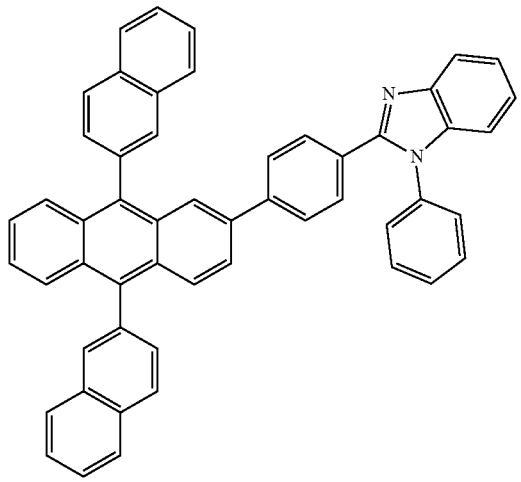

ET1

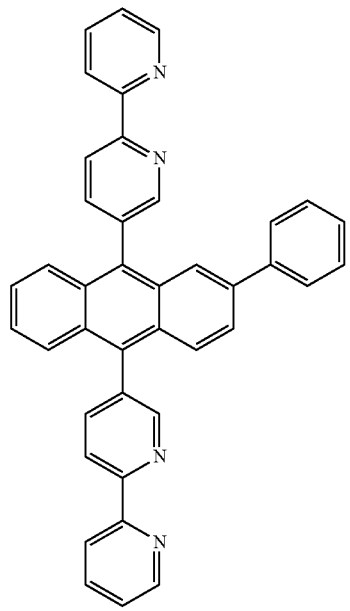

ET2

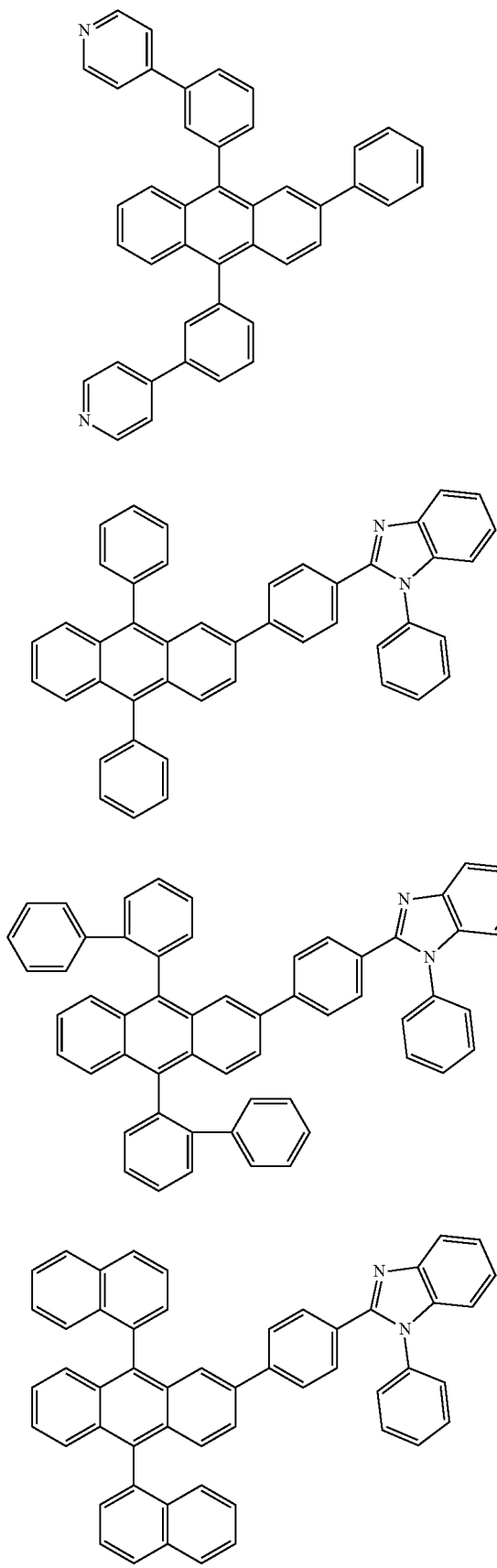

ET10
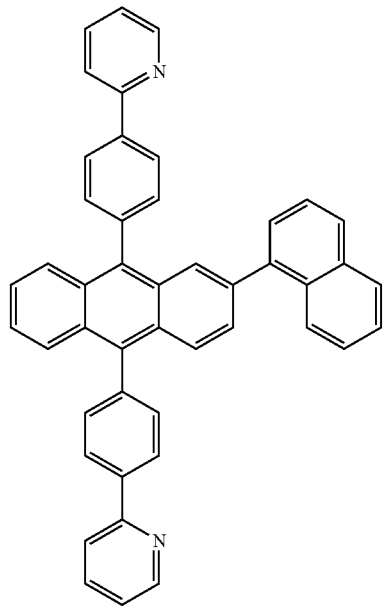
ET11
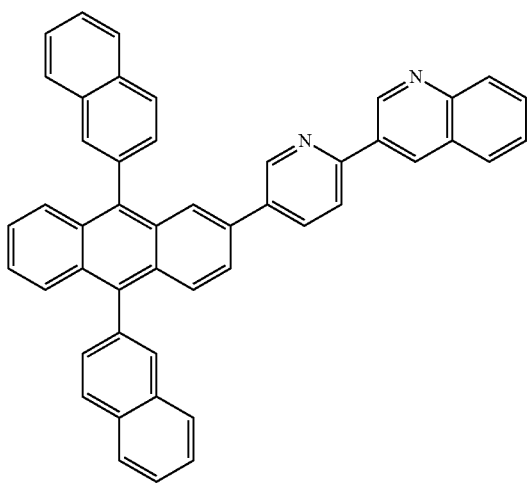
ET12
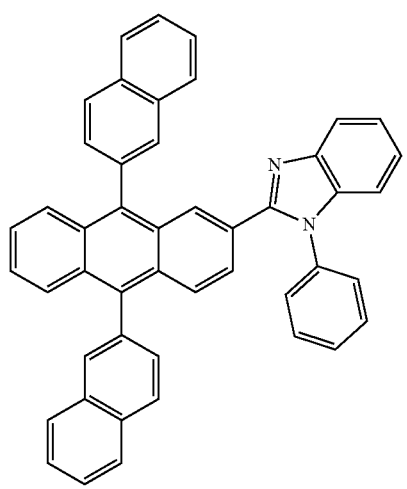
ET13
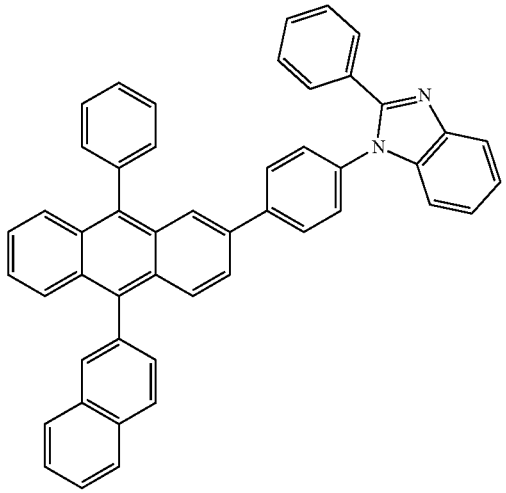
ET14
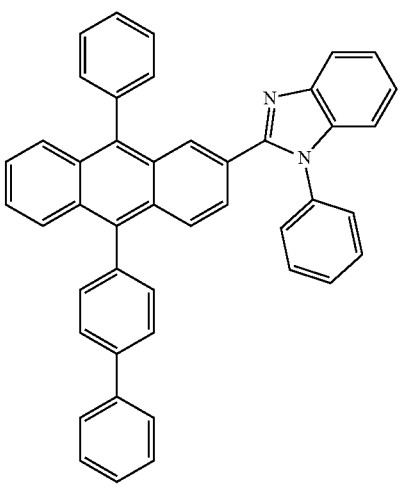
ET15
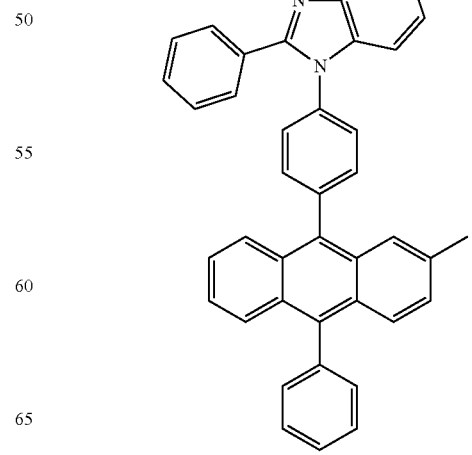

ET16
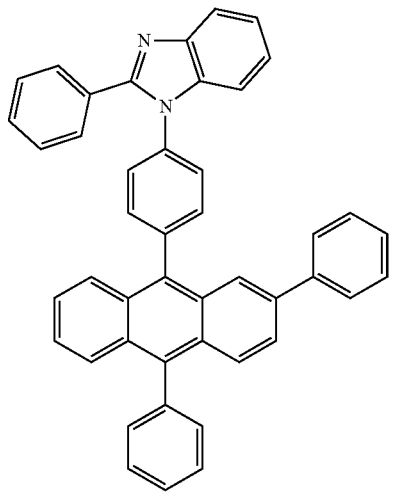
ET17
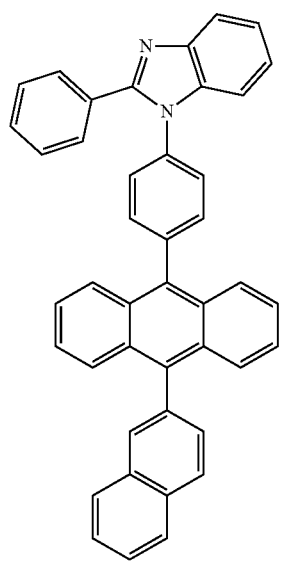
ET18
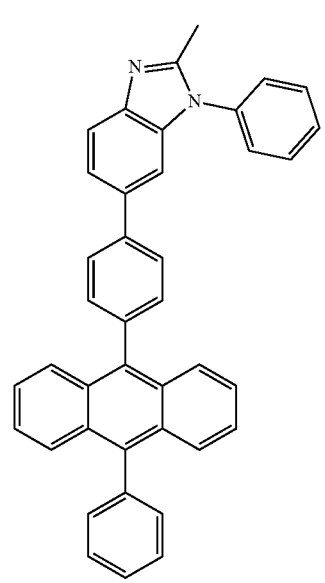
ET19
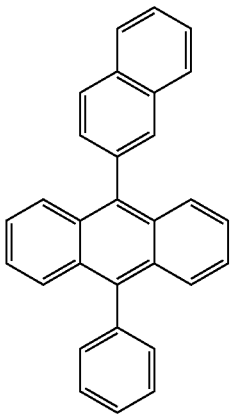
ET20
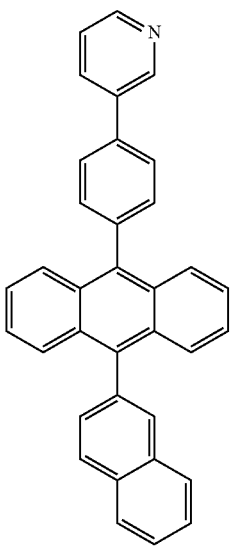
ET21
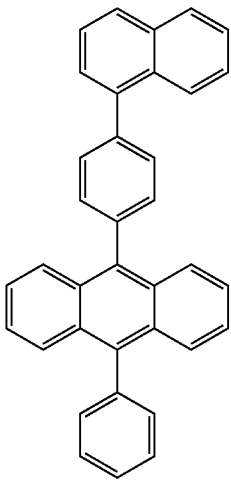

ET22
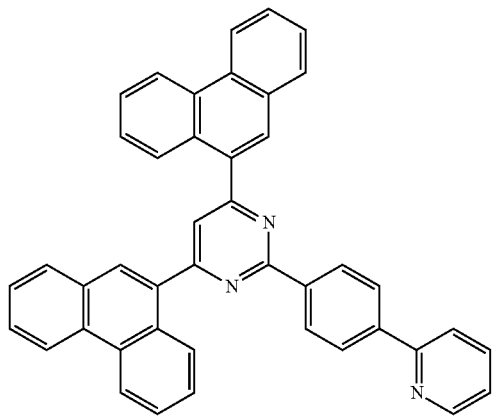
ET23
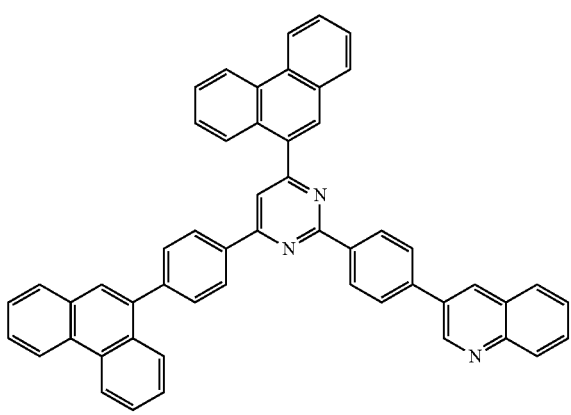
ET24
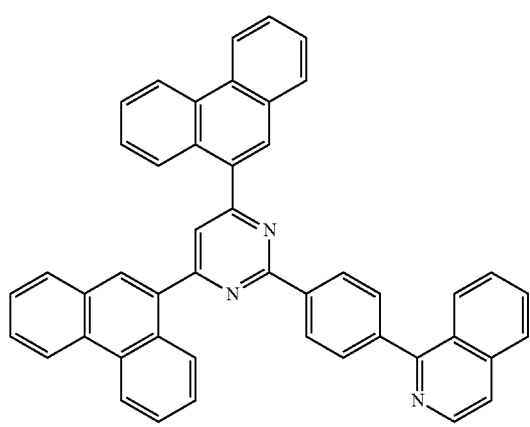
ET25
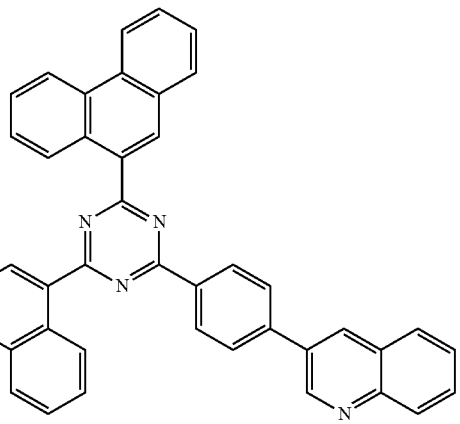
ET26
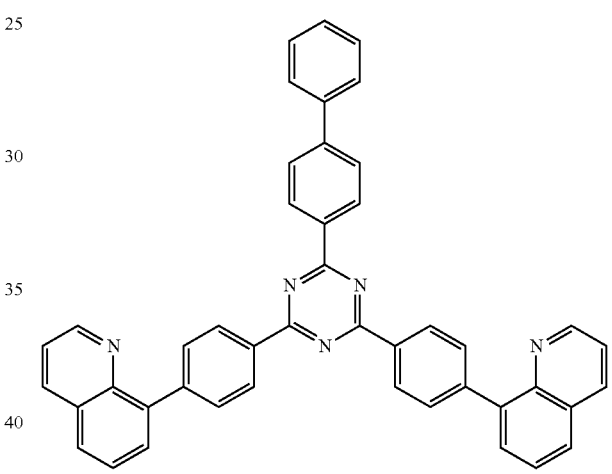
ET27
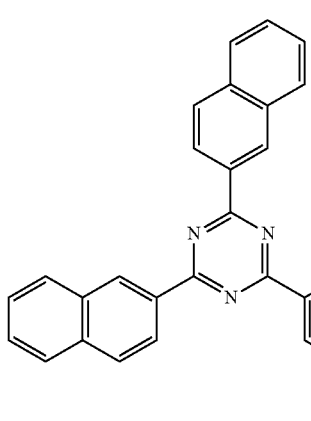

ET28
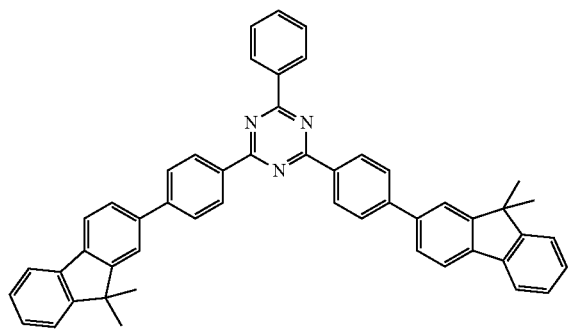
ET29
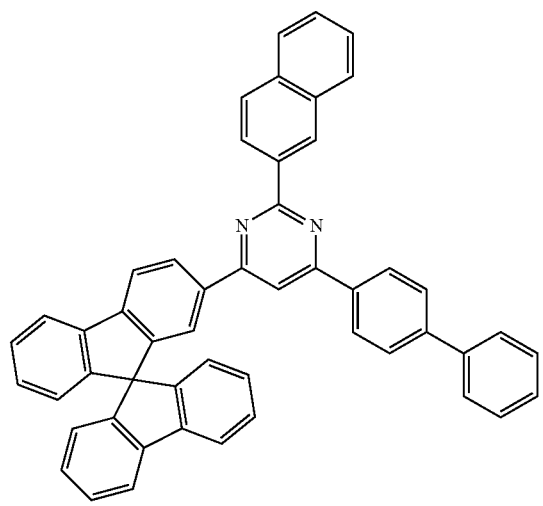
ET30
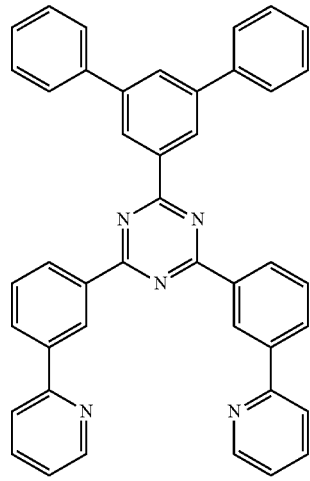
ET31
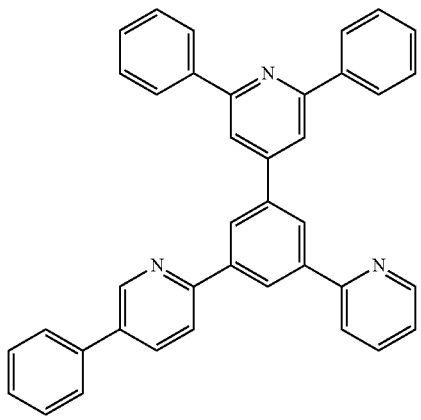
ET32
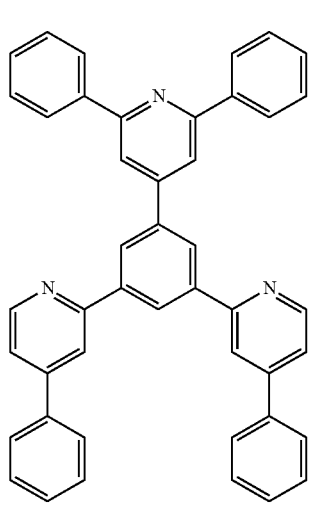
ET33
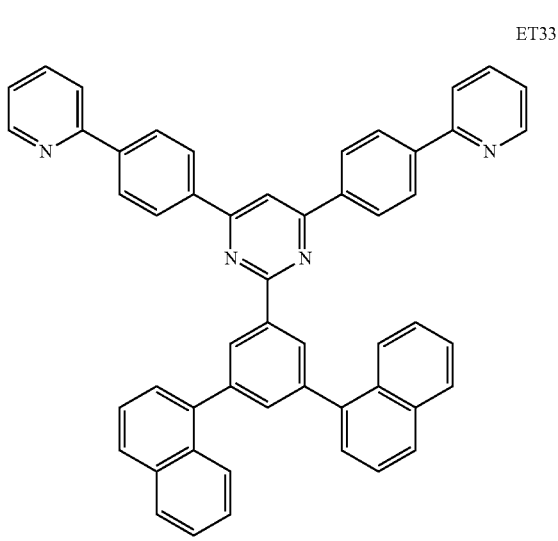

ET34

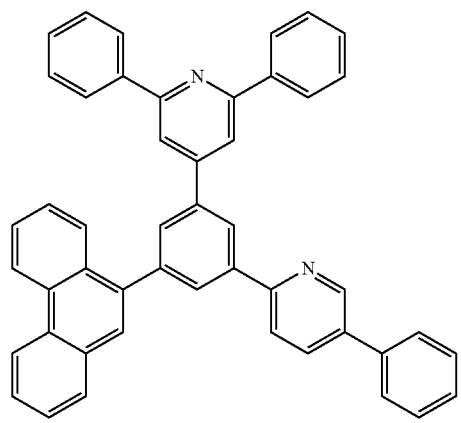

ET35

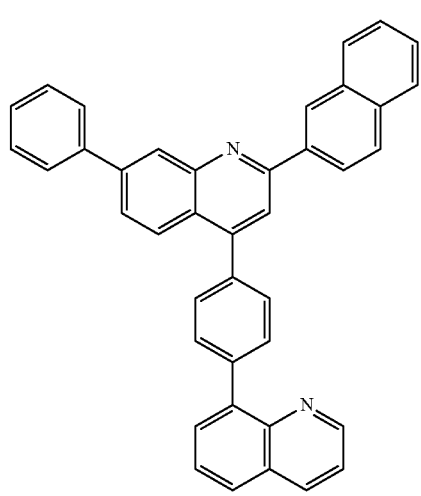

ET36

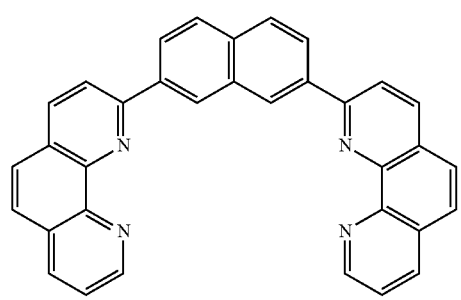

In one or more embodiments, the electron transport region may include at least one selected from 2,9-dimethyl-4,7-diphenyl-1,10-phenanthroline (BCP), 4,7-dphenyl-1,10-phenanthroline (Bphen), Alq₃, BAlq, 3-(biphenyl-4-yl)-5-(4-tert-butylphenyl)-4-phenyl-4H-1,2,4-triazole (TAZ), and NTAZ.

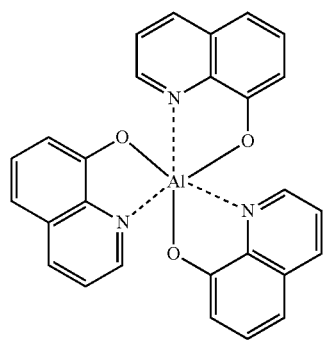

Alq₃

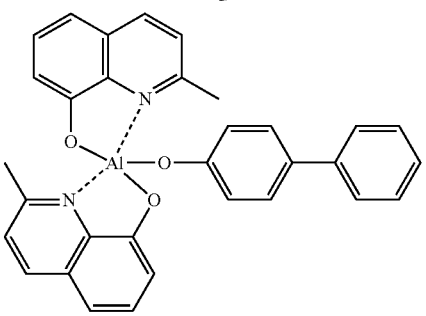

BAlq

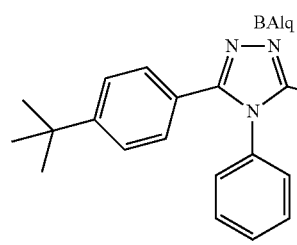

TAZ

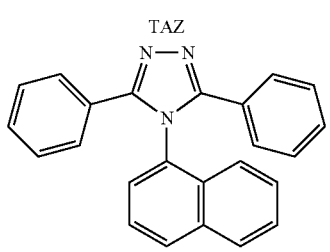

NTAZ

The thickness of the buffer layer, the hole blocking layer, or the electron controlling layer may each independently be in a range of about 20 Å to about 1,000 Å, for example, about 30 Å to about 300 Å. When the thicknesses of the buffer layer, the hole blocking layer, and the electron control layer are within these ranges, the electron blocking layer may have excellent electron blocking characteristics or electron control characteristics without a substantial increase in driving voltage.

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

The electron transport region (for example, the electron transport layer in the electron transport region) may further include, in addition to the materials described above, a metal-containing material.

The metal-containing material may include at least one selected from alkali metal complex and alkaline earth-metal complex. The alkali metal complex may include a metal ion selected from a Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy phenyloxadiazole, a hydroxy diphenylthiadiazol, a hydroxy phenylpyridine, a hydroxy phenylbenzimidazole, a hydroxy phenylbenzothiazole, a bipyridine, a phenanthroline, and a cyclopentadiene, but embodiments of the present disclosure are not limited thereto.

For example, the metal-containing material may include a Li complex. The Li complex may include, for example, Compound ET-D1 (lithium quinolate, LiQ) or ET-D2.

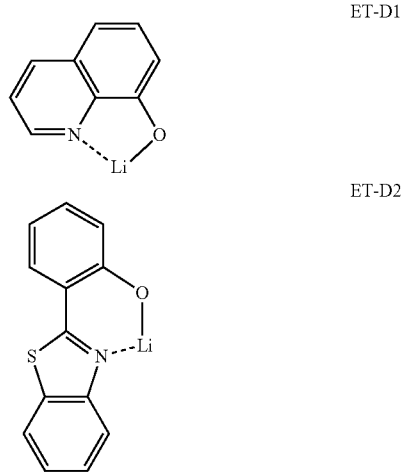

ET-D1

ET-D2

The electron transport region may include an electron injection layer that facilitates injection of electrons from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof.

The alkali metal may be selected from Li, Na, K, Rb, and Cs. In one embodiment, the alkali metal may be Li, Na, or Cs. In one or more embodiments, the alkali metal may be Li or Cs, but embodiments of the present disclosure are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth-metal compound, and the rare earth metal compound may be selected from oxides and halides (for example, fluorides, chlorides, bromides, or iodides) of the alkali metal, the alkaline earth-metal, and the rare earth metal.

The alkali metal compound may be selected from alkali metal oxides, such as $Li_2O$, $Cs_2O$, or $K_2O$, and alkali metal halides, such as LiF, NaF, CsF, KF, LiI, NaI, CsI, KI, or RbI. In one embodiment, the alkali metal compound may be selected from LiF, $Li_2O$, NaF, LiI, NaI, CsI, and KI, but embodiments of the present disclosure are not limited thereto.

The alkaline earth-metal compound may be selected from alkaline earth-metal oxides, such as BaO, SrO, CaO, $Ba_xSr_{1-x}O$ (0<x<1), or $Ba_xCa_{1-x}O$ (0<x<1). In one embodiment, the alkaline earth-metal compound may be selected from BaO, SrO, and CaO, but embodiments of the present disclosure are not limited thereto.

The rare earth metal compound may be selected from $YbF_3$, $ScF_3$, $ScO_3$, $Y_2O_3$, $Ce_2O_3$, $GdF_3$, and $TbF_3$. In one embodiment, the rare earth metal compound may be selected from $YbF_3$, $ScF_3$, $TbF_3$, $YbI_3$, $ScI_3$, and $TbI_3$, but embodiments of the present disclosure are not limited thereto.

The alkali metal complex, the alkaline earth metal complex, and the rare earth metal complex may include an ion of alkali metal, alkaline earth-metal, and rare earth metal as described above, and a ligand coordinated with a metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenyloxazole, hydroxy phenylthiazole, hydroxy diphenyloxadiazole, hydroxy diphenylthiadiazol, hydroxy phenylpyridine, hydroxy phenylbenzimidazole, hydroxy phenylbenzothiazole, bipyridine, phenanthroline, and cyclopentadiene, but embodiments of the present disclosure are not limited thereto.

The electron injection layer may consist of an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof, as described above. In one or more embodiments, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

[Second Electrode 190]

The second electrode 190 may be disposed on the organic layer 150 having such a structure. The second electrode 190 may be a cathode that is an electron injection electrode, and in this regard, a material for forming the second electrode 190 may be a material having a low work function, and such a material may be metal, alloy, an electrically conductive compound, or a combination thereof.

The second electrode 190 may include at least one selected from lithium (Li), silver (Si), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode 190 may be a transmissive electrode, a semi-transmissive electrode, or a reflective electrode.

The second electrode 190 may have a single-layered structure, or a multi-layered structure including two or more layers.

Figure 3:
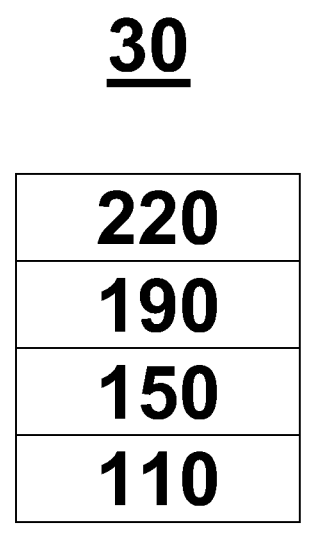
Figure 4:
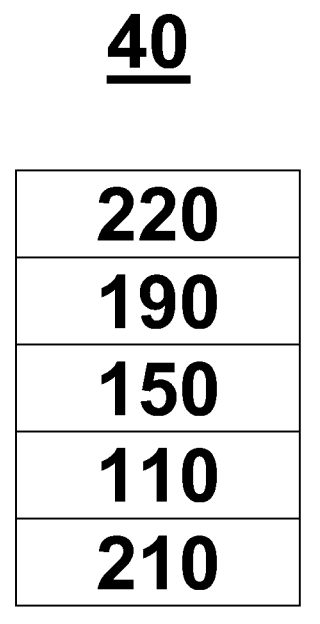

[Description of FIGS. 2 to 4]

Figure 2:
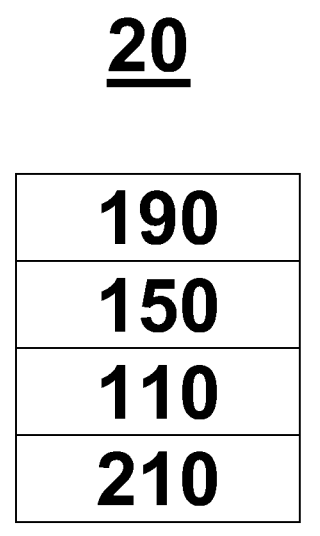

An organic light-emitting device 20 of FIG. 2 includes a first capping layer 210, a first electrode 110, an organic layer 150, and a second electrode 190 which are sequentially stacked in this stated order. An organic light-emitting device 30 of FIG. 3 includes a first electrode 110, an organic layer 150, a second electrode 190, and a second capping layer 220 which are sequentially stacked in this stated order. An organic light-emitting device 40 of FIG. 4 includes a first capping layer 210, a first electrode 110, an organic layer 150, a second electrode 190, and a second capping layer 220.

Regarding FIGS. 2 to 4, the first electrode 110, the organic layer 150, and the second electrode 190 may be understood by referring to the description presented in connection with FIG. 1.

In the organic layer 150 of each of the organic light-emitting devices 20 and 40, light generated in an emission layer may pass through the first electrode 110, which is a semi-transmissive electrode or a transmissive electrode, and the first capping layer 210 toward the outside. In the organic layer 150 of each of the organic light-emitting devices 30 and 40, light generated in an emission layer may pass through the second electrode 190, which is a semi-transmissive electrode or a transmissive electrode, and the second capping layer 220 toward the outside.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may each independently include at least one material selected from carbocyclic compounds, heterocyclic compounds, amine-based compounds, porphyrine derivatives, phthalocyanine derivatives, a naphthalocyanine derivatives, alkali metal complexes, and alkaline earth-based complexes. The carbocyclic compound, the heterocyclic compound, and the amine-based compound may be optionally substituted with a substituent containing at least one element selected from O, N, S, Se, Si, F, Cl, Br, and I. In one embodiment, at least one selected from the first capping layer 210 and the second capping layer 220 may each independently include an amine-based compound.

In one embodiment, at least one selected from the first capping layer 210 and the second capping layer 220 may each independently include the compound represented by Formula 201 or the compound represented by Formula 202.

In one or more embodiments, at least one selected from the first capping layer 210 and the second capping layer 220 may each independently include a compound selected from Compounds HT28 to HT33 and Compounds CP1 to CP5, but embodiments of the present disclosure are not limited thereto.

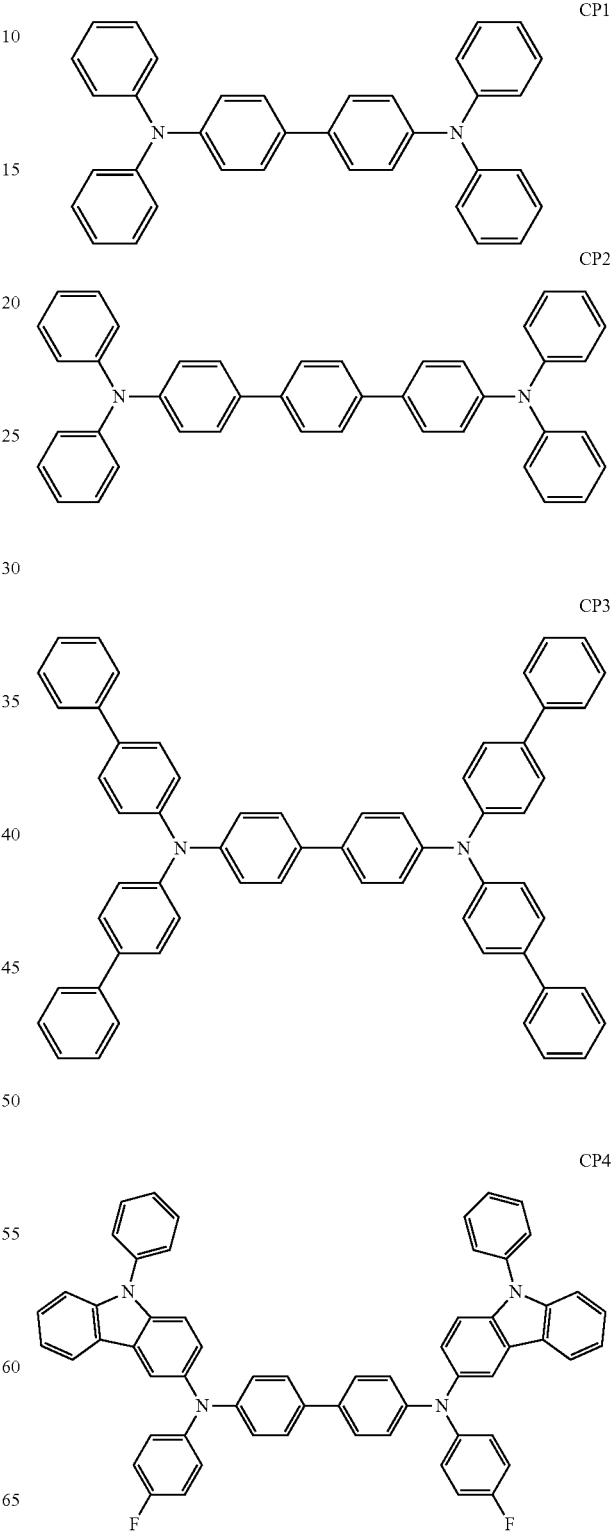

CP5

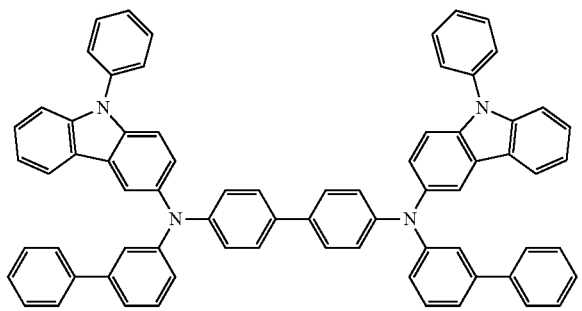

Hereinbefore, the organic light-emitting device according to an embodiment has been described in connection with FIGS. 1 to 4. However, embodiments of the present disclosure are not limited thereto.

Layers constituting the hole transport region, an emission layer, and layers constituting the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec by taking into account a material to be included in a layer to be formed, and the structure of a layer to be formed.

When layers constituting the hole transport region, an emission layer, and layers constituting the electron transport region are formed by spin coating, the spin coating may be performed at a coating speed of about 2,000 rpm to about 5,000 rpm and at a heat treatment temperature of about 80° C. to 200° C., depending on a material to be included in a layer and the structure of each layer to be formed.

[General Definition of Substituents]

The term "$C_1$-$C_{60}$ alkyl group" as used herein refers to a linear or branched saturated aliphatic hydrocarbon monovalent group having 1 to 60 carbon atoms, and non-limiting examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group" as used herein refers to a divalent group having the same structure as the $C_1$-$C_{60}$ alkyl group.

The term "$C_2$-$C_{60}$ alkenyl group" as used herein refers to a hydrocarbon group formed by substituting at least one carbon-carbon double bond in the middle or at the terminus of the $C_2$-$C_{60}$ alkyl group, and non-limiting examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group formed by substituting at least one carbon-carbon triple bond in the middle or at the terminus of the $C_2$-$C_{60}$ alkyl group, and non-limiting examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and non-limiting examples thereof include a methoxy group, an ethoxy group, and an isopropyloxy group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_1$ heterocycloalkyl group" as used herein refers to a monovalent saturated monocyclic group having at least one heteroatom selected from N, O, Si, P, and S as a ring-forming atom and 1 to 10 carbon atoms, and non-limiting examples thereof include a 1,2,3,4-oxatriazolidinyl group, a tetrahydrofuranyl group, a tetrahydrothiophenyl group. The term "$C_1$-$C_1$ heterocycloalkylene group" as used herein refers to a divalent group having the same structure as the $C_1$-$C_1$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, Si, P, and S as a ring-forming atom, 1 to 10 carbon atoms, and at least one carbon-carbon double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_1$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a heterocyclic aromatic system that has at least one heteroatom selected from N, O, Si, P, and S as a ring-forming atom, in addition to 1 to 60 carbon atoms. The term "$C_1$-$C_{60}$ heteroarylene group" as used herein refers to a divalent group having a heterocyclic aromatic system that has at least one heteroatom selected from N, O, Si, P, and S as a ring-forming atom, in addition to 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" as used herein refers to —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

The term "monovalent non-aromatic condensed polycyclic group" as used herein refers to a monovalent group (for example, having 8 to 60 carbon atoms) having two or more rings condensed with each other, only carbon atoms as ring-forming atoms, and no aromaticity in its entire molecular structure. A detailed example of the monovalent non-aromatic condensed polycyclic group is a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 1 to 60 carbon atoms) having two or more rings condensed to each other, at least one heteroatom selected from N, O, Si, P, and S, other than carbon atoms, as a ring-forming atom, and no aromaticity in its entire molecular structure. An example of the monovalent non-aromatic condensed heteropolycyclic group is a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{60}$ carbocyclic group" as used herein refers to a monocyclic or polycyclic group having 5 to 60 carbon atoms in which a ring-forming atom is a carbon atom only. The $C_5$-$C_{60}$ carbocyclic group may be an aromatic carbocyclic group or a non-aromatic carbocyclic group. The $C_5$-$C_{60}$ carbocyclic group may be a ring, such as benzene, a monovalent group, such as a phenyl group, or a divalent group, such as a phenylene group. In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having the same structure as the $C_1$-$C_{60}$ carbocyclic group, except that as a ring-forming atom, at least one heteroatom selected from N, O, Si, P, and S is used in addition to carbon (the number of carbon atoms may be in a range of 1 to 60).

At least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph", as used herein, may refer to a phenyl group; the term "Me", as used herein, may refer to a methyl group; the term "Et", as used herein, may refer to an ethyl group; the terms "ter-Bu" or "But", as used herein, may refer to a tert-butyl group; and the term "OMe" as used herein may refer to a methoxy group.

The term "biphenyl group" as used herein refers to "a phenyl group substituted with a phenyl group." In other words, the "biphenyl group" is a substituted phenyl group having a $C_6$-$C_{60}$ aryl group as a substituent.

The term "terphenyl group" as used herein refers to "a phenyl group substituted with a biphenyl group." In other words, the "terphenyl group" is a phenyl group having, as a substituent, a $C_6$-$C_{60}$ aryl group substituted with a $C_6$-$C_{60}$ aryl group.

* and *' used herein, unless defined otherwise, each refer to a binding site to a neighboring atom in a corresponding formula.

Hereinafter, a compound according to embodiments and an organic light-emitting device according to embodiments will be described in detail with reference to Synthesis Examples and Examples. The wording "B was used instead of A" used in describing Synthesis Examples and Examples refers to that an identical molar equivalent of B was used in place of A.

EXAMPLES

Synthesis Example 1: Synthesis of Compound A5

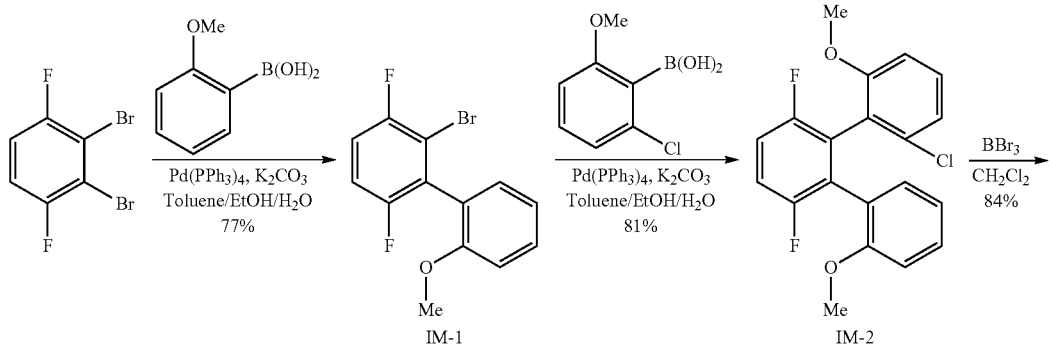

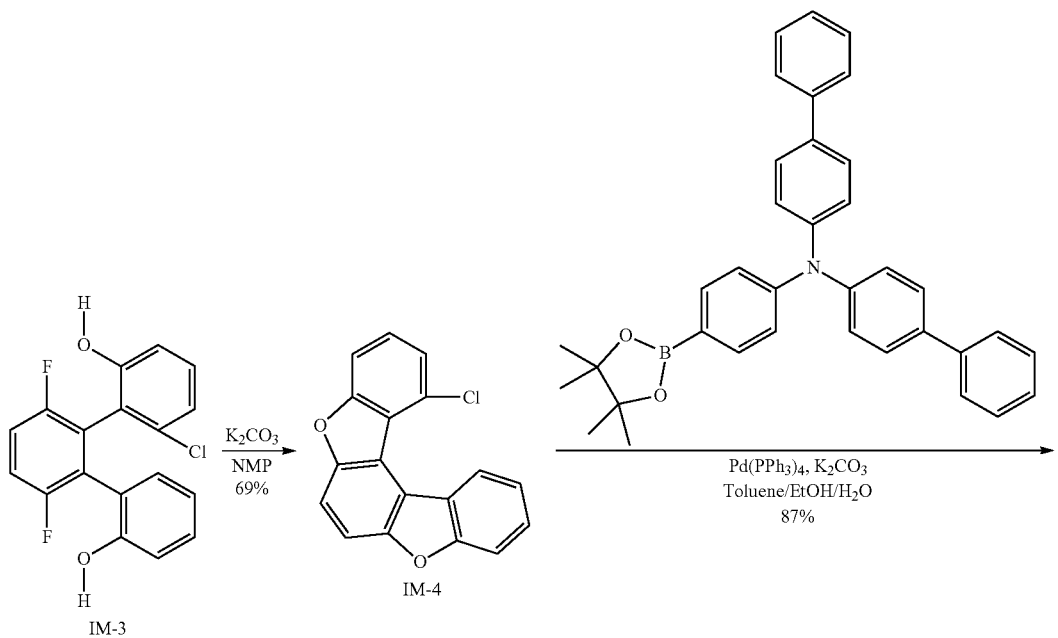

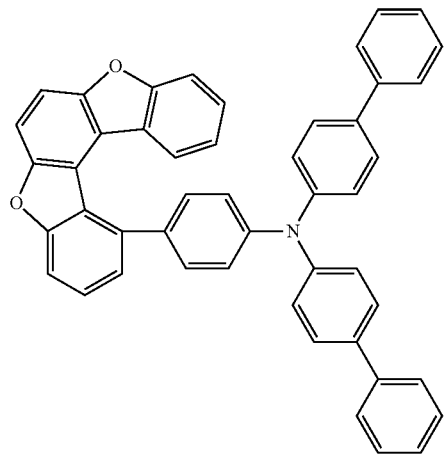

A6

(Synthesis of Intermediate IM-1)

In an Ar atmosphere, 20.00 g (73.56 mmol) of 2,3-dibromo-1,4-difluorobenzene, 12.30 g (1.1 equiv, 80.9 mmol) of 2-methoxyphenylboronic acid, 80.92 g (3 equiv, 220.7 mmol) of $K_2CO_3$, 4.25 g (0.05 equiv, 3.7 mmol) of $Pd(PPh_3)_4$, and 515 mL of a mixed solution of toluene/EtOH/$H_2O$ (4/2/1) were sequentially added to a 1,000-mL three-neck flask, and heated and stirred at a temperature of 80° C. for 5 hours. After cooling to room temperature, the reaction solution was extracted therefrom by using toluene. A water layer was removed therefrom, and an organic layer was cleaned by using saturated saline and dried by using $MgSO_4$. $MgSO_4$ was filtered and separated and the organic layer was concentrated. A crude product obtained therefrom was purified by silica gel column chromatography (mixed solvent of hexane and toluene was used in a development layer) to obtain Intermediate IM-1 (16.94 g, yield of 77%).

Intermediate IM-1 was identified by observing the mass number m/z=299 as the molecular ion peak through FAB-MS.

(Synthesis of Intermediate IM-2)

In an Ar atmosphere, 15.00 g (50.1 mmol) of Intermediate IM-1, 10.28 g (1.1 equiv, 55.2 mmol) of 2-chloro-6-methoxyphenylboronic acid, 20.79 g (3 equiv, 150.4 mmol) of $K_2CO_3$, 2.90 g (0.05 equiv, 2.5 mmol) of $Pd(PPh_3)_4$, and 350 mL of a mixed solution of toluene/EtOH/$H_2O$ (4/2/1) were sequentially added to a 500-mL three-neck flask, and heated and stirred at a temperature of 80° C. for 5 hours. After cooling to room temperature, the reaction solution was extracted therefrom by using toluene. A water layer was removed therefrom, and an organic layer was cleaned by using saturated saline and dried by using $MgSO_4$. $MgSO_4$ was filtered and separated and the organic layer was concentrated. A crude product obtained therefrom was purified by silica gel column chromatography (mixed solvent of hexane and toluene was used in a development layer) to obtain Intermediate IM-2 (14.66 g, yield of 81%).

Intermediate IM-2 was identified by observing the mass number m/z=360 as the molecular ion peak through FAB-MS.

(Synthesis of Intermediate IM-3)

In an Ar atmosphere, 13.00 g (36.0 mmol) of Intermediate IM-2, 120 mL of $CH_2Cl_2$, and 216 mL (6 equiv, 216.2 mmol) of $CH_2Cl_2$ solution of 1 M $BBr_3$ were sequentially added to a 500-mL three-neck flask, and heated and stirred at room temperature for 24 hours. The reaction solution was neutralized by using saturated $NaHCO_3$ aqueous solution, and an organic layer was extracted therefrom by using $CH_2Cl_2$ and cleaned by using saturated saline. A crude product obtained therefrom was purified by silica gel column chromatography (mixed solvent of hexane and toluene was used in a development layer) to obtain Intermediate IM-3 (10.07 g, yield of 84%).

Intermediate IM-3 was identified by observing the mass number m/z=332 as the molecular ion peak through FAB-MS.

(Synthesis of Intermediate IM-4)

In an Ar atmosphere, 10.00 g (30.0 mmol) of Intermediate IM-3, 150 mL of NMP, and 16.62 g (4 equiv, 120.2 mmol) of $K_2CO_3$ were sequentially added to a 300-mL three-neck flask, and heated and stirred at a temperature of 180° C. for 5 hours. After the reaction solution was cooled to room temperature, $H_2O$ was added to the reaction solution and an organic layer was extracted therefrom by using toluene. The organic layer was cleaned by using saturated saline and dried by using $MgSO_4$. $MgSO_4$ was filtered and separated and the organic layer was concentrated. A crude product obtained therefrom was purified by silica gel column chromatography (mixed solvent of hexane and toluene was used in a development layer) to obtain Intermediate IM-4 (6.07 g, yield of 69%).

Intermediate IM-4 was identified by observing the mass number m/z=292 as the molecular ion peak through FAB-MS.

(Synthesis of Compound A5)

In an Ar atmosphere, 5.00 g (17.08 mmol) of Intermediate IM-4, 9.84 g (1.1 equiv, 18.8 mmol) of N, N-Di(4-biphenylyl)-4-(4,4,5,5-tetramethyl-1,3,2-dioxaborolan-2-yl)aniline, 7.08 g (3 equiv, 51.2 mmol) of $K_2CO_3$, 0.98 g (0.05 equiv, 0.9 mmol) of $Pd(PPh_3)_4$, and 120 mL of mixed solution of toluene/EtOH/$H_2O$ (4/2/1) were sequentially added to a 500-mL three-neck flask, and heated and stirred at a temperature of 80° C. for 5 hours. The reaction mixture was cooled to room temperature, and the reaction solution was extracted therefrom by using toluene. A water layer was removed therefrom, and an organic layer was cleaned by using saturated saline and dried by using $MgSO_4$. $MgSO_4$ was filtered and separated and the organic layer was concentrated. A crude product obtained therefrom was purified by silica gel column chromatography (mixed solvent of hexane and toluene was used in a development layer) to obtain Compound A5 (9.51 g, yield of 87%) that was a white solid.

Compound A5 was identified by observing the mass number m/z=653 as the molecular ion peak through FAB-MS.

Synthesis Example 2: Synthesis of Compound A21

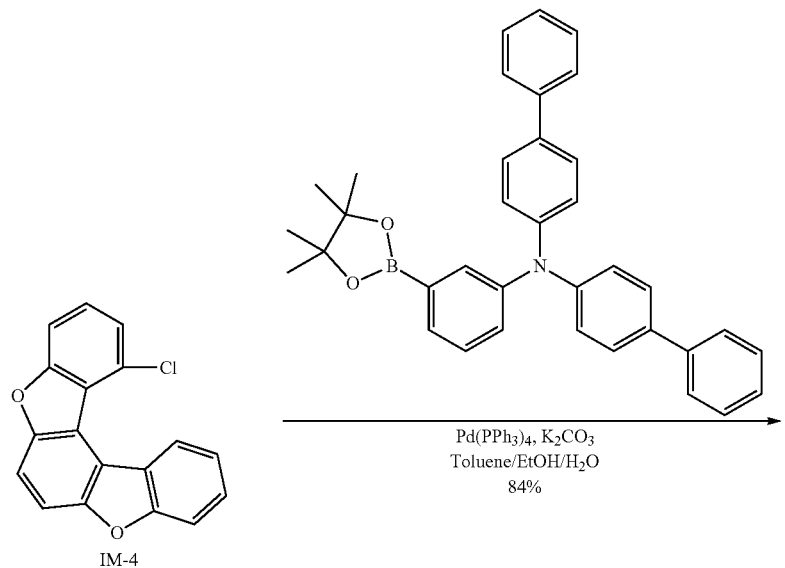

IM-4

500-mL three-neck flask, and heated and stirred at a temperature of 80° C. for 5 hours. After cooling to room temperature, the reaction solution was extracted therefrom by using toluene. A water layer was removed therefrom, and an organic layer was cleaned by using saturated saline and dried by using $MgSO_4$. $MgSO_4$ was filtered and separated and the organic layer was concentrated. A crude product obtained therefrom was purified by silica gel column chromatography (mixed solvent of hexane and toluene was used

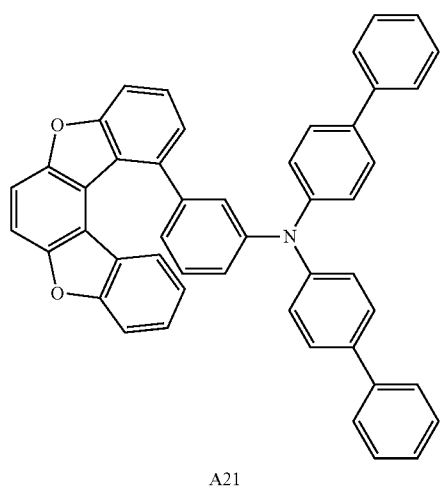

A21

In an Ar atmosphere, 5.00 g (73.56 mmol) of Intermediate IM-4, 9.84 g (1.1 equiv, 18.8 mmol) of N,N-di(4-biphenylyl)-3-(4,4,5,5-tetramethyl-1,3,2-dioxaborolan-2-yl)aniline, 7.08 g (3 equiv, 51.2 mmol) of $K_2CO_3$, 0.98 g (0.05 equiv, 0.9 mmol) of $Pd(PPh_3)_4$, and 120 mL of mixed solution of toluene/EtOH/$H_2O$ (4/2/1) were sequentially added to a in a development layer) to obtain Compound A21 (9.18 g, yield of 84%) that was a white solid.

Compound A21 was identified by observing the mass number m/z=653 as the molecular ion peak through FAB-MS.

Synthesis Example 3: Synthesis of Compound A73

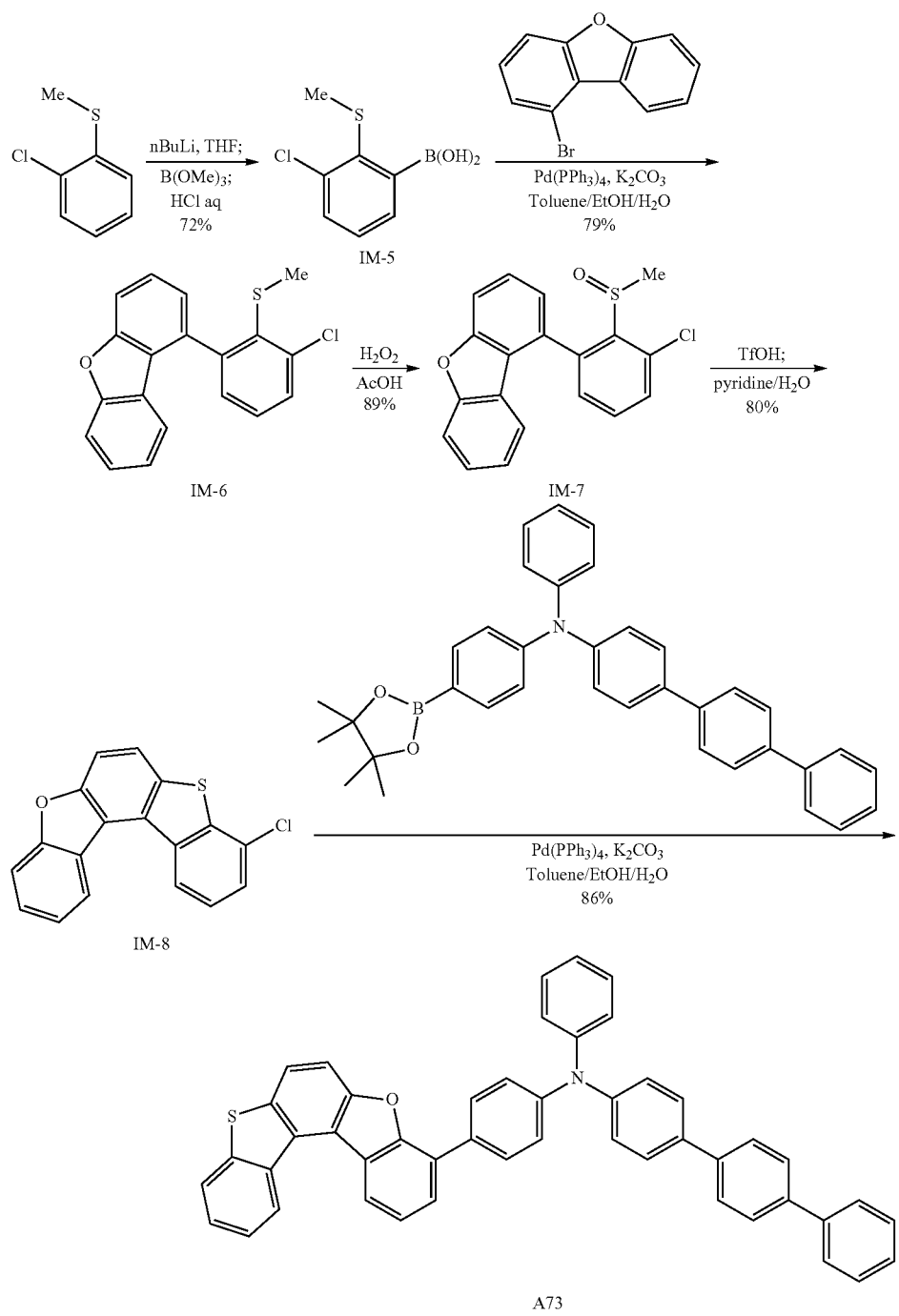

(Synthesis of Intermediate IM-5)

In an Ar atmosphere, 20.00 g (126.07 mmol) of 2-chlorophenyl methyl sulfide and 420 mL (0.3 M) of THF were stirred at a temperature of −78° C. in a 1,000-mL three-neck flask, and 86.7 mL (1.1 equiv) of 1.6 mol/L n-BuLi/n-hexane solution was added dropwise thereto. After the reaction mixture was stirred at the same temperature for 1 hour, 65.50 g (5 equiv, 630.4 mmol) of trimethyl borate was added dropwise thereto and stirred at the same temperature for 2 hours, and the reaction mixture was heated to room temperature and stirred again for 2 hours. 250 mL of 1 N HCl was added thereto, and the reaction solution was extracted therefrom by using toluene. A water layer was removed therefrom, and an organic layer was sequentially cleaned by aqueous solution of sodium hydrogen carbonate and saturated saline and dried by using MgSO₄. MgSO₄ was filtered and separated and the organic layer was concentrated. A crude product obtained therefrom was purified by silica gel column chromatography (mixed solvent of hexane and toluene was used in a development layer) to obtain Intermediate IM-5 (18.38 g, yield of 72%).

Intermediate IM-5 was identified by observing the mass number m/z=202 as the molecular ion peak through FAB-MS.

(Synthesis of Intermediate IM-6)

In an Ar atmosphere, 15.00 g (74.1 mmol) of Intermediate IM-5, 20.14 g (1.1 equiv, 81.5 mmol) of 1-bromo-dibenzofuran, 30.72 g (3 equiv, 222.3 mmol) of $K_2CO_3$, 4.28 g (0.05 equiv, 3.7 mmol) of $Pd(PPh_3)_4$, and 518 mL of mixed solution of toluene/EtOH/$H_2O$ (4/2/1) were sequentially added to a 1,000-mL three-neck flask, and heated and stirred at a temperature of 80° C. for 5 hours. After cooling to room temperature, the reaction solution was extracted therefrom by using toluene. A water layer was removed therefrom, and an organic layer was cleaned by using saturated saline and dried by using $MgSO_4$. $MgSO_4$ was filtered and separated and the organic layer was concentrated. A crude product obtained therefrom was purified by silica gel column chromatography (mixed solvent of hexane and toluene was used in a development layer) to obtain Intermediate IM-6 (19.01 g, yield of 79%).

Intermediate IM-6 was identified by observing the mass number m/z=324 as the molecular ion peak through FAB-MS.

(Synthesis of Intermediate IM-7)

In an Ar atmosphere, 15.00 g (46.2 mmol) of Intermediate IM-6 and 184 mL (0.25 M) of AcOH were added to a 500-mL three-neck flask and stirred at a temperature of 0° C., and 184 mL of AcOH solution containing 35% hydrogen peroxide (4.62 g) was added dropwise thereto. The reaction solution was heated and stirred at the same temperature for 2 hours, and AcOH of the reaction solution was distilled under reduced pressure. A crude product obtained therefrom was purified by silica gel column chromatography (mixed solvent of hexane and toluene was used in a development layer) to obtain Intermediate IM-7 (14.01 g, yield of 89%).

Intermediate IM-7 was identified by observing the mass number m/z=340 as the molecular ion peak through FAB-MS.

(Synthesis of Intermediate IM-8)

In an Ar atmosphere, 10.00 g (29.3 mmol) of Intermediate IM-7 and 44.0 g (10 equiv, 293.4 mmol) of trifluoromethanesulfonic acid were sequentially added to a 300-mL three-neck flask, and stirred at room temperature for 24 hours. The reaction solution was slowly added to 98 mL of mixed solution of $H_2O$/pyridine (8:1) and heated and stirred for 1 hour under reflux. After cooling to room temperature, the reaction solution was extracted therefrom by using toluene. A water layer was removed therefrom, and an organic layer was cleaned by using saturated saline and dried by using $MgSO_4$. $MgSO_4$ was filtered and separated and the organic layer was concentrated. A crude product obtained therefrom was purified by silica gel column chromatography (mixed solvent of hexane and toluene was used in a development layer) to obtain Intermediate IM-8 (7.25 g, yield of 80%).

Intermediate IM-8 was identified by observing the mass number m/z=308 as the molecular ion peak through FAB-MS.

(Synthesis of Compound A73)

In an Ar atmosphere, 5.00 g (16.2 mmol) of Intermediate IM-8, 9.32 g (1.1 equiv, 17.8 mmol) of N-phenyl-N-[4-(4,4,5,5-tetramethyl-1,3,2-dioxaborolan-2-yl)phenyl]-(1,1':4',1''-terphenyl)-4-amine, 6.71 g (3 equiv, 48.6 mmol) of $K_2CO_3$, 0.94 g (0.05 equiv, 0.8 mmol) of $Pd(PPh_3)_4$, and 113 mL of mixed solution of toluene/EtOH/$H_2O$ (4/2/1) were sequentially added to a 500-mL three-neck flask, and heated and stirred at a temperature of 80° C. for 5 hours. After cooling to room temperature, the reaction solution was extracted therefrom by using toluene. A water layer was removed therefrom, and an organic layer was cleaned by using saturated saline and dried by using $MgSO_4$. $MgSO_4$ was filtered and separated and the organic layer was concentrated. A crude product obtained therefrom was purified by silica gel column chromatography (mixed solvent of hexane and toluene was used in a development layer) to obtain Compound A73 (9.33 g, yield of 86%) that was a white solid.

Compound A73 was identified by observing the mass number m/z=669 as the molecular ion peak through FAB-MS.

Synthesis Example 4: Synthesis of Compound A100

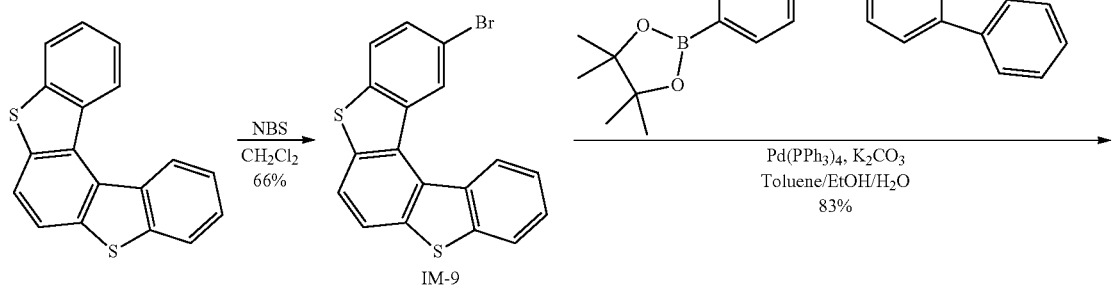

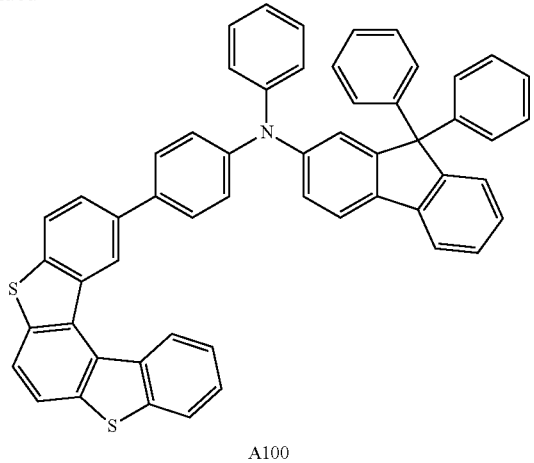

A100

(Synthesis of Intermediate IM-9)

In an Ar atmosphere, 10.00 g (34.4 mmol) of benzo[1,2-b:4,3-b']bis[1]benzothiophene, 172 mL of $CH_2Cl_2$, and 7.35 g (1.2 equiv, 41.3 mmol) of N-bromosuccinimide were sequentially added to a 300-mL three-neck flask, and stirred at room temperature for 4 hours. $H_2O$ was added to the reaction solution, and the reaction solution was extracted therefrom. A water layer was removed therefrom, and an organic layer was cleaned by using saturated saline and dried by using $MgSO_4$. $MgSO_4$ was filtered and separated and the organic layer was concentrated. A crude product obtained therefrom was purified by silica gel column chromatography (mixed solvent of hexane and toluene was used in a development layer) to obtain Intermediate IM-9 (8.39 g, yield of 66%).

Intermediate IM-9 was identified by observing the mass number m/z=369 as the molecular ion peak through FAB-MS.

(Synthesis of Compound A100)

In an Ar atmosphere, 5.00 g (13.5 mmol) of Intermediate IM-9, 9.11 g (1.1 equiv, 14.9 mmol) of N,9,9-triphenyl-N-[4-(4,4,5,5-tetramethyl-1,3,2-dioxaborolan-2-yl)phenyl]-9H-fluoren-2-amine, 5.61 g (3 equiv, 40.6 mmol) of $K_2CO_3$, 0.78 g (0.05 equiv, 0.7 mmol) of $Pd(PPh_3)_4$, and 95 mL of mixed solution of toluene/EtOH/$H_2O$ (4/2/1) were sequentially added to a 300-mL three-neck flask, and heated and stirred at a temperature of 80° C. for 5 hours. After cooling to room temperature, the reaction solution was extracted therefrom by using toluene. A water layer was removed therefrom, and an organic layer was cleaned by using saturated saline and dried by using $MgSO_4$. $MgSO_4$ was filtered and separated and the organic layer was concentrated. A crude product obtained therefrom was purified by silica gel column chromatography (mixed solvent of hexane and toluene was used in a development layer) to obtain Compound A100 (8.70 g, yield of 83%) that was a white solid.

Compound A100 was identified by observing the mass number m/z=774 as the molecular ion peak through FAB-MS.

Synthesis Example 5: Synthesis of Compound B5

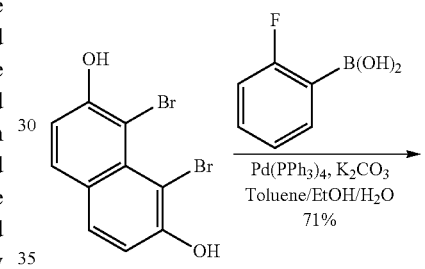

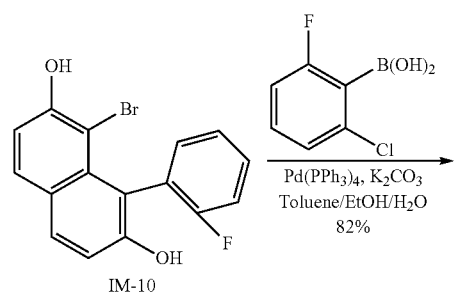

IM-10

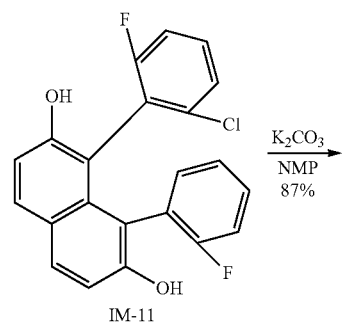

IM-11

-continued

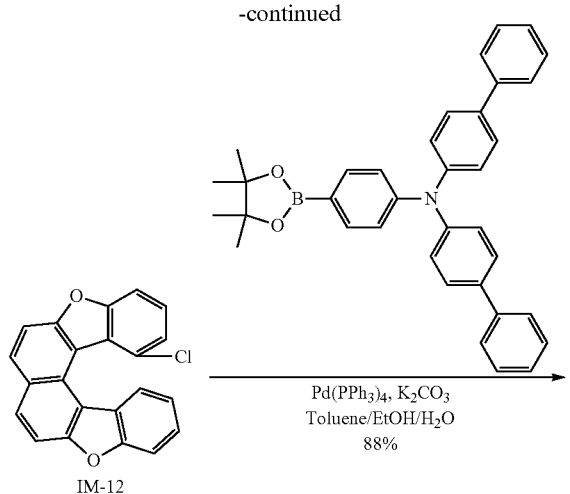

IM-12

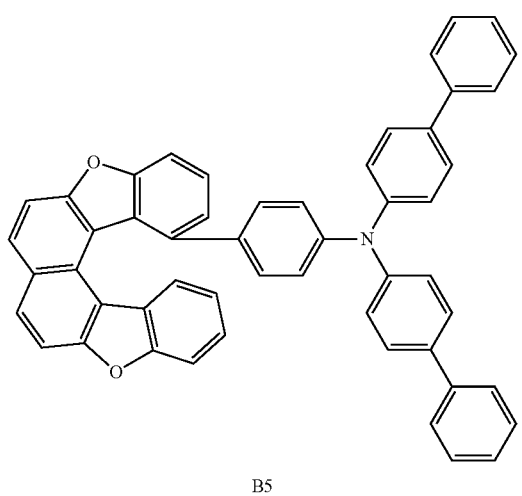

B5

(Synthesis of Intermediate IM-10)

In an Ar atmosphere, 25.00 g (78.63 mmol) of 1,8-dibromo-2,7-dihydroxynaphthalene, 12.10 g (1.1 equiv, 86.49 mmol) of 2-fluorophenylboronic acid, 32.60 g (3 equiv, 235.9 mmol) of $K_2CO_3$, 4.54 g (0.05 equiv, 3.9 mmol) of $Pd(PPh_3)_4$, and 550 mL of mixed solution of toluene/EtOH/$H_2O$ (4/2/1) were sequentially added to a 1,000-mL flask, and heated and stirred at a temperature of 80° C. for 5 hours. After cooling to room temperature, the reaction solution was extracted therefrom by using toluene. A water layer was removed therefrom, and an organic layer was cleaned by using saturated saline and dried by using $MgSO_4$. $MgSO_4$ was filtered and separated and the organic layer was concentrated. A crude product obtained therefrom was purified by silica gel column chromatography (mixed solvent of hexane and toluene was used in a development layer) to obtain Intermediate IM-10 (18.60 g, yield of 71%).

Intermediate IM-10 was identified by observing the mass number m/z=333 as the molecular ion peak through FAB-MS.

(Synthesis of Intermediate IM-11)

In an Ar atmosphere, 12.00 g (36.02 mmol) of Intermediate IM-10, 6.91 g (1.1 equiv, 39.6 mmol) of 2-chloro-6-fluorophenylboronic acid, 14.93 g (3 equiv, 108.06 mmol) of $K_2CO_3$, 2.08 g (0.05 equiv, 1.8 mmol) of $Pd(PPh_3)_4$, and 252 mL of mixed solution of toluene/EtOH/$H_2O$ (4/2/1) were sequentially added to a 500-mL three-neck flask, and heated and stirred at a temperature of 80° C. for 5 hours. After cooling to room temperature, the reaction solution was extracted therefrom by using toluene. A water layer was removed therefrom, and an organic layer was cleaned by using saturated saline and dried by using $MgSO_4$. $MgSO_4$ was filtered and separated and the organic layer was concentrated. A crude product obtained therefrom was purified by silica gel column chromatography (mixed solvent of hexane and toluene was used in a development layer) to obtain Intermediate IM-11 (11.30 g, yield of 82%).

Intermediate IM-11 was identified by observing the mass number m/z=382 as the molecular ion peak through FAB-MS.

(Synthesis of Intermediate IM-12)

In an Ar atmosphere, 10.00 g (26.1 mmol) of Intermediate IM-11, 130 mL of NMP, and 14.44 g (4 equiv, 104.5 mmol) of $K_2CO_3$ were sequentially added to a 300-mL three-neck flask, and heated and stirred at a temperature of 180° C. for 5 hours. After cooling to room temperature, $H_2O$ was added to the reaction solution, and the reaction solution was extracted therefrom. A water layer was removed therefrom, and an organic layer was cleaned by using saturated saline and dried by using $MgSO_4$. $MgSO_4$ was filtered and separated and the organic layer was concentrated. A crude product obtained therefrom was purified by silica gel column chromatography (mixed solvent of hexane and toluene was used in a development layer) to obtain Intermediate IM-12 (7.79 g, yield of 87%).

Intermediate IM-12 was identified by observing the mass number m/z=342 as the molecular ion peak through FAB-MS.

(Synthesis of Compound B5)

In an Ar atmosphere, 5.00 g (14.6 mmol) of Intermediate IM-12, 8.66 g (1.1 equiv, 16.0 mmol) of N, N-Di(4-biphenylyl)-4-(4,4,5,5-tetramethyl-1,3,2-dioxaborolan-2-yl)aniline, 6.05 g (3 equiv, 43.8 mmol) of $K_2CO_3$, 0.84 g (0.05 equiv, 0.7 mmol) of $Pd(PPh_3)_4$, and 102 mL of mixed solution of toluene/EtOH/$H_2O$ (4/2/1) were sequentially mixed to a 500-mL three-neck flask, and heated and stirred at a temperature of 80° C. for 5 hours. After cooling to room temperature, the reaction solution was extracted therefrom by using toluene. A water layer was removed therefrom, and an organic layer was cleaned by using saturated saline and dried by using MgSO$_4$. MgSO$_4$ was filtered and separated and the organic layer was concentrated. A crude product obtained therefrom was purified by silica gel column chromatography (mixed solvent of hexane and toluene was used in a development layer) to obtain Compound B5 (9.03 g, yield of 88%).

Compound B5 was identified by observing the mass number m/z=703 as the molecular ion peak through FAB-MS.

Synthesis Example 6: Synthesis of Compound B14

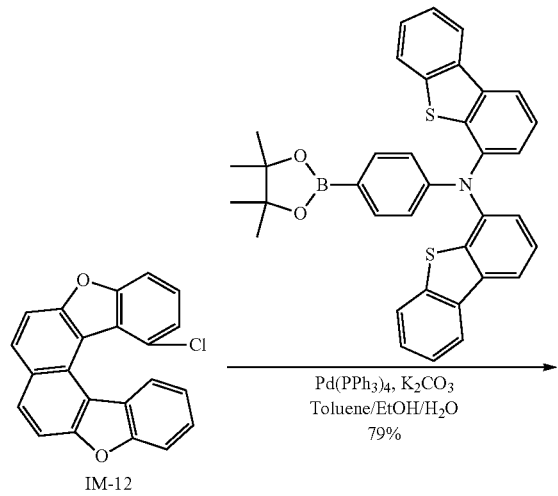

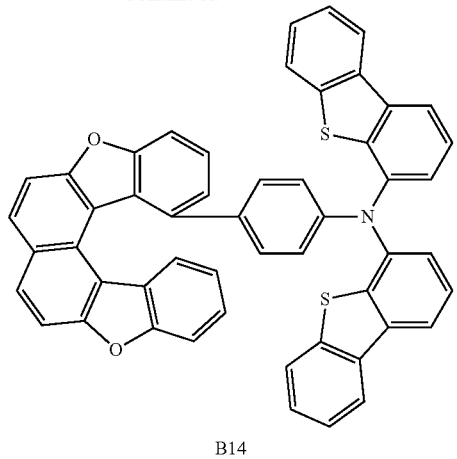

B14

(Synthesis of Compound B14)

In an Ar atmosphere, 5.00 g (14.6 mmol) of Intermediate IM-12, 8.98 g (1.1 equiv, 16.0 mmol) of N-(dibenzo[b,d]thiophen-4-yl)-N-(4-(4,4,5,5-tetramethyl-1,3,2-dioxaborolan-2-yl)phenyl)dibenzo[b, d]thiophen-4-amine, 6.05 g (3 equiv, 43.8 mmol) of K$_2$CO$_3$, 0.84 g (0.05 equiv, 0.7 mmol) of Pd(PPh$_3$)$_4$, and 102 mL of mixed solution of toluene/EtOH/H$_2$O (4/2/1) were sequentially added to a 500-mL three-neck flask, and heated and stirred at a temperature of 80° C. for 5 hours. After cooling to room temperature, the reaction solution was extracted therefrom by using toluene. A water layer was removed therefrom, and an organic layer was cleaned by using saturated saline and dried by using MgSO$_4$. MgSO$_4$ was filtered and separated and the organic layer was concentrated. A crude product obtained therefrom was purified by silica gel column chromatography (mixed solvent of hexane and toluene was used in a development layer) to obtain Compound B14 (8.08 g, yield of 79%) that was a white solid.

Compound B14 was identified by observing the mass number m/z=763 as the molecular ion peak through FAB-MS.

Synthesis Example 7: Synthesis of Compound B35

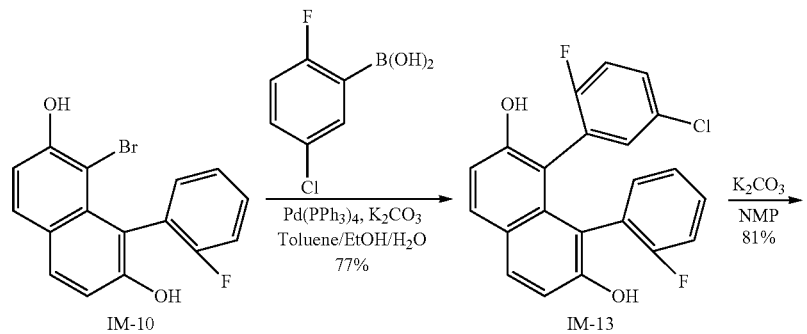

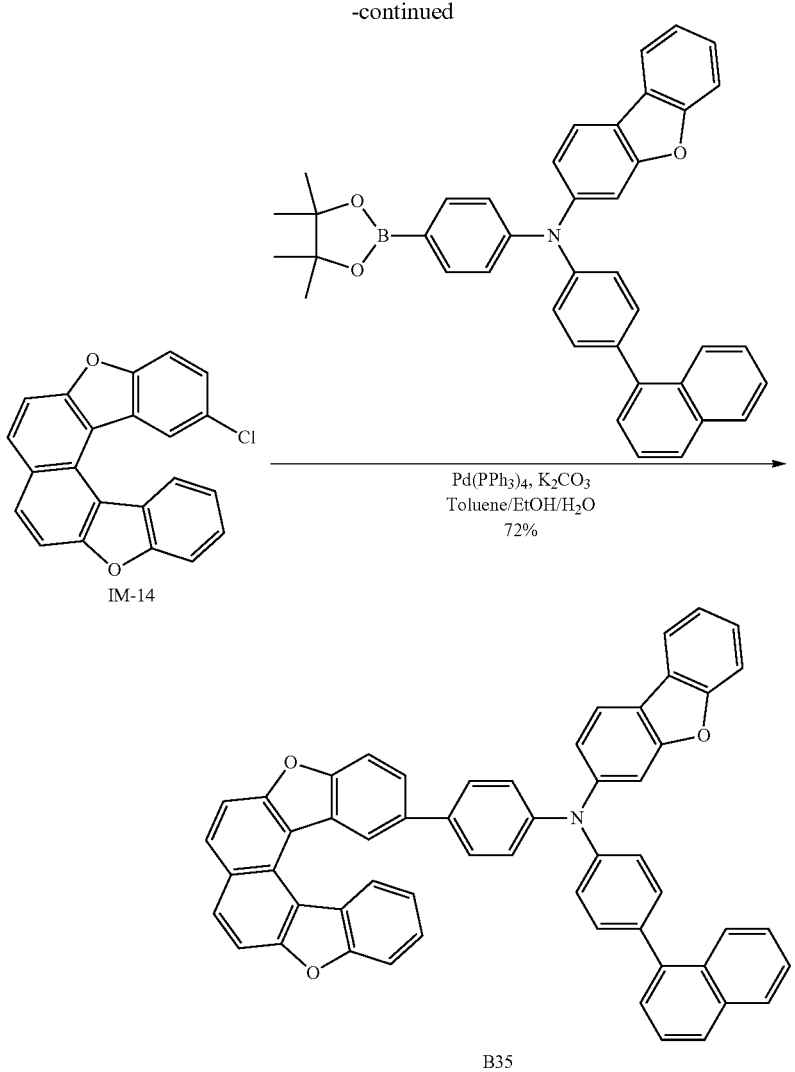

(Synthesis of Intermediate IM-13)

In an Ar atmosphere, 12.00 g (36.02 mmol) of Intermediate IM-10, 6.91 g (1.1 equiv, 39.6 mmol) of 3-chloro-6-fluorophenylboronic acid, 14.93 g (3 equiv, 108.06 mmol) of $K_2CO_3$, 2.08 g (0.05 equiv, 1.8 mmol) of $Pd(PPh_3)_4$, and 252 mL of mixed solution of toluene/EtOH/$H_2O$ (4/2/1) were sequentially added to a 500-mL three-neck flask, and heated and stirred at a temperature of 80° C. for 5 hours. After cooling to room temperature, the reaction solution was extracted therefrom by using toluene. A water layer was removed therefrom, and an organic layer was cleaned by using saturated saline and dried by using $MgSO_4$. $MgSO_4$ was filtered and separated and the organic layer was concentrated. A crude product obtained therefrom was purified by silica gel column chromatography (mixed solvent of hexane and toluene was used in a development layer) to obtain Intermediate IM-13 (10.62 g, yield of 77%).

Compound B13 was identified by observing the mass number m/z=382 as the molecular ion peak through FAB-MS.

(Synthesis of Intermediate IM-14)

In an Ar atmosphere, 10.00 g (26.1 mmol) of Intermediate IM-13, 130 mL of NMP, and 14.44 g (4 equiv, 104.5 mmol) of $K_2CO_3$ were sequentially added to a 300-mL three-neck flask, and heated and stirred at a temperature of 180° C. for 5 hours. After cooling to room temperature, $H_2O$ was added to the reaction solution, and the reaction solution was extracted therefrom. An organic layer was cleaned by using saturated saline and dried by using $MgSO_4$. $MgSO_4$ was filtered and separated and the organic layer was concentrated.

A crude product obtained therefrom was purified by silica gel column chromatography (mixed solvent of hexane and toluene was used in a development layer) to obtain Intermediate IM-14 (7.26 g, yield of 81%).

Intermediate IM-14 was identified by observing the mass number m/z=342 as the molecular ion peak through FAB-MS.

(Synthesis of Compound B35)

In an Ar atmosphere, 5.00 g (14.6 mmol) of Intermediate IM-12, 9.68 g (1.1 equiv, 16.0 mmol) of N-[4-(naphthalen-1-yl)phenyl[-N-[4-(4,4,5,5-tetramethyl-1,3,2-dioxaborolan-2-yl)phenyl]dibenzofuran-3-amine, 6.05 g (3 equiv, 43.8 mmol) of $K_2CO_3$, 0.84 g (0.05 equiv, 0.7 mmol) of $Pd(PPh_3)_4$, and 500 mL of mixed solution of toluene/EtOH/$H_2O$ (4/2/1) were sequentially added to a 500-mL three-neck flask, and heated and stirred at a temperature of 80° C. for 5 hours. After cooling to room temperature, the reaction solution was extracted therefrom by using toluene. A water layer was removed therefrom, and an organic layer was cleaned by using saturated saline and dried by using MgSO$_4$. MgSO$_4$ was filtered and separated and the organic layer was concentrated. A crude product obtained therefrom was purified by silica gel column chromatography (mixed solvent of hexane and toluene was used in a development layer) to obtain Compound B35 (8.06 g, yield of 72%) that was a white solid.

Compound B35 was identified by observing the mass number m/z=767 as the molecular ion peak through FAB-MS.

Synthesis Example 8: Synthesis of Compound B41

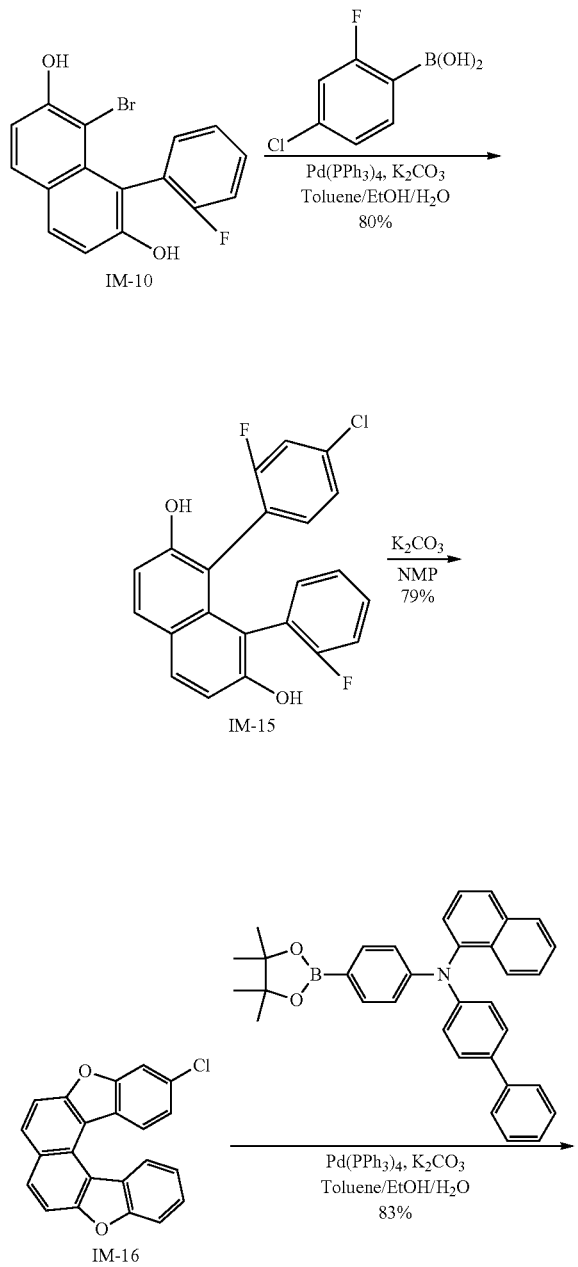

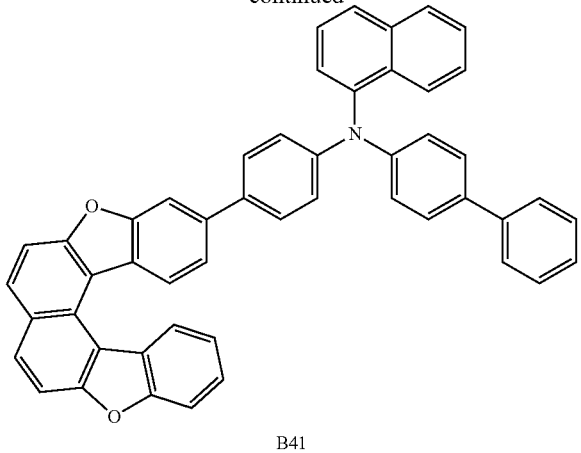

B41

(Synthesis of Intermediate IM-15)

In an Ar atmosphere, 12.00 g (36.02 mmol) of Intermediate IM-10, 6.91 g (1.1 equiv, 39.6 mmol) of 4-chloro-2-fluorophenylboronic acid, 14.93 g (3 eqiv, 108.06 mmol) of K$_2$CO$_3$, 2.08 g (0.05 equiv, 1.8 mmol) of Pd(PPh$_3$)$_4$, and 252 mL of mixed solution of toluene/EtOH/H$_2$O (4/2/1) were sequentially mixed to a 500-mL three-neck flask, and heated and stirred at a temperature of 80° C. for 5 hours. After cooling to room temperature, the reaction solution was extracted therefrom by using toluene. A water layer was removed therefrom, and an organic layer was cleaned by using saturated saline and dried by using MgSO$_4$. MgSO$_4$ was filtered and separated and the organic layer was concentrated. A crude product obtained therefrom was purified by silica gel column chromatography (mixed solvent of hexane and toluene was used in a development layer) to obtain Intermediate IM-15 (11.03 g, yield of 80%).

Intermediate IM-15 was identified by observing the mass number m/z=382 as the molecular ion peak through FAB-MS.

(Synthesis of Intermediate IM-16)

In an Ar atmosphere, 10.00 g (26.1 mmol) of IM-15, 130 mL of NMP, and 14.44 g (4 equiv, 104.5 mmol) of K$_2$CO$_3$ were sequentially added to a 300-mL three-neck flask, and heated and stirred at a temperature of 180° C. for 5 hours. After cooling to room temperature, H$_2$O was added to the reaction solution, and the reaction solution was extracted therefrom. An organic layer was cleaned by using saturated saline and dried by using MgSO$_4$. MgSO$_4$ was filtered and separated and the organic layer was concentrated. A crude product obtained therefrom was purified by silica gel column chromatography (mixed solvent of hexane and toluene was used in a development layer) to obtain Intermediate IM-16 (7.07 g, yield of 79%).

Intermediate IM-16 was identified by observing the mass number m/z=342 as the molecular ion peak through FAB-MS.

(Synthesis of Compound B41)

In an Ar atmosphere, 5.00 g (14.6 mmol) of Intermediate IM-16, 8.24 g (1.1 equiv, 16.0 mmol) of N-[(1,1'-biphenyl)-4-yl]-N-[4-(4,4,5,5-tetramethyl-1,3,2-dioxaborolan-2-yl)phenyl]naphthalen-1-amine, 6.05 g (3 equiv, 43.8 mmol) of K$_2$CO$_3$, 0.84 g (0.05 equiv, 0.7 mmol) of Pd(PPh$_3$)$_4$, and 102 mL of mixed solution of toluene/EtOH/H$_2$O (4/2/1) were sequentially added to a 500-mL three-neck flask, and heated and stirred at a temperature of 80° C. for 5 hours. After cooling to room temperature, the reaction solution was extracted therefrom by using toluene. A water layer was removed therefrom, and an organic layer was cleaned by using saturated saline and dried by using MgSO$_4$. MgSO$_4$ was filtered and separated and the organic layer was concentrated. A crude product obtained therefrom was purified by silica gel column chromatography (mixed solvent of hexane and toluene was used in a development layer) to obtain Compound B41 (8.21 g, yield of 83%) that was a white solid.

Compound B41 was identified by observing the mass number m/z=677 as the molecular ion peak through FAB-MS.

Synthesis methods of compounds other than Compounds synthesized according to Synthesis Examples may also be easily recognized by those of ordinary skill in the art by referring to the synthesis mechanisms and source materials described above.

Example 1

As an anode, a Corning 15 Ω/cm$^2$ (1,500 Å) ITO glass substrate was cut to a size of 50 mm×50 mm×0.7 mm, sonicated with isopropyl alcohol and pure water each for 5 minutes, and then cleaned by exposure to ultraviolet rays and ozone for 30 minutes. Then, the ITO glass substrate was provided to a vacuum deposition apparatus.

1-TNATA as a known material for a hole injection layer was vacuum-deposited on the ITO glass substrate to a thickness of 600 Å, and Compound A5 as a hole transport compound was vacuum-deposited to a thickness of 300 Å, thereby forming a hole transport layer.

9,10-di(naphthalen-2-yl)anthracene (ADN) as a known blue fluorescent host and 2,5,8,11-tetra-t-butylperylene (TBPe) as a known blue fluorescent dopant were co-deposited on the hole transport layer at a weight ratio of 97:3 to form an emission layer having a thickness of 250 Å.

Alq$_3$ was deposited on the emission layer to form an electron transport layer having a thickness of 250 Å, LiF, which is an alkali metal halide, was deposited on the electron transport layer to form an electron injection layer having a thickness of 10 Å, Al was vacuum-deposited to form a cathode electrode having a thickness of 1,000 Å to form a LiF/Al electrode, thereby completing the manufacture of an organic light-emitting device.

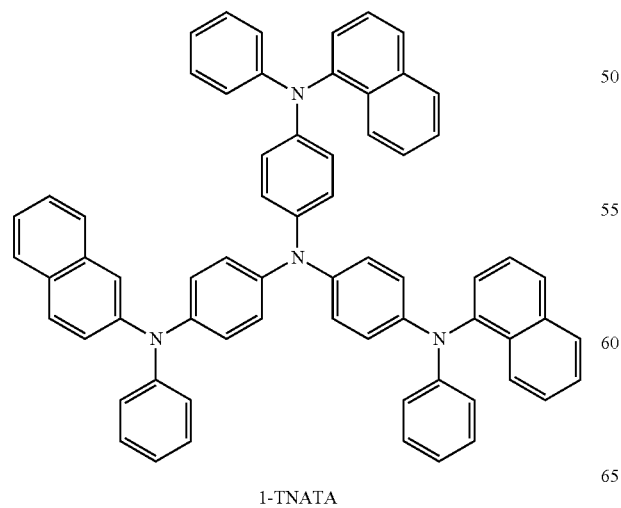

1-TNATA

-continued

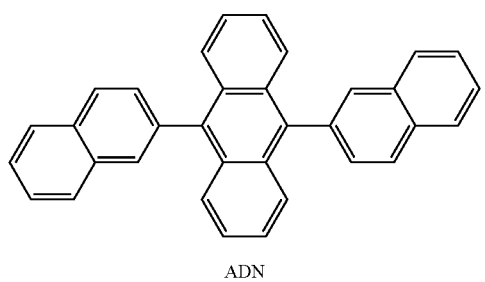

ADN

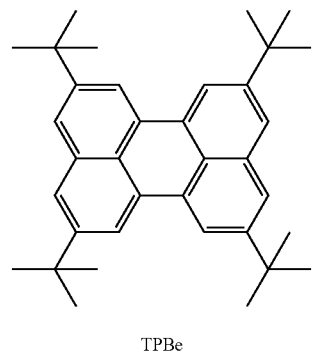

TPBe

Examples 2 to 8

Organic light-emitting devices were manufactured in the same manner as in Example 1, except that Compounds shown in Table 1 were each used instead of Compound A5 in forming a hole transport layer.

Comparative Examples 1 to 6

Organic light-emitting devices were manufactured in the same manner as in Comparative Example 1, except that Compounds R$_1$ to R$_6$ were each used instead of Compound A5 in forming a hole transport layer.

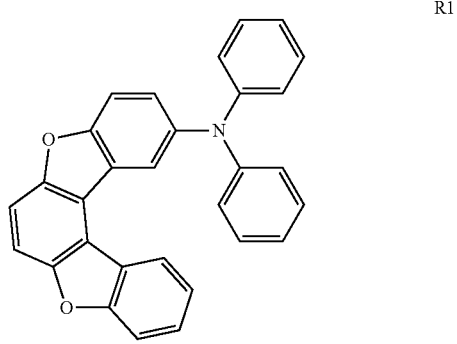

R1

-continued

R2
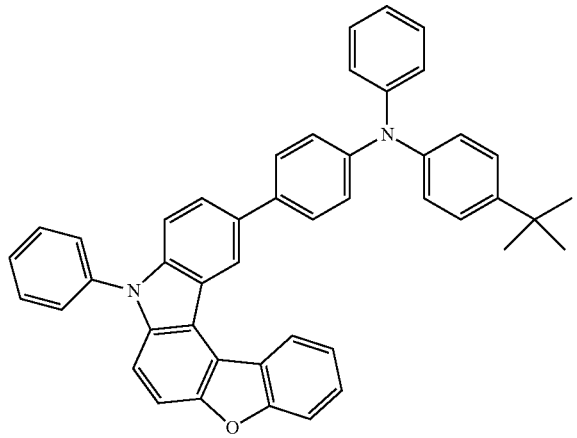

R3
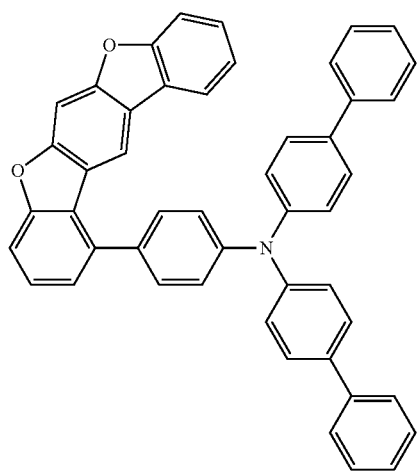

R4
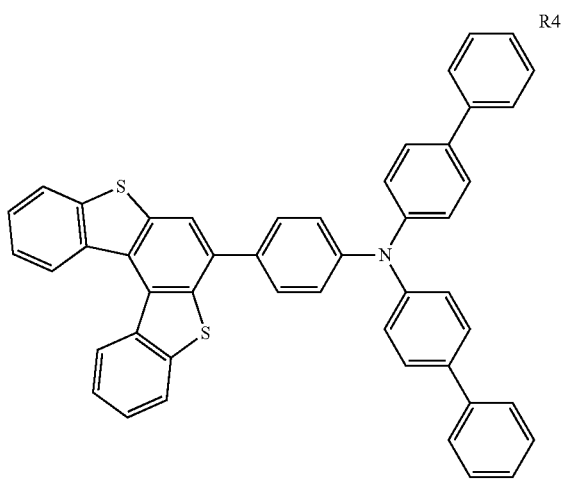

-continued

R5
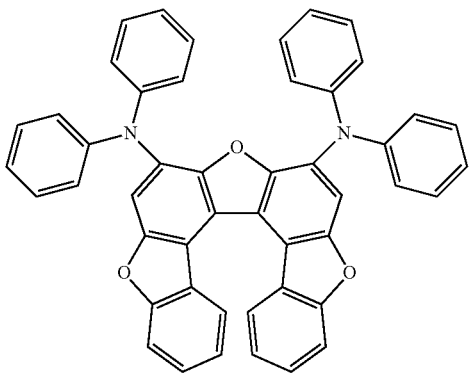

R6
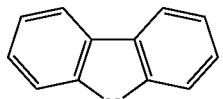
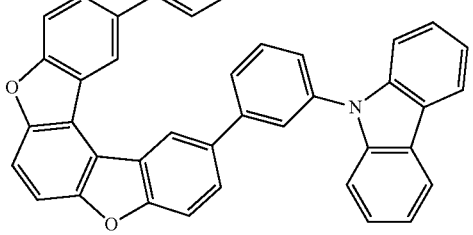

Evaluation Example 1

The current density, driving voltage, luminescent efficiency, and half lifespan of the organic light-emitting devices manufactured according to Examples 1 to 8 and Comparative Examples 1 to 6 were measured at dark room by using Source Meter (manufactured by Keithley Instrument 2400 series), a chrominance luminance meter CS-200 (manufactured by Konica Minolta), and measurement program LabVIEW 8.2, and results thereof are shown in Table 1. The half lifespan is a luminance half time from luminance 1000 cd/m$^2$.

TABLE 1

| | Hole transport material | Driving voltage (V) | Current density (mA/cm$^2$) | Efficiency (cd/A) | Half lifespan (LT50(h)) |
|---|---|---|---|---|---|
| Example 1 | Compound A5 | 5.7 | 10 | 7.9 | 2050 |
| Example 2 | Compound A21 | 5.8 | 10 | 8.1 | 2000 |
| Example 3 | Compound A73 | 5.6 | 10 | 7.6 | 2150 |
| Example 4 | Compound A100 | 5.7 | 10 | 7.7 | 2200 |
| Example 5 | Compound B5 | 5.6 | 10 | 8.2 | 2100 |
| Example 6 | Compound B14 | 5.8 | 10 | 8.3 | 2050 |
| Example 7 | Compound B35 | 5.8 | 10 | 8.0 | 2150 |

TABLE 1-continued
|  | Hole transport material | Driving voltage (V) | Current density (mA/cm$^2$) | Efficiency (cd/A) | Half lifespan (LT50(h)) |
|---|---|---|---|---|---|
| Example 8 | Compound B41 | 5.8 | 10 | 8.0 | 2100 |
| Comparative Example 1 | Compound R1 | 6.0 | 10 | 5.6 | 1400 |
| Comparative Example 2 | Compound R2 | 6.0 | 10 | 6.0 | 1500 |
| Comparative Example 3 | Compound R3 | 5.9 | 10 | 6.0 | 1750 |
| Comparative Example 4 | Compound R4 | 6.0 | 10 | 6.3 | 1700 |
| Comparative Example 5 | Compound R5 | 6.0 | 10 | 5.9 | 1750 |
| Comparative Example 6 | Compound R6 | 6.4 | 10 | 5.7 | 1500 |
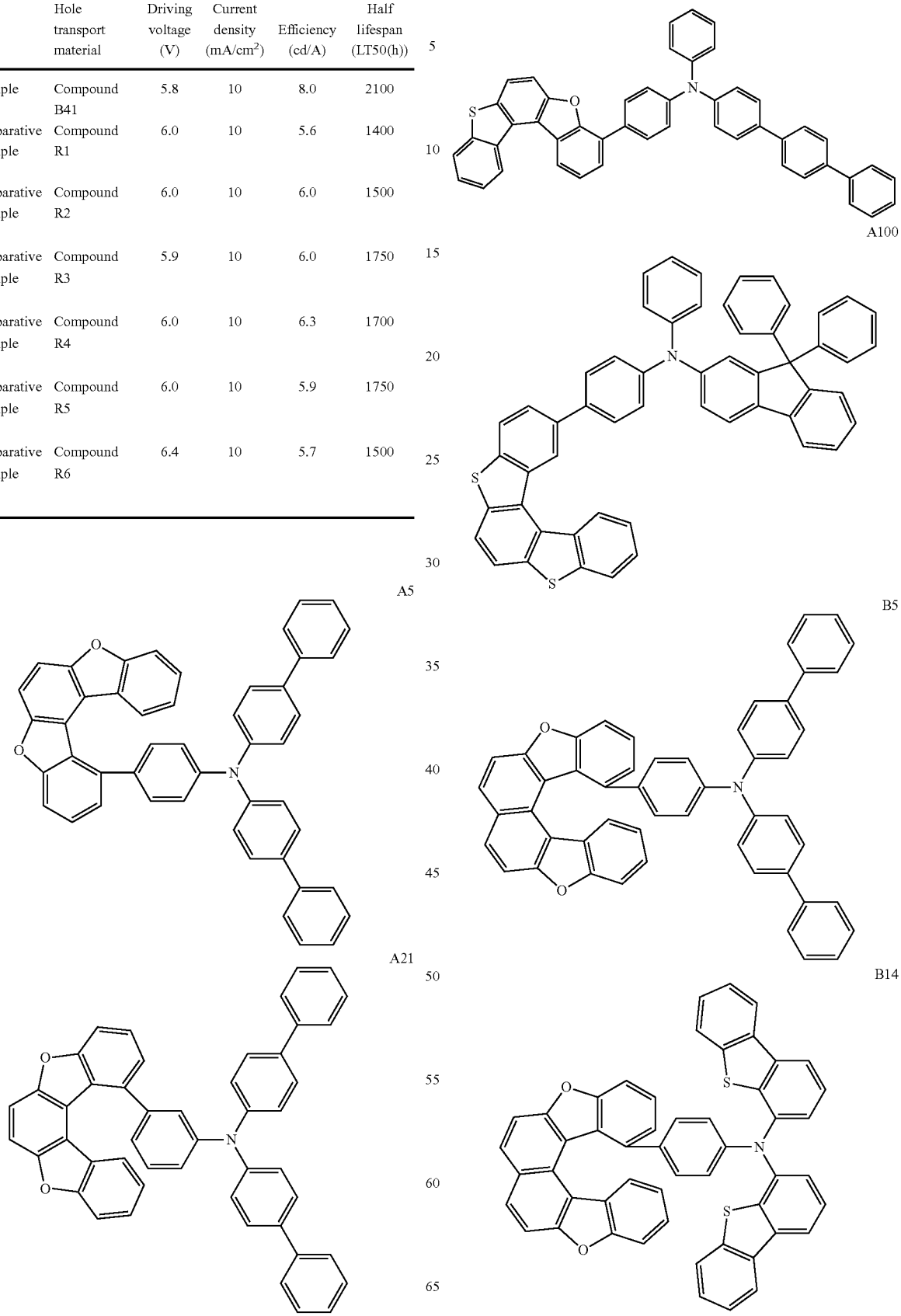

-continued

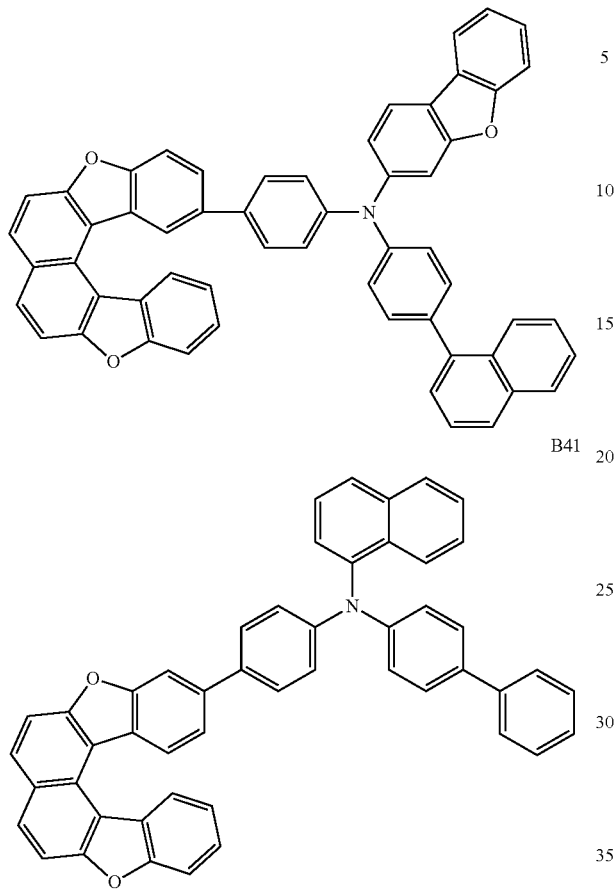

Referring to Table 1, it is confirmed that the organic light-emitting devices of Examples 1 to 8 have a low driving voltage and high efficiency, as compared with the organic light-emitting devices of Comparative Examples 1 to 6. In addition, it is confirmed that the organic light-emitting devices of Examples 1 to 8 have a long lifespan, as compared with the organic light-emitting devices of Comparative Examples 1 to 6.

The organic light-emitting device including the condensed cyclic compound may have a low driving voltage, high efficiency, and a long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

-continued
B111
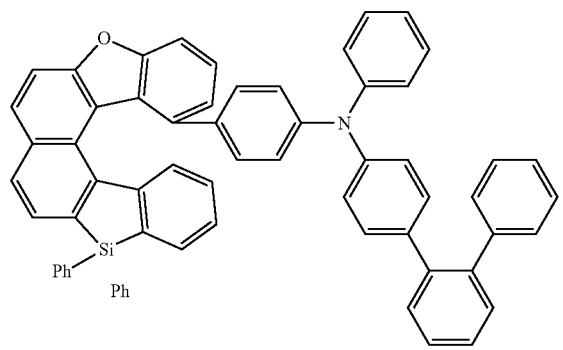
B112
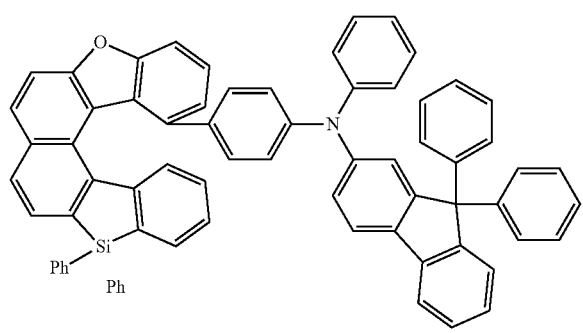
B115
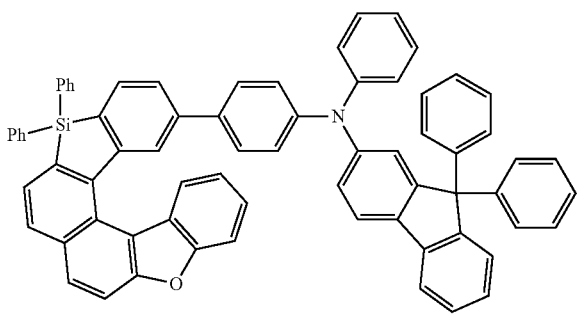
B116
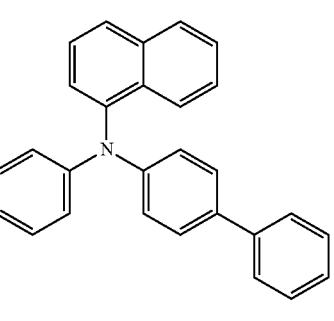
B113
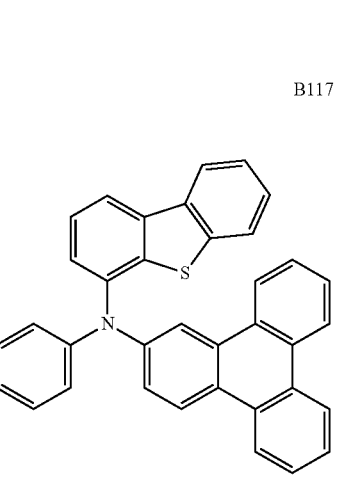
B117
B114
B118
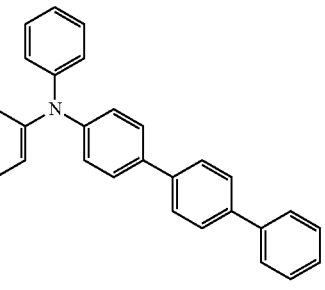

B119
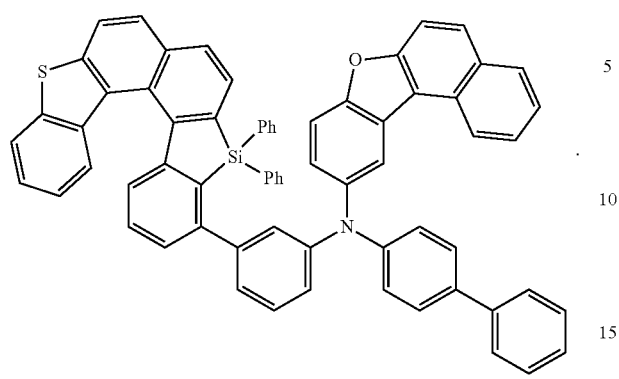

What is claimed is:
1. An organic light-emitting device comprising:
a first electrode;
a second electrode facing the first electrode; and
an organic layer between the first electrode and the second electrode and comprising an emission layer,
wherein the organic layer comprises at least one of a condensed cyclic compound represented by Formula 1-1 or 1-2:

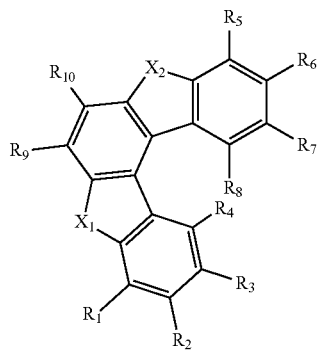

<Formula 1-1>

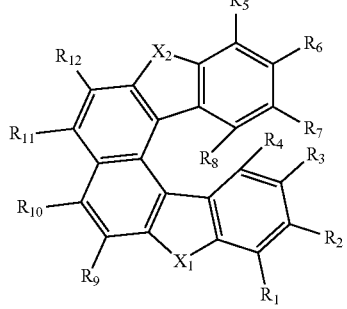

<Formula 1-2>

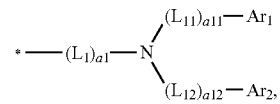

<Formula 2> wherein, in Formulae 1-1 and 1-2,
$X_1$ and $X_2$ are each independently O, S, and $Si(R_{13})(R_{14})$, and at least one selected from $X_1$ and $X_2$ is $Si(R_{13})(R_{14})$,
wherein, in Formula 2,
$L_1$, $L_{11}$, and $L_{12}$ are each independently selected from *—O—*', a substituted or unsubstituted $C_3$-$C_{60}$ carbocyclic group, and a substituted or unsubstituted $C_1$-$C_{60}$ heterocyclic group,
a1 is an integer from 1 to 5,
a11 and a12 are each independently an integer from 0 to 4,
$Ar_1$ and $Ar_2$ are each independently selected from a substituted or unsubstituted $C_3$-$C_{60}$ carbocyclic group and a substituted or unsubstituted $C_1$-$C_{60}$ heterocyclic group,
wherein, in Formulae 1-1 and 1-2,
$R_5$ to $R_{14}$ are each independently selected from a group represented by Formula 2, hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —S(=O)$_2$($Q_1$), and —P(=O)($Q_1$)($Q_2$), at least one selected from $R_5$ to $R_8$ is a group represented by Formula 2, $R_1$ to $R_4$ are each independently selected from a group represented by hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), and —B($Q_1$)($Q_2$), $R_1$ to $R_4$ do not include a carbazole group, any two neighboring groups among $R_1$ to $R_{14}$ are optionally linked to form a substituted or unsubstituted $C_3$-$C_{60}$ carbocyclic group or a $C_1$-$C_{60}$ heterocyclic group, at least one substituent of the substituted $C_3$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is selected from:

deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* and *' each indicate a binding site to a neighboring atom.

2. The organic light-emitting device of claim 1, wherein, the first electrode is an anode,
the second electrode is a cathode,
the organic layer comprises a hole transport region between the first electrode and the emission layer and an electron transport region between the emission layer and the second electrode, the hole transport region comprises a hole injection layer, a hole transport layer, an emission auxiliary layer, an electron blocking layer, or any combination thereof, and the electron transport region comprises a buffer layer, a hole blocking layer, an electron control layer, an electron transport layer, an electron injection layer, or any combination thereof.

3. The organic light-emitting device of claim 2, wherein, the hole transport region comprises the condensed cyclic compound.

4. The organic light-emitting device of claim 2, wherein, the hole transport region comprises the hole transport layer, and the hole transport layer comprises the condensed cyclic compound.

5. The organic light-emitting device of claim 4, wherein, the hole transport region comprises the emission auxiliary layer, and the emission auxiliary layer comprises the condensed cyclic compound.

6. The organic light-emitting device of claim 1, wherein, the emission layer comprises a host and a dopant.

7. The organic light-emitting device of claim 6, wherein, the host comprises an anthracene-based compound, a pyrene-based compound, a fluoranthene-based compound, a chrysene-based compound, a dihydrobenzanthracene-based compound, a triphenylene-based compound, or any combination thereof.

8. The organic light-emitting device of claim 1, wherein, the emission layer is a first emission layer for emitting a first color light, the organic light-emitting device further comprises i) at least one second emission layer for emitting a second color light or ii) at least one second emission layer for emitting the second color light and at least one third emission layer for emitting a third color light, between the first electrode and the second electrode, a maximum emission wavelength of the first color light, a maximum emission wavelength of the second color light, and a maximum emission wavelength of the third color light are identical to or different from each other, and the first color light and the second color light are emitted in the form of a mixed light, or the first color light, the second color light, and the third color light are emitted in the form of the mixed light.

9. A condensed cyclic compound represented by Formula 1-1 or 1-2:

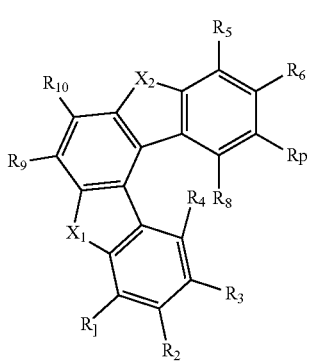

<Formula 1-1>

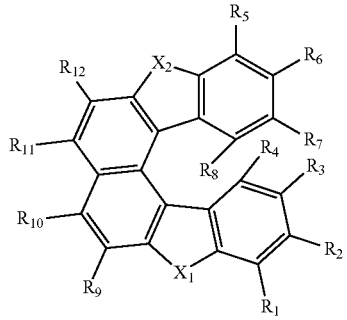

<Formula 1-2>

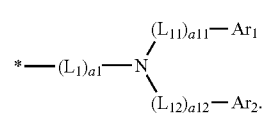

<Formula 2> wherein, in Formulae 1-1 and 1-2, $X_1$ and $X_2$ are each independently O, S, and $Si(R_{13})(R_{14})$, and at least one selected from $X_1$ and $X_2$ is $Si(R_{13})(R_{14})$, wherein, in Formula 2, $L_1$, $L_{11}$, and $L_{12}$ are each independently selected from *—O—*', a substituted or unsubstituted $C_3$-$C_{60}$ carbocyclic group, and a substituted or unsubstituted $C_1$-$C_{60}$ heterocyclic group, a1 is an integer from 1 to 5, a11 and a12 are each independently an integer from 0 to 4, $Ar_1$ and $Ar_2$ are each independently selected from a substituted or unsubstituted $C_3$-$C_{60}$ carbocyclic group and a substituted or unsubstituted $C_1$-$C_{60}$ heterocyclic group, wherein, in Formulae 1-1 and 1-2, $R_5$ to $R_{14}$ are each independently selected from a group represented by Formula 2, hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$B(Q_1)(Q_2)$, —$S(=O)_2(Q_1)$, and —$P(=O)(Q_1)(Q_2)$, at least one selected from $R_5$ to $R_8$ is a group represented by Formula 2, $R_1$ to $R_4$ are each independently selected from a group represented by hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), and —B($Q_1$)($Q_2$), $R_1$ to $R_4$ do not include a carbazole group, any two neighboring groups among $R_1$ to $R_{14}$ are optionally linked to form a substituted or unsubstituted $C_3$-$C_{60}$ carbocyclic group or a $C_1$-$C_{60}$ heterocyclic group, at least one substituent of the substituted $C_3$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is selected from:

deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* and *' each indicate a binding site to a neighboring atom.

10. The condensed cyclic compound of claim 9, wherein, $L_1$, $L_{11}$, and $L_{12}$ are each independently selected from:

*—O—*', a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a benzosilole group, a dibenzosilole group, a quinoline group, an isoquinoline group, a benzimidazole group, an imidazopyridine group, and an imidazopyrimidine group;

a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a benzosilole group, a dibenzosilole group, a quinoline group, an isoquinoline group, a benzimidazole group, an imidazopyridine group, and an imidazopyrimidine group, each substituted with at least one selected from deuterium, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a pyridinyl group, a pyrazinyl group, a pyrimidinyl group, a pyridazinyl group, a quinolinyl group, an isoquinolinyl group, a benzofuranyl group, a benzothiophenyl group, —Si($Q_{31}$)($Q_{32}$)($Q_{33}$), —N($Q_{31}$)($Q_{32}$), and —B($Q_{31}$)($Q_{32}$), and $Q_1$ and $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, and a pyridinyl group.

11. The condensed cyclic compound of claim 9, wherein, $L_1$, $L_{11}$, and $L_{12}$ are each independently selected from *—O—*' and groups represented by Formulae 3-1 to 3-29:

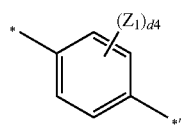

3-1

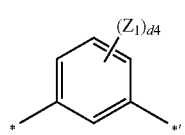

3-2

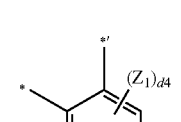

3-3

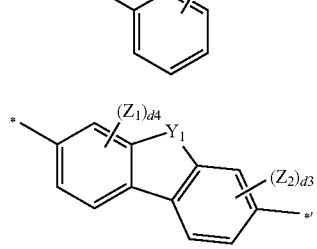

3-4

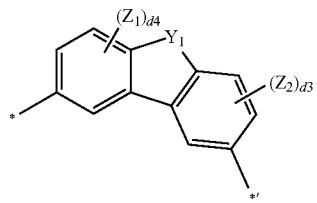

3-5

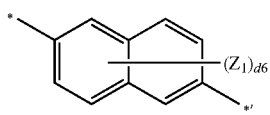

3-6

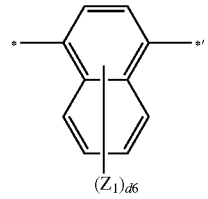

3-7

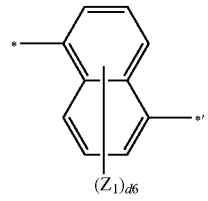

3-8

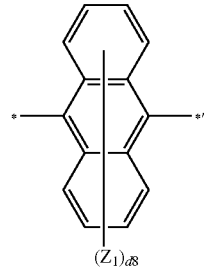

3-9

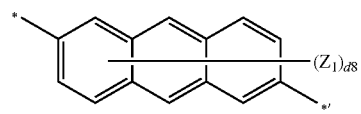

3-10

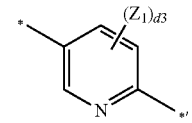

3-11

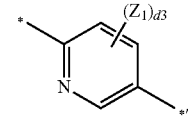

3-12

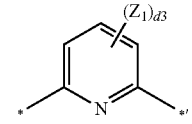

3-13

213
-continued
3-14
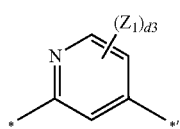
3-15
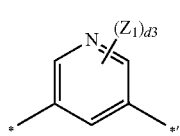
3-16
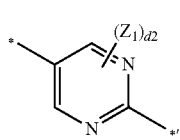
3-17
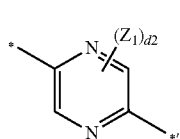
3-18
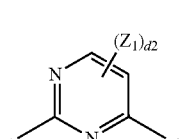
3-19
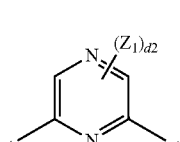
3-20
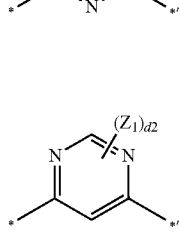
3-21
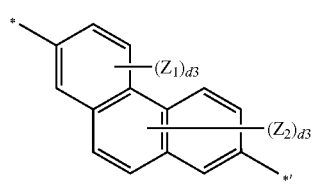
3-22
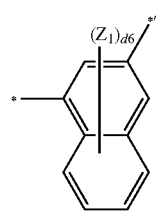
214
-continued
3-23
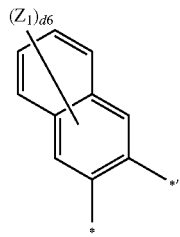
3-24
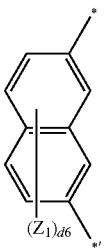
3-25
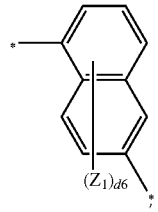
3-26
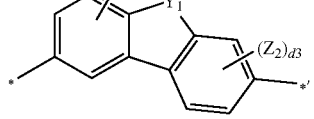
3-27
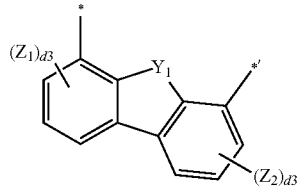
3-28
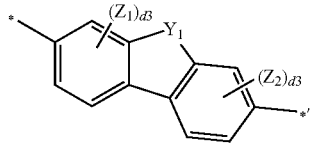
3-29
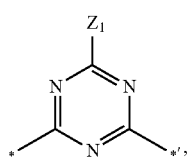
wherein, in Formulae 3-1 to 3-29,
$Y_1$ is selected from $C(Z_3)(Z_4)$, $N(Z_5)$, $Si(Z_6)(Z_7)$, O, and S,
$Z_1$ to $Z_7$ are each independently selected from hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a pyrenyl group, a chrysenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a benzofuranyl group, a benzothiophenyl group, a benzosilolyl group, a dibenzosilolyl group, and —Si($Q_{31}$)($Q_{32}$)($Q_{33}$), $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, and a pyridinyl group, d2 is an integer from 0 to 2,
d3 is an integer from 0 to 3,
d4 is an integer from 0 to 4,
d6 is an integer from 0 to 6,
d8 is an integer from 0 to 8, and
* and *' each indicate a binding site to a neighboring atom.

12. The condensed cyclic compound of claim 9, wherein, a1 is 1 or 2.

13. The condensed cyclic compound of claim 9, wherein, $Ar_1$ and $Ar_2$ are each independently selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a triphenylenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, an adamantanyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, a benzonaphtho silolyl group, a dinaphtho silolyl group, a benzimidazolyl group, a phenanthrolinyl group, and an imidazopyridinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a triphenylenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, an adamantanyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, a benzonaphtho silolyl group, a dinaphtho silolyl group, a benzimidazolyl group, a phenanthrolinyl group, and an imidazopyridinyl group, each substituted with at least one selected from deuterium, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a triphenylenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, an adamantanyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, a benzonaphtho silolyl group, a dinaphtho silolyl group, a benzimidazolyl group, a phenanthrolinyl group, an imidazopyridinyl group, —N($Q_{31}$)($Q_{32}$), —Si($Q_{31}$)($Q_{32}$)($Q_{33}$), and —P(=O)($Q_{31}$)($Q_{32}$); and —N($Q_1$)($Q_2$), —B($Q_1$)($Q_2$), —S(=O)$_2$($Q_1$), and —P(=O)($Q_1$)($Q_2$), and $Q_1$, $Q_2$, and $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, and a pyridinyl group.

14. The condensed cyclic compound of claim 9, wherein, $Ar_1$ and $Ar_2$ are each independently selected from groups represented by Formulae 4-1 to 4-15:

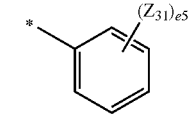

4-1

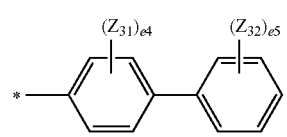

4-2

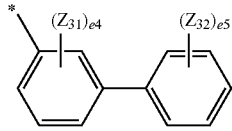

4-3

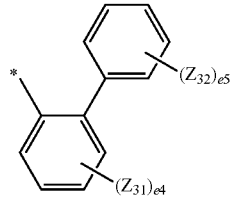

4-4

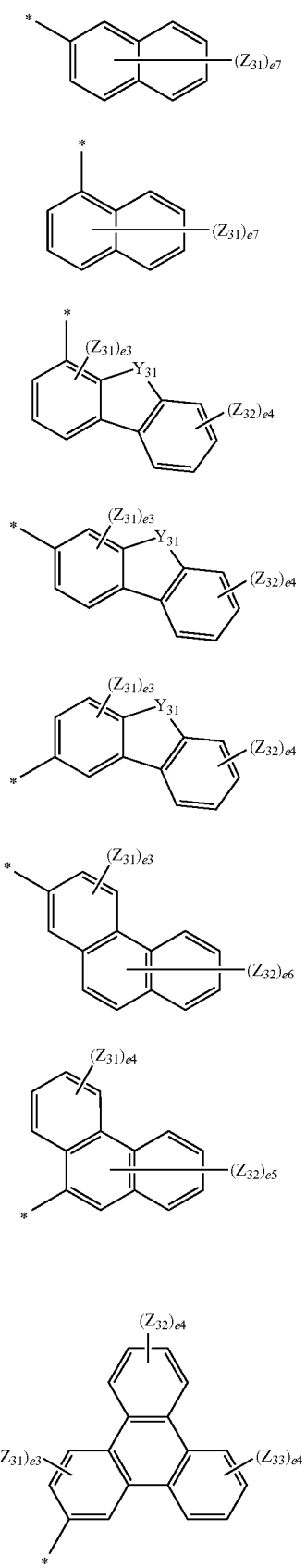
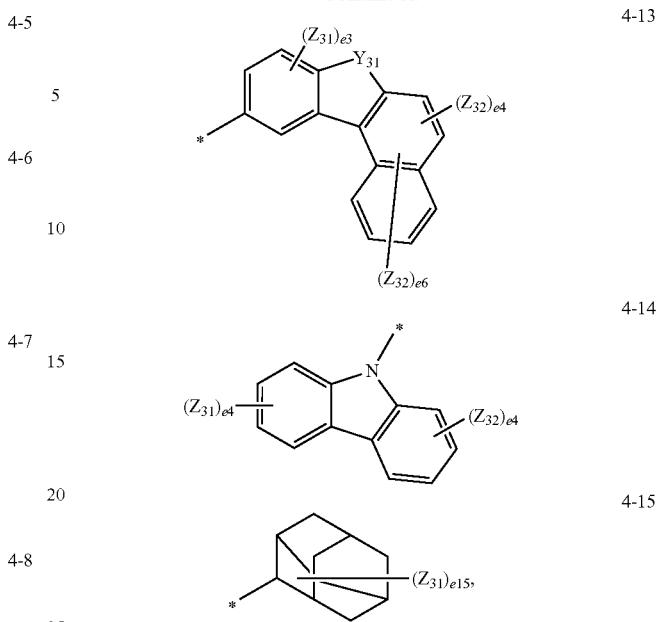

wherein, in Formulae 4-1 to 4-15, $Y_{31}$ is selected from $C(Z_{34})(Z_{35})$, $N(Z_{36})$, $Si(Z_{37})(Z_{38})$, O, and S, $Z_{31}$ to $Z_{38}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a triazinyl group, a biphenyl group, a terphenyl group, a phenyl group substituted with a $C_1$-$C_{20}$ alkyl group, and —$Si(Q_{31})(Q_{32})(Q_{33})$, $Q_{31}$ to $Q_{33}$ are each independently selected from a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and a phenyl group substituted with a $C_1$-$C_{20}$ alkyl group, e3 is an integer from 0 to 3,
e4 is an integer from 0 to 4,
e5 is an integer from 0 to 5,
e6 is an integer from 0 to 6,
e7 is an integer from 0 to 7,
e15 is an integer from 0 to 15, and
* indicates a binding site to a neighboring atom.

15. The condensed cyclic compound of claim 9, wherein, $R_5$ to $R_{14}$ are each independently selected from:
a group represented by Formula 2, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a triphenylenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, an adamantanyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, a benzonaphtho silolyl group, a dinaphtho silolyl group, a benzimidazolyl group, a phenanthrolinyl group, and an imidazopyridinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a triphenylenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, an adamantanyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, a benzonaphtho silolyl group, a dinaphtho silolyl group, a benzimidazolyl group, a phenanthrolinyl group, and an imidazopyridinyl group, each substituted with at least one selected from deuterium, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a triphenylenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, an adamantanyl group, a pyridinyl group, a pyrazinyl group, a pyrimidinyl group, a pyridazinyl group, a triazinyl group, a thiophenyl group, a furanyl group, a quinolinyl group, an isoquinolinyl group, a benzofuranyl group, a benzothiophenyl group, a dibenzosilolyl group, a benzonaphtho silolyl group, a dinaphtho silolyl group, a benzimidazolyl group, a phenanthrolinyl group, an imidazopyridinyl group, —N($Q_{31}$)($Q_{32}$), —Si($Q_{31}$)($Q_{32}$)($Q_{33}$), and —P(=O)($Q_{31}$)($Q_{32}$); and —B($Q_1$)($Q_2$), —S(=O)$_2$($Q_1$), and —P(=O)($Q_1$)($Q_2$), and $Q_1$, $Q_2$, and $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, and a pyridinyl group.

16. The condensed cyclic compound of claim 9, wherein, in Formula 1-1, i) $R_1$ to $R_4$ and $R_9$ to $R_{10}$ are each hydrogen, or ii) $R_1$ to $R_4$ are each hydrogen, and $R_9$ to $R_{10}$ are linked to form a benzene group.

17. The condensed cyclic compound of claim 9, wherein, in Formula 1-2, i) $R_1$ to $R_4$ and $R_9$ to $R_{12}$ are each hydrogen, ii) $R_1$ to $R_4$ and $R_9$ to $R_{10}$ are each hydrogen, and Ru and $R_{12}$ are linked to form a benzene group, or iii) $R_1$ to $R_2$ and $R_9$ to $R_{12}$ are each hydrogen, and $R_3$ and $R_4$ are linked to form a benzene group or a pyridine group.

18. The condensed cyclic compound of claim 9, wherein, i) $R_5$ is a group represented by Formula 2, and $R_6$ to $R_8$ are each hydrogen, ii) $R_6$ is a group represented by Formula 2, and $R_5$, $R_7$, and $R_8$ are each hydrogen, iii) $R_7$ is a group represented by Formula 2, and $R_5$, $R_6$, and $R_8$ are each hydrogen, or iv) $R_8$ is a group represented by Formula 2, and $R_5$ to $R_7$ are each hydrogen.

19. The condensed cyclic compound of claim 9, wherein, the condensed cyclic compound is selected from Compounds A105 to A119 and B105 to B119:

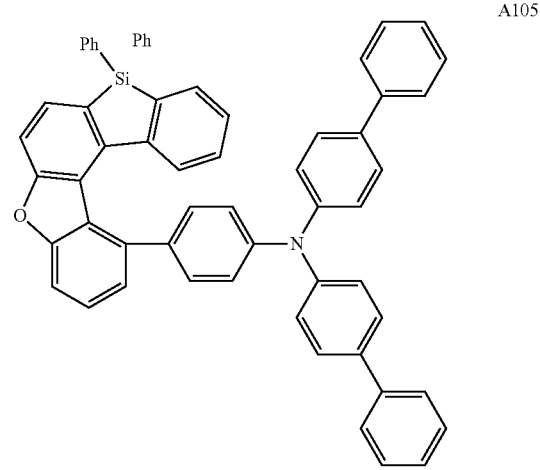

A105

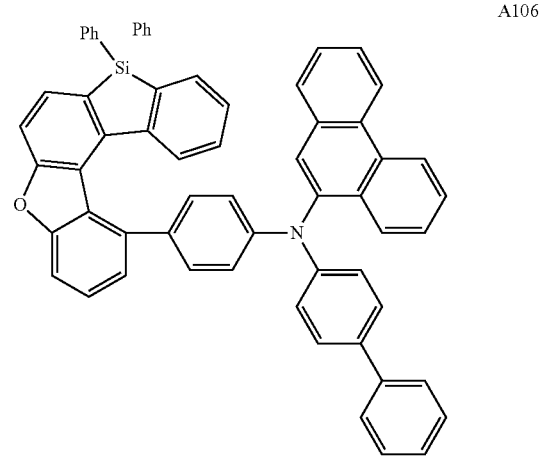

A106

-continued
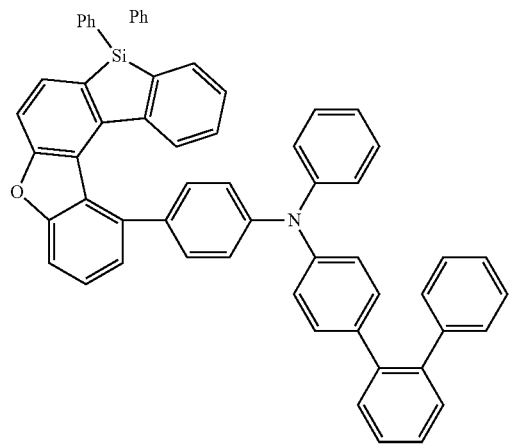
A107
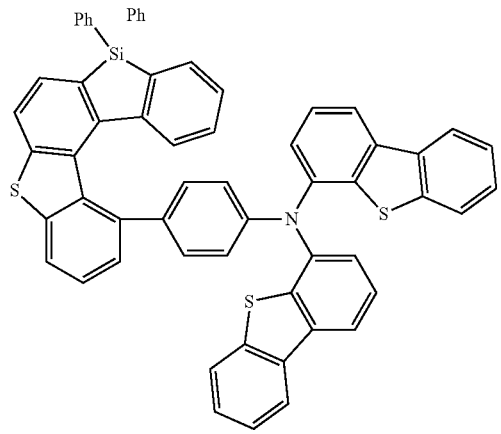
A110
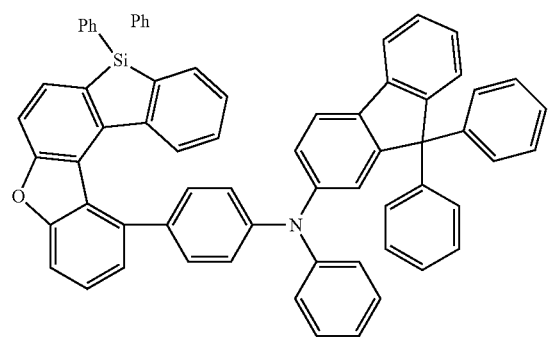
A108
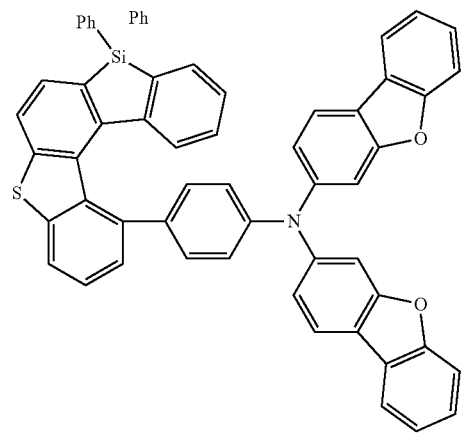
A111
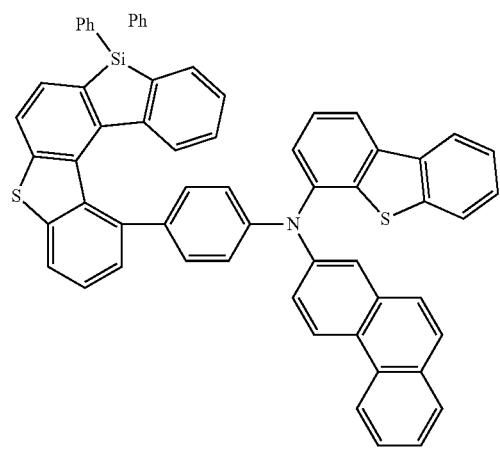
A109
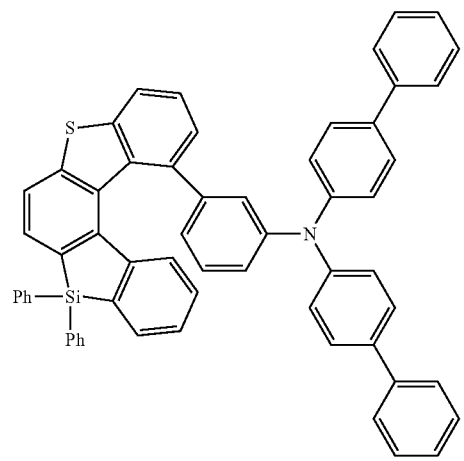
A112

A113
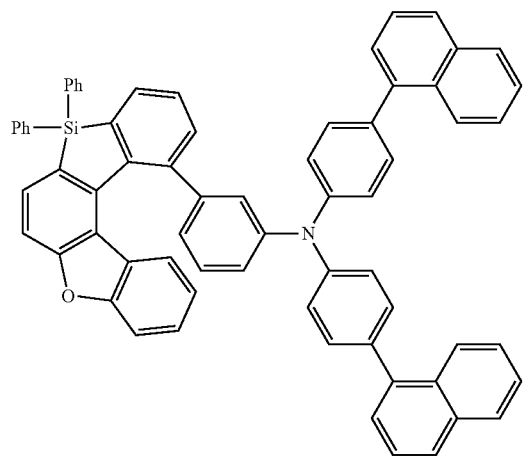
A114
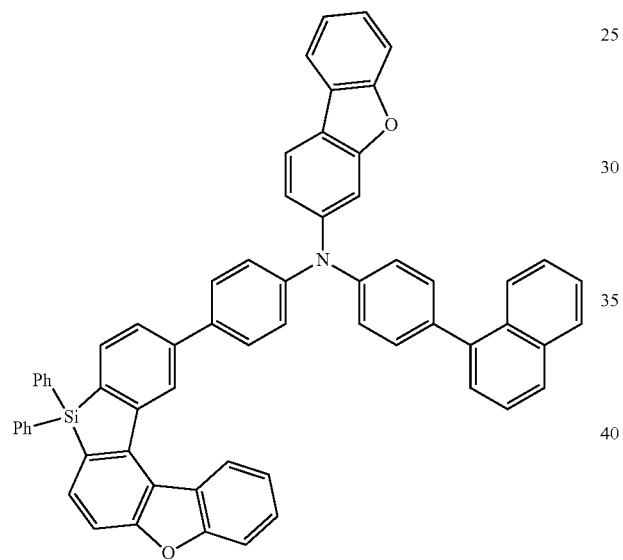
A115
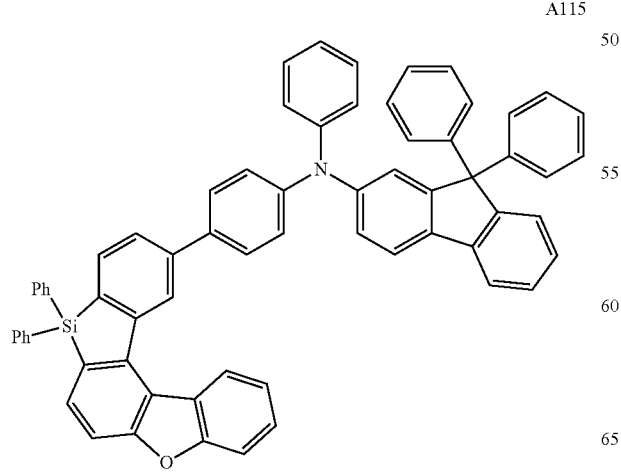
A116
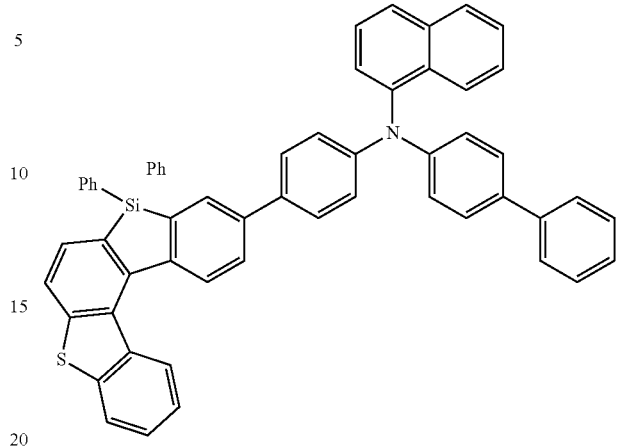
A117
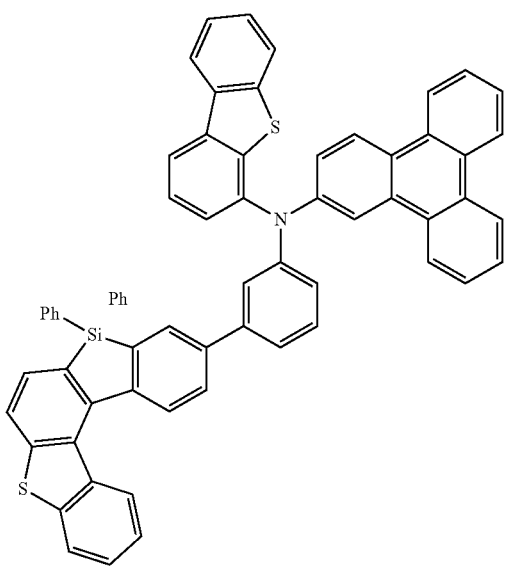
A118
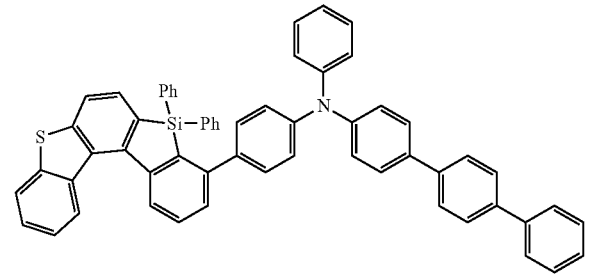

A119
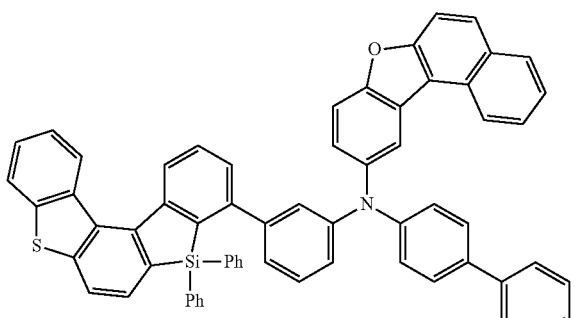
B105
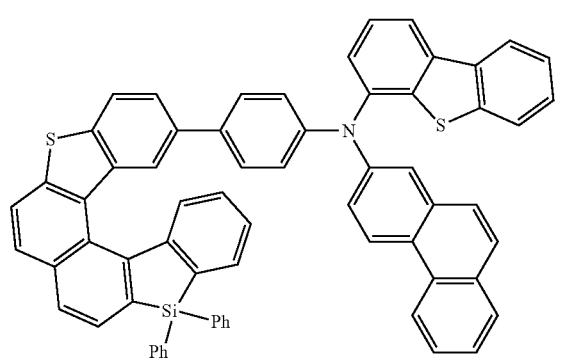
B106
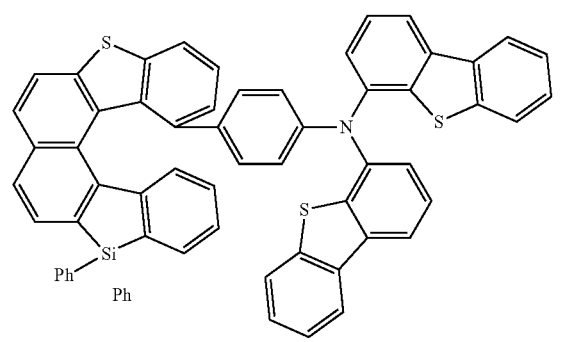
B107
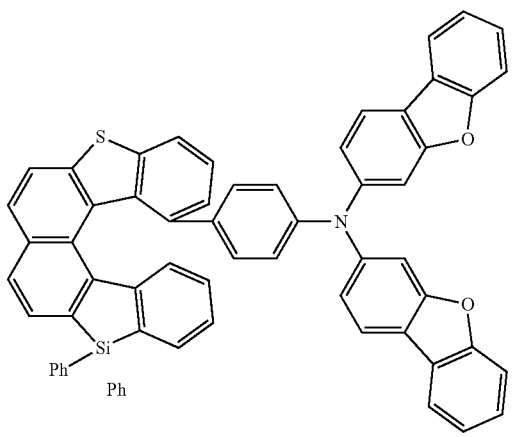
B108
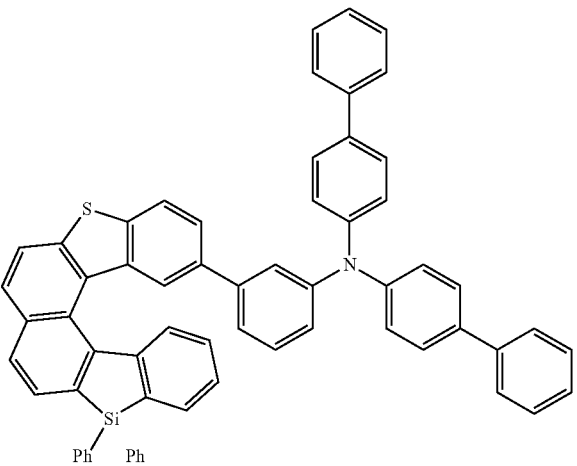
B109
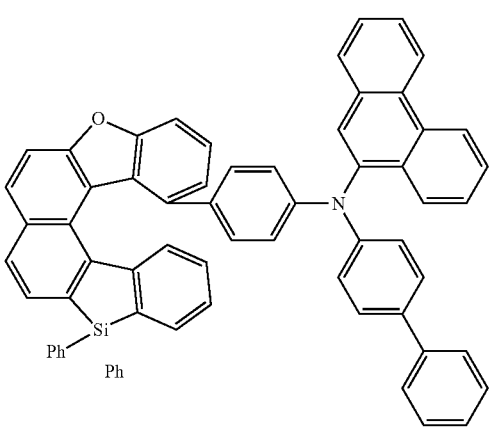
B110